(12) United States Patent
Künzl et al.

(10) Patent No.: US 11,661,398 B2
(45) Date of Patent: May 30, 2023

(54) CELLULAR TRANSPORT SYSTEM FOR TRANSFERRING A SULFONIC ACID CONSTRUCT CARRYING A CARGO INTO THE CYTOPLASM OF A CELL

(71) Applicant: Scientist of Fortune, S.A., Luxembourg (LU)

(72) Inventors: Tilmann Künzl, Basel (CH); Sven Panke, Zürich (CH); Philippe Marlière, Luxembourg (LU)

(73) Assignee: Scientist of Fortune, S.A., Luxembourg (LU)

( * ) Notice: Subject to any disclaimer, the term of this patent is extended or adjusted under 35 U.S.C. 154(b) by 291 days.

(21) Appl. No.: 16/652,949

(22) PCT Filed: Oct. 2, 2018

(86) PCT No.: PCT/EP2018/076826
§ 371 (c)(1),
(2) Date: Apr. 1, 2020

(87) PCT Pub. No.: WO2019/068726
PCT Pub. Date: Apr. 11, 2019

(65) Prior Publication Data
US 2021/0009513 A1    Jan. 14, 2021

(30) Foreign Application Priority Data
Oct. 2, 2017 (EP) .................................. 17194345

(51) Int. Cl.
*C07C 309/17* (2006.01)
*C12N 9/10* (2006.01)

(52) U.S. Cl.
CPC ............ *C07C 309/17* (2013.01); *C12N 9/104* (2013.01); *C12Y 203/02002* (2013.01)

(58) Field of Classification Search
None
See application file for complete search history.

(56) References Cited

U.S. PATENT DOCUMENTS 4,469,689 A    9/1984 Anderson et al.

OTHER PUBLICATIONS

Nierman et al. Proc. Nat. Acad. Sci. (2001) 98(7): 4136-4141 (Year: 2001).*
Kunst et al. Nature (1997) 390(20): 249-256, with Table 1 being shown at the end of the article) (Year: 1997).*
EPO Office Action dated Jan. 29, 2018 received in corresponding EP Application 17194345.9.
Holt et al., "Major Sultanate Transporter Soa1 in Saccharomyces Cerevisiae and Considerable Substrate Diversity in its Fungal Family", Nature Communications, vol. 8, pp. 1-13 (2017).
International Search Report and Written Opinion dated Nov. 22, 2018 and received in PCT/EP2018/076826.
Kuenzl et al., "Overcoming the Membrane Barrier: Recruitment of γ-glutamyl Transferase for Intracellular Release of Metabolic Cargo from Peptide Vectors", Metabolic Engineering, vol. 39 pp. 60-70 (2017).
Bataller-Sifre et al., "New Clinical and Toxicological Scenario of Gammaglutamyltranspeptidase", New Clinical and Toxicological Scenario of Gammaglutamyltranspeptidase, vol. 103, No. 11, pp. 586-590 (2011).
European Office Action dated Nov. 25, 2021 received in corresponding EP Application 18 782 409.9.

* cited by examiner

*Primary Examiner* — Susan M Hanley
(74) *Attorney, Agent, or Firm* — Michele Wales; InHouse Patent Counsel, LLC

(57) ABSTRACT

The present invention relates to a cellular transport system for bringing a sulfonic acid construct which carries a cargo into a cell and releasing the cargo in the cell's cytoplasm, the cellular transport system comprising: (i) a sulfonate transporter located in the cytoplasm membrane of the cell wherein said sulfonate transporter is capable of transporting said sulfonic acid construct across the cytoplasm membrane into the cytoplasm; (ii) a γ-glutamyl transferase (GGT; EC 2.3.2.2) which is modified to be located in the cytoplasm of the cell, wherein said γ-glutamyl transferase is capable of hydrolyzing said sulfonic acid construct so as to release the cargo. Moreover, the present invention relates to the use of a cellular transport system for bringing a sulfonic acid construct which contains a cargo into a cell and releasing the cargo in the cell's cytoplasm. Further, the present invention relates to a γ-glutamyl transferase for hydrolyzing a sulfonic acid construct which contains a cargo.

Figure 1:
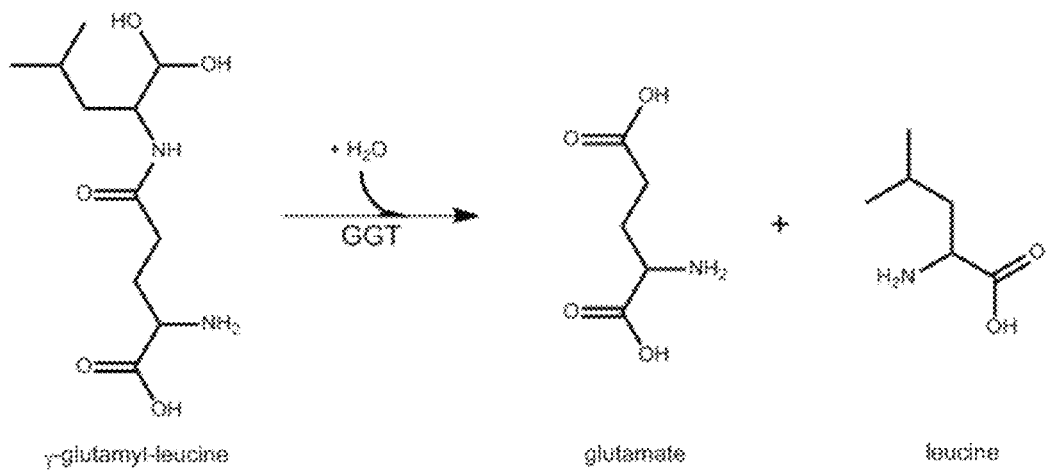

14 Claims, 18 Drawing Sheets
Specification includes a Sequence Listing.

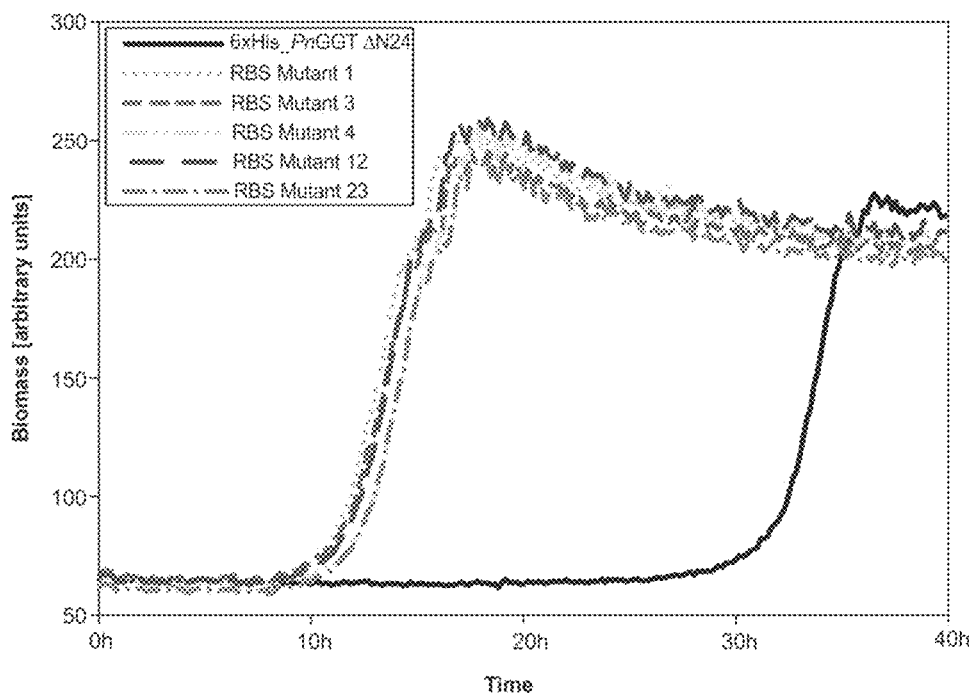
Figure 14
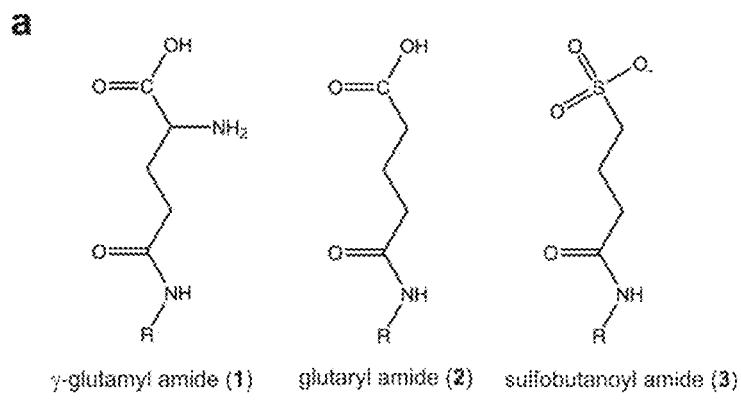
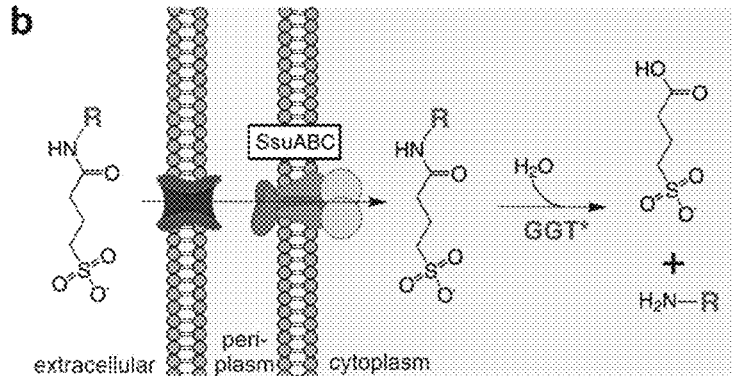
Figure 15

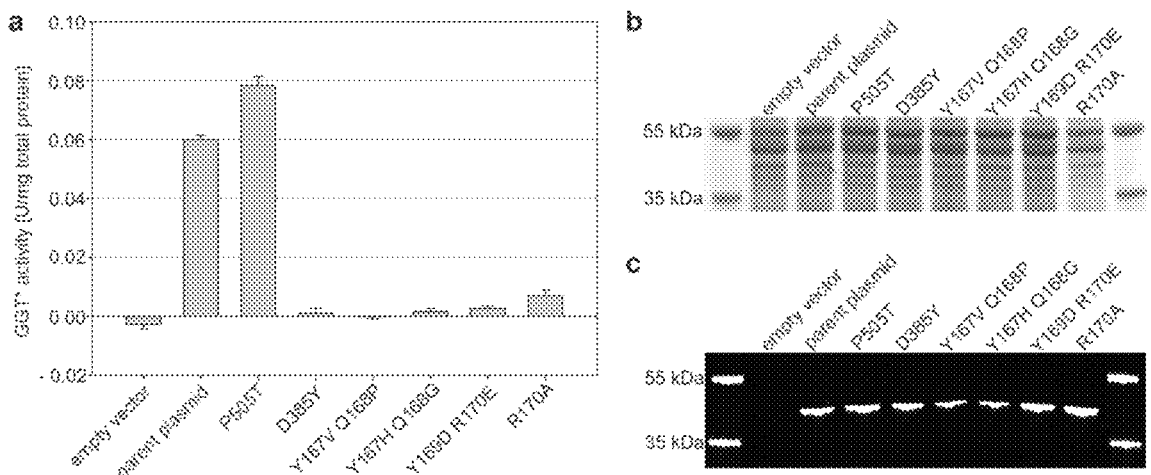

Figure 29

| | | |
|---|---|---|
| *Pseudomonas nitroreducens* | AVAAQRVHHQLLPKDTTYYDAYAP■GKVADELKAMGYTLEDQGWNMGDIQAIRVNGKAL | 539 |
| *Pseudomonas denitrificans* | AVAAQRVHHQLLPKDTTYYDAYAP■GKVADELKGMGYTLEDQGWNMGDIQAIRVNGKAL | 540 |
| *Pseudomonas aeruginosa* | AVAAQRVHHQLLPKDTTYYDAYAP■GKVAEELKAMGYTLEDQGWNMGDIQAIRVDGKAL | 540 |
| *Pseudomonas putida* | AVAAQRVHHQLLPKDTTYYDAYAP■GKVAEELKAMGYTLEDQGWNMGDIQAIRVDGKAL | 540 |
| *Pseudomonas syringae* | AVGAQRVHHQLLPKDTIYYDAYAP■GKPAEDLKAMGYKLEDQGWEMGNVQAIKIDGTKL | 539 |
| *Pseudomonas fluorescens* | AVAAQRVHHQLLPKDTTYYDAYAP■GKVAEELKAMGYTLEDQGWEMGDIQAIRVNGTAL | 520 |

Figure 30

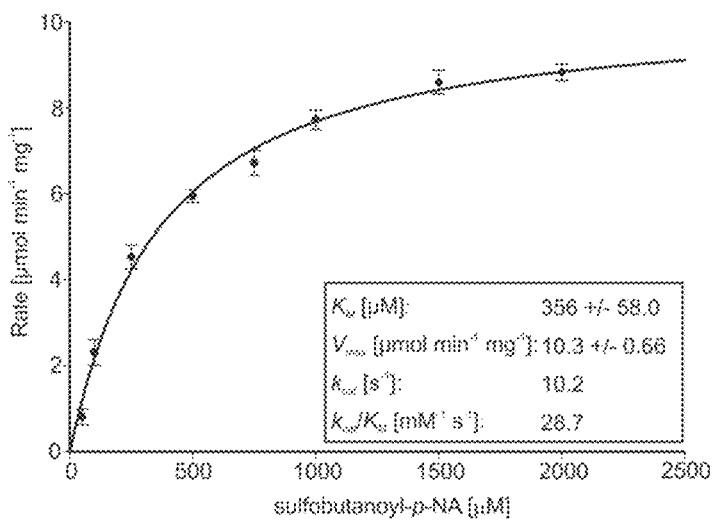

Figure 31

CELLULAR TRANSPORT SYSTEM FOR TRANSFERRING A SULFONIC ACID CONSTRUCT CARRYING A CARGO INTO THE CYTOPLASM OF A CELL

PRIORITY

This application is a § 371 National Stage Application of PCT/EP2018/076826 filed on Oct. 2, 2018, which claims priority to EP 17194345.9 filed on Oct. 2, 2017, each of which are hereby incorporated by reference in their entirety.

The present invention relates to a cellular transport system for bringing a sulfonic acid construct as defined herein which carries a cargo into a cell and releasing the cargo in the cell's cytoplasm, the cellular transport system comprising: (i) a sulfonate transporter located in the cytoplasm membrane of the cell wherein said sulfonate transporter is capable of transporting said sulfonic acid construct across the cytoplasm membrane into the cytoplasm; (ii) a γ-glutamyl transferase (GGT; EC 2.3.2.2) which is modified to be located in the cytoplasm of the cell, wherein said γ-glutamyl transferase is capable of hydrolyzing said sulfonic acid construct so as to release the cargo. Moreover, the present invention relates to the use of a cellular transport system for bringing a sulfonic acid construct as defined herein which contains a cargo into a cell and releasing the cargo in the cell's cytoplasm. Further, the present invention relates to a γ-glutamyl transferase for hydrolyzing a sulfonic acid construct as defined herein which contains a cargo.

Semipermeable membranes of cells frequently pose an obstacle for metabolic engineering and synthetic biology approaches by limiting the uptake of potentially interesting compounds and thus interfere with a broad variety of possible enzyme engineering or metabolic reconstruction strategies. Previous attempts to overcome this barrier relied on the unspecific nature of peptide transport systems, but often suffered from low versatility or chemical instability.

Bacteria developed several ways to control the uptake of low molecular weight compounds from their surroundings. Many compounds reach the cell with active or passive assistance by transport proteins that evolved for a specific group of molecules. Others simply diffuse into the cell across membranes if the physicochemical properties allow that. However, most compounds do not reach the cytoplasm as they are neither recognized by existing carrier proteins nor do they diffuse across membranes due to their polar or charged nature. This can include intermediates of new artificial biochemical pathways, which limits pathway implementation to step-by-step development starting from a branching point in canonical metabolism rather than from both ends in parallel (Birmingham et al., 2014). Also, the uptake of many unnatural amino acids or nucleic acid analogs for xenobiology approaches remains difficult, unless specific transporters can be identified (Malyshev et al., 2014).

An alternative strategy for the transport of non-membrane going compounds into the cytoplasm of for example the model bacterium *Escherichia coli* is based on the promiscuous nature of peptide import. For this approach, also known as portage transport (Boehm et al., 1983), a compound of interest is attached to short peptides and smuggled into the cell via peptide transporters, where it is released. The two best-studied peptide transporters in *E. coli* are the dipeptide and oligopeptide permease systems DppABCDF and OppABCDF, which are both known to display broad substrate specificity (Guyer et al., 1986; Smith et al., 1999).

Both transport systems have spacious hydrated binding pockets in their periplasmic binding proteins DppA and OppA that allow coping with a broad diversity of peptide substrates (Dunten and Mowbray, 1995; Nickitenko et al., 1995; Sleigh et al., 1999; Tame et al., 1995). Upon entering of a peptide into the binding pocket, water molecules are displaced while the remaining water molecules stabilize the peptide in the binding pocket and prevent strong interactions with the protein. Due to this high degree of flexibility, binding of peptides containing different side-chains or side-chain modifications is possible (Payne et al., 1984; Perry and Gilvarg, 1984).

In earlier studies, it was shown that several impermeable amino acid analogs and phosphorylated metabolic intermediates like histidinol phosphate and o-phosphohomoserine are transported into the cell by the oligopeptide permease (Opp) system as the C-terminal residue of a tripeptide (Ames et al., 1973; Fickel and Gilvarg, 1973). However, it is known that the permease's periplasmic peptide binding protein OppA forms several salt bridges with the backbone and C-terminus of the peptide substrate, suggesting that this approach is applicable mainly to amino acid analogs or closely related structures that do not significantly alter the conformation of the peptide backbone (Klepsch et al., 2011; Tame et al., 1995). This limits substantially the scope of the compounds that can be portaged. In a different approach, nucleophilic compounds were attached to the α-carbon atom of a glycine residue in a tripeptide and transported into the cell via the Opp system. The α-substituted glycine is stable only if it is part of a peptide but will decompose rapidly once it is liberated by cytoplasmic peptidases, releasing the leaving group (Hong and Park, 1993; Hwang et al., 1989; Kingsbury et al., 1984). The drawback of this method is that those peptides which contain a glycine residue with substituents that can function as good leaving groups are rather instable and have a half-life of only several minutes, making the system difficult to use in practical terms (Kingsbury et al., 1984).

Figure 3:
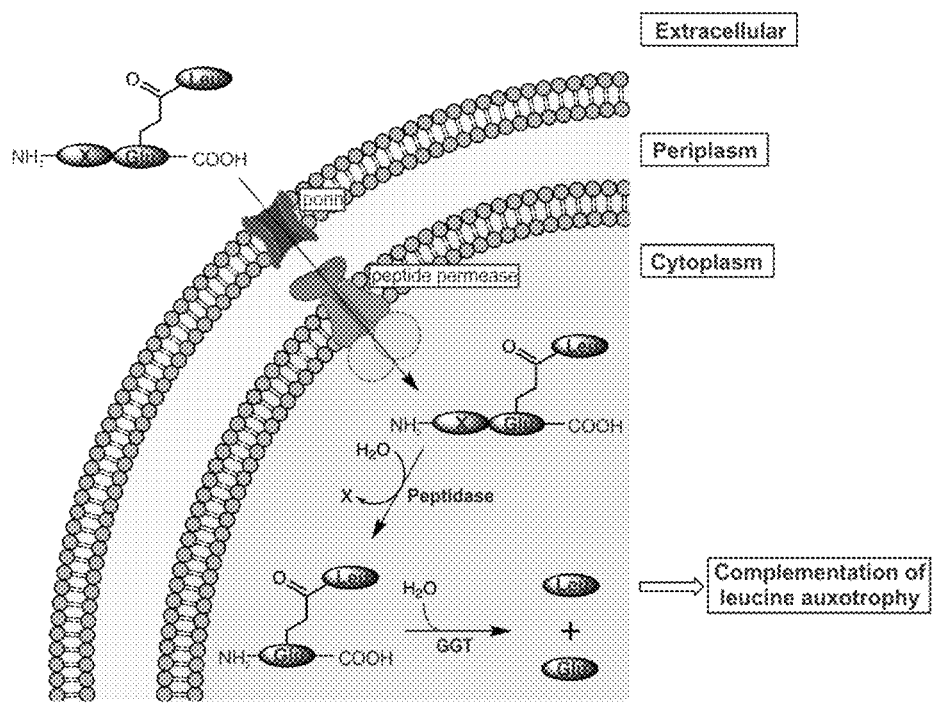

Recently, a new strategy has been shown to retain the advantages of promiscuous peptide transport but would allow circumventing the above mentioned disadvantages (FIG. 3). This synthetic transport system combines the promiscuity of peptide transport with efficient intracellular release of the cargo using the enzyme γ-glutamyl transferase (GGT) and has been described in the literature (Kuenzel et al., 2016) and in the poster presentation of Kuenzel and Panke, 2016. In short, different cargo molecules were attached to the glutamate side chain of the dipeptide alanyl-glutamate via stable amide linkages. Once the peptide is taken up and the alanine residue is removed by intracellular peptidases, the cargo molecule can be released from the glutamate by GGT. Implementation of this system required changing the localization of GGT from the periplasmic space to the cytoplasm. As it has been shown (see also the Examples further below), this can be achieved by deleting amino acids of the signal peptide of *Pseudomonas nitroreducens* GGT which was used as a model GGT.

In general, it is chemically easy to attach a compound of interest to the γ-carboxyl side chain of a glutamate residue in a small oligopeptide via a stable amide linkage. Such a strategy is suitable for a wide range of amine-containing cargo molecules, the resulting substrate does not display a significantly altered peptide backbone, and the substrate is chemically stable. Once arrived in the cytoplasm, the oligopeptide is hydrolyzed by one of *E. coli*'s intracellular peptidases and the γ-substituted glutamate released. Such γ-glutamyl compounds can be hydrolyzed by the enzyme γ-glutamyl transferase (GGT; EC 2.3.2.2) to unload the cargo molecule within the cytoplasm.

GGT is well conserved among prokaryotic and eukaryotic organisms and is mainly responsible for the degradation of glutathione in the periplasmic space, but in addition, it is known to catalyze the hydrolysis of a broad range of other γ-substituted glutamyl compounds (Hanigan, 2014; Imaoka et al., 2010; Minami et al., 2003). Binding of a γ-glutamyl compound to the active site of the enzyme leads to the formation of a γ-glutamyl-enzyme intermediate and results in release of an amine cargo. The intermediate is then attacked by either water (hydrolase activity) or by an amino acid or peptide (transpeptidase activity) as a nucleophile (FIG. 4a) (Okada et al., 2006). Importantly, the enzyme displays a broad substrate specificity as regards the substituent at the γ-carboxyl group, which can be easily rationalized from the crystal structure of for example the *E. coli* GGT (EcGGT): Only the γ-glutamyl moiety of the substrate is tightly bound within the substrate binding pocket while the substituent at the γ-carboxyl group remains solvent exposed and does not or hardly interact with the active site (Okada et al., 2006). The binding of the γ-glutamyl moiety also implies that it has to be released from the oligopeptide first.

Even though it has been shown that the substrate specificity of EcGGT seems to be favorable for the above described approach, the cellular location of GGTs requires further attention. GGT is usually secreted from the cytoplasm of bacteria or anchored in the eukaryotic membrane with the catalytic activity in the extracellular domain (Finidori et al., 1984; Hanigan, 2014; Suzuki et al., 1986). In *E. coli*, GGT is expressed as an inactive proenzyme and secreted to the periplasmic space where it undergoes maturation into a (previously N-terminal) large and a (previously C-terminal) small subunit of approximately 40 and 20 kDa in size, respectively. The maturation process is essential for enzyme activity, as the threonine residue at the newly formed N-terminus of the small subunit is the catalytic residue of the enzyme (Suzuki and Kumagai, 2002). However, in the above described approach, it has to be assured that GGT is retained in the cytoplasm.

As shown in the Examples of the present invention, in the above approach described in the literature (Kuenzl et al., 2016) and in the poster presentation of Kuenzl and Panke, 2016 it is possible to change the cellular localization of GGT from the periplasmic space to the cytoplasm. However although it has been demonstrated that portage of a cargo molecule and unloading of this cargo is possible, this approach has disadvantages which pose major hurdles when trying to implement this system in various xeno- or synthetic biology applications. This is because it turned out that the cytoplasmic expression of GGT leads to toxic effects. These toxic effects are speculated to be caused by the fact that GGT is known to hydrolyze glutamine to glutamate (Imaoka et al., 2010) and thus, a futile cycle of glutamine synthesis is established when expressed in the cytoplasm. It is also speculated that, alternatively, glutamine levels are simply reduced, leading to toxic effects. As shown in the Examples of the present invention, these toxic effects required elaborate fine-tuning of the cytoplasmic GGT expression. In particular, a fine-tuning of the expression level by using specifically engineered ribosome binding sites was necessary, thereby reducing the expression level of the cytoplasmic GGT to a level which is tolerated by the cells. Moreover, it turned out to be beneficial to introduce mutations in the pcnB gene encoding the enzyme poly(A) polymerase I (PAP I). These modifications make it difficult to universally implement the above described system on a broader scale.

Therefore, there is still a need for improvements, in particular as regards avoiding toxic effects of the cytoplasmic GGT. The present application addresses this need by providing the embodiments as defined in the claims.

In particular, the present invention provides a system which utilizes a carrier for a cargo other than a γ-substituted glutamyl compound. The present invention is based on the finding that there exist GGT enzymes and that it is possible to provide GGT enzymes which prefer as substrates sulfonic acid compounds instead of γ-substituted glutamyl compounds. This allows the provision of a cellular transport system for carrying a desired cargo into a cell which is advantageous in comparison to the known systems described above.

By using a different carrier for the cargo, i.e., a compound which is based on a sulfonic acid composition, and GGT enzymes which prefer such a carrier as a substrate instead of their natural substrate (i.e., a γ-substituted glutamyl compound) the above-mentioned toxic effects can be prevented. The present invention is predominantly based on the surprising finding that γ-glutamyl transferases (GGT) exist and can be provided which, when intracellularly expressed, are capable of hydrolyzing a sulfonic acid construct which carries a cargo so as to set free said cargo.

Moreover, using a different carrier for the cargo (i.e., a carrier based on a sulfonic acid composition) and GGT enzymes which prefer such a carrier as a substrate instead of their natural substrate has the beneficial effect that this carrier is highly versatile since a broad range of (chemically) diverse cargos may be employed given the fact that the cargo is only limited as far as it has to be capable of forming an amide linkage, a thioester linkage or an ester linkage.

As demonstrated in the Examples of the present invention, it has surprisingly been found that certain variants of GGT can actually accept such substrates which differ from the natural substrate, i.e., a γ-substituted glutamyl compound, and can hydrolyze them so as to set free the cargo which is contained in the sufonic acid construct. In the Examples of the present invention it is, e.g., shown that GGT mutants which have been described in the art can accept as substrate a 4-sulfobutanoyl conjugate (which is also referred to herein as "sulfobutanoyl conjugate" or "sulfobutyryl conjugate"). This is exemplified by using 4-sulfobutanoic acid (which is also referred to herein as "sulfobutanoic acid", "sulfobutyric acid" or "sulfobutyrate") which carries at its carboxyl group a leucine as a cargo and which is hydrolyzed by the used GGT mutants into sulfobutyric acid and leucine (see FIG. 2). In another Example, this has been demonstrated by using sulfobutanoyl-p-nitroanilidine as a substrate, carrying the dye 4-nitroaniline as a cargo. This substrate has been shown to be hydrolyzed into sulfobutanoic acid and the yellow dye 4-nitroaniline (see FIG. 16). The GGT mutants used in the Examples are GGT mutants from *E. coli* and from *Pseudomonas nitroreducens*.

The surprising finding of the present invention provides the basis for the general concept of the present invention of using a γ-glutamyl transferase (GGT; EC 2.3.2.2) which is modified to be located in the cytoplasm of the cell and which is capable of accepting a sulfonic acid construct as defined herein as a substrate.

Accordingly, the present invention relates to a cellular transport system for bringing a sulfonic acid construct of the following formula (I) or a physiologically acceptable salt thereof

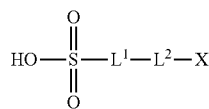

(I)

wherein:
- L¹ is a group —(CH$_2$)$_{1-6}$—, wherein said group —(CH$_2$)$_{1-6}$— is optionally substituted with one or more groups R$^{L11}$, and further wherein one or more —CH$_2$— units comprised in said group —(CH$_2$)$_{1-6}$— are each optionally replaced by a group R$^{L12}$;
- L² is —C(=O)— or —C(=S)—;
- X is a chemical moiety which is attached to L² via a heteroatom comprised in said chemical moiety, wherein said heteroatom is selected from oxygen, sulfur, nitrogen and selenium;
- each R$^{L11}$ is independently selected from C$_{1-5}$ alkyl, C$_{2-5}$ alkenyl, C$_{2-5}$ alkynyl, —(C$_{0-3}$ alkylene)-OH, —(C$_{0-3}$ alkylene)-O(C$_{1-5}$ alkyl), —(C$_{0-3}$ alkylene)-O(C$_{1-5}$ alkylene)-OH, —(C$_{0-3}$ alkylene)-O(C$_{1-5}$ alkylene)-O(C$_{1-5}$ alkyl), —(C$_{0-3}$ alkylene)-SH, —(C$_{0-3}$ alkylene)-S(C$_{1-5}$ alkyl), —(C$_{0-3}$ alkylene)-S(C$_{1-5}$ alkylene)-SH, —(C$_{0-3}$ alkylene)-S(C$_{1-5}$ alkylene)-S(C$_{1-5}$ alkyl), —(C$_{0-3}$ alkylene)-NH$_2$, —(C$_{0-3}$ alkylene)-NH(C$_{1-5}$ alkyl), —(C$_{0-3}$ alkylene)-N(C$_{1-5}$ alkyl)(C$_{1-5}$ alkyl), —(C$_{0-3}$ alkylene)-halogen, —(C$_{0-3}$ alkylene)-(C$_{1-5}$ haloalkyl), —(C$_{0-3}$ alkylene)-O—(C$_{1-5}$ haloalkyl), —(C$_{0-3}$ alkylene)-CF$_3$, —(C$_{0-3}$ alkylene)-CN, —(C$_{0-3}$ alkylene)-NO$_2$, —(C$_{0-3}$ alkylene)-CHO, —(C$_{0-3}$ alkylene)-CO—(C$_{1-5}$ alkyl), —(C$_{0-3}$ alkylene)-COOH, —(C$_{0-3}$ alkylene)-CO—O—(C$_{1-5}$ alkyl), —(C$_{0-3}$ alkylene)-O—CO—(C$_{1-5}$ alkyl), —(C$_{0-3}$ alkylene)-CO—NH$_2$, —(C$_{0-3}$ alkylene)-CO—NH(C$_{1-5}$ alkyl), —(C$_{0-3}$ alkylene)-CO—N(C$_{1-5}$ alkyl)(C$_{1-5}$ alkyl), —(C$_{0-3}$ alkylene)-NH—CO—(C$_{1-5}$ alkyl), —(C$_{0-3}$ alkylene)-N(C$_{1-5}$ alkyl)-CO—(C$_{1-5}$ alkyl), —(C$_{0-3}$ alkylene)-SO$_2$—NH$_2$, —(C$_{0-3}$ alkylene)-SO$_2$—NH(C$_{1-5}$ alkyl), —(C$_{0-3}$ alkylene)-SO$_2$—N(C$_{1-5}$ alkyl)(C$_{1-5}$ alkyl), —(C$_{0-3}$ alkylene)-NH—SO$_2$—(C$_{1-5}$ alkyl), —(C$_{0-3}$ alkylene)-N(C$_{1-5}$ alkyl)-SO$_2$—(C$_{1-5}$ alkyl), —(C$_{0-3}$ alkylene)-carbocyclyl, and —(C$_{0-3}$ alkylene)-heterocyclyl, wherein the carbocyclyl moiety comprised in said —(C$_{0-3}$ alkylene)-carbocyclyl and the heterocyclyl moiety comprised in said —(C$_{0-3}$ alkylene)-heterocyclyl are each optionally substituted with one or more groups R$^{L15}$, and further wherein any two groups R$^{L11}$ that are attached to different carbon atoms comprised in L¹ may also be mutually linked to form together a group —R$^{L13}$—, and wherein any two groups R$^{L11}$ that are attached to the same carbon atom comprised in L¹ may also be mutually linked to form, together with the carbon atom that they are attached to, a cycloalkyl or a heterocycloalkyl, wherein said cycloalkyl or said heterocycloalkyl is optionally substituted with one or more groups R$^{L15}$;
- each R$^{L12}$ is independently selected from —O—, —CO—, —C(=O)O—, —O—C(=O)—, —N(R$^{L14}$)—, —N(R$^{L14}$)—CO—, —CO—N(R$^{L14}$)—, —S—, —SO—, —SO$_2$—, —SO$_2$—N(R$^{L14}$)— and —N(R$^{L14}$)—SO$_2$—;
- each R$^{L13}$ is independently selected from C$_{1-6}$ alkylene and C$_{2-6}$ alkenylene, wherein said alkylene or said alkenylene is optionally substituted with one or more groups independently selected from C$_{1-4}$ alkyl, —OH, —O(C$_{1-4}$ alkyl), —NH$_2$, —NH(C$_{1-4}$ alkyl), —N(C$_{1-4}$ alkyl)(C$_{1-4}$ alkyl), halogen, —CF$_3$, and —CN, and further wherein one or more —CH$_2$— units comprised in said alkylene or in said alkenylene are each optionally replaced by a group independently selected from —O—, —CO—, —NH—, —N(C$_{1-5}$ alkyl)- and —S—;
- each R$^{L14}$ is independently selected from hydrogen and C$_{1-5}$ alkyl; and
- each R$^{L15}$ is independently selected from C$_{1-5}$ alkyl, C$_{2-5}$ alkenyl, C$_{2-5}$ alkynyl, —(C$_{0-3}$ alkylene)-OH, —(C$_{0-3}$ alkylene)-O(C$_{1-5}$ alkyl), —(C$_{0-3}$ alkylene)-O(C$_{1-5}$ alkylene)-OH, —(C$_{0-3}$ alkylene)-O(C$_{1-5}$ alkylene)-O(C$_{1-5}$ alkyl), —(C$_{0-3}$ alkylene)-SH, —(C$_{0-3}$ alkylene)-S(C$_{1-5}$ alkyl), —(C$_{0-3}$ alkylene)-S(C$_{1-5}$ alkylene)-SH, —(C$_{0-3}$ alkylene)-S(C$_{1-5}$ alkylene)-S(C$_{1-5}$ alkyl), —(C$_{0-3}$ alkylene)-NH$_2$, —(C$_{0-3}$ alkylene)-NH(C$_{1-5}$ alkyl), —(C$_{0-3}$ alkylene)-N(C$_{1-5}$ alkyl)(C$_{1-5}$ alkyl), —(C$_{0-3}$ alkylene)-halogen, —(C$_{0-3}$ alkylene)-(C$_{1-5}$ haloalkyl), —(C$_{0-3}$ alkylene)-O—(C$_{1-5}$ haloalkyl), —(C$_{0-3}$ alkylene)-CF$_3$, —(C$_{0-3}$ alkylene)-CN, —(C$_{0-3}$ alkylene)-NO$_2$, —(C$_{0-3}$ alkylene)-CHO, —(C$_{0-3}$ alkylene)-CO—(C$_{1-5}$ alkyl), —(C$_{0-3}$ alkylene)-COOH, —(C$_{0-3}$ alkylene)-CO—O—(C$_{1-5}$ alkyl), —(C$_{0-3}$ alkylene)-O—CO—(C$_{1-5}$ alkyl), —(C$_{0-3}$ alkylene)-CO—NH$_2$, —(C$_{0-3}$ alkylene)-CO—NH(C$_{1-5}$ alkyl), —(C$_{0-3}$ alkylene)-CO—N(C$_{1-5}$ alkyl)(C$_{1-5}$ alkyl), —(C$_{0-3}$ alkylene)-NH—CO—(C$_{1-5}$ alkyl), —(C$_{0-3}$ alkylene)-N(C$_{1-5}$ alkyl)-CO—(C$_{1-5}$ alkyl), —(C$_{0-3}$ alkylene)-SO$_2$—NH$_2$, —(C$_{0-3}$ alkylene)-SO$_2$—NH(C$_{1-5}$ alkyl), —(C$_{0-3}$ alkylene)-SO$_2$—N(C$_{1-5}$ alkyl)(C$_{1-5}$ alkyl), —(C$_{0-3}$ alkylene)-NH—SO$_2$—(C$_{1-5}$ alkyl), and —(C$_{0-3}$ alkylene)-N(C$_{1-5}$ alkyl)-SO$_2$—(C$_{1-5}$ alkyl);

into a cell and releasing a cargo from the sulfonic acid construct of formula (I) in the cell's cytoplasm, wherein said cargo is a compound H—X wherein X is as defined in formula (I), and wherein the cellular transport system comprises (i) a sulfonate transporter located in the cytoplasm membrane of the cell wherein said sulfonate transporter is capable of transporting said sulfonic acid construct of formula (I) across the cytoplasm membrane into the cytoplasm;

(ii) a γ-glutamyl transferase (GGT; EC 2.3.2.2) which is modified to be located in the cytoplasm of the cell, wherein said γ-glutamyl transferase is capable of hydrolyzing said sulfonic acid construct of formula (I) to release the compound X—H.

The present invention is based on the surprising finding that certain GGT variants prefer sulfonic acid constructs over their natural substrate and can hydrolyze them, thereby allowing to provide a transport system that can use sulfonate compounds as transport vectors for bringing non-membrane going cargo molecules into the cell. More specifically, it is shown in the Examples that *E. coli* GGT mutant D433N (EcGGT D433N) is able to accept a 4-sulfobutanoyl conjugate as a substrate and to hydrolyze it so as to set free a cargo which is linked to the 4-sulfobutanoic acid via the carboxyl group.

It is also demonstrated in the Examples that a corresponding mutant derived from *Pseudomonas nitroreducens* (PnGGT), i.e., the mutant variant PnGGT D405N fulfils the same function as the above *E. coli* GGT mutant D433N.

Position D433 of *E. coli* corresponds to position D405 in *Pseudomonas nitroreducens* as shown by sequence alignment and homology modeling between both sequences. In fact, it is known that most of the residues directly interacting with the substrate were shown to be highly conserved in GGT enzymes from various organisms and are important for correct functionality of the enzyme, among them residue D433 which forms a salt bridge with the α-amino group of the γ-glutamyl substrate (Okada et al., 2006; Suzuki et al., 2004). It was demonstrated earlier that replacement of the aspartyl residue at position 433 with an asparaginyl residue allows the enzyme to deacylate glutaryl-7-aminocephalosporanic acid (GL-7-ACA), suggesting that single amino acid mutations in the substrate binding pocket of GGT can alter the substrate spectrum of the enzyme (Suzuki et al., 2004; Yamada et al., 2008).

By using EcGGT D433N or PnGGT D405N as a starting point, variants from GGT enzymes from other organisms can be identified or constructed for which the substrate specificity is shifted towards sulfonic acid constructs and which can hydrolyze such sulfonic acid constructs so as to release a cargo contained in the cargo. Such variants can also be used in the scope of the present invention for intracellular discharge of cargo molecules from a sulfonic acid construct (FIG. 15B).

As described above, the cellular transport system according to the present invention allows to bring a sulfonic acid construct of formula (I) or a physiologically acceptable salt thereof into a cell and to release a compound H—X (which is also referred to herein as "cargo") from the sulfonic acid construct of formula (I) into the cytoplasm of the cell. When the sulfonic acid construct of formula (I) is hydrolyzed by the γ-glutamyl transferase, the cargo is set free as H—X and at the same time the remainder of the construct is set free as a compound of the formula $HO_3S\text{-}L^1\text{-}L^2\text{-}OH$, wherein $L^1$ and $L^2$ are as defined in formula (I).

The sulfonic acid construct of formula (I) and the physiologically acceptable salts thereof will be described in more detail in the following:

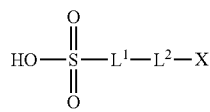
(I)

In formula (I), $L^1$ is a group —$(CH_2)_{1-6}$—, wherein said group —$(CH_2)_{1-6}$— is optionally substituted with one or more (e.g., one, two or three) groups $R^{L11}$, and further wherein one or more (e.g., one or two) —$CH_2$— units comprised in said group —$(CH_2)_{1-6}$— are each optionally replaced by a group $R^{L12}$.

Said group —$(CH_2)_{1-6}$—, which may be substituted with one or more groups $R^{L11}$ and/or in which one or more —$CH_2$— units may be replaced by $R^{L12}$ (as defined above), is preferably —$(CH_2)_{2-4}$—, and is more preferably —$(CH_2)_3$—.

Each $R^{L11}$ is independently selected from $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-5}$ alkyl), —($C_{0-3}$ alkylene)-O($C_{1-5}$ alkylene)-OH, —($C_{0-3}$ alkylene)-O($C_{1-5}$ alkylene)-O($C_{1-5}$ alkyl), —($C_{0-3}$ alkylene)-SH, —($C_{0-3}$ alkylene)-S($C_{1-5}$ alkyl), —($C_{0-3}$ alkylene)-S($C_{1-5}$ alkylene)-SH, —($C_{0-3}$ alkylene)-S($C_{1-5}$ alkylene)-S($C_{1-5}$ alkyl), —($C_{0-3}$ alkylene)-NH$_2$, —($C_{0-3}$ alkylene)-NH($C_{1-5}$ alkyl), —($C_{0-3}$ alkylene)-N($C_{1-5}$ alkyl)($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-CF$_3$, —($C_{0-3}$ alkylene)-CN, —($C_{0-3}$ alkylene)-NO$_2$, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—NH$_2$, —($C_{0-3}$ alkylene)-CO—NH($C_{1-5}$ alkyl), —($C_{0-3}$ alkylene)-CO—N($C_{1-5}$ alkyl)($C_{1-5}$ alkyl), —($C_{0-3}$ alkylene)-NH—CO—($C_{1-5}$ alkyl), —($C_{0-3}$ alkylene)-N($C_{1-5}$ alkyl)-CO—($C_{1-5}$ alkyl), —($C_{0-3}$ alkylene)-SO$_2$—NH$_2$, —($C_{0-3}$ alkylene)-SO$_2$—NH($C_{1-5}$ alkyl), —($C_{0-3}$ alkylene)-SO$_2$—N($C_{1-5}$ alkyl)($C_{1-5}$ alkyl), —($C_{0-3}$ alkylene)-NH—SO$_2$—($C_{1-5}$ alkyl), —($C_{0-3}$ alkylene)-N($C_{1-5}$ alkyl)-SO$_2$—($C_{1-5}$ alkyl), —($C_{0-3}$ alkylene)-carbocyclyl, and —($C_{0-3}$ alkylene)-heterocyclyl, wherein the carbocyclyl moiety comprised in said —($C_{0-3}$ alkylene)-carbocyclyl and the heterocyclyl moiety comprised in said —($C_{0-3}$ alkylene)-heterocyclyl are each optionally substituted with one or more groups $R^{L15}$; furthermore, any two groups $R^{L11}$ that are attached to different carbon atoms comprised in $L^1$, if such groups $R^{L11}$ are present, may also be mutually linked to form together a group —$R^{L13}$— (where it is preferred that at most two groups $R^{L11}$ that are attached to different carbon atoms comprised in $L^1$, but not more than two such groups $R^{L11}$, may be mutually linked to form together a group —$R^{L13}$—); moreover, any two groups $R^{L11}$ that are attached to the same carbon atom comprised in $L^1$, if such groups $R^{L11}$ are present, may also be mutually linked to form, together with the carbon atom that they are attached to, a cycloalkyl or a heterocycloalkyl, wherein said cycloalkyl or said heterocycloalkyl is optionally substituted with one or more groups $R^{L15}$.

Preferably, each $R^{L11}$ is independently selected from $C_{1-5}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —NH$_2$, —NH($C_{1-5}$ alkyl), —N($C_{1-5}$ alkyl)($C_{1-5}$ alkyl), halogen, $C_{1-5}$ haloalkyl, —O—($C_{1-5}$ haloalkyl), —CF$_3$, —CN, —CHO, —CO—($C_{1-5}$ alkyl), —COOH, —CO—O—($C_{1-5}$ alkyl), —O—CO—($C_{1-5}$ alkyl), —CO—NH$_2$, —CO—NH($C_{1-5}$ alkyl), —CO—N($C_{1-5}$ alkyl)($C_{1-5}$ alkyl), —NH—CO—($C_{1-5}$ alkyl), —N($C_{1-5}$ alkyl)-CO—($C_{1-5}$ alkyl), —SO$_2$—NH$_2$, —SO$_2$—NH($C_{1-5}$ alkyl), —SO$_2$—N($C_{1-5}$ alkyl)($C_{1-5}$ alkyl), —NH—SO$_2$—($C_{1-5}$ alkyl), and —N($C_{1-5}$ alkyl)-SO$_2$—($C_{1-5}$ alkyl); furthermore, two groups $R^{L11}$ that are attached to different carbon atoms comprised in $L^1$ may also be mutually linked to form together a group —$R^{L13}$—. More preferably, each $R^{L11}$ is independently selected from $C_{1-5}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —NH$_2$, —NH($C_{1-5}$ alkyl), —N($C_{1-5}$ alkyl)($C_{1-5}$ alkyl), halogen, $C_{1-5}$ haloalkyl, —CF$_3$, and —CN. Even more preferably, each $R^{L11}$ is independently selected from $C_{1-4}$ alkyl (e.g., methyl or ethyl), —OH, —O($C_{1-4}$ alkyl) (e.g., —OCH$_3$ or —OCH$_2$CH$_3$), —NH$_2$, —NH($C_{1-4}$ alkyl) (e.g., —NHCH$_3$), —N($C_{1-4}$ alkyl)($C_{1-4}$ alkyl) (e.g., —N(CH$_3$)$_2$), halogen (e.g., —F, —Cl, —Br, or —I), —CF$_3$, and —CN.

Each $R^{L12}$ is independently selected from —O—, —CO—, —C(=O)O—, —O—C(=O)—, —N($R^{L14}$)—, —N($R^{L14}$)—CO—, —CO—N($R^{L14}$)—, —S—, —SO—, —SO$_2$—, —SO$_2$—N($R^{L14}$)— and —N($R^{L14}$)—SO$_2$—. Preferably, each $R^{L12}$ is independently selected from —O—, —CO—, —C(=O)O—, —O—C(=O)—, —N($R^{L14}$)—, —N($R^{L14}$)—CO—, —CO—N($R^{L14}$)— and —S—, more preferably from —O—, —CO—, —N($R^{L14}$)— and —S—.

Each $R^{L13}$ is independently selected from $C_{1-6}$ alkylene and $C_{2-6}$ alkenylene, wherein said alkylene or said alkenylene is optionally substituted with one or more (e.g., one, two or three) groups independently selected from $C_{1-4}$ alkyl, —OH, —O($C_{1-4}$ alkyl), —NH$_2$, —NH($C_{1-4}$ alkyl), —N($C_{1-4}$ alkyl)($C_{1-4}$ alkyl), halogen, —CF$_3$, and —CN, and further wherein one or more (e.g., one or two) —CH$_2$— units comprised in said alkylene or in said alkenylene are each optionally replaced by a group independently selected from —O—, —CO—, —NH—, —N($C_{1-5}$ alkyl)- and —S—. Preferably, each $R^{L13}$ is independently selected from linear $C_{1-6}$ alkylene and linear $C_{2-6}$ alkenylene.

Each $R^{L14}$ is independently selected from hydrogen and $C_{1-5}$ alkyl. Preferably, each $R^{L14}$ is independently selected from hydrogen, methyl and ethyl.

Each $R^{L15}$ is independently selected from $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-5}$ alkyl), —($C_{0-3}$ alkylene)-O($C_{1-5}$ alkylene)-OH, —($C_{0-3}$ alkylene)-O($C_{1-5}$ alkylene)-O($C_{1-5}$ alkyl), —($C_{0-3}$ alkylene)-SH, —($C_{0-3}$ alkylene)-S($C_{1-5}$ alkyl), —($C_{0-3}$ alkylene)-S($C_{1-5}$ alkylene)-SH, —($C_{0-3}$ alkylene)-S($C_{1-5}$ alkylene)-S($C_{1-5}$ alkyl), —($C_{0-3}$ alkylene)-NH$_2$, —($C_{0-3}$ alkylene)-NH($C_{1-5}$ alkyl), —($C_{0-3}$ alkylene)-N($C_{1-5}$ alkyl)($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-CF$_3$, —($C_{0-3}$ alkylene)-CN, —($C_{0-3}$ alkylene)-NO$_2$, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—NH$_2$, —($C_{0-3}$ alkylene)-CO—NH($C_{1-5}$ alkyl), —($C_{0-3}$ alkylene)-CO—N($C_{1-5}$ alkyl)($C_{1-5}$ alkyl), —($C_{0-3}$ alkylene)-NH—CO—($C_{1-5}$ alkyl), —($C_{0-3}$ alkylene)-N($C_{1-5}$ alkyl)-CO—($C_{1-5}$ alkyl), —($C_{0-3}$ alkylene)-SO$_2$—NH$_2$, —($C_{0-3}$ alkylene)-SO$_2$—NH($C_{1-5}$ alkyl), —($C_{0-3}$ alkylene)-SO$_2$—N($C_{1-5}$ alkyl)($C_{1-5}$ alkyl), —($C_{0-3}$ alkylene)-NH—SO$_2$—($C_{1-5}$ alkyl), and —($C_{0-3}$ alkylene)-N($C_{1-5}$ alkyl)-SO$_2$—($C_{1-5}$ alkyl).

With respect to $L^1$, it is preferred that a —CH$_2$— unit (i.e., a —CH$_2$— unit comprised in said group —(CH$_2$)$_{1-6}$—) that is adjacent (i.e., directly attached) to $L^2$ or to the sulfonic acid group comprised in the sulfonic acid construct of formula (I) is not replaced by $R^{L12}$. It is furthermore preferred that at most one —CH$_2$— unit comprised in said group —(CH$_2$)$_{1-6}$— is optionally replaced by $R^{L12}$, and more preferably none of the —CH$_2$— unit(s) comprised in said group —(CH$_2$)$_{1-6}$— is/are replaced by $R^{L12}$. Moreover, it is preferred that said group —(CH$_2$)$_{1-6}$— is optionally substituted with one or two groups $R^{L11}$ (particularly one group $R^{L11}$), and it is even more preferred that said group —(CH$_2$)$_{1-6}$— is not substituted with any group $R^{L11}$. Accordingly, it is most preferred that none of the —CH$_2$— unit(s) comprised in said group —(CH$_2$)$_{1-6}$— is/are replaced by $R^{L12}$, and that said group —(CH$_2$)$_{1-6}$— is not substituted with any $R^{L11}$.

In accordance with the above-described definitions, it is particularly preferred that $L^1$ is —(CH$_2$)$_{1-6}$—, even more preferably —(CH$_2$)$_{2-4}$—, and most preferably $L^1$ is —(CH$_2$)$_3$—.

$L^2$ is —C(=O)— or —C(=S)—. Preferably, $L^2$ is —C(=O)—.

X is a chemical moiety which is attached to $L^2$ via a heteroatom comprised in said chemical moiety, wherein said heteroatom is selected from oxygen, sulfur, nitrogen and selenium. Said heteroatom is preferably selected from oxygen, sulfur and nitrogen; more preferably, said heteroatom is oxygen or nitrogen; even more preferably, said heteroatom is nitrogen.

The chemical moiety X is not particularly limited and can, in principle, be any chemical moiety that is desired to be transported into a cell and to be released inside the cell in the form of a compound X—H.

For example, X may be a chemical moiety which is attached to $L^2$ via a heteroatom comprised in said chemical moiety, wherein the heteroatom is as defined above, and wherein the chemical moiety is selected from:

an amino acid (e.g., an α-amino acid, particularly any one of the 20 standard proteinogenic α-amino acids—i.e., Ala, Arg, Asn, Asp, Cys, Glu, Gln, Gly, His, Ile, Leu, Lys, Met, Phe, Pro, Ser, Thr, Trp, Tyr, or Val—or any non-proteinogenic and/or non-standard α-amino acid, such as, e.g., ornithine, citrulline, homolysine, pyrrolysine, 4-hydroxyproline, α-methylalanine (i.e., 2-aminoisobutyric acid), norvaline, norleucine, terleucine (tert-leucine), labionin, or an alanine or glycine that is substituted at the side chain with a cyclic group (e.g., a cycloalkyl group, a heterocycloalkyl group, an aryl group, or a heteroaryl group) like, e.g., cyclopentylalanine, cyclohexylalanine, phenylalanine, naphthylalanine, pyridylalanine, thienylalanine, cyclohexylglycine, or phenylglycine; or a β-amino acid (e.g., β-alanine), a γ-amino acid (e.g., γ-aminobutyric acid, isoglutamine, or statine), a δ-amino acid, or a dehydroamino acid (e.g., an α,β-dehydroamino acid, such as, e.g., dehydrobutyrine or dehydroalanine); or any other compound comprising at least one carboxylic acid group and at least one amino group), an amino acid analog, a peptide (e.g., a dipeptide or a tripeptide, which may be composed of two or three of the aforementioned amino acids), a glycopeptide, a lipopeptide, a peptide analog, an amine, a diamine (e.g., hexamethylenediamine or putrescine), a polyamine (e.g., spermidine or spermine), a sugar (e.g., a monosaccharide, a disaccharide, a trisaccharide, a sugar alcohol, a deoxy sugar, an amino sugar, a fluoro sugar, a thio-sugar, or an aza-sugar; specific examples include, in particular, glycolaldehyde, glyceraldehyde, dihydroxyacetone, erythrose, threose, erythrulose, arabinose, lyxose, ribose, xylose, ribulose, xylulose, deoxyribose, allose, altrose, galactose, glucose, gulose, idose, mannose, talose, fructose, psicose, sorbose, tagatose, fucose, fuculose, rhamnose, mannoheptulose, sedoheptulose, neuraminic acid, cellobiose, isomaltose, lactose, lactulose, maltose, sucrose, trehalose, turanose, maltotriose, melezitose, raffinose, cladinose, or desosamine), a nucleobase (particularly a purine base or a pyrimidine base; e.g., adenine, thymine, uracil, guanine, cytosine, isocytosine, 5-methylcytosine, 5-hydroxymethylcytosine, 7-methylguanine, xanthine, hypoxanthine, 5-trifluoromethyluracil (trifluorothymine), 5,6-dihydrouracil, 7-deazaguanine, or queuine), a nucleobase analog, a nucleoside (e.g., a ribonucleoside, which may be composed of ribose and any one of the aforementioned nucleobases, or a deoxyribonucleoside, which may be composed of 2-deoxyribose and any one of the aforementioned nucleobases; specific examples include, in particular, adenosine, guanosine, 5-methyluridine, uridine, 5-methylcytidine, cytidine, inosine, xanthosine, wybutosine, deoxyadenosine, deoxyguanosine, thymidine, deoxyuridine, deoxycytidine, deoxyinosine, or deoxyxanthosine), a nucleoside analog, a nucleotide (e.g., a nucleoside monophosphate, a nucleoside diphosphate, a nucleoside triphosphate, or a cyclic nucleotide, wherein the nucleoside comprised in any of the aforementioned nucleoside phosphates may be, e.g., a ribonucleoside or a deoxyribonucleoside containing any of the aforementioned nucleobases; specific examples include, in particular, AMP, GMP, m5UMP, UMP, CMP, IMP, XMP, dAMP, dGMP, dTMP, dUMP, dCMP, dIMP, dXMP, cAMP, cGMP, c-di-GMP, cADPR, ADP, GDP, m5UDP, UDP, CDP, dADP, dGDP, dTDP, dUDP, dCDP, ATP, GTP, m5UTP, UTP, CTP, ITP, XTP, dATP, dGTP, dTTP, dUTP, dCTP, dITP, or dXTP), a nucleotide analog, a nucleic acid (e.g., a DNA or an RNA, either of which may be single-stranded or double-stranded and may be composed of, e.g., 2 to 10 bases/nucleotides or 2 to 10 base pairs), a phosphate-containing organic group, a phosphonate-containing organic group (e.g., a bisphosphonate), metaphosphate, a lipid (e.g., a fatty acid, an eicosanoid or a steroid), a phospholipid, a glycolipid, a sphingolipid (e.g., a ceramide), a glycosphingolipid, a vitamin (e.g., thiamine, niacin, pyridoxine, vitamin B12, cobalamine, biotin, pantothenic acid, folic acid, vitamin K, vitamin C, or riboflavin), a cofactor or a coenzyme (e.g., thiamine pyrophosphate, NAD$^+$, NADH, NADP$^+$, NADPH, pyridoxal 5'-phosphate (PLP), pyridoxamine phosphate (PMP), methylcobalamin, adenosylcobalamin, cobalamine, biotin, coenzyme A, tetrahydrofolic acid, dihydrofolic acid, menaquinone, phytomenadione, ascorbic acid, flavin mononucleotide (FMN), flavin adenine dinucleotide (FAD), coenzyme F420, adenosine triphosphate (ATP), S-adenosyl methionine (SAM), coenzyme B, coenzyme M, coenzyme Q, cytidine triphosphate (CTP), glutathione, heme (e.g., heme A, heme B, heme C, or heme O), lipoamide, methanofuran, molybdopterin, a nucleotide sugar (such as, e.g., CDP-glucose, GDP-mannose, TDP-glucose, UDP-glucose, UDP-galactose, UDP-glucuronic acid, or UDP-N-acetylglucosamine), 3'-phosphoadenosine-5'-phosphosulfate, pyrroloquinoline quinone, tetrahydrobiopterin, tetrahydromethanopterin, or tetrahydrosarcinapterin), a coenzyme analog, a metabolic intermediate (e.g., an unnatural metabolic intermediate), a pharmaceutical drug, an anti-infective agent, an analgesic, an anti-inflammatory agent, an anthelmintic, an antibacterial agent, an antidepressant, an antidiabetic agent, an antiepileptic, an antifungal agent, an antigout agent, an antihistamine, an antimigraine agent, an antimuscarinic agent, an antineoplastic agent, an immunosuppressant, an antiprotozoal agent, an antiviral agent, an anxiolytic, a sedative, a hypnotic, an antipsychotic, a haemostatic, a calcium regulating agent, a cardiovascular agent, a cough suppressant, an expectorant, a mucolytic, a dermatological agent, a dopaminergic agent, a gastro-intestinal agent, an anaesthetic, a vitamin, an anti-asthma agent, a radiopharmaceutical, a stimulant, a thyroid agent, an antibiotic (e.g., puromycin, a puromycin derivative or analog, streptomycin, dihydrostreptomycin, neomycin, framycetin, paromomycin, ribostamycin, kanamycin, amikacin, arbekacin, bekanamycin, dibekacin, tobramycin, spectinomycin, hygromycin B, paromomycin, gentamicin, netilmicin, sisomicin, plazomicin, isepamicin, verdamicin, astromicin, doxycycline, chlortetracycline, clomocycline, demeclocycline, lymecycline, meclocycline, metacycline, minocycline, oxytetracycline, penimepicycline, rolitetracycline, tetracycline, tigecycline, eravacycline, eperezolid, linezolid, posizolid, radezolid, ranbezolid, sutezolid, tedizolid, chloramphenicol, azidamfenicol, thiamphenicol, florfenicol, retapamulin, tiamulin, valnemulin, azithromycin, clarithromycin, dirithromycin, erythromycin, flurithromycin, josamycin, midecamycin, miocamycin, oleandomycin, rokitamycin, roxithromycin, spiramycin, troleandomycin, tylosin, a ketolide, telithromycin, cethromycin, solithromycin, clindamycin, lincomycin, pirlimycin, pristinamycin, quinupristin, dalfopristin, virginiamycin, or fusidic acid), a toxin, a pesticide, or any one of the above-mentioned compounds/moieties which is connected via a linker (e.g., an alkylene linker or a poly(oxyalkylene) linker) to the heteroatom that is attached to $L^2$, wherein the linker may further comprise a cleavable group (e.g., an enzymatically cleavable group or a chemically cleavable group).

Moreover, X may also be selected from —O—$R^{X1}$, —S—$R^{X1}$, —N(—$R^{X2}$)—$R^{X3}$ and —Se—$R^{X1}$, preferably from —O—$R^{X1}$, —S—$R^{X1}$ and —N(—$R^{X2}$)—$R^{X3}$.

$R^{X1}$ is selected from $C_{1-15}$ alkyl, $C_{2-15}$ alkenyl, $C_{2-15}$ alkynyl, —($C_{0-12}$ alkylene)-carbocyclyl, and —($C_{0-12}$ alkylene)-heterocyclyl, wherein said alkyl, said alkenyl, said alkynyl, the alkylene moiety comprised in said —($C_{0-12}$ alkylene)-carbocyclyl and the alkylene moiety comprised in said —($C_{0-12}$ alkylene)-heterocyclyl are each optionally substituted with one or more (e.g., one, two or three) groups $R^{X4}$, wherein one or more (e.g., one, two or three) —CH$_2$— units comprised in said alkyl, in said alkenyl, in said alkynyl, in the alkylene moiety comprised in said —($C_{0-12}$ alkylene)-carbocyclyl or in the alkylene moiety comprised in said —($C_{0-12}$ alkylene)-heterocyclyl are each optionally replaced by a group $R^{X5}$, and further wherein the carbocyclyl moiety comprised in said —($C_{0-12}$ alkylene)-carbocyclyl and the heterocyclyl moiety comprised in said —($C_{0-12}$ alkylene)-heterocyclyl are each optionally substituted with one or more (e.g., one, two or three) groups $R^{X6}$. The carbocyclyl moiety comprised in said —($C_{0-12}$ alkylene)-carbocyclyl may be, e.g., a cycloalkyl, a cycloalkenyl, or an aryl. The heterocyclyl moiety comprised in said —($C_{0-12}$ alkylene)-heterocyclyl may be, e.g., a heterocycloalkyl, a heterocycloalkenyl, or a heteroaryl.

$R^{X2}$ and $R^{X3}$ are each independently a group $R^{X1}$, or $R^{X2}$ and $R^{X3}$ are mutually linked to form, together with the nitrogen atom that they are attached to, a nitrogen ring atom-containing heterocyclyl which is optionally substituted with one or more (e.g., one, two or three) groups $R^{X6}$.

Each $R^{X4}$ is independently selected from —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —S($C_{1-5}$ alkylene)-SH, —S($C_{1-5}$ alkylene)-S($C_{1-5}$ alkyl), —NH$_2$, —NH($C_{1-5}$ alkyl), —N($C_{1-5}$ alkyl)($C_{1-5}$ alkyl), halogen, $C_{1-5}$ haloalkyl, —O—($C_{1-5}$ haloalkyl), —CF$_3$, —CN, —NO$_2$, —CHO, —CO—($C_{1-5}$ alkyl), —OOH, —CO—O—($C_{1-5}$ alkyl), —O—CO—($C_{1-5}$ alkyl), —CO—NH$_2$, —CO—NH($C_{1-5}$ alkyl), —CO—N($C_{1-5}$ alkyl)($C_{1-5}$ alkyl), —NH—CO—($C_{1-5}$ alkyl), —N($C_{1-5}$ alkyl)-CO—($C_{1-5}$ alkyl), —SO$_2$—NH$_2$, —SO$_2$—NH($C_{1-5}$ alkyl), —SO$_2$—N($C_{1-5}$ alkyl)($C_{1-5}$ alkyl), —NH—SO$_2$—($C_{1-5}$ alkyl), —N($C_{1-5}$ alkyl)-SO$_2$—($C_{1-5}$ alkyl), carbocyclyl and heterocyclyl, wherein said carbocyclyl and said heterocyclyl are each optionally substituted with one or more (e.g., one, two or three) groups $R^{X6}$.

Each $R^{X5}$ is independently selected from —O—, —CO—, —C(=O)O—, —C(=O)—, —N($R^{X7}$)—, —N($R^{X7}$)—CO—, —CO—N($R^{X7}$)—, —N($R^{X7}$)—CO—N($R^{X7}$)—, —N($R^{X7}$)—C(=O)—O—, —O—C(=O)—N($R^{X7}$)—, —N($R^{X7}$)—C(NH$_2$)=N—, —N=C(NH$_2$)—N($R^{X7}$)—, —N($R^{X7}$)—C(=N—CN)—N($R^{X7}$)—, —N($R^{X7}$)—C (=N—R$^{X7}$)—N(R$^{X7}$)—, —N(R$^{X7}$)—C(=N—R$^{X7}$)—, —C(=N—R$^{X7}$)—N(R$^{X7}$)—, —N(R$^{X7}$)—C(=N—NO$_2$)—N(R$^{X7}$)—, —N(R$^{X7}$)—C(=N—CN)—, —C(=N—CN)—N(R$^{X7}$)—, —N(R$^{X7}$)—C(=CH—NO$_2$)—, —C(=CH—NO$_2$)—N(R$^{X7}$)—, —N(R$^{X7}$)—C(=N—NO$_2$)—, —C(=N—NO$_2$)—N(R$^{X7}$)—, —S—, —SO—, —SO$_2$—, —SO$_2$—N(R$^{X7}$)—, —N(R$^{X7}$)—SO$_2$—, —N(R$^{X7}$)—SO$_2$—N(R$^{X7}$)—, —SO—N(R$^{X7}$)—, —N(R$^{X7}$)—SO—, —N(R$^{X7}$)—SO—N(R$^{X7}$)—, —C(=S)O—, —O—C(=S)—, —C(=O)S—, —S—C(=O)—, —N(R$^{X7}$)—C(=S)—, —C(=S)—N(R$^{X7}$)—, —N(R$^{X7}$)—C(=S)—N(R$^{X7}$)—, —N(R$^{X7}$)—C(=S)—O—, —O—C(=S)—N(R$^{X7}$)—, —N(R$^{X7}$)—C(=O)—S—, —S—C(=O)—N(R$^{X7}$)—, —S—C(=N—R$^{X7}$)—N(R$^{X7}$)—, —N(R$^{X7}$)—C(=N—R$^{X7}$)—S—, —O—C(=N—R$^{X7}$)—N(R$^{X7}$)—, and —N(R$^{X7}$)—C(=N—R$^{X7}$)—O—. Preferably, each R$^{X5}$ is independently selected from —O—, —CO—, —C(=O)—, —O—C(=O)—, —N(R$^{X7}$)—, —N(R$^{X7}$)—CO—, —CO—N(R$^{X7}$)—, —S—, —SO—, —SO$_2$—, —SO$_2$—N(R$^{X7}$)—, and —N(R$^{X7}$)—SO$_2$—.

Each R$^{X6}$ is independently selected from $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-5}$ alkyl), —($C_{0-3}$ alkylene)-O($C_{1-5}$ alkylene)-OH, —($C_{0-3}$ alkylene)-O($C_{1-5}$ alkylene)-O($C_{1-5}$ alkyl), —($C_{0-3}$ alkylene)-SH, —($C_{0-3}$ alkylene)-S($C_{1-5}$ alkyl), —($C_{0-3}$ alkylene)-S($C_{1-5}$ alkylene)-SH, —($C_{0-3}$ alkylene)-S($C_{1-5}$ alkylene)-S($C_{1-5}$ alkyl), —($C_{0-3}$ alkylene)-NH$_2$, —($C_{0-3}$ alkylene)-NH($C_{1-5}$ alkyl), —($C_{0-3}$ alkylene)-N($C_{1-5}$ alkyl)($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-CF$_3$, —($C_{0-3}$ alkylene)-CN, —($C_{0-3}$ alkylene)-NO$_2$, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—NH$_2$, —($C_{0-3}$ alkylene)-CO—NH($C_{1-5}$ alkyl), —($C_{0-3}$ alkylene)-CO—N($C_{1-5}$ alkyl)($C_{1-5}$ alkyl), —($C_{0-3}$ alkylene)-NH—CO—($C_{1-5}$ alkyl), —($C_{0-3}$ alkylene)-N($C_{1-5}$ alkyl)-CO—($C_{1-5}$ alkyl), —($C_{0-3}$ alkylene)-SO$_2$—NH$_2$, —($C_{0-3}$ alkylene)-SO$_2$—NH($C_{1-5}$ alkyl), —($C_{0-3}$ alkylene)-SO$_2$—N($C_{1-5}$ alkyl)($C_{1-5}$ alkyl), —($C_{0-3}$ alkylene)-NH—SO$_2$—($C_{1-5}$ alkyl), —($C_{0-3}$ alkylene)-N($C_{1-5}$ alkyl)-SO$_2$—($C_{1-5}$ alkyl), —($C_{0-3}$ alkylene)-carbocyclyl and —($C_{0-3}$ alkylene)-heterocyclyl, wherein the carbocyclyl moiety comprised in said —($C_{0-3}$ alkylene)-carbocyclyl and the heterocyclyl moiety comprised in said —($C_{0-3}$ alkylene)-heterocyclyl are each optionally substituted with one or more (e.g., one, two or three) groups R$^{X8}$.

Each R$^{X7}$ is independently selected from hydrogen and $C_{1-5}$ alkyl. Preferably, each R$^{X7}$ is independently selected from hydrogen, methyl and ethyl.

Each R$^{X8}$ is independently selected from $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-5}$ alkyl), —($C_{0-3}$ alkylene)-O($C_{1-5}$ alkylene)-OH, —($C_{0-3}$ alkylene)-O($C_{1-5}$ alkylene)-O($C_{1-5}$ alkyl), —($C_{0-3}$ alkylene)-SH, —($C_{0-3}$ alkylene)-S($C_{1-5}$ alkyl), —($C_{0-3}$ alkylene)-S($C_{1-5}$ alkylene)-SH, —($C_{0-3}$ alkylene)-S($C_{1-5}$ alkylene)-S($C_{1-5}$ alkyl), —($C_{0-3}$ alkylene)-NH$_2$, —($C_{0-3}$ alkylene)-NH($C_{1-5}$ alkyl), —($C_{0-3}$ alkylene)-N($C_{1-5}$ alkyl)($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-CF$_3$, —($C_{0-3}$ alkylene)-CN, —($C_{0-3}$ alkylene)-NO$_2$, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—NH$_2$, —($C_{0-3}$ alkylene)-CO—NH($C_{1-5}$ alkyl), —($C_{0-3}$ alkylene)-CO—N($C_{1-5}$ alkyl)($C_{1-5}$ alkyl), —($C_{0-3}$ alkylene)-NH—CO—($C_{1-5}$ alkyl), —($C_{0-3}$ alkylene)-N($C_{1-5}$ alkyl)-CO—($C_{1-5}$ alkyl), —($C_{0-3}$ alkylene)-SO$_2$—NH$_2$, —($C_{0-3}$ alkylene)-SO$_2$—NH($C_{1-5}$ alkyl), —($C_{0-3}$ alkylene)-SO$_2$—N($C_{1-5}$ alkyl)($C_{1-5}$ alkyl), —($C_{0-3}$ alkylene)-NH—SO$_2$—($C_{1-5}$ alkyl), —($C_{0-3}$ alkylene)-N($C_{1-5}$ alkyl)-SO$_2$—($C_{1-5}$ alkyl), —($C_{0-3}$ alkylene)-carbocyclyl and —($C_{0-3}$ alkylene)-heterocyclyl.

It is preferred that the sulfonic acid construct of formula (I) has a molecular weight of equal to or less than about 1 kDa, more preferably of equal to or less than about 800 Da, even more preferably of equal to or less than about 500 Da, and still more preferably of equal to or less than about 300 Da.

The molecular weight of the sulfonic acid construct of formula (I) is indicated herein in dalton (Da), which is an alternative name for the unified atomic mass unit (u). A molecular weight of, e.g., 500 Da is thus equivalent to 500 g/mol. The term "kDa" (kilodalton) refers to 1000 Da.

The molecular weight of a molecule, such as the sulfonic acid construct of formula (I), can be determined using methods known in the art, such as, e.g., mass spectrometry (e.g., electrospray ionization mass spectrometry (ESI-MS) or matrix-assisted laser desorption/ionization mass spectrometry (MALDI-MS)), gel electrophoresis (e.g., polyacrylamide gel electrophoresis using sodium dodecyl sulfate (SDS-PAGE)), hydrodynamic methods (e.g., gel filtration chromatography or gradient sedimentation), or static light scattering (e.g., multi-angle light scattering (MALS)). It is preferred that the molecular weight of the sulfonic acid construct of formula (I) is determined using mass spectrometry.

Preferred examples of the sulfonic acid construct of formula (I) include the following compounds as well as physiologically acceptable salts of any one of these compounds:

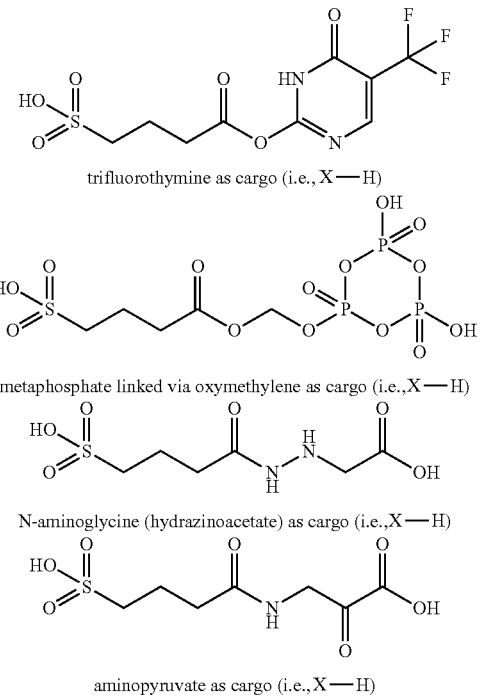

trifluorothymine as cargo (i.e., X—H)

metaphosphate linked via oxymethylene as cargo (i.e., X—H)

N-aminoglycine (hydrazinoacetate) as cargo (i.e., X—H)

aminopyruvate as cargo (i.e., X—H)

-continued

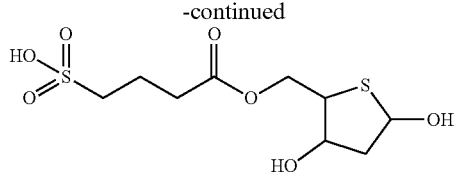
2-deoxy-4-thiaribofuranose as cargo (i.e., X—H)

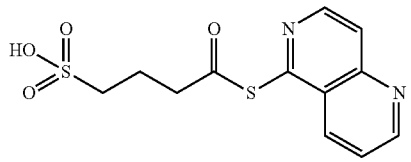
5-mercapto-1,6-diazanaphthalene as cargo (i.e., X—H)

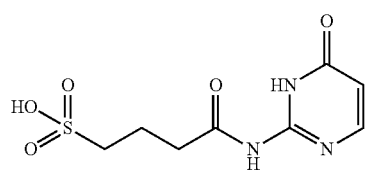
isocytosine as cargo (i.e., X—H)

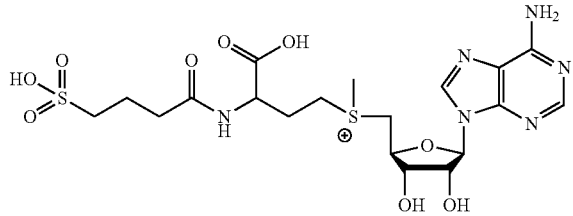
S-adenosylmethionine as cargo (i.e., X—H)

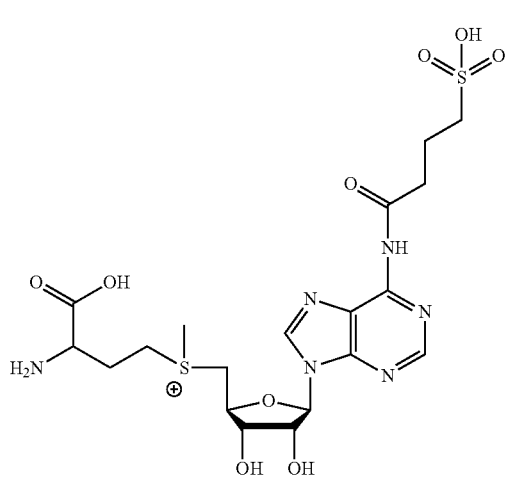
S-adenosylmethionine as cargo (i.e., X—H)

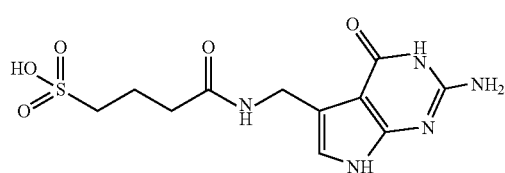
7-(aminomethyl)-7-deazaguanine (queunine precursor) as cargo (i.e., X—H)

-continued

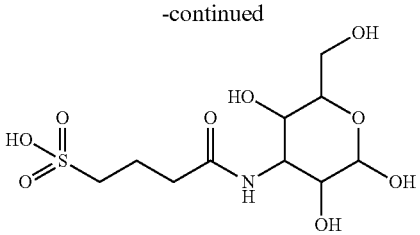
kanosamine as cargo (i.e., X—H)

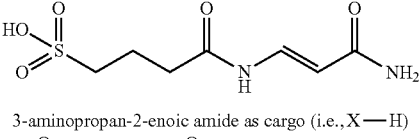
3-aminopropan-2-enoic amide as cargo (i.e., X—H)

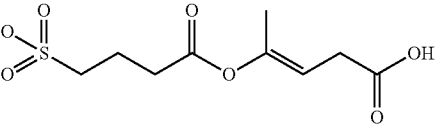
levulinate as cargo (i.e., X—H)

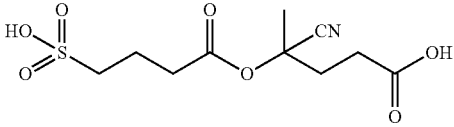
4-cyano-4-hydroxy-pentanoic as cargo (i.e., X—H)

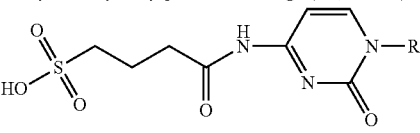
cytocine conjugate as cargo (i.e., X—H);
the group R can be hydrogen or any substituent, as desired
(e.g., a sugar, a phosphosugar, etc.)

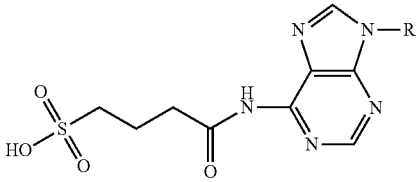
adenine conjugate as cargo (i.e., X—H);
the group R can be hydrogen or any substituent, as desired
(e.g., a sugar, a phosphosugar, etc.)

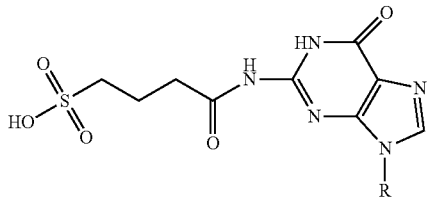
guanine conjugate as cargo (i.e., X—H);
the group R can be hydrogen or any substituent, as desired
(e.g., a sugar, a phosphosugar, etc.)

The term "cellular" in the term "cellular transport system" means that the required components for the transport of the sulfonic acid construct in terms of the present invention are present or implemented in a cell. Thus, the present invention also relates to a cell comprising a transport system as described herein. Such a cell is in particular characterized by the fact that it contains nucleic acid sequences which encode the elements of the cellular transport system as described herein.

A cell in accordance with the present invention is the basic structural, functional, and biological unit of all known living organisms. A cell is the smallest unit of life that can replicate independently, and cells are often called the "building blocks of life". Cells consist of cytoplasm enclosed within a semipermeable membrane.

A cellular transport system as used in accordance with the present invention relates to a system which overcomes cellular semipermeable membranes which often pose a barrier for bringing desired molecules (herein called "cargos") into a cell. The cellular transport system of the present invention is based on the interplay between a specifically designed cargo-carrier construct, i.e. the sulfonic acid construct according to formula (I) in which X represents the cargo, which can be transported across the semipermeable membrane into the cytoplasm of the cell and a specific enzymatic activity which is capable of intracellularly hydrolyzing the chemical linkage between the cargo and the carrier, thereby releasing the cargo from the sulfonic acid construct while it is crucial that this enzymatic activity is located in the cytoplasm of a cell.

In the following, the two above-mentioned components of the cellular transport system of the present invention are described in more detail.

The first component is the sulfonate transporter located in the membrane of the cell wherein said sulfonate transporter is capable of transporting said sulfonic acid construct across the cytoplasm membrane into the cytoplasm. This component is described in the following.

The second component is a γ-glutamyl transferase (GGT; EC 2.3.2.2) which is modified to be located in the cytoplasm of the cell, wherein said γ-glutamyl transferase is capable of hydrolyzing said sulfonic acid construct. This second component is described in more detail further below.

The present invention is not particularly limited to a specific sulfonate transporter. In fact, most or even all cells express one or several proteins involved in scavenging sulfur (compounds) and in up-taking these compounds into the cell. Sulfonate transporters are membrane transport proteins (often simply referred to as transporters) which are located in the membrane of a cell and which are involved in the movement of sulfur (compounds) across a biological membrane. Transport proteins are integral transmembrane proteins, i.e., they exist permanently within and span the membrane across which they transport substances. The proteins may assist in the movement of substances by facilitated diffusion or active transport.

Accordingly, any sulfonate transporter, endogenously or recombinantly expressed in a cell, may be used in the cellular transport system of the present invention as long as it is capable of transporting the sulfonic acid construct across the cytoplasm membrane into the cytoplasm.

As an example, the sulfonate transporter located in the cytoplasm membrane of the cell is a TauABC transporter or an SsuABC transporter derived from *E. coli*.

*E. coli* possesses two transport systems for the uptake of sulfonates. While the TauABC system is mostly responsible for the uptake of taurine, the SsuABC system is less specific and facilitates transport of a broad range of structurally diverse sulfonates (Eichhorn et al., 2000). Once sulfonates are transported into the cytoplasm they can be desulfonated by the enzymes TauD or SsuDE, resulting in the formation of an aldehyde and a sulfite ion that can be further utilized as sulfur source (Eichhorn et al., 1997; Eichhorn et al., 1999).

In *E. coli*, the genes encoding the TauABC transporter and the SsuABC transporter are organized in the tauABCD and ssuEADCB gene clusters, respectively. While the TauABC transporter and the SsuABC transporter are the actual membrane transport proteins located in the membrane of the cell, the proteins encoded by tauD and ssuDE of the above-mentioned gene clusters are cytoplasmic enzymes responsible for desulfonation.

Thus, in a preferred embodiment, in the cellular transport system of the present invention, the sulfonate transporter located in the cytoplasm membrane of the cell is a TauABC transporter or an SsuABC transporter derived from *E. coli*.

The above-mentioned sulfonate transporters from *E. coli* are of course only examples for sulfonate transporters which can be employed in a cellular transport system according to the present invention. Any other sulfonate transporter can be employed as long as it is capable of transporting the sulfonic acid construct as defined above into the cytoplasm of a cell. Such sulfonate transporters, in particular ABC-type sulfonate transporters, are not only known from *E. coli* but also from other organisms, in particular microorganisms. Sulfur transporters of the ABC type actually occur in basically all organisms from prokaryotes to higher mammalians. Thus, any sulfonate transporter, in particular any ABC-type sulfonate transporter derivable from eukaryotic or prokaryotic organisms, such as plants, animals, fungi and bacteria can be employed in a cellular transport system according to the present invention as long as it is capable of transporting the sulfonic acid construct into the cytoplasm of a cell. ABC-type sulfonate transporters have, e.g. been described in *Pseudomonas putida*, Corynebacteria, such as *Corynebacterium glutamicum* and in *Bacillus subtilis* which may be preferably used in a cellular transport system according to the present invention. Furthermore, Pereira et al. (BMC Genomics 16 (2015), 524) describes an ABC-type sulfur/sulfonate transport system in *Xanthomonas citri* pv. *citri*.

Thus, in one preferred embodiment the sulfonate transporter is an ABC-type sulfonate transporter. Known ABC transporters have in common that they comprise multiple subunits and are essential for the uptake of hydrophilic nutrients. Solutes are translocated through two transmembrane proteins and, on the cytoplasmic side of the membrane, two nucleotide binding domains bind and hydrolyze ATP to provide the energy for the translocation process. In addition to that, most ABC transporters possess an extracytoplasmic substrate-binding protein which is responsible for recognition and binding of the solute. Sulfonate ABC transporters have the ability to recognize sulfonate compounds with its periplasmic binding protein and the ability to channel sulfonates through transmembrane proteins into the cytoplasm of a cell. More preferably it is a transporter which is a homolog of the SsuABC transporter or of the TauABC transporter of *E. coli*. The term "homolog" in this context means that there is functional homology, i.e. the transporter fulfills the same function as the SsuABC transporter or of the TauABC transporter of *E. coli*. Preferably, the term "homolog" in this context means that there is also a structural homology in the sense that the corresponding transporter is encoded by genes which belong to a similar gene cluster as the ssuEADCB gene cluster or the TauABCD gene cluster of *E. coli*, preferably by genes which encode proteins with a certain minimal degree of sequence identity to the SsuABC transporter of *E. coli* (see below).

In a more preferred embodiment, the sulfonate transporter located in the cytoplasm membrane of the cell is a TauABC transporter which comprises the amino acid sequence of any one of SEQ ID NOs:5 to 7 or a combination thereof or a sequence which is at least n % identical to any one of SEQ ID NOs:5 to 7 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 or a combination of such sequences and wherein the transporter is located in the membrane of a cell and has the activity of transporting a sulfonate, preferably the sulfonic acid construct as described herein, across the cytoplasm membrane into the cytoplasm.

In another preferred embodiment, the sulfonate transporter located in the cytoplasm membrane of the cell is a SsuABC transporter which comprises the amino acid sequence of any one of SEQ ID NOs:8 to 10 or a combination thereof or a sequence which is at least n % identical to any one of SEQ ID NOs:8 to 10 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 or a combination of such sequences and wherein the transporter is located in the membrane of a cell and has the activity of transporting a sulfonate, preferably the sulfonic acid construct as described herein, across the cytoplasm membrane into the cytoplasm.

As regards the determination of sequence identity, the following should apply: When the sequences which are compared do not have the same length, the degree of identity either refers to the percentage of amino acid residues in the shorter sequence which are identical to amino acid residues in the longer sequence or to the percentage of amino acid residues in the longer sequence which are identical to amino acid residues in the shorter sequence. Preferably, it refers to the percentage of amino acid residues in the shorter sequence which are identical to amino acid residues in the longer sequence. The degree of sequence identity can be determined according to methods well known in the art using preferably suitable computer algorithms such as CLUSTAL.

When using the Clustal analysis method to determine whether a particular sequence is, for instance, at least 60% identical to a reference sequence default settings may be used or the settings are preferably as follows: Matrix: blosum 30; Open gap penalty: 10.0; Extend gap penalty: 0.05; Delay divergent: 40; Gap separation distance: 8 for comparisons of amino acid sequences. For nucleotide sequence comparisons, the Extend gap penalty is preferably set to 5.0.

In a preferred embodiment ClustalW2 is used for the comparison of amino acid sequences. In the case of pairwise comparisons/alignments, the following settings are preferably chosen: Protein weight matrix: BLOSUM 62; gap open: 10; gap extension: 0.1. In the case of multiple comparisons/alignments, the following settings are preferably chosen: Protein weight matrix: BLOSUM 62; gap open: 10; gap extension: 0.2; gap distance: 5; no end gap.

Preferably, the degree of identity is calculated over the complete length of the sequence.

Amino acid residues located at a position corresponding to a position as indicated herein-below in the amino acid sequence shown in any one of SEQ ID NOs:5 to 10 can be identified by the skilled person by methods known in the art. For example, such amino acid residues can be identified by aligning the sequence in question with the sequence shown in any one of SEQ ID NOs:5 to 10 and by identifying the positions which correspond to the above indicated positions of any one of SEQ ID NOs:5 to 10. The alignment can be done with means and methods known to the skilled person, e.g. by using a known computer algorithm such as the Lipman-Pearson method (Science 227 (1985), 1435) or the CLUSTAL algorithm. It is preferred that in such an alignment maximum homology is assigned to conserved amino acid residues present in the amino acid sequences.

In a preferred embodiment ClustalW2 is used for the comparison of amino acid sequences. In the case of pairwise comparisons/alignments, the following settings are preferably chosen: Protein weight matrix: BLOSUM 62; gap open: 10; gap extension: 0.1. In the case of multiple comparisons/alignments, the following settings are preferably chosen: Protein weight matrix: BLOSUM 62; gap open: 10; gap extension: 0.2; gap distance: 5; no end gap.

Preferably, the degree of identity is calculated over the complete length of the sequence.

Whether a protein is located in the membrane of a cell may be determined by methods known to the person skilled in the art.

The activity of (a) sulfonate transporter(s) may be determined by methods known in the art. As an example, reference is made to Eichhorn et al. (Journal of Bacteriology 182(10), 2000) which assesses the effects of deletions of the E. coli taurine and alkanesulfonate transport systems.

More specifically, the activity of a protein of transporting a sulfonate, preferably the sulfonic acid construct of the present invention, across the cytoplasm membrane into the cytoplasm of a cell may be determined by methods known to the person skilled in the art. In fact, there are many methods known in the art to determine the cellular localization of a molecule (i.e., of a sulfonate in the present case) by, e.g., determining whether it is localized in the cytoplasm of the cell or whether the molecule is localized outside the cell. In one embodiment, this activity of transporting a sulfonate, preferably the sulfonic acid construct of the present invention, across the cytoplasm membrane into the cytoplasm of a cell is determined as described in the Examples appended hereto (see, e.g., Example 8). The assay described in the Examples can be adapted according to known methods so as to assess whether a transporter at hand can transport a sulfonate via the cytoplasm membrane or not. One possible approach is to provide a cell which does not have the capacity to transport sulfonates over the cytoplasm membrane and to transform it with nucleic acid molecules encoding a possible sulfonate transporter and incubating it in a medium containing a sulfonate. Presence of the sulfonate in the cell indicates that the encoded protein has sulfonate transporter activity. The presence of the sulfonate in the cell can be determined by the skilled person by methods known in the art.

In a preferred embodiment, the cell of the cellular transport system of the present invention has been genetically modified by the introduction of one or more nucleic acid molecules containing nucleotide sequences encoding the sulfonate transporter of the cellular transport system of the present invention as described above. The nucleic acid molecule(s) can be stably integrated into the genome of the cell or may be present in an extrachromosomal manner. In a more preferred embodiment, the nucleic acid molecule(s) can be present on a plasmid.

Means and methods for correspondingly genetically modifying the cell of the cellular transport system are described in more detail further below.

The second component of the cellular transport system of the present invention is a γ-glutamyl transferase (GGT; EC 2.3.2.2). A GGT to be employed in a cellular transport system according to the present invention is characterized by the features that:
(i) it is modified to be located in the cytoplasm of the cell; and (ii) it is capable of hydrolyzing the sulfonic acid construct of formula (I) to release the compound H—X.

As explained above, the present invention is based on the finding that there exist versions of GGT enzymes which prefer as substrates sulfonic acid compounds instead of γ-substituted glutamyl compounds. This allows to provide a cellular transport system for carrying a cargo into a cell and have it set free by the action of the GGT which is advantageous in comparison to the known systems for the reasons as outlined above.

γ-glutamyl transferases (GGT; EC 2.3.2.2) are known to occur in a variety of organisms, including eukaryotic and prokaryotic organisms, such as plants, animals, fungi and bacteria.

GGT is known to be mainly responsible for the degradation of glutathione in the periplasmic space, but in addition, it is known to catalyze the hydrolysis of a broad range of other γ-substituted glutamyl compounds (Imaoka et al., 2010; Minami et al., 2003). Binding of a γ-glutamyl compound to the active site of the enzyme leads to the formation of a γ-glutamyl-enzyme intermediate and results in release of an amine cargo. The intermediate is then attacked by either water (hydrolase activity) or by an amino acid or peptide (transpeptidase activity) as a nucleophile (see FIG. 4a) (Okada et al., 2006).

GGT has been described to occur in a large number of organisms, including animals, plants, fungi and bacteria, e.g., in *Arabidopsis* sp. (SwissProt accession number Q9M0G0), *Bacillus licheniformis* (SwissProt accession number Q65KZ6), *Bacillus subtilis* (UniProt accession number Q83XQ6), *Escherichia coli* (UniProt accession number P18956), *Picrophilus torridus* (UniProt accession number Q6KZT2), *Pseudomonas fluorescens* (UniProt accession number Q4KIM5), and *Schizosaccharomyces pombe* (SwissProt accession number O14194). The enzyme has also been described in *Allium cepa, Allium sativum, Aphidius ervi, Arabidopsis thaliana, Ascaris suum, Aspergillus oryzae, Bacillus pumilis, Blighia sapida, Bos taurus, Campylobacter jejuni, Canis lupus familaris, Equus caballus, Heliobacter pylori, Histoplasma capsulatum, Homo sapiens, Hordeum vulgare, Lentinula edodes, Lepidochelys kempii, Marthasterias glacialis, Morchella esculenta, Mus musculus, Neisseria gonorrhoeae, Oncornavirus, Oncornavirus cuniculus, Ovis aries, Penicillinum roqueforti, Phaseolus vulgaris, Proteus mirabilis, Raphanus sativus, Rattus norvegicus, Saccharomyces cerevisiae, Setaria cervi, Sonanum lycopersicum, Sus scrofa* and *Treponema denticola*.

In bacteria, GGT is usually secreted from the cytoplasm or anchored in the cytoplasmic membrane with the catalytic activity in the extracellular domain (Finidori et al., 1984; Hanigan, 2014; Suzuki et al., 1986). In *E. coli*, GGT is expressed as an inactive proenzyme and secreted to the periplasmic space where it undergoes maturation into a (previously N-terminal) large and a (previously C-terminal) small subunit of approximately 40 and 20 kDa in size, respectively. The maturation process is essential for enzyme activity, as the threonine residue at the newly formed N-terminus of the small subunit is the catalytic residue of the enzyme (Suzuki and Kumagai, 2002).

Yet, as mentioned above, in accordance with the rationale of the present invention, the GGT to be used in the cellular transport system of the present invention is modified to be located in the cytoplasm of the cell since it is desired that the release of the cargo takes place in the cytoplasm. As shown in the Examples, it is possible to modify GGT enzymes so as to be located in the cytoplasm and to be enzymatically active. This is demonstrated for the wildtype enzymes of *E. coli* (EcGGT) and *Pseudomonas nitroreducens* (PnGGT) as well as for the mutants EcGGT D433N and PnGGT D405N by effecting deletions of the N-terminus of the enzyme. It was shown that already a partial deletion (ΔN16) of the signal peptide leads to a cytoplasmic location and an active enzyme as well as a nearly complete deletion of the signal peptide (ΔN24.)

Thus, a GGT which is modified so as to be located in the cytoplasm of the cell can be a GGT in which the signal peptide is partially or completely deleted. Utilizing bioinformatic analysis tools, the skilled person can determine the signal peptide within a given protein. Accordingly, the skilled person can identify the amino acids which form the signal peptide of the γ-glutamyl transferase (GGT) to be used in the cellular transport system of the present invention.

Once determined, a signal-peptide truncation can be introduced by, e.g., deleting or mutating/modifying (parts of) the amino acid sequence of the γ-glutamyl transferase (GGT) in order to be located in the cell by methods known in the art.

Preferably, the GGT is a GGT in which at least n amino acids are deleted from the N-terminus in comparison to the corresponding wildtype GGT with n being an integer selected from 10, 11, 12, 13, 14, 15, 16, 17, 18, 19, 20, 21, 22, 23, 24 or 25, preferably 16, even more preferably 24. Preferably the deletion of the N-terminus is not longer than 29, 28, 27, 26 or 25 amino acids.

Whether a protein is localized in the cytoplasm of a cell may be determined by methods known to the person skilled in the art. In fact, there are many methods known in the art to determine the localization of a protein within a cell or even a subcellular compartment. Moreover, there are methods known in the art to determine whether a protein is localized in the cytoplasm of the cell or whether the protein is secreted and, accordingly, localized outside the cell. In a preferred embodiment, it may be determined as described in the Examples appended hereto whether the γ-glutamyl transferase is located in the cytoplasm of the cell.

In the scope of the present invention, a GGT is employed which is able to accept a sulfonic acid construct as a substrate. It has been found that certain variants of GGT can actually accept such substrates, in particular sulfonic acid constructs of formula (I) which carry a cargo (indicated as X in formula (I)), which differ from the natural substrate, i.e., a γ-substituted glutamyl compound, and can hydrolyze them so as to set free the cargo. In the Examples of the present invention it is, e.g., shown that GGT mutants which have been described in the art can accept a 4-sulfobutanoyl conjugate as a substrate. This is exemplified by using 4-sulfobutanoic acid which carries at its carboxyl group a leucine or p-nitroanilide as a cargo and which is hydrolyzed by the used GGT mutants into sulfobutyric acid and leucine and 4-nitroaniline, respectively (see FIGS. 2 and 16). The GGT mutants used in the Examples are GGT mutants from *E. coli* and from *Pseudomonas nitroreducens*.

These GGT mutants show an amino acid substitution at corresponding positions, i.e. at position 433 in the *E. coli* GGT which corresponds to position 405 in the GGT from *Pseudomonas nitroreducens*. These substitutions in both enzymes lead to a shift in substrate specificity so that the GGT accepts 4-sulfobutanoyl conjugates as substrates and even prefers such substrates over their natural substrates, i.e. γ-substituted glutamyl compounds.

The position which corresponds to position D433 in the *E. coli* GGT and position D405 of the *P. nitroreducens* GGT is known to be highly conserved among the GGTs from different organisms. This position is known to be important for the enzymatic activity and to form a salt bridge with the α-amine group of the γ-glutamyl substrate (Okada et al., 2006; Suzuki et al., 2004).

Based on this knowledge, it is possible for the skilled person to provide GGT variants derived from GGT enzymes from other organisms which are capable of using a sulfonic acid construct as defined herein as a substrate and which can therefore be employed in a transport system according to the present invention. Thus, in one embodiment the GGT enzyme employed in the cellular transport system according to the present invention is a GGT enzyme in which the amino acid at the position corresponding to position D433 of the E. coli GGT (shown in SEQ ID NO: 1) or to position D405 of the P. nitroreducens GGT (shown in SEQ ID NO: 4) is replaced by another amino acid, preferably by an asparagine (N; Asn). Such variants can be produced by starting out from any known GGT enzyme, e.g., any known naturally occurring GGT enzyme and by effecting the amino acid substitution at the position indicated above according to routine measures, such as site directed mutagenesis.

Thus, the γ-glutamyl transferase (GGT; EC 2.3.2.2) to be used in the cellular transport system of the present invention can be derived from any existing GGT enzyme from any suitable source as long as it is modified to be located in the cytoplasm of the cell and as long as it is capable of accepting a sulfonic acid construct as described herein as a substrate and of hydrolyzing it. The latter feature, i.e. the ability to accept and hydrolyze a sulfonic acid construct, may be achieved by effecting the above described substitution at a position corresponding to position D433 of the E. coli GGT (or D405 of the P. nitroreducens GGT).

In a preferred embodiment, the γ-glutamyl transferase (GGT; EC 2.3.2.2) to be used in the cellular transport system of the present invention is an enzyme selected from the group consisting of the enzymes derived from a GGT of the above-mentioned organisms.

In a more preferred embodiment, the γ-glutamyl transferase (GGT; EC 2.3.2.2) is an enzyme which is derived from a GGT of Escherichia coli or Pseudomonas nitroreducens, preferably by deletion of all or part of the N-terminal signal sequence and substitution of D433 (in the case of E. coli) or D405 (in the case of P. nitroreducens) by another amino acid, preferably by asparagine (N; Asn).

The γ-glutamyl transferase from Escherichia coli has an amino acid sequence as set forth in SEQ ID NO:1. SEQ ID NO:3 shows an amino acid sequence of the γ-glutamyl transferase from Escherichia coli which has been used in the Examples and which harbours a His-tag amino acid sequence at its N-terminal end but lacks the 24 N-terminal amino acids of SEQ ID NO:1 which correspond to the major part of the GGT's signal peptide for its secretion as explained in more detail further below.

The γ-glutamyl transferase from Pseudomonas nitroreducens has an amino acid sequence as set forth in SEQ ID NO:2. SEQ ID NO:4 shows an amino acid sequence of the γ-glutamyl transferase from Pseudomonas nitroreducens which has been used in the Examples and which harbours a His-tag amino acid sequence at its N-terminal end but lacks the 24 N-terminal amino acids of SEQ ID NO:2 which correspond to the major part of the GGT's signal peptide for its secretion as explained in more detail further below.

Thus, in a preferred embodiment, the γ-glutamyl transferase (GGT; EC 2.3.2.2) is an enzyme which comprises the amino acid sequence of SEQ ID NOs:1 or 2 or sequences which are at least n % identical to SEQ ID NO:1 or 2 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme is modified to be located in the cytoplasm of the cell and is modified so as to be able of hydrolyzing a sulfonic acid construct of formula (I) so as to release the compound H—X.

As regards the determination of sequence identity, the same applies as has been set forth above.

The enzymatic activity of a γ-glutamyl transferase to hydrolyze a sulfonic acid construct of formula (I) so as to release the compound H—X may be determined by methods known to the person skilled in the art. The chemical nature of these linkages has been described above. There are methods known in the art to determine whether an enzyme is capable of catalyzing such a chemical reaction. In one embodiment, the activity of a γ-glutamyl transferase to hydrolyze a sulfonic acid construct of formula (I) so as to release the compound H—X is determined as described in the Examples appended hereto.

The activity of a γ-glutamyl transferase to hydrolyze a sulfonic acid construct of formula (I) so as to release the compound H—X can be assessed by an enzymatic in vitro assay in whole cell lysates, thereby assessing the release of a cargo molecule, i.e. group "X" in formula (I) from a sulfonic acid construct of formula (I). More specifically, to test for the desired activity, a colorimetric enzyme assay can be used, utilizing as the substrate sulfobutanoyl-p-nitroanilide in 50 mM Tris-HCl (pH 9.0) or a corresponding nitroanilide. For that, cytoplasmic GGT variants are first expressed and a whole cell extract/lysate is prepared by standard methods. To start the reaction, the substrate sulfobutanoyl-p-nitroanilide is added to a final concentration of 4 mM. Hydrolysis of this colorless substrate by a GGT variant into sulfobutanoic acid and the yellow dye 4-nitroaniline can be quantified photometrically at 410 nm. More specifically, absorption at 410 nm is constantly measured at 37° C. in a Tecan Infinite 200 Pro plate reader (Tecan, Männedorf, Switzerland). One unit is defined as the amount of enzyme required to catalyze the formation of 1 μmol of 4-nitroaniline per minute.

To test the activity of a γ-glutamyl transferase to hydrolyze a sulfonic acid construct, the above colorimetric enzyme assay may be used with the exception that, sulfobutanoyl-p-nitrophenyl and sulfobutanoyl-p-nitrothiophenol, respectively, is used as a substrate instead of the substrate sulfobutanoyl-p-nitroanilide.

In a preferred embodiment the GGT employed in the cellular transport system according to the present invention shows a preference for accepting a sulfonic acid construct as a substrate instead of a γ-substituted glutamyl compound (i.e. the natural substrate). The term "preference" in this context preferably means that the GGT shows an activity on a sulfonic acid construct which is at least 10%, preferably at least 20%, 30%, 40%, 50%, 60%, 70%, 80% or 90% higher than on a corresponding γ-substituted glutamyl compound. The activity is preferably measured in the form of the kcat value. Alternatively, the term "preference" means that the GGT has a higher affinity for a sulfonic acid construct than for a corresponding γ-substituted glutamyl compound. The affinity may be indicated as the $K_M$ value. Preferably the $K_M$ for a γ-substituted glutamyl compound is at least 2 times, preferably 3 times, 4 times, 5 times, 10 times, 20 times or 100 times higher than that for a corresponding sulfonic acid construct.

In a particularly preferred embodiment the GGT employed in a cellular transport system according to the invention does no longer accept a γ-carboxyl substituted glutamyl compound as a substrate or only shows a negligible affinity for such a compound.

γ-glutamyl transferases (GGT; EC 2.3.2.2) known in the art are not very well conserved over large regions of the enzyme and, accordingly, the overall degree of sequence identity referred to above may be rather low. However, it has been shown that γ-glutamyl transferases contain common sequence motifs/signatures which are highly conserved, in particular motifs/signatures which form the active site of the enzyme.

Accordingly, in a preferred embodiment, the γ-glutamyl transferase (GGT; EC 2.3.2.2) is a GGT in which the sequence of the amino acid residues corresponding to the region of positions 390 to 469 of SEQ ID NO:1 (or corresponding to the region of positions 362 to 441 in SEQ ID NO:2) is highly conserved. "Highly conserved" in this context means that the γ-glutamyl transferase (GGT; EC 2.3.2.2) is a GGT in which the sequence of the amino acid residues corresponding to the region of positions 390 to 469 of SEQ ID NO:1 (or corresponding to the region of positions 362 to 441 in SEQ ID NO:2) shows a sequence identity of at least 60% to the region of positions 390 to 469 of SEQ ID NO:1 (or to the region of positions 362 to 441 in SEQ ID NO:2). Preferably, in such a GGT the amino acid which corresponds to position D433 of the *E. coli* GGT or to position D405 of the *P. nitroreducens* GGT is substituted by another amino acid, preferably by asparagine (N, Asn).

In more preferred embodiments, the sequence identity in this region is at least 65, 70, 75, 80, 85, 90, 91, 92, 93, 94, 95, 96, 97, 98 or 99%.

In an even more preferred embodiment the GGT contains a region which is identical to the amino acid sequence of positions 391 to 469 of SEQ ID NO: 1 with the exception that position D433 is replaced by another amino acid, preferably asparagine (N; Asn) or identical to the amino acid sequence of positions 362 to 441 of SEQ ID NO: 2 with the exception that position D405 is replaced by another amino acid, preferably asparagine.

Within the motif corresponding to amino acid residues from position 391 to 469 of SEQ ID NO:1 (or from position 362 to 441 in SEQ ID NO:2) γ-glutamyl transferases (GGT; EC 2.3.2.2) have a motif which is even more conserved.

Accordingly, in another preferred embodiment, the γ-glutamyl transferase (GGT; EC 2.3.2.2) is a GGT in which the sequence of the amino acid residues corresponding to the region of positions 426 to 438 of SEQ ID NO:1 (or corresponding to the region of positions 398 to 410 in SEQ ID NO:2) is highly conserved. "Highly conserved" in this context means that the γ-glutamyl transferase (GGT; EC 2.3.2.2) is a GGT in which the sequence of the amino acid residues corresponding to the region of positions 426 to 438 of SEQ ID NO:1 (or corresponding to the region of positions 398 to 410 in SEQ ID NO:2) shows a sequence identity of at least 70% sequence to the region of positions 426 to 438 of SEQ ID NO:1 (or to the region of positions 398 to 410 in SEQ ID NO:2). Preferably, in such a GGT the amino acid which corresponds to position D433 of the *E. coli* GGT or to position D405 of the *P. nitroreducens* GGT is substituted by another amino acid, preferably by asparagine (N, Asn).

In more preferred embodiments, the sequence identity in this region is at least 75, 80, 85, 90, 91, 92, 93, 94, 95, 96, 97, 98 or 99%.

In an even more preferred embodiment the GGT contains a region which is identical to the amino acid sequence of positions 426 to 438 of SEQ ID NO: 1 with the exception that position D433 is replaced by another amino acid, preferably asparagine (N; Asn) or identical to the amino acid sequence of positions 398 to 410 of SEQ ID NO: 2 with the exception that D405 is replaced by another amino acid, preferably asparagine (N; Asn).

In a more preferred embodiment, in the cellular transport system of the present invention as described herein above, the γ-glutamyl transferase (GGT) has an amino acid sequence as shown in SEQ ID NO:1 or SEQ ID NO:2 or an amino acid sequence having at least 30% sequence identity to SEQ ID NO:1 or SEQ ID NO:2 and lacking at least 16 preferably at least 24 N-terminal amino acids, wherein said γ-glutamyl transferase is modified so as to be able to hydrolyze a sulfonic acid construct as defined herein so as to set free the compound H—X.

In other more preferred embodiments, the γ-glutamyl transferase (GGT) has an amino acid sequence as shown in SEQ ID NO:1 or SEQ ID NO:2 or an amino acid sequence having at least 30% sequence identity to SEQ ID NO:1 or SEQ ID NO:2 and lacking at least the 16, 17, 18, 19, 20, 21, 23 or 24 N-terminal amino acids and is capable of hydrolyzing a sulfonic acid construct as defined herein so as to set free the compound H—X.

In another more preferred embodiment, the γ-glutamyl transferase (GGT) has an amino acid sequence as shown in SEQ ID NO:1 or SEQ ID NO:2 or an amino acid sequence having at least 30% sequence identity to SEQ ID NO:1 or SEQ ID NO:2 and lacking the entire signal peptide, i.e., the 25 N-terminal amino acids and is capable of hydrolyzing a sulfonic acid construct as defined herein so as to set free the compound H—X.

In another preferred embodiment the GGT does not lack more than 29, even more preferably not more than 25 amino acids at the N-terminus.

In more preferred embodiments, the degree of sequence identity is at least 35, 40, 45, 50, 55, 60, 65, 70, 75, 80, 85, 90, 91, 92, 93, 94, 95, 96, 97, 98 or 99%.

The cellular transport system of the present invention is not particularly limited to a particular cell type. It can be established in any desired cell which either naturally expresses one or more of the above components of the cellular transport system or which had been genetically modified so that it expresses (including overexpresses) one or more of the above components of the cellular transport system of the present invention. Thus, any cell can be engineered to express the above components of the cellular transport system.

In a preferred embodiment, the present invention relates to a cellular transport system in accordance with any of the foregoing, wherein the cell is a eukaryotic cell or a prokaryotic cell, preferably a fungal or a yeast cell, a bacterial cell, a gram negative bacterial cell, more preferably an *E. coli* cell.

In principle any bacterium can be used. Preferred bacteria to be employed in accordance with the present invention are bacteria of the genus *Bacillus, Clostridium, Corynebacterium, Pseudomonas, Zymomonas* or *Escherichia*. In a particularly preferred embodiment the bacterium belongs to the genus *Escherichia* and even more preferred to the species *Escherichia coli*. In another preferred embodiment the bacterium belongs to the species *Pseudomonas putida* or to the species *Zymomonas mobilis* or to the species *Corynebacterium glutamicum* or to the species *Bacillus subtilis*.

Preferably, the cell is a fungus, more preferably a fungus of the genus *Saccharomyces, Schizosaccharomyces, Aspergillus, Trichoderma, Kluyveromyces* or *Pichia* and even more preferably of the species *Saccharomyces cerevisiae, Schizosaccharomyces pombe, Aspergillus niger, Trichoderma reesei, *Kluyveromyces marxianus, Kluyveromyces lactis, Pichia pastoris, Pichia torula* or *Pichia utilis.*

In another embodiment, the cell is a photosynthetic microorganism. Preferably, the microorganism is a photosynthetic bacterium, or a microalgae. In a further embodiment the microorganism is an algae, more preferably an algae belonging to the diatomeae.

In case a gram-negative bacterium like, e.g., *E. coli* is used, the size of the sulfonic acid construct to be employed in the transport system may be limited by the cut-off of the porin channels which are known to allow the uptake of molecules having a size of up to about 400 Da to 800 Da. It has previously been reported that porin channels have a cut-off size of approximately 600 Dalton (Cowan et al., 1992).

Therefore, in a preferred embodiment, the present invention relates to a cellular transport system in accordance with any of the foregoing, wherein the cell is a gram negative bacterial cell, like, e.g., an *E. coli* cell, wherein one or more of the porin channels are mutated to enlarge the size of said porin channels.

Approaches to enlarge the porin size are known to the person skilled in the art and are described in the literature.

In one preferred embodiment, in the cellular transport system in accordance with any of the foregoing, the porin channels OmpC and/or OmpF are mutated to enlarge the size of said porin channels and to allow the transfer of the sulfonic acid construct of the present invention into the periplasm.

OmpC and OmpF are the main porin channels of *E. coli*. Both allow the passage of various molecules with a size of up to about 600 Dalton. These porin channels are known to have no strong preference for any specific kind of molecule. In order to increase the cut-off size for bringing a sulfonic acid construct into a cell in accordance with the present invention, (a) mutation(s) may be introduced in OmpC and/or OmpF.

As an example, it was demonstrated for OmpF that the pore size can be enlarged by mutations and, therefore, the cut-off of the porin can be increased.

Corresponding mutations are, e.g., described in Cowan et al., 1992, Lou et al., 1996 and Saint et al., 1996.

In another preferred embodiment, in the cellular transport system in accordance with any of the foregoing, the porin channel FhuA is mutated to enlarge the size of said porin channel and to allow the transfer of the sulfonic acid construct of the present invention into the periplasm.

FhuA is known to be responsible for the uptake of siderophores across the outer membrane. As an example, it was reported previously that the pore of this channel can be enlarged by deleting a part of the protein.

This mutation as well as other mutations of the porin channel for enlarging its size are described in Muhammed et al., 2011 and Krewinkel et al., 2011.

In another preferred embodiment, in the cellular transport system in accordance with any of the foregoing, the porin channel LamB is mutated to enlarge the size of said porin channel and to allow the transfer of the sulfonic acid construct of the present invention into the periplasm.

LamB is known to be a porin in the outer membrane responsible for the uptake of maltose and other sugars. It was shown that the specificity of this protein can be altered by introducing mutations.

Corresponding mutations are described in Van Gelder et al., 2002 and Van Gelder et al., 2001.

In a preferred embodiment, the γ-glutamyl transferase employed in the cellular transport system has an amino acid sequence as shown in SEQ ID NO:1 or an amino acid sequence having at least 30% sequence identity to SEQ ID NO:1 in which the amino acid residue at position 433 in the amino acid sequence shown in SEQ ID NO:1 or at a position corresponding to this position is substituted with another amino acid residue, wherein the enzyme is modified to be located in the cytoplasm of the cell as defined herein above.

In more preferred embodiments, the degree of sequence identity is at least 35, 40, 45, 50, 55, 60, 65, 70, 75, 80, 85, 90, 91, 92, 93, 94, 95, 96, 97, 98 or 99%.

As regards the determination of sequence identity, the same applies as has been set forth above.

When the amino acid sequences of γ-glutamyl transferases are aligned by means of such a method, regardless of insertions or deletions that occur in the amino acid sequences, the positions of the corresponding amino acid residues can be determined in each of the γ-glutamyl transferases.

In the context of the present invention, "substituted with another amino acid residue" means that the respective amino acid residues at the indicated position can be substituted with any other possible amino acid residues, e.g. naturally occurring amino acids or non-naturally occurring amino acids (Brustad and Arnold, Curr. Opin. Chem. Biol. 15 (2011), 201-210), preferably with an amino acid residues selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine, most preferably asparagine (N; Asn) or an amino acid which constitutes a conservative replacement instead of asparagine. Moreover, the term "substituted" or "substitution" also means that the respective amino acid residue at the indicated position is modified.

Such modifications include naturally occurring modifications and non-naturally occurring modifications. Naturally occurring modifications include but are not limited to eukaryotic post-translational modification, such as attachment of functional groups (e.g. acetate, phosphate, hydroxyl, lipids (myristoylation of glycine residues) and carbohydrates (e.g. glycosylation of arginine, asparagines etc.). Naturally occurring modifications also encompass the change in the chemical structure by citrullination, carbamylation and disulphide bond formation between cysteine residues; attachment of co-factors (FMN or FAD that can be covalently attached) or the attachment of peptides (e.g. ubiquitination or sumoylation).

Non-naturally occurring modifications include, e.g., in vitro modifications such as biotinylation of lysine residue or the inclusion of non-canonical amino acids (see Liu and Schultz, Annu. Rev. Biochem. 79 (2010), 413-44 and Wang et al., Chem. Bio. 2009 Mar. 27; 16 (3), 323-336; doi:01016/jchembiol.2009.03.001).

Whether a γ-glutamyl transferase, once having introduced a modification at position 433 (or at a position corresponding to this position) is capable of hydrolyzing a sulfonic acid construct as defined herein can be determined as outlined above.

According to another embodiment, the γ-glutamyl transferase employed in the cellular transport system has an amino acid sequence as shown in SEQ ID NO:1 or an amino acid sequence having at least 30% sequence identity to SEQ ID NO:1 in which the amino acid residue at position 433 in the amino acid sequence shown in SEQ ID NO:1 or at a position corresponding to this position is substituted with another amino acid residue and wherein said γ-glutamyl transferase furthermore shows at least one amino acid substitution at position 444 and/or 484 in the amino acid sequence shown in SEQ ID NO:1 or at a position corresponding to one of these positions, wherein the enzyme is modified to be located in the cytoplasm of the cell as defined herein above.

As regards the possible substitutions, the same applies as has been set forth above in connection with position D433 of SEQ ID NO: 1.

Preferably, such a γ-glutamyl transferase has the following substitution in the amino acid sequence shown in SEQ ID NO:1 or at a position corresponding to this position: Y444A and/or G484H.

In more preferred embodiments, the degree of sequence identity is at least 35, 40, 45, 50, 55, 60, 65, 70, 75, 80, 85, 90, 91, 92, 93, 94, 95, 96, 97, 98 or 99%.

The invention also relates to such γ-glutamyl transferases as defined above, wherein the amino acid residue indicated as substituting the amino acid residue at the position in SEQ ID NO:1 is not that particular amino acid residue but an amino acid residue which is conservative in relation to the indicated substituting amino acid.

Whether an amino acid is conservative with respect to another amino acid can be judged according to means and methods known in the art and as described herein above. One possibility is the PAM 250 matrix; alternatively, the Blosum Family Matrices can be used.

The affinity of a GGT for a sulfonic acid construct of formula (I) may be further enhanced by effecting additional substitutions of amino acids in the substrate binding pocket of the enzyme. Positions which are of interest in this context are the following positions in the GGT enzymes from *E. coli* and *P. nitroreducens* or corresponding positions from GGT enzymes of other organisms:

*E. coli* GGT: R114, T409, N411, Q430, S462, S463, G483
*P. nitroreducens* GGT: R94, T381, N383, E402, F416, S434, S435, G455, G456

Thus, the GGT employed in a cellular transport system according to the present invention is preferably an enzyme which shows a substitution at at least one position corresponding to the above indicated positions in the GGT enzymes from *E. coli* and from *P. nitroreducens*.

The affinity of a GGT for a sulfonic acid construct of formula (I) may be further enhanced by effecting additional substitutions of amino acids. Positions which are of interest in this context are the following positions in the GGT enzyme from *P. nitroreducens* or corresponding positions from GGT enzymes of other organisms:

*P. nitroreducens* GGT: D385, P505, Y167, Q168, Y169, R170

Thus, the GGT employed in a cellular transport system according to the present invention is preferably an enzyme which shows a substitution at at least one position corresponding to the above indicated positions in the GGT enzymes from *P. nitroreducens*.

According to another embodiment, the γ-glutamyl transferase employed in the cellular transport system has an amino acid sequence as shown in SEQ ID NO:2 or an amino acid sequence having at least 30% sequence identity to SEQ ID NO:2 in which the amino acid residue at position 405 in the amino acid sequence shown in SEQ ID NO:2 or at a position corresponding to this position is substituted with another amino acid residue and wherein said γ-glutamyl transferase furthermore shows at least one amino acid substitution at position 385 in the amino acid sequence shown in SEQ ID NO:2 or at a position corresponding to one of these positions, wherein the enzyme is modified to be located in the cytoplasm of the cell as defined herein above and wherein the enzyme is modified so as to be able of hydrolyzing a sulfonic acid construct of formula (I) so as to release the compound H—X.

As regards the determination of the sequence identity, the same applies as has been set forth above.

As regards the possible substitutions, the same applies as has been set forth above.

In more preferred embodiments, the degree of sequence identity is at least 35, 40, 45, 50, 55, 60, 65, 70, 75, 80, 85, 90, 91, 92, 93, 94, 95, 96, 97, 98 or 99%.

Preferably, such a γ-glutamyl transferase has the following substitution in the amino acid sequence shown in SEQ ID NO:2 or at a position corresponding to this position: D385Y.

According to another embodiment, the γ-glutamyl transferase employed in the cellular transport system has an amino acid sequence as shown in SEQ ID NO:2 or an amino acid sequence having at least 30% sequence identity to SEQ ID NO:2 in which the amino acid residue at position 405 in the amino acid sequence shown in SEQ ID NO:2 or at a position corresponding to this position is substituted with another amino acid residue and wherein said γ-glutamyl transferase furthermore shows at least one amino acid substitution at position 505 in the amino acid sequence shown in SEQ ID NO:2 or at a position corresponding to one of these positions, wherein the enzyme is modified to be located in the cytoplasm of the cell as defined herein above and wherein the enzyme is modified so as to be able of hydrolyzing a sulfonic acid construct of formula (I) so as to release the compound H—X.

As regards the determination of the sequence identity, the same applies as has been set forth above.

As regards the possible substitutions, the same applies as has been set forth above.

In more preferred embodiments, the degree of sequence identity is at least 35, 40, 45, 50, 55, 60, 65, 70, 75, 80, 85, 90, 91, 92, 93, 94, 95, 96, 97, 98 or 99%.

Preferably, such a γ-glutamyl transferase has the following substitution in the amino acid sequence shown in SEQ ID NO:2 or at a position corresponding to this position: P505T.

According to another embodiment, the γ-glutamyl transferase employed in the cellular transport system has an amino acid sequence as shown in SEQ ID NO:2 or an amino acid sequence having at least 30% sequence identity to SEQ ID NO:2 in which the amino acid residue at position 405 in the amino acid sequence shown in SEQ ID NO:2 or at a position corresponding to this position is substituted with another amino acid residue and wherein said γ-glutamyl transferase furthermore shows at least one amino acid substitution at position 167 in the amino acid sequence shown in SEQ ID NO:2 or at a position corresponding to one of these positions, wherein the enzyme is modified to be located in the cytoplasm of the cell as defined herein above and wherein the enzyme is modified so as to be able of hydrolyzing a sulfonic acid construct of formula (I) so as to release the compound H—X.

As regards the determination of the sequence identity, the same applies as has been set forth above.

As regards the possible substitutions, the same applies as has been set forth above.

In more preferred embodiments, the degree of sequence identity is at least 35, 40, 45, 50, 55, 60, 65, 70, 75, 80, 85, 90, 91, 92, 93, 94, 95, 96, 97, 98 or 99%.

Preferably, such a γ-glutamyl transferase has the following substitution in the amino acid sequence shown in SEQ ID NO:2 or at a position corresponding to this position: Y167K, Y167H or Y167V.

According to another embodiment, the γ-glutamyl transferase employed in the cellular transport system has an amino acid sequence as shown in SEQ ID NO:2 or an amino acid sequence having at least 30% sequence identity to SEQ ID NO:2 in which the amino acid residue at position 405 in the amino acid sequence shown in SEQ ID NO:2 or at a position corresponding to this position is substituted with another amino acid residue and wherein said γ-glutamyl transferase furthermore shows at least one amino acid substitution at position 168 in the amino acid sequence shown in SEQ ID NO:2 or at a position corresponding to one of these positions, wherein the enzyme is modified to be located in the cytoplasm of the cell as defined herein above and wherein the enzyme is modified so as to be able of hydrolyzing a sulfonic acid construct of formula (I) so as to release the compound H—X.

As regards the determination of the sequence identity, the same applies as has been set forth above.

As regards the possible substitutions, the same applies as has been set forth above.

In more preferred embodiments, the degree of sequence identity is at least 35, 40, 45, 50, 55, 60, 65, 70, 75, 80, 85, 90, 91, 92, 93, 94, 95, 96, 97, 98 or 99%.

Preferably, such a γ-glutamyl transferase has the following substitution in the amino acid sequence shown in SEQ ID NO:2 or at a position corresponding to this position: Q168P or Q168G.

According to another embodiment, the γ-glutamyl transferase employed in the cellular transport system has an amino acid sequence as shown in SEQ ID NO:2 or an amino acid sequence having at least 30% sequence identity to SEQ ID NO:2 in which the amino acid residue at position 405 in the amino acid sequence shown in SEQ ID NO:2 or at a position corresponding to this position is substituted with another amino acid residue and wherein said γ-glutamyl transferase furthermore shows at least one amino acid substitution at position 169 in the amino acid sequence shown in SEQ ID NO:2 or at a position corresponding to one of these positions, wherein the enzyme is modified to be located in the cytoplasm of the cell as defined herein above and wherein the enzyme is modified so as to be able of hydrolyzing a sulfonic acid construct of formula (I) so as to release the compound H—X.

As regards the determination of the sequence identity, the same applies as has been set forth above.

As regards the possible substitutions, the same applies as has been set forth above.

In more preferred embodiments, the degree of sequence identity is at least 35, 40, 45, 50, 55, 60, 65, 70, 75, 80, 85, 90, 91, 92, 93, 94, 95, 96, 97, 98 or 99%.

Preferably, such a γ-glutamyl transferase has the following substitution in the amino acid sequence shown in SEQ ID NO:2 or at a position corresponding to this position: Y169D.

According to another embodiment, the γ-glutamyl transferase employed in the cellular transport system has an amino acid sequence as shown in SEQ ID NO:2 or an amino acid sequence having at least 30% sequence identity to SEQ ID NO:2 in which the amino acid residue at position 405 in the amino acid sequence shown in SEQ ID NO:2 or at a position corresponding to this position is substituted with another amino acid residue and wherein said γ-glutamyl transferase furthermore shows at least one amino acid substitution at position 170 in the amino acid sequence shown in SEQ ID NO:2 or at a position corresponding to one of these positions, wherein the enzyme is modified to be located in the cytoplasm of the cell as defined herein above and wherein the enzyme is modified so as to be able of hydrolyzing a sulfonic acid construct of formula (I) so as to release the compound H—X.

As regards the determination of the sequence identity, the same applies as has been set forth above.

As regards the possible substitutions, the same applies as has been set forth above.

In more preferred embodiments, the degree of sequence identity is at least 35, 40, 45, 50, 55, 60, 65, 70, 75, 80, 85, 90, 91, 92, 93, 94, 95, 96, 97, 98 or 99%.

Preferably, such a γ-glutamyl transferase has the following substitution in the amino acid sequence shown in SEQ ID NO:2 or at a position corresponding to this position: R170E or R170A.

In order to optimize the cellular transport system of the present invention, the activity/activities of enzymes capable of desulfonation may be reduced, or lost/inactivated in the cell of the cellular transport system.

"Desulfonation" in the context of the present invention relates to the removal of a sulfur group from a substrate.

Thus, according to another embodiment, the present invention relates to the cellular transport system in accordance with the above, wherein the activity/activities of enzymes capable of desulfonation is/are reduced or lost/inactivated.

Preferably, this reduction (or complete loss) of the activity is achieved by a genetic modification of the cell which leads to said inactivation or reduction. This can be achieved e.g., by random mutagenesis or site-directed mutagenesis of the promoter and/or the enzyme and subsequent selection of promoters and/or enzymes having the desired properties or by complementary nucleotide sequences or RNAi effect.

In the context of the present invention, a "reduced activity" means that the expression and/or the activity of an enzyme capable of desulfonation in the cell, preferably the genetically modified cell, is at least 10%, preferably at least 20%, more preferably at least 30% or 50%, even more preferably at least 70% or 80% and particularly preferred at least 90% or 100% lower than in the corresponding non-modified cell.

Methods for measuring the level of expression of a given protein in a cell are well known to the person skilled in the art. In short, these methods may, e.g., employ methods of measuring the expression on the RNA-level (by, e.g., RT-PCR technologies) or on the protein level (by, e.g., Western blot methods).

Assays for measuring the reduced enzyme activity of desulfonation of are known in the art.

A genetic modification of the cell which leads to said inactivation or reduction of the desulfonation activity/activities is preferably achieved by inactivation of the gene(s) encoding enzymes capable of desulfonation.

The inactivation of the gene(s) encoding an enzyme having desulfonation activity in the context of the present invention means that the gene(s) coding for enzyme(s) having desulfonation activity which is (are) present in the cell is (are) inactivated so that they are no longer expressed and/or do not lead to the synthesis of a functional enzyme having desulfonation activity. Inactivation can be achieved by many different ways known in the art. The inactivation can, e.g., be achieved by the disruption of the gene(s) encoding the enzyme having desulfonation activity or by clean deletion of said gene(s) through the introduction of a selection marker. Alternatively, the promoter of the gene(s) encoding the enzyme having desulfonation activity can be mutated in a way that the gene(s) is/are no longer transcribed into mRNA. Other ways to inactivate the gene(s) encoding the enzyme having desulfonation activity known in the art are: to express a polynucleotide encoding RNA having a nucleotide sequence complementary to the transcript of the gene encoding the enzyme having desulfonation activity so that the mRNA can no longer be translated into a protein, to express a polynucleotide encoding RNA that suppresses the expression of said gene(s) through RNAi effect; to express a polynucleotide encoding RNA having an activity of specifically cleaving a transcript of said gene(s); or to express a polynucleotide encoding RNA that suppresses expression of said gene(s) through co-suppression effect. These polynucleotides can be incorporated into a vector, which can be introduced into the cell by transformation to achieve the inactivation of the gene(s) encoding enzyme having desulfonation activity.

The term "inactivation" in the context of the present invention preferably means complete inactivation, i.e. that the cell does not show an enzyme having desulfonation activity.

Preferably, "inactivation" means that the gene(s) encoding the enzyme having desulfonation activity which are present in the cell are genetically modified so as to prevent the expression of the enzyme. This can be achieved, e.g., by deletion of the gene or parts thereof wherein the deletion of parts thereof prevents expression of the enzyme, or by disruption of the gene either in the coding region or in the promoter region wherein the disruption has the effect that no protein is expressed or a dysfunctional protein is expressed.

Preferably, the enzyme having desulfonation activity is SsuDE and/or TauD.

In another embodiment, the present invention also relates to the use of the cellular transport system as described herein above for bringing a sulfonic acid construct as defined herein into a cell and releasing the cargo, i.e. the chemical moiety "X" in formula (I) as H—X, in the cell's cytoplasm.

As regards the preferred embodiments, the same applies as has been set forth above in the context of the cellular transport system.

The present invention also relates to the use of a γ-glutamyl transferase as defined herein above for hydrolyzing a sulfonic acid construct of formula (I) so as to set free the cargo contained in said construct (moiety X in formula (I)) as H—X. The present invention also relates to the use of a γ-glutamyl transferase as defined herein above in a cellular transport system according to the present invention for hydrolyzing a sulfonic acid construct of formula (I) so as to set free the cargo contained in said construct (moiety X in formula (I)) as H—X.

As regards the preferred embodiments, the same applies as has been set forth above in the context of the cellular transport system.

As mentioned above, the nature of the cell of the cellular transport system in accordance with any of the foregoing is not particularly limited and may be a eukaryotic cell, preferably a fungal or a yeast cell, or a prokaryotic cell, preferably a bacterial cell, more preferably a gram negative bacterial cell, even more preferably an *E. coli* cell.

Thus, in accordance with the present invention, the cell of the cellular transport system described above and the cell of the uses of the cellular transport system described above is a cell which produces the components of the transport system of the present invention as described above. A use which employs such a cellular transport system according to the invention is referred to as an "in vivo" use. It is possible to use a cell in the cellular transport system of the present invention which had been genetically modified so that it expresses (including overexpresses) the components of the cellular transport system as described above. Thus, the cell employed in the cellular transport system of the present invention can be an engineered cell which expresses (enzymatic and transport) components described above, i.e. which has in its genome a nucleotide sequence encoding such a component and which has been modified to (over)express it/them. The expression may occur constitutively or in an induced or regulated manner.

As mentioned above, in preferred embodiments of the present invention, certain other components of the present invention do necessarily have to be overexpressed. In fact, as mentioned above, a reduction or inactivation of the activity/activities of enzymes capable of desulfonation may be preferred.

Accordingly, as regards this/these activity/activities of enzymes capable of desulfonation the following also applies, with the exception that a "reduction" or an "inactivation" is meant as outlined above instead of an "increase" or and "overexpression".

In a preferred embodiment the cell of the cellular transport system of the present invention has been genetically modified by the introduction of one or more nucleic acid molecules containing nucleotide sequences encoding one or more components of the cellular transport system of the present invention as described above. The nucleic acid molecule(s) can be stably integrated into the genome of the cell or may be present in an extrachromosomal manner, e.g. on a plasmid.

Such a genetically modified cell of the cellular transport system of the present invention can, e.g., be a cell that does not naturally express enzymes/proteins/components/transporters described above and which has been genetically modified to express such enzymes/proteins/components/transporters or a cell which naturally expresses such enzymes/proteins/components/transporters and which has been genetically modified, e.g. transformed with a nucleic acid, e.g. a vector, encoding the respective component(s), and/or insertion of a desired (modified) promoter in front of the endogenous nucleotide sequence encoding the enzyme in order to increase the respective activity in said cell.

However, the invention preferably excludes naturally occurring cells as found in nature expressing a component of the cellular transport system of the present invention as described above at levels as they exist in nature. Instead, the cell of the cellular transport system of the present invention and employed in a use of the present invention is preferably a non-naturally occurring microorganism, whether it has been genetically modified to express (including overexpression) an exogenous component of the invention not normally existing in its genome or whether it has been engineered to overexpress an exogenous component.

Thus, the components and cells employed in connection with the present invention are preferably non-naturally occurring components or cells, i.e. they are components or cells which differ significantly from naturally occurring components (i.e., proteins or enzymes) or cells and which do not occur in nature. As regards the enzymes, they are preferably variants of naturally occurring enzymes which do not as such occur in nature. Such variants include, for example, mutants, in particular prepared by molecular biological methods, which show improved/modified properties, such as a higher enzyme activity, higher substrate specificity, higher temperature resistance and the like. As regards the cells, they are preferably genetically modified cells as described herein above which differ from naturally occurring cells due to a genetic modification. Genetically modified cells are cells which do not naturally occur, i.e., which cannot be found in nature, and which differ substantially from naturally occurring cells due to the introduction of a foreign nucleic acid molecule.

By overexpressing an exogenous or endogenous component as described herein above, the concentration of the enzyme/protein/component/transporter is substantially higher than what is found in nature, which can then unexpectedly force the reaction of the present invention which uses a non-natural for the respective enzyme. Preferably, the concentration of the overexpressed enzyme is at least 5%, 10%, 20%, 30% or 40% of the total host cell protein.

It is also possible in the context of the present invention that the cell is a cell which naturally does not have the respective enzyme activity or transporter activity but which is genetically modified so as to comprise a nucleotide sequence allowing the expression of a corresponding enzyme/protein/component/transporter of the cellular transport system of the present invention. Similarly, the cell may also be a cell which naturally has the respective enzyme activity or transporter activity but which is genetically modified so as to enhance such an activity, e.g. by the introduction of an exogenous nucleotide sequence encoding a corresponding enzyme or transporter or by the introduction of a (modified) promoter for the endogenous gene encoding the enzyme or transporter to increase endogenous production to overexpressed (non-natural) levels.

If a cell is used which naturally expresses a corresponding enzyme or transporter, it is possible to modify such a cell so that the respective activity is overexpressed in the cell. This can, e.g., be achieved by effecting mutations in the promoter region of the corresponding gene or introduction of a high expressing promoter so as to lead to a promoter which ensures a higher expression of the gene. Alternatively, it is also possible to mutate the gene as such so as to lead to an enzyme showing a higher activity.

In one embodiment the cell employed in the cellular transport system according to the invention is a cell which has been genetically modified to contain a foreign nucleic acid molecule encoding at least one enzyme/protein/component/transporter described above. The term "foreign" or "exogenous" in this context means that the nucleic acid molecule does not naturally occur in said cell. This means that it does not occur in the same structure or at the same location in the cell. In one preferred embodiment, the foreign nucleic acid molecule is a recombinant molecule comprising a promoter and a coding sequence encoding the respective enzyme/protein/component/transporter of the cellular transport system of the present invention in which the promoter driving expression of the coding sequence is heterologous with respect to the coding sequence. "Heterologous" in this context means that the promoter is not the promoter naturally driving the expression of said coding sequence but is a promoter naturally driving expression of a different coding sequence, i.e., it is derived from another gene, or is a synthetic promoter or a chimeric promoter. Preferably, the promoter is a promoter heterologous to the microorganism, i.e. a promoter which does naturally not occur in the respective microorganism. Even more preferably, the promoter is an inducible promoter. Promoters for driving expression in different types of cells, in particular in microorganisms, are well known to the person skilled in the art.

In a further embodiment the nucleic acid molecule is foreign to the cell in that the encoded enzyme/protein/component/transporter is not endogenous to the cell, i.e. is naturally not expressed by the cell when it is not genetically modified. In other words, the encoded enzyme is heterologous with respect to the cell. The foreign nucleic acid molecule may be present in the cell in extrachromosomal form, e.g. as a plasmid, or stably integrated in the chromosome. A stable integration is preferred. Thus, the genetic modification can consist, e.g. in integrating the corresponding gene(s) encoding the enzyme(s)/protein(s)/component(s)/transporter(s) of the cellular transport system of the present invention into the chromosome, or in expressing the enzyme(s)/protein(s)/component(s)/transporter(s) from a plasmid containing a promoter upstream of the enzyme-coding sequence, the promoter and coding sequence preferably originating from different organisms, or any other method known to one of skill in the art.

In a preferred embodiment, the cell is a microorganism. The term "microorganism" in the context of the present invention refers to bacteria, as well as to fungi, such as yeasts, and also to algae and archaea. In one preferred embodiment, the microorganism is a bacterium. In principle any bacterium can be used. Preferred bacteria to be employed in the process according to the invention are bacteria of the genus *Bacillus, Clostridium, Corynebacterium, Pseudomonas, Zymomonas* or *Escherichia*. In a particularly preferred embodiment the bacterium belongs to the genus *Escherichia* and even more preferred to the species *Escherichia coli*. In another preferred embodiment the bacterium belongs to the species *Pseudomonas putida* or to the species *Zymomonas mobilis* or to the species *Corynebacterium glutamicum* or to the species *Bacillus subtilis*.

It is also possible to employ an extremophilic bacterium such as *Thermus thermophilus*, or anaerobic bacteria from the family Clostridiae.

In another preferred embodiment the microorganism is a fungus, more preferably a fungus of the genus *Saccharomyces, Schizosaccharomyces, Aspergillus, Trichoderma, Kluyveromyces* or *Pichia* and even more preferably of the species *Saccharomyces cerevisiae, Schizosaccharomyces pombe, Aspergillus niger, Trichoderma reesei, Kluyveromyces marxianus, Kluyveromyces lactis, Pichia pastoris, Pichia torula* or *Pichia utilis*.

In another embodiment, the cell, preferably the microorganism, may be a photosynthetic microorganism expressing at least one enzyme/protein/component of the cellular transport system of the present invention as described above. Preferably, the microorganism is a photosynthetic bacterium, or a microalgae. In a further embodiment the microorganism is an algae, more preferably an algae belonging to the diatomeae.

The transporter(s) used in the cellular transport system according to the invention can be naturally occurring transporters or transporters which are derived from naturally occurring transporters, e.g. by the introduction of mutations or other alterations which, e.g., alter or improve the transporter activity, the stability, etc.

Methods for modifying and/or improving the desired activities of proteins are well-known to the person skilled in the art and include, e.g., random mutagenesis or site-directed mutagenesis and subsequent selection of proteins/transporters having the desired properties or approaches of the so-called "directed evolution".

For example, for genetic modification in prokaryotic cells, a nucleic acid molecule encoding a corresponding enzyme/protein/transporter can be introduced into plasmids which permit mutagenesis or sequence modification by recombination of DNA sequences. Standard methods (see Sambrook and Russell (2001), Molecular Cloning: A Laboratory Manual, CSH Press, Cold Spring Harbor, N.Y., USA) allow base exchanges to be performed or natural or synthetic sequences to be added. DNA fragments can be ligated by using adapters and linkers complementary to the fragments. Moreover, engineering measures which provide suitable restriction sites or remove surplus DNA or restriction sites can be used. In those cases, in which insertions, deletions or substitutions are possible, in vitro mutagenesis, "primer repair", restriction or ligation can be used. In general, a sequence analysis, restriction analysis and other methods of biochemistry and molecular biology are carried out as analysis methods. The resulting enzyme/protein/transporter variants are then tested for the desired activity, e.g., enzymatic activity or transport, with an assay as described above and in particular for their increased enzyme activity or transport activity.

As described above, the cell of the cellular transport system of the present invention is a cell which has been genetically modified by the introduction of a nucleic acid molecule encoding a modified GGT to be located in the cytoplasm of a cell. Such a cell may be a cell which has been genetically modified by the introduction of a nucleic acid molecule encoding a further enzyme/protein/component/transporter. Thus, in a preferred embodiment, the cell is a recombinant cell which has been genetically modified to have an increased activity of at least one enzyme/protein/component/transporter described above. This can be achieved e.g. by transforming the cell with a nucleic acid encoding a corresponding enzyme/protein/component/transporter. A detailed description of genetic modification of cells will be given further below. Preferably, the nucleic acid molecule introduced into the cell is a nucleic acid molecule which is heterologous with respect to the cell, i.e. it does not naturally occur in said cell.

In the context of the present invention, an "increased activity" means that the expression and/or the activity of an enzyme or a transporter in the genetically modified cell is at least 10%, preferably at least 20%, more preferably at least 30% or 50%, even more preferably at least 70% or 80% and particularly preferred at least 90% or 100% higher than in the corresponding non-modified cell. In even more preferred embodiments the increase in expression and/or activity may be at least 150%, at least 200% or at least 500%. In particularly preferred embodiments the expression is at least 10-fold, more preferably at least 100-fold and even more preferred at least 1000-fold higher than in the corresponding non-modified cell.

The term "increased" expression/activity also covers the situation in which the corresponding non-modified cell does not express a corresponding enzyme so that the corresponding expression/activity in the non-modified cell is zero. Preferably, the concentration of the overexpressed enzyme is at least 5%, 10%, 20%, 30%, or 40% of the total host cell protein.

Methods for measuring the level of expression of a given protein in a cell are well known to the person skilled in the art. In one embodiment, the measurement of the level of expression is done by measuring the amount of the corresponding protein. Corresponding methods are well known to the person skilled in the art and include Western Blot, ELISA etc. In another embodiment the measurement of the level of expression is done by measuring the amount of the corresponding RNA. Corresponding methods are well known to the person skilled in the art and include, e.g., Northern Blot.

In the context of the present invention the term "recombinant" means that the cell is genetically modified so as to contain a nucleic acid molecule encoding an enzyme or a transporter as defined above as compared to a wild-type or non-modified cell. A nucleic acid molecule encoding an enzyme or a transporter as defined above can be used alone or as part of a vector.

The nucleic acid molecules can further comprise expression control sequences operably linked to the polynucleotide comprised in the nucleic acid molecule. The term "operatively linked" or "operably linked", as used throughout the present description, refers to a linkage between one or more expression control sequences and the coding region in the polynucleotide to be expressed in such a way that expression is achieved under conditions compatible with the expression control sequence.

Expression comprises transcription of the heterologous DNA sequence, preferably into a translatable mRNA. Regulatory elements ensuring expression in fungi as well as in bacteria, are well known to those skilled in the art. They encompass promoters, enhancers, termination signals, targeting signals and the like. Examples are given further below in connection with explanations concerning vectors.

Promoters for use in connection with the nucleic acid molecule may be homologous or heterologous with regard to its origin and/or with regard to the gene to be expressed. Suitable promoters are for instance promoters which lend themselves to constitutive expression. However, promoters which are only activated at a point in time determined by external influences can also be used. Artificial and/or chemically inducible promoters may be used in this context.

The vectors can further comprise expression control sequences operably linked to said polynucleotides contained in the vectors. These expression control sequences may be suited to ensure transcription and synthesis of a translatable RNA in eukaryotic cells, bacteria or fungi.

In addition, it is possible to insert different mutations into the polynucleotides by methods usual in molecular biology (see for instance Sambrook and Russell (2001), Molecular Cloning: A Laboratory Manual, CSH Press, Cold Spring Harbor, N.Y., USA), leading to the synthesis of polypeptides possibly having modified biological properties. The introduction of point mutations is conceivable at positions at which a modification of the amino acid sequence for instance influences the biological activity or the regulation of the polypeptide.

Moreover, mutants possessing a modified substrate specificity can be prepared. Preferably, such mutants show an increased activity.

Furthermore, the introduction of mutations into the polynucleotides encoding an enzyme/protein/component/transporter as defined above allows the gene expression rate and/or the activity of the enzyme/protein/component/transporters encoded by said polynucleotides to be increased.

For genetically modifying eukaryotic cells, bacteria or fungi, the polynucleotides encoding an enzyme or transporter as defined above or parts of these molecules can be introduced into plasmids which permit mutagenesis or sequence modification by recombination of DNA sequences. Standard methods (see Sambrook and Russell (2001), Molecular Cloning: A Laboratory Manual, CSH Press, Cold Spring Harbor, N.Y., USA) allow base exchanges to be performed or natural or synthetic sequences to be added. DNA fragments can be connected to each other by applying adapters and linkers to the fragments. Moreover, engineering measures which provide suitable restriction sites or remove surplus DNA or restriction sites can be used. In those cases, in which insertions, deletions or substitutions are possible, in vitro mutagenesis, "primer repair", restriction or ligation can be used. In general, a sequence analysis, restriction analysis and other methods of biochemistry and molecular biology are carried out as analysis methods.

Thus, in accordance with the present invention a cell of the cellular transport system of the present invention can be produced by genetically modifying cells comprising introducing the above-described polynucleotides, nucleic acid molecules or vectors into a desired cell.

The polynucleotide encoding the respective enzyme/protein/component/transporter is expressed so as to lead to the production of a polypeptide having any of the activities described above. An overview of different expression systems is for instance contained in Methods in Enzymology 153 (1987), 385-516, in Bitter et al. (Methods in Enzymology 153 (1987), 516-544) and in Sawers et al. (Applied Microbiology and Biotechnology 46 (1996), 1-9), Billman-Jacobe (Current Opinion in Biotechnology 7 (1996), 500-4), Hockney (Trends in Biotechnology 12 (1994), 456-463), Griffiths et al., (Methods in Molecular Biology 75 (1997), 427-440). An overview of yeast expression systems is for instance given by Hensing et al. (Antonie van Leuwenhoek 67 (1995), 261-279), Bussineau et al. (Developments in Biological Standardization 83 (1994), 13-19), Gellissen et al. (Antonie van Leuwenhoek 62 (1992), 79-93, Fleer (Current Opinion in Biotechnology 3 (1992), 486-496), Vedvick (Current Opinion in Biotechnology 2 (1991), 742-745) and Buckholz (Bio/Technology 9 (1991), 1067-1072).

Expression vectors have been widely described in the literature. As a rule, they contain not only a selection marker gene and a replication-origin ensuring replication in the host selected, but also a bacterial or viral promoter, and in most cases a termination signal for transcription. Between the promoter and the termination signal there is in general at least one restriction site or a polylinker which enables the insertion of a coding DNA sequence. The DNA sequence naturally controlling the transcription of the corresponding gene can be used as the promoter sequence, if it is active in the selected host organism. However, this sequence can also be exchanged for other promoter sequences. It is possible to use promoters ensuring constitutive expression of the gene and inducible promoters which permit a deliberate control of the expression of the gene. Bacterial and viral promoter sequences possessing these properties are described in detail in the literature. Regulatory sequences for the expression in microorganisms (for instance *E. coli, S. cerevisiae*) are sufficiently described in the literature. Promoters permitting a particularly high expression of a downstream sequence are for instance the T7 promoter (Studier et al., Methods in Enzymology 185 (1990), 60-89), lacUV5, trp, trp-acUV5 (DeBoer et al., in Rodriguez and Chamberlin (Eds), Promoters, Structure and Function; Praeger, New York, (1982), 462-481; DeBoer et al., Proc. Natl. Acad. Sci. USA (1983), 21-25), Ip1, rac (Boros et al., Gene 42 (1986), 97-100). Inducible promoters are preferably used for the synthesis of polypeptides. These promoters often lead to higher polypeptide yields than do constitutive promoters. In order to obtain an optimum amount of polypeptide, a two-stage process is often used. First, the host cells are cultured under optimum conditions up to a relatively high cell density. In the second step, transcription is induced depending on the type of promoter used. In this regard, a tac promoter is particularly suitable which can be induced by lactose or IPTG (=isopropyl-β-D-thiogalactopyranoside) (deBoer et al., Proc. Natl. Acad. Sci. USA 80 (1983), 21-25). Termination signals for transcription are also described in the literature.

The transformation of the host cell with a polynucleotide or vector as described above can be carried out by standard methods, as for instance described in Sambrook and Russell (2001), Molecular Cloning: A Laboratory Manual, CSH Press, Cold Spring Harbor, N.Y., USA; Methods in Yeast Genetics, A Laboratory Course Manual, Cold Spring Harbor Laboratory Press, 1990. The host cell is cultured in nutrient media meeting the requirements of the particular host cell used, in particular in respect of the pH value, temperature, salt concentration, aeration, antibiotics, vitamins, trace elements etc.

The present invention also relates to a composition comprising:
(a) a sulfonic acid construct of formula (I) as described herein above; and
(b) a cell harbouring a transport system as described herein above.

The present invention also relates to a kit or kit of parts comprising
(a) a sulfonic acid construct of formula (I) as described herein above; and
(b) a cell harbouring a transport system as described herein above.

In a further aspect, the present invention relates to a method for bringing a sulfonic acid construct as defined herein into a cell and releasing from said sulfonic acid construct the cargo (moiety "X" in formula (I)) in the cell's cytoplasm wherein the method employs the cellular transport system as described herein above. In particular, the present invention also relates to a method for transporting a cargo molecule into a cell comprising incubating a cell harbouring a transport system according to the present invention in a medium containing a sulfonic acid construct as defined herein whereby said construct is transported into the cell and is cleaved within the cell by the GGT and the cargo is set free in the cell.

As regards the preferred embodiments, the same applies as has been set forth above in the context of the cellular transport system.

In a further aspect, the present invention relates to a method for hydrolyzing a sulfonic acid construct of formula (I) shown above so as to set free a compound H—X wherein the method employs the γ-glutamyl transferase as defined herein above.

As regards the preferred embodiments, the same applies as has been set forth above in the context of the cellular transport system.

In yet another aspect the present invention relates to the use of a sulfonic acid construct of formula (I) as defined herein above in a transport system according to the present invention as described herein.

As regards the preferred embodiments, the same applies as has been set forth above in the context of the cellular transport system.

The present invention also relates to a composition comprising:
(c) a sulfonic acid construct of formula (I) as described herein above; and
(d) a γ-glutamyl transferase as described herein which is capable of hydrolyzing said sulfonic acid construct of formula (I) so as to set free the compound H—X, wherein X is as defined in formula (I), or a nucleic acid sequence encoding a γ-glutamyl transferase as described herein which is capable of hydrolyzing said sulfonic acid construct of formula (I) so as to set free the compound H—X, wherein X is as defined in formula (I); and optionally (e) a nucleic acid sequence encoding a sulfonate transporter.

In such a composition, the moiety X contained in the sulfonic acid construct of formula (I) can, for example, be a compound which is suitable for selecting cells in which the compound H—X is set free. Examples are molecules which allow to select the cells, e.g., on the basis of color or other selectable characteristics.

In another preferred embodiment the moiety X is a molecule which is pharmaceutically active, e.g. cytotoxic, once it is released as H—X from the sulfonic acid construct upon hydrolyzation by the γ-glutamyl transferase. Thus, a composition as defined above could be useful for killing cells in a targeted manner by first bringing a γ-glutamyl transferase as described in connection with the cellular transport system according to the present invention into a cell and then bringing into the cell a sulfonic acid construct of formula (I) in which X is pharmaceutically active, e.g. cytotoxic, once it is released as H—X from the sulfonic acid construct. If the cell does not endogenously express a sulfonate transporter which allows to transport the sulfonic acid construct into the cells, it may also be useful to transform the cell with a corresponding nucleic acid sequence which encodes a suitable sulfonate transporter. Thus, in a preferred embodiment the above described composition is a pharmaceutical composition. If H—X is cytotoxic, such a composition may, for example, be employed in cancer therapy for killing cancer cells in a targeted manner or as antibiotics for addressing bacterial infections.

Specific cells, like cancer cells, can specifically be targeted by introducing in a targeted manner a nucleic acid encoding a γ-glutamyl transferase which is capable of hydrolyzing the sulfonic acid construct into such cells (using methods known in the art).

Accordingly, the present invention also relates to a sulfonic acid construct of formula (I) for use in therapy, preferably for use in cancer treatment or in the treatment of infections, e.g. bacterial infections.

In the context of the present invention the sulfonic acid construct of formula (I) may be used in non-salt form or in the form of a salt, particularly in the form of a physiologically acceptable salt. The present invention embraces all physiologically acceptable salt forms of the sulfonic acid construct of formula (I) which may be formed, e.g., by protonation of an atom carrying an electron lone pair which is susceptible to protonation, such as an amino group, with an inorganic or organic acid, or as a salt of an acid group (such as a carboxylic acid group) with a physiologically acceptable cation. Exemplary base addition salts comprise, for example: alkali metal salts such as sodium or potassium salts; alkaline earth metal salts such as calcium or magnesium salts; zinc salts; ammonium salts; aliphatic amine salts such as trimethylamine, triethylamine, dicyclohexylamine, ethanolamine, diethanolamine, triethanolamine, procaine salts, meglumine salts, ethylenediamine salts, or choline salts; aralkyl amine salts such as N,N-dibenzylethylenediamine salts, benzathine salts, benethamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts, lysine salts, or histidine salts. Exemplary acid addition salts comprise, for example: mineral acid salts such as hydrochloride, hydrobromide, hydroiodide, sulfate salts (such as, e.g., sulfate or hydrogensulfate salts), nitrate salts, phosphate salts (such as, e.g., phosphate, hydrogenphosphate, or dihydrogenphosphate salts), carbonate salts, hydrogencarbonate salts, perchlorate salts, borate salts, or thiocyanate salts; organic acid salts such as acetate, propionate, butyrate, pentanoate, hexanoate, heptanoate, octanoate, cyclopentanepropionate, decanoate, undecanoate, oleate, stearate, lactate, maleate, oxalate, fumarate, tartrate, malate, citrate, succinate, adipate, gluconate, glycolate, nicotinate, benzoate, salicylate, ascorbate, pamoate (embonate), camphorate, glucoheptanoate, or pivalate salts; sulfonate salts such as methanesulfonate (mesylate), ethanesulfonate (esylate), 2-hydroxyethanesulfonate (isethionate), benzenesulfonate (besylate), p-toluenesulfonate (tosylate), 2-naphthalenesulfonate (napsylate), 3-phenylsulfonate, or camphorsulfonate salts; glycerophosphate salts; and acidic amino acid salts such as aspartate or glutamate salts.

Moreover, the sulfonic acid construct of formula (I) may exist in the form of different isomers, in particular stereoisomers (including, e.g., geometric isomers (or cis/trans isomers), enantiomers and diastereomers) or tautomers. All such isomers of the sulfonic acid construct of formula (I) are contemplated as being part of the present invention, either in admixture or in pure or substantially pure form. As for stereoisomers, the invention embraces the use of the isolated optical isomers of the sulfonic acid construct of formula (I) as well as any mixtures thereof (including, in particular, racemic mixtures/racemates). The racemates can be resolved by physical methods, such as, e.g., fractional crystallization, separation or crystallization of diastereomeric derivatives, or separation by chiral column chromatography. The individual optical isomers can also be obtained from the racemates via salt formation with an optically active acid followed by crystallization. The present invention further encompasses any tautomers of the sulfonic acid construct of formula (I).

The scope of the invention also embraces the use of a sulfonic acid construct of formula (I) or a physiologically acceptable salt thereof, wherein one or more atoms of the sulfonic acid construct of formula (I), particularly of group X comprised in said construct, are replaced by a specific isotope of the corresponding atom. For example, the invention encompasses the use of a sulfonic acid construct of formula (I), in which (e.g., wherein in group X) one or more hydrogen atoms (or, e.g., all hydrogen atoms) are replaced by deuterium atoms (i.e., $^2$H; also referred to as "D"). Accordingly, the invention also embraces the use of sulfonic acid constructs of formula (I) which are enriched in deuterium (particularly in group X). Naturally occurring hydrogen is an isotopic mixture comprising about 99.98 mol-% hydrogen-1 ($^1$H) and about 0.0156 mol-% deuterium ($^2$H or D). The content of deuterium in one or more hydrogen positions in the sulfonic acid constructs of formula (I) can be increased using deuteration techniques known in the art. For example, a construct of formula (I) or a reactant or precursor to be used in the synthesis of the construct of formula (I) can be subjected to an H/D exchange reaction using, e.g., heavy water (D2O). Further suitable deuteration techniques are described in: Atzrodt J et al., *Bioorg Med Chem*, 20(18), 5658-5667, 2012; William J S et al., *Journal of Labelled Compounds and Radiopharmaceuticals*, 53(11-12), 635-644, 2010; Modvig A et al., *J Org Chem*, 79, 5861-5868, 2014. The content of deuterium can be determined, e.g., using mass spectrometry or NMR spectroscopy. Unless specifically indicated otherwise, it is preferred that the sulfonic acid construct of formula (I) is not enriched in deuterium. Accordingly, the presence of naturally occurring hydrogen atoms or $^1$H hydrogen atoms in the sulfonic acid constructs of formula (I) is preferred.

The present invention also embraces the use of sulfonic acid constructs of formula (I), in which one or more atoms (particularly one or more atoms in group X) are replaced by a positron-emitting isotope of the corresponding atom, such as, e.g., $^{18}$F, $^{11}$C, $^{13}$N, $^{15}$O, $^{76}$Br, $^{77}$Br, $^{120}$I and/or $^{124}$I. Such compounds can be used as tracers, imaging probes or trackers in positron emission tomography (PET). The invention thus includes (i) constructs of formula (I), in which (e.g., wherein in group X) one or more fluorine atoms (or, e.g., all fluorine atoms) are replaced by $^{18}$F atoms, (ii) constructs of formula (I), in which (e.g., wherein in group X) one or more carbon atoms (or, e.g., all carbon atoms) are replaced by $^{11}$C atoms, (iii) constructs of formula (I), in which (e.g., wherein in group X) one or more nitrogen atoms (or, e.g., all nitrogen atoms) are replaced by $^{13}$N atoms, (iv) constructs of formula (I), in which (e.g., wherein in group X) one or more oxygen atoms (or, e.g., all oxygen atoms) are replaced by $^{15}$O atoms, (v) constructs of formula (I), in which (e.g., wherein in group X) one or more bromine atoms (or, e.g., all bromine atoms) are replaced by $^{76}$Br atoms, (vi) constructs of formula (I), in which (e.g., wherein in group X) one or more bromine atoms (or, e.g., all bromine atoms) are replaced by $^{77}$Br atoms, (vii) constructs of formula (I), in which (e.g., wherein in group X) one or more iodine atoms (or, e.g., all iodine atoms) are replaced by $^{120}$I atoms, and (viii) constructs of formula (I), in which (e.g., wherein in group X) one or more iodine atoms (or, e.g., all iodine atoms) are replaced by $^{124}$I atoms. In general, it is preferred that none of the atoms in the sulfonic acid constructs of formula (I) are replaced by specific isotopes.

The following definitions apply throughout the present specification, unless specifically indicated otherwise.

The term "hydrocarbon group" refers to a group consisting of carbon atoms and hydrogen atoms.

The term "alicyclic" is used in connection with cyclic groups and denotes that the corresponding cyclic group is non-aromatic.

As used herein, the term "alkyl" refers to a monovalent saturated acyclic (i.e., non-cyclic) hydrocarbon group which may be linear or branched. Accordingly, an "alkyl" group does not comprise any carbon-to-carbon double bond or any carbon-to-carbon triple bond. A "$C_{1-5}$ alkyl" denotes an alkyl group having 1 to 5 carbon atoms. Preferred exemplary alkyl groups are methyl, ethyl, propyl (e.g., n-propyl or isopropyl), or butyl (e.g., n-butyl, isobutyl, sec-butyl, or tert-butyl).

As used herein, the term "alkenyl" refers to a monovalent unsaturated acyclic hydrocarbon group which may be linear or branched and comprises one or more (e.g., one or two) carbon-to-carbon double bonds while it does not comprise any carbon-to-carbon triple bond. The term "$C_{2-5}$ alkenyl" denotes an alkenyl group having 2 to 5 carbon atoms. Preferred exemplary alkenyl groups are ethenyl, propenyl (e.g., prop-1-en-1-yl, prop-1-en-2-yl, or prop-2-en-1-yl), butenyl, butadienyl (e.g., buta-1,3-dien-1-yl or buta-1,3-dien-2-yl), pentenyl, or pentadienyl (e.g., isoprenyl).

As used herein, the term "alkynyl" refers to a monovalent unsaturated acyclic hydrocarbon group which may be linear or branched and comprises one or more (e.g., one or two) carbon-to-carbon triple bonds and optionally one or more carbon-to-carbon double bonds. The term "$C_{2-5}$ alkynyl" denotes an alkynyl group having 2 to 5 carbon atoms. Preferred exemplary alkynyl groups are ethynyl, propynyl (e.g., propargyl), or butynyl.

As used herein, the term "alkylene" refers to an alkanediyl group, i.e. a divalent saturated acyclic hydrocarbon group which may be linear or branched. A "$C_{1-5}$ alkylene" denotes an alkylene group having 1 to 5 carbon atoms, and the term "$C_{0-3}$ alkylene" indicates that a covalent bond (corresponding to the option "$C_0$ alkylene") or a $C_{1-3}$ alkylene is present. Preferred exemplary alkylene groups are methylene (—CH$_2$—), ethylene (e.g., —CH$_2$—CH$_2$— or —CH(—CH$_3$)—), propylene (e.g., —CH$_2$—CH$_2$—CH$_2$—, —CH(—CH$_2$—CH$_3$)—, —CH$_2$—CH(—CH$_3$)—, or —CH(—CH$_3$)—CH$_2$—), or butylene (e.g., —CH$_2$—CH$_2$—CH$_2$—CH$_2$—).

As used herein, the term "alkenylene" refers to an alkenediyl group, i.e. a divalent unsaturated acyclic hydrocarbon group which may be linear or branched and comprises one or more (e.g., one or two) carbon-to-carbon double bonds while it does not comprise any carbon-to-carbon triple bond. A "$C_{2-5}$ alkenylene" denotes an alkenylene group having 2 to 5 carbon atoms. Unless defined otherwise, the term "alkenylene" preferably refers to $C_{2-4}$ alkenylene (including, in particular, linear $C_{2-4}$ alkenylene).

As used herein, the term "carbocyclyl" refers to a hydrocarbon ring group, including monocyclic rings as well as bridged ring, spiro ring and/or fused ring systems (which may be composed, e.g., of two or three rings), wherein said ring group may be saturated, partially unsaturated (i.e., unsaturated but not aromatic) or aromatic. Unless defined otherwise, "carbocyclyl" preferably refers to aryl, cycloalkyl or cycloalkenyl.

As used herein, the term "heterocyclyl" refers to a ring group, including monocyclic rings as well as bridged ring, spiro ring and/or fused ring systems (which may be composed, e.g., of two or three rings), wherein said ring group comprises one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, wherein one or more carbon ring atoms may optionally be oxidized (i.e., to form an oxo group), and further wherein said ring group may be saturated, partially unsaturated (i.e., unsaturated but not aromatic) or aromatic. For example, each heteroatom-containing ring comprised in said ring group may contain one or two O atoms and/or one or two S atoms (which may optionally be oxidized) and/or one, two, three or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. Unless defined otherwise, "heterocyclyl" preferably refers to heteroaryl, heterocycloalkyl or heterocycloalkenyl.

As used herein, the term "aryl" refers to an aromatic hydrocarbon ring group, including monocyclic aromatic rings as well as bridged ring and/or fused ring systems containing at least one aromatic ring (e.g., ring systems composed of two or three fused rings, wherein at least one of these fused rings is aromatic; or bridged ring systems composed of two or three rings, wherein at least one of these bridged rings is aromatic). "Aryl" may, e.g., refer to phenyl, naphthyl, dialinyl (i.e., 1,2-dihydronaphthyl), tetralinyl (i.e., 1,2,3,4-tetrahydronaphthyl), indanyl, indenyl (e.g., 1H-indenyl), anthracenyl, phenanthrenyl, 9H-fluorenyl, or azulenyl. Unless defined otherwise, an "aryl" preferably has 6 to 14 ring atoms, more preferably 6 to 10 ring atoms, even more preferably refers to phenyl or naphthyl, and most preferably refers to phenyl.

As used herein, the term "heteroaryl" refers to an aromatic ring group, including monocyclic aromatic rings as well as bridged ring and/or fused ring systems containing at least one aromatic ring (e.g., ring systems composed of two or three fused rings, wherein at least one of these fused rings is aromatic; or bridged ring systems composed of two or three rings, wherein at least one of these bridged rings is aromatic), wherein said aromatic ring group comprises one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, and further wherein one or more carbon ring atoms may optionally be oxidized (i.e., to form an oxo group). For example, each heteroatom-containing ring comprised in said aromatic ring group may contain one or two O atoms and/or one or two S atoms (which may optionally be oxidized) and/or one, two, three or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. "Heteroaryl" may, e.g., refer to thienyl (i.e., thiophenyl), benzo[b]thienyl, naphtho[2,3-b]thienyl, thianthrenyl, furyl (i.e., furanyl), benzofuranyl, isobenzofuranyl, chromanyl, chromenyl (e.g., 2H-1-benzopyranyl or 4H-1-benzopyranyl), isochromenyl (e.g., 1H-2-benzopyranyl), chromonyl, xanthenyl, phenoxathiinyl, pyrrolyl (e.g., 1H-pyrrolyl), imidazolyl, pyrazolyl, pyridyl (i.e., pyridinyl; e.g., 2-pyridyl, 3-pyridyl, or 4-pyridyl), pyrazinyl, pyrimidinyl, pyridazinyl, indolyl (e.g., 3H-indolyl), isoindolyl, indazolyl, indolizinyl, purinyl, quinolyl, isoquinolyl, phthalazinyl, naphthyridinyl, quinoxalinyl, cinnolinyl, pteridinyl, carbazolyl, 3-carbolinyl, phenanthridinyl, acridinyl, perimidinyl, phenanthrolinyl (e.g., [1,10]phenanthrolinyl, [1,7]phenanthrolinyl, or [4,7]phenanthrolinyl), phenazinyl, thiazolyl, isothiazolyl, phenothiazinyl, oxazolyl, isoxazolyl, oxadiazolyl (e.g., 1,2,4-oxadiazolyl, 1,2,5-oxadiazolyl (i.e., furazanyl), or 1,3,4-oxadiazolyl), thiadiazolyl (e.g., 1,2,4-thiadiazolyl, 1,2,5-thiadiazolyl, or 1,3,4-thiadiazolyl), phenoxazinyl, pyrazolo[1,5-a]pyrimidinyl (e.g., pyrazolo[1,5-a]pyrimidin-3-yl), 1,2-benzoisoxazol-3-yl, benzothiazolyl, benzothiadiazolyl, benzoxazolyl, benzisoxazolyl, benzimidazolyl, benzo[b]thiophenyl (i.e., benzothienyl), triazolyl (e.g., 1H-1,2,3-triazolyl, 2H-1,2,3-triazolyl, 1H-1,2,4-triazolyl, or 4H-1,2,4-triazolyl), benzotriazolyl, 1H-tetrazolyl, 2H-tetrazolyl, triazinyl (e.g., 1,2,3-triazinyl, 1,2,4-triazinyl, or 1,3,5-triazinyl), furo[2,3-c]pyridinyl, dihydrofuropyridinyl (e.g., 2,3-dihydrofuro[2,3-c]pyridinyl or 1,3-dihydrofuro[3,4-c]pyridinyl), imidazopyridinyl (e.g., imidazo[1,2-a]pyridinyl or imidazo[3,2-a]pyridinyl), quinazolinyl, thienopyridinyl, tetrahydrothienopyridinyl (e.g., 4,5,6,7-tetrahydrothieno[3,2-c]pyridinyl), dibenzofuranyl, 1,3-benzodioxolyl, benzodioxanyl (e.g., 1,3-benzodioxanyl or 1,4-benzodioxanyl), or coumarinyl. Unless defined otherwise, the term "heteroaryl" preferably refers to a 5 to 14 membered (more preferably 5 to 10 membered) monocyclic ring or fused ring system comprising one or more (e.g., one, two, three or four) ring heteroatoms independently selected from O, S and N, wherein one or more S ring atoms (if present) and/or one or more N ring atoms (if present) are optionally oxidized, and wherein one or more carbon ring atoms are optionally oxidized; even more preferably, a "heteroaryl" refers to a 5 or 6 membered monocyclic ring comprising one or more (e.g., one, two or three) ring heteroatoms independently selected from O, S and N, wherein one or more S ring atoms (if present) and/or one or more N ring atoms (if present) are optionally oxidized, and wherein one or more carbon ring atoms are optionally oxidized. Moreover, unless defined otherwise, the term "heteroaryl" particularly preferably refers to pyridinyl (e.g., 2-pyridyl, 3-pyridyl, or 4-pyridyl), imidazolyl, thiazolyl, 1H-tetrazolyl, 2H-tetrazolyl, thienyl (i.e., thiophenyl), or pyrimidinyl.

As used herein, the term "cycloalkyl" refers to a saturated hydrocarbon ring group, including monocyclic rings as well as bridged ring, spiro ring and/or fused ring systems (which may be composed, e.g., of two or three rings; such as, e.g., a fused ring system composed of two or three fused rings). "Cycloalkyl" may, e.g., refer to cyclopropyl, cyclobutyl, cyclopentyl, cyclohexyl, cycloheptyl, decalinyl (i.e., decahydronaphthyl), or adamantyl. Unless defined otherwise, "cycloalkyl" preferably refers to a $C_{3-11}$ cycloalkyl, and more preferably refers to a $C_{3-7}$ cycloalkyl. A particularly preferred "cycloalkyl" is a monocyclic saturated hydrocarbon ring having 3 to 7 ring members. Moreover, unless defined otherwise, the term "cycloalkyl" even more preferably refers to cyclohexyl or cyclopropyl, and yet even more preferably refers to cyclohexyl.

As used herein, the term "heterocycloalkyl" refers to a saturated ring group, including monocyclic rings as well as bridged ring, spiro ring and/or fused ring systems (which may be composed, e.g., of two or three rings; such as, e.g., a fused ring system composed of two or three fused rings), wherein said ring group contains one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, and further wherein one or more carbon ring atoms may optionally be oxidized (i.e., to form an oxo group). For example, each heteroatom-containing ring comprised in said saturated ring group may contain one or two O atoms and/or one or two S atoms (which may optionally be oxidized) and/or one, two, three or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. "Heterocycloalkyl" may, e.g., refer to aziridinyl, azetidinyl, pyrrolidinyl, imidazolidinyl, pyrazolidinyl, piperidinyl, piperazinyl, azepanyl, diazepanyl (e.g., 1,4-diazepanyl), oxazolidinyl, isoxazolidinyl, thiazolidinyl, isothiazolidinyl, morpholinyl (e.g., morpholin-4-yl), thiomorpholinyl (e.g., thiomorpholin-4-yl), oxazepanyl, oxiranyl, oxetanyl, tetrahydrofuranyl, 1,3-dioxolanyl, tetrahydropyranyl, 1,4-dioxanyl, oxepanyl, thiiranyl, thietanyl, tetrahydrothiophenyl (i.e., thiolanyl), 1,3-dithiolanyl, thianyl, thiepanyl, decahydroquinolinyl, decahydroisoquinolinyl, or 2-oxa-5-aza-bicyclo[2.2.1]hept-5-yl. Unless defined otherwise, "heterocycloalkyl" preferably refers to a 3 to 11 membered saturated ring group, which is a monocyclic ring or a fused ring system (e.g., a fused ring system composed of two fused rings), wherein said ring group contains one or more (e.g., one, two, three, or four) ring heteroatoms independently selected from O, S and N, wherein one or more S ring atoms (if present) and/or one or more N ring atoms (if present) are optionally oxidized, and wherein one or more carbon ring atoms are optionally oxidized; more preferably, "heterocycloalkyl" refers to a 5 to 7 membered saturated monocyclic ring group containing one or more (e.g., one, two, or three) ring heteroatoms independently selected from O, S and N, wherein one or more S ring atoms (if present) and/or one or more N ring atoms (if present) are optionally oxidized, and wherein one or more carbon ring atoms are optionally oxidized. Moreover, unless defined otherwise, "heterocycloalkyl" even more preferably refers to tetrahydropyranyl, piperidinyl, piperazinyl, morpholinyl, pyrrolidinyl, or tetrahydrofuranyl.

As used herein, the term "cycloalkenyl" refers to an unsaturated alicyclic (non-aromatic) hydrocarbon ring group, including monocyclic rings as well as bridged ring, spiro ring and/or fused ring systems (which may be composed, e.g., of two or three rings; such as, e.g., a fused ring system composed of two or three fused rings), wherein said hydrocarbon ring group comprises one or more (e.g., one or two) carbon-to-carbon double bonds and does not comprise any carbon-to-carbon triple bond. "Cycloalkenyl" may, e.g., refer to cyclopropenyl, cyclobutenyl, cyclopentenyl, cyclohexenyl, cyclohexadienyl, cycloheptenyl, or cycloheptadienyl. Unless defined otherwise, "cycloalkenyl" preferably refers to a $C_{3-11}$ cycloalkenyl, and more preferably refers to a $C_{3-7}$ cycloalkenyl. A particularly preferred "cycloalkenyl" is a monocyclic unsaturated alicyclic hydrocarbon ring having 3 to 7 ring members and containing one or more (e.g., one or two; preferably one) carbon-to-carbon double bonds.

As used herein, the term "heterocycloalkenyl" refers to an unsaturated alicyclic (non-aromatic) ring group, including monocyclic rings as well as bridged ring, spiro ring and/or fused ring systems (which may be composed, e.g., of two or three rings; such as, e.g., a fused ring system composed of two or three fused rings), wherein said ring group contains one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, wherein one or more carbon ring atoms may optionally be oxidized (i.e., to form an oxo group), and further wherein said ring group comprises at least one double bond between adjacent ring atoms and does not comprise any triple bond between adjacent ring atoms. For example, each heteroatom-containing ring comprised in said unsaturated alicyclic ring group may contain one or two O atoms and/or one or two S atoms (which may optionally be oxidized) and/or one, two, three or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. "Heterocycloalkenyl" may, e.g., refer to imidazolinyl (e.g., 2-imidazolinyl (i.e., 4,5-dihydro-1H-imidazolyl), 3-imidazolinyl, or 4-imidazolinyl), tetrahydropyridinyl (e.g., 1,2,3,6-tetrahydropyridinyl), dihydropyridinyl (e.g., 1,2-dihydropyridinyl or 2,3-dihydropyridinyl), pyranyl (e.g., 2H-pyranyl or 4H-pyranyl), thiopyranyl (e.g., 2H-thiopyranyl or 4H-thiopyranyl), dihydropyranyl, dihydrofuranyl, dihydropyrazolyl, dihydropyrazinyl, dihydroisoindolyl, octahydroquinolinyl (e.g., 1,2,3,4,4a,5,6,7-octahydroquinolinyl), or octahydroisoquinolinyl (e.g., 1,2,3,4,5,6,7,8-octahydroisoquinolinyl). Unless defined otherwise, "heterocycloalkenyl" preferably refers to a 3 to 11 membered unsaturated alicyclic ring group, which is a monocyclic ring or a fused ring system (e.g., a fused ring system composed of two fused rings), wherein said ring group contains one or more (e.g., one, two, three, or four) ring heteroatoms independently selected from O, S and N, wherein one or more S ring atoms (if present) and/or one or more N ring atoms (if present) are optionally oxidized, wherein one or more carbon ring atoms are optionally oxidized, and wherein said ring group comprises at least one double bond between adjacent ring atoms and does not comprise any triple bond between adjacent ring atoms; more preferably, "heterocycloalkenyl" refers to a 5 to 7 membered monocyclic unsaturated non-aromatic ring group containing one or more (e.g., one, two, or three) ring heteroatoms independently selected from O, S and N, wherein one or more S ring atoms (if present) and/or one or more N ring atoms (if present) are optionally oxidized, wherein one or more carbon ring atoms are optionally oxidized, and wherein said ring group comprises at least one double bond between adjacent ring atoms and does not comprise any triple bond between adjacent ring atoms.

As used herein, the term "halogen" refers to fluoro (—F), chloro (—Cl), bromo (—Br), or iodo (—I).

As used herein, the term "haloalkyl" refers to an alkyl group substituted with one or more (preferably 1 to 6, more preferably 1 to 3) halogen atoms which are selected independently from fluoro, chloro, bromo and iodo, and are preferably all fluoro atoms. It will be understood that the maximum number of halogen atoms is limited by the number of available attachment sites and, thus, depends on the number of carbon atoms comprised in the alkyl moiety of the haloalkyl group. "Haloalkyl" may, e.g., refer to —CF$_3$, —CHF$_2$, —CH$_2$F, —CF$_2$—CH$_3$, —CH$_2$—CF$_3$, —CH$_2$—CHF$_2$, —CH$_2$—CF$_2$—CH$_3$, —CH$_2$—CF$_2$—CF$_3$, or —CH(CF$_3$)$_2$. A particularly preferred "haloalkyl" group is —CF$_3$.

As used herein, the term "sulfonic acid group" refers to a group —SO$_3$H.

As used herein, the terms "optional", "optionally" and "may" denote that the indicated feature may be present but can also be absent. Whenever the term "optional", "optionally" or "may" is used, the present invention specifically relates to both possibilities, i.e., that the corresponding feature is present or, alternatively, that the corresponding feature is absent. For example, the expression "X is optionally substituted with Y" (or "X may be substituted with Y") means that X is either substituted with Y or is unsubstituted. Likewise, if a component of a composition is indicated to be "optional", the invention specifically relates to both possibilities, i.e., that the corresponding component is present (contained in the composition) or that the corresponding component is absent from the composition.

Various groups are referred to as being "optionally substituted" in this specification. Generally, these groups may carry one or more substituents, such as, e.g., one, two, three or four substituents. It will be understood that the maximum number of substituents is limited by the number of attachment sites available on the substituted moiety. Unless defined otherwise, the "optionally substituted" groups referred to in this specification carry preferably not more than two substituents and may, in particular, carry only one substituent. Moreover, unless defined otherwise, it is preferred that the optional substituents are absent, i.e. that the corresponding groups are unsubstituted.

As used herein, the term "peptide" refers to a polymer of two or more amino acids linked via amide bonds that are formed between an amino group of one amino acid and a carboxyl group of another amino acid. The amino acids comprised in the peptide, which are also referred to as amino acid residues, may be selected from the 20 standard proteinogenic α-amino acids (i.e., Ala, Arg, Asn, Asp, Cys, Glu, Gln, Gly, His, Ile, Leu, Lys, Met, Phe, Pro, Ser, Thr, Trp, Tyr, and Val) but also from non-proteinogenic and/or non-standard α-amino acids (such as, e.g., ornithine, citrulline, homolysine, pyrrolysine, 4-hydroxyproline, α-methylalanine (i.e., 2-aminoisobutyric acid), norvaline, norleucine, terleucine (tert-leucine), labionin, or an alanine or glycine that is substituted at the side chain with a carbocyclyl or a heterocyclyl group (e.g., a cycloalkyl group, a heterocycloalkyl group, an aryl group, or a heteroaryl group) like, e.g., cyclopentylalanine, cyclohexylalanine, phenylalanine, naphthylalanine, pyridylalanine, thienylalanine, cyclohexylglycine, or phenylglycine) as well as β-amino acids (e.g., β-alanine), γ-amino acids (e.g., γ-aminobutyric acid, isoglutamine, or statine), δ-amino acids and dehydroamino acids (e.g., an α,β-dehydroamino acid, such as, e.g., dehydrobutyrine or dehydroalanine). Preferably, the amino acid residues comprised in the peptide are selected from α-amino acids, more preferably from the 20 standard proteinogenic α-amino acids (which can be present as the L-isomer or the D-isomer, and are preferably all present as the L-isomer). The peptide may be unmodified or may be modified, e.g., at its N-terminus, at its C-terminus and/or at a functional group in the side chain of any of its amino acid residues (particularly at the side chain functional group of one or more Lys, His, Ser, Thr, Tyr, Cys, Asp, Glu, and/or Arg residues). Such modifications may include, e.g., the attachment of any of the protecting groups described for the corresponding functional groups in: Wuts P G & Greene T W, Greene's protective groups in organic synthesis, John Wiley & Sons, 2006. Such modifications may also include the covalent attachment of one or more polyethylene glycol (PEG) chains (forming a PEGylated peptide), the glycosylation and/or the acylation with one or more fatty acids (e.g., one or more $C_{8-30}$ alkanoic or alkenoic acids; forming a fatty acid acylated peptide). Moreover, such modified peptides may also include peptidomimetics, provided that they contain at least two amino acids that are linked via an amide bond (formed between an amino group of one amino acid and a carboxyl group of another amino acid). The amino acid residues comprised in the peptide may, e.g., be present as a linear molecular chain (forming a linear peptide) or may form one or more rings (corresponding to a cyclic peptide). The peptide may also form oligomers consisting of two or more identical or different molecules.

As used herein, the term "amino acid" refers, in particular, to any one of the 20 standard proteinogenic α-amino acids (i.e., Ala, Arg, Asn, Asp, Cys, Glu, Gln, Gly, His, Ile, Leu, Lys, Met, Phe, Pro, Ser, Thr, Trp, Tyr, or Val) but also to a non-proteinogenic and/or non-standard α-amino acid (such as, e.g., ornithine, citrulline, homolysine, pyrrolysine, 4-hydroxyproline, α-methylalanine (i.e., 2-aminoisobutyric acid), norvaline, norleucine, terleucine (tert-leucine), labionin, or an alanine or glycine that is substituted at the side chain with a cyclic group (e.g., a cycloalkyl group, a heterocycloalkyl group, an aryl group, or a heteroaryl group) like, e.g., cyclopentylalanine, cyclohexylalanine, phenylalanine, naphthylalanine, pyridylalanine, thienylalanine, cyclohexylglycine, or phenylglycine), or a β-amino acid (e.g., β-alanine), a γ-amino acid (e.g., γ-aminobutyric acid, isoglutamine, or statine), a δ-amino acid, a dehydroamino acid (e.g., an α,β-dehydroamino acid, such as, e.g., dehydrobutyrine or dehydroalanine), or any other compound comprising at least one carboxylic acid group and at least one amino group. Unless defined otherwise, the term "amino acid" preferably refers to an α-amino acid, more preferably to any one of the 20 standard proteinogenic α-amino acids (which may be in the form of the L-isomer or the D-isomer but are preferably in the form of the L-isomer).

As used herein, unless explicitly indicated otherwise or contradicted by context, the terms "a", "an" and "the" are used interchangeably with "one or more" and "at least one".

As used herein, the term "about" preferably refers to ±10% of the indicated numerical value, more preferably to ±5% of the indicated numerical value, and in particular to the exact numerical value indicated. If the term "about" is used in connection with the endpoints of a range, it preferably refers to the range from the lower endpoint −10% of its indicated numerical value to the upper endpoint +10% of its indicated numerical value, more preferably to the range from of the lower endpoint −5% to the upper endpoint +5%, and even more preferably to the range defined by the exact numerical values of the lower endpoint and the upper endpoint. If the term "about" is used in connection with the endpoint of an open-ended range, it preferably refers to the corresponding range starting from the lower endpoint −10% or from the upper endpoint +10%, more preferably to the range starting from the lower endpoint −5% or from the upper endpoint +5%, and even more preferably to the open-ended range defined by the exact numerical value of the corresponding endpoint. If the term "about" is used in connection with a parameter that is quantified in integers, such as the number of nucleotides in a nucleic acid, the numbers corresponding to ±10% or ±5% of the indicated numerical value are to be rounded to the nearest integer.

As used herein, the term "comprising" (or "comprise", "comprises", "contain", "contains", or "containing"), unless explicitly indicated otherwise or contradicted by context, has the meaning of "containing, inter alia", i.e., "containing, among further optional elements, . . . ". In addition thereto, this term also includes the narrower meanings of "consisting essentially of" and "consisting of". For example, the term "A comprising B and C" has the meaning of "A containing, inter alia, B and C", wherein A may contain further optional elements (e.g., "A containing B, C and D" would also be encompassed), but this term also includes the meaning of "A consisting essentially of B and C" and the meaning of "A consisting of B and C" (i.e., no other components than B and C are comprised in A).

It is to be understood that the present invention specifically relates to each and every combination of features and embodiments described herein, including any combination of general and/or preferred features/embodiments. In particular, the invention specifically relates to each combination of meanings (including general and/or preferred meanings) for the various groups and variables comprised in formula (I).

The reference in this specification to any prior publication (or information derived therefrom) is not and should not be taken as an acknowledgment or admission or any form of suggestion that the corresponding prior publication (or the information derived therefrom) forms part of the common general knowledge in the technical field to which the present specification relates.

In this specification, a number of documents including patent applications are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

FIG. 1: Hydrolysis of γ-glutamyl-leucine catalyzed by GGT.

Figure 2:
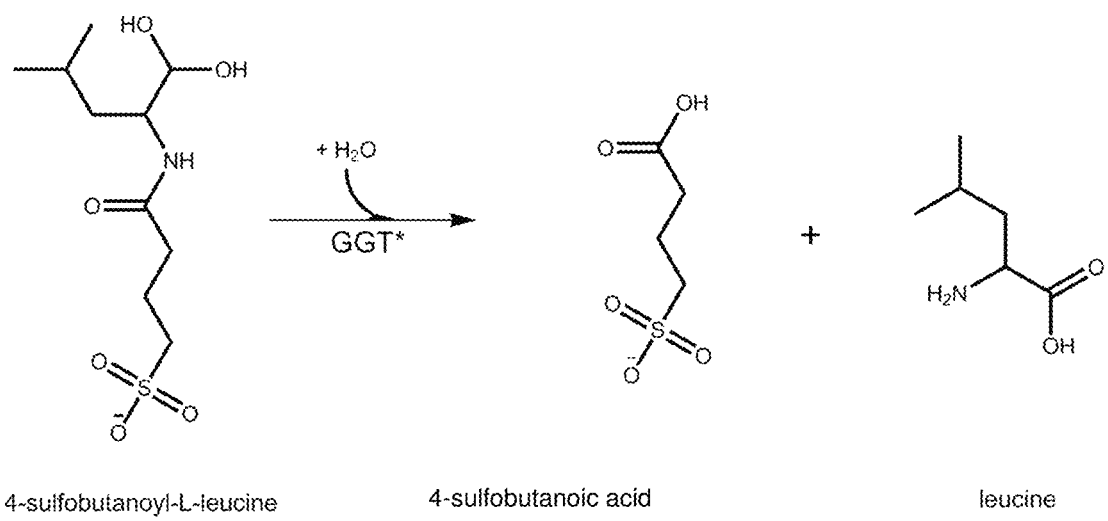

FIG. 2: Hydrolysis of the corresponding sulfonate catalyzed by GGT* (EcGGT D433N or PnGGT D405N).

FIG. 3: Scheme of a synthetic transport system and the proof-of-concept. A peptide loaded with leucine is transported into the cytoplasm of *E. coli* through porin channels and peptide permease systems. Inside the cell, the N-terminal amino acid is cleaved off by a peptidase and leucine is released by the activity of 6×His_PnGGT ΔN24.

Figure 4:
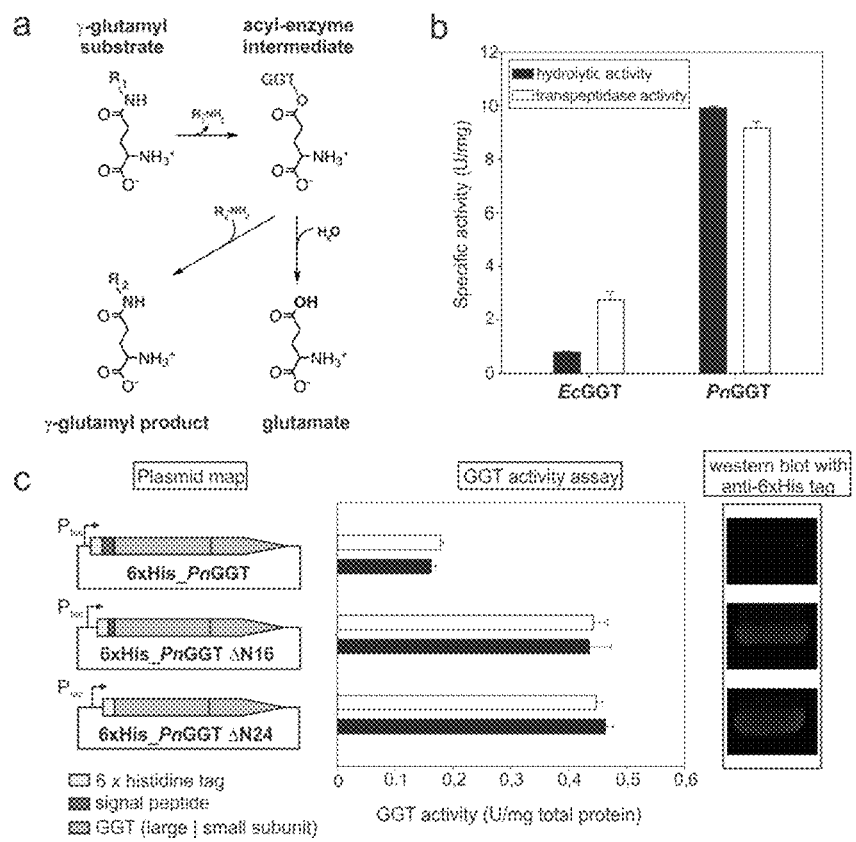

FIG. 4: Main characteristics of γ-glutamyl transferases. (a) Cleavage of γ-glutamyl substrates is initiated by the formation of an acyl-enzyme intermediate and accompanied by the release of an amine substituent. Formation of the intermediate is followed by a nucleophilic substitution with either water (hydrolase activity) or amino acids/peptides (transpeptidase activity) as the nucleophile. (b) Specific activities of purified EcGGT and PnGGT. EcGGT shows elevated transpeptidase activity in the presence of the peptide acceptor glycyl-glycine. For PnGGT no additional enzyme activity can be detected in the presence of the peptide acceptor. Error bars indicate the standard deviation from 3 individual measurements. (c) Expression of PnGGT either with a full or a truncated signal peptide. The western blot data is an excerpt from a larger blot (for the complete picture, see FIG. 9) focusing only on the large GGT subunit.

Figure 5:
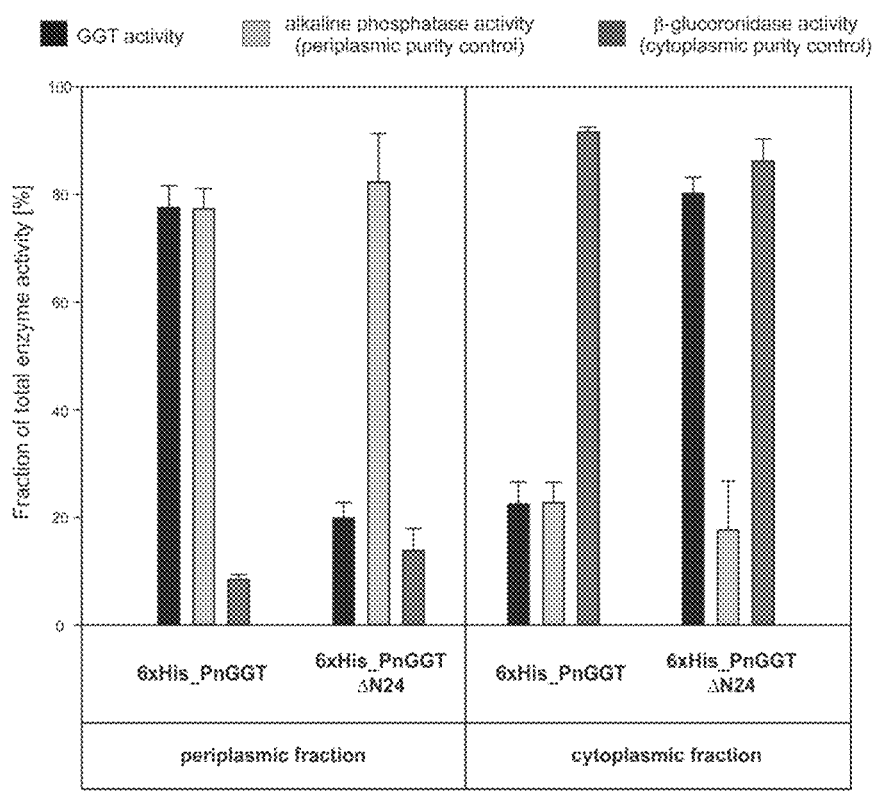

FIG. 5: Cellular localization of PnGGT variants with full (6×His_PnGGT) or truncated signal peptide (6×His_PnGGT ΔN24). Alkaline phosphatase and β-glucuronidase activities were measured to determine the purity of the periplasmic and cytoplasmic fractions. Error bars indicate the standard deviation from three individual separation experiments.

Figure 6:
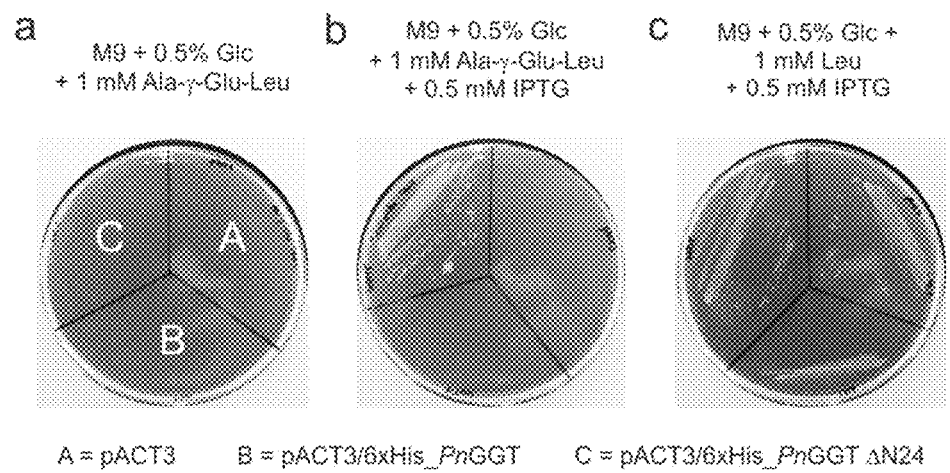

FIG. 6: Demonstration of the synthetic transport system in the pcnB knockout strain TK054 ΔpcnB. (a) On M9 minimal medium supplemented with 0.5% glucose and 1 mM Ala-γ-Glu-Leu no growth can be observed in the absence of the inducer IPTG. (b) In the presence of IPTG, growth is only possible if cells are transformed with pACT3/6×His_ PnGGT ΔN24. (c) All transformed strains show similar growth in the presence of free leucine.

Figure 7:
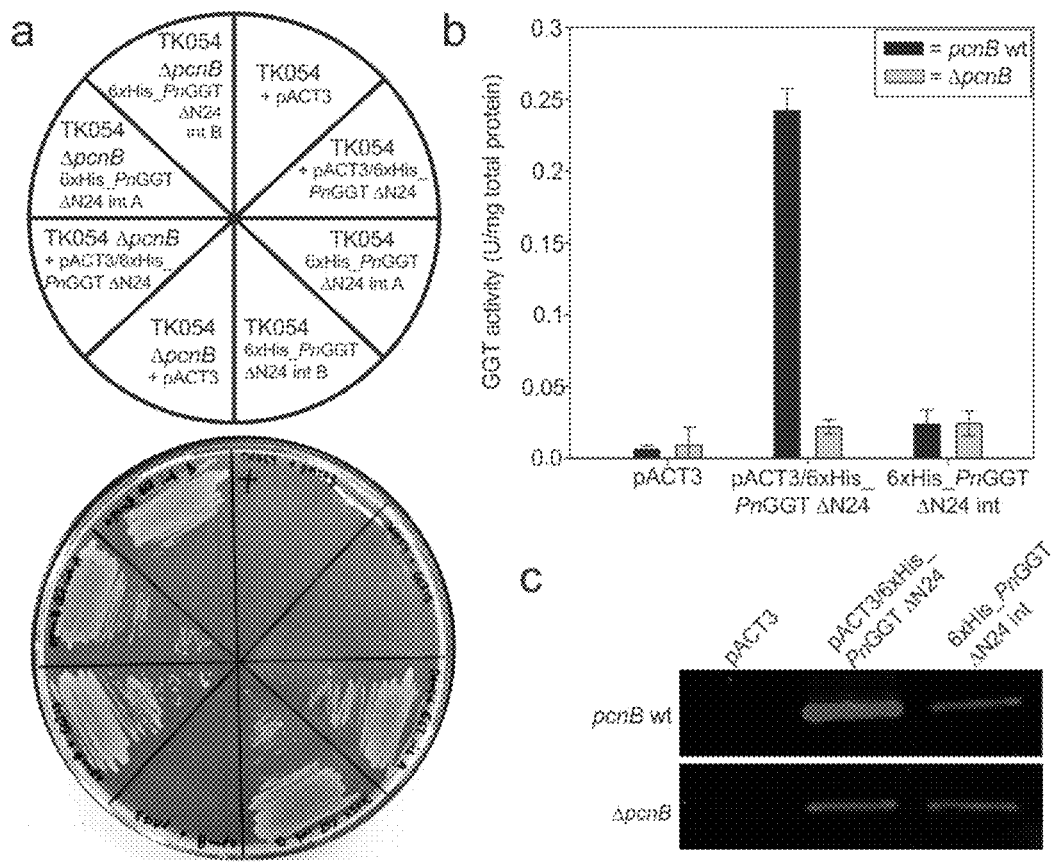

FIG. 7: Chromosomal integration of 6×His_PnGGT ΔN24. (a) Growth after 2 days of leucine auxotrophic strains either with a functional pcnB copy (TK054) or a knockout in pcnB (TK054 ΔpcnB) on minimal medium supplemented with 0.5% glucose, 1 mM Ala-γ-Glu-Leu and 0.5 mM IPTG. Strains were transformed with the empty vector pACT3, the 6×His_PnGGT ΔN24 expression vector or a copy of the gene for 6×His_PnGGT ΔN24 was integrated into the chromosome (identical strains 6×His_PnGGT ΔN24 int A & B). (b) Expression levels of 6×His_PnGGT ΔN24 were quantified in a colorimetric enzyme assay or (c) by western blot with an antibody against the 6×His-tag at the N-terminus of PnGGT.

Figure 8:
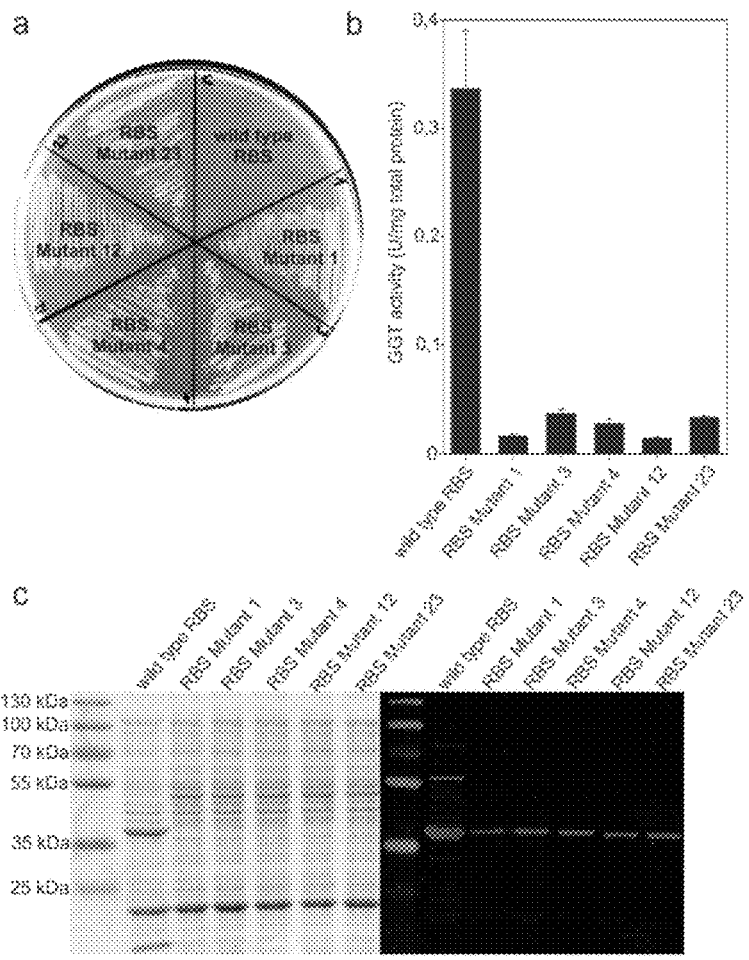

FIG. 8: Optimizing 6×His_PnGGT ΔN24 expression levels through engineering of the RBS sequence. (a) Growth of the leucine auxotrophic strain TK054 expressing 6×His_ PnGGT ΔN24 from different expression plasmids, differing in the RBS in front of the start of the gene. Strains were plated on solid M9 medium supplemented with 0.5% glucose, 1 mM Ala-γ-Glu-Leu and 0.5 mM IPTG. (b) Determination of GGT activity in cell extracts and (c) determination of GGT expression levels by western blotting for the same strains as in (a).

Figure 9:
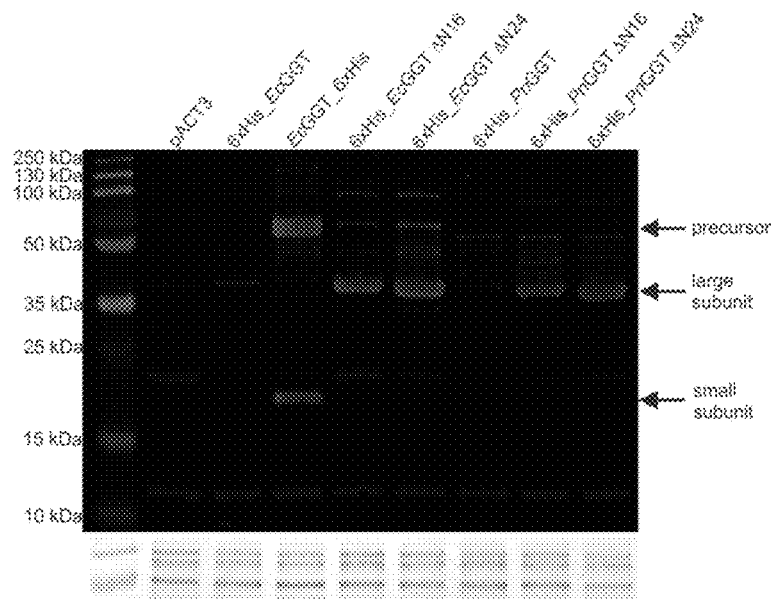

FIG. 9: Expression of different GGT variants. Expression of the following GGT variants was compared by western blot analysis: full length EcGGT or PnGGT with N-terminal 6×His-tag (6×His_EcGGT, 6×His_PnGGT); full length EcGGT with C-terminal 6×His-tag (EcGGT_6×His); EcGGT or PnGGT with truncated signal peptide and N-terminal 6×His-tag (6×His_EcGGT ΔN16, 6×His_PnGGT ΔN16); EcGGT or PnGGT with deleted signal peptide and N-terminal 6×His-tag (6×His_EcGGT ΔN24, 6×His_ PnGGT ΔN24). Below the western blot, the SDS-PAGE gel is shown to confirm loading of equal amounts of protein per lane.

Figure 10:
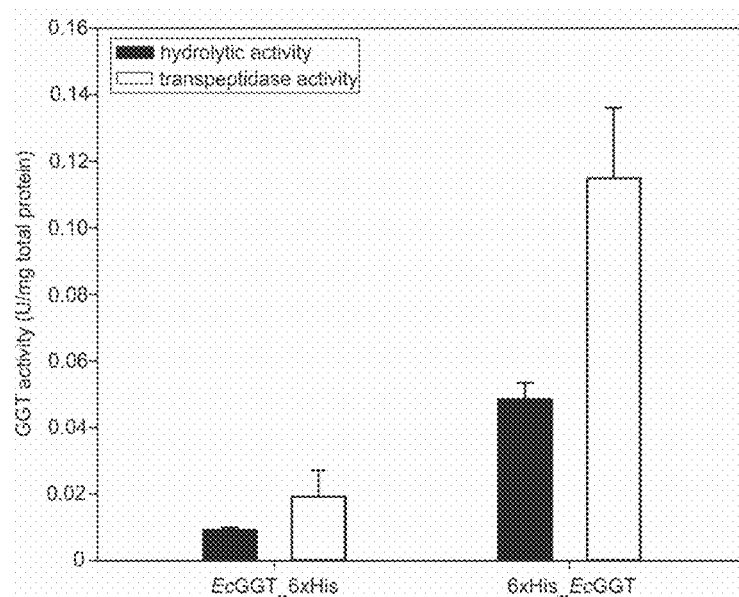

FIG. 10: Comparison of GGT activity in cell extracts of strains producing either the C-terminally (EcGGT_6×His) or the N-terminally (6×His_EcGGT) His-tagged EcGGT variants. GGT activity in whole cell lysates is significantly higher if EcGGT is expressed with an N-terminal 6×His-Tag compared to a variant with a C-terminal 6×His-tag.

Figure 11:
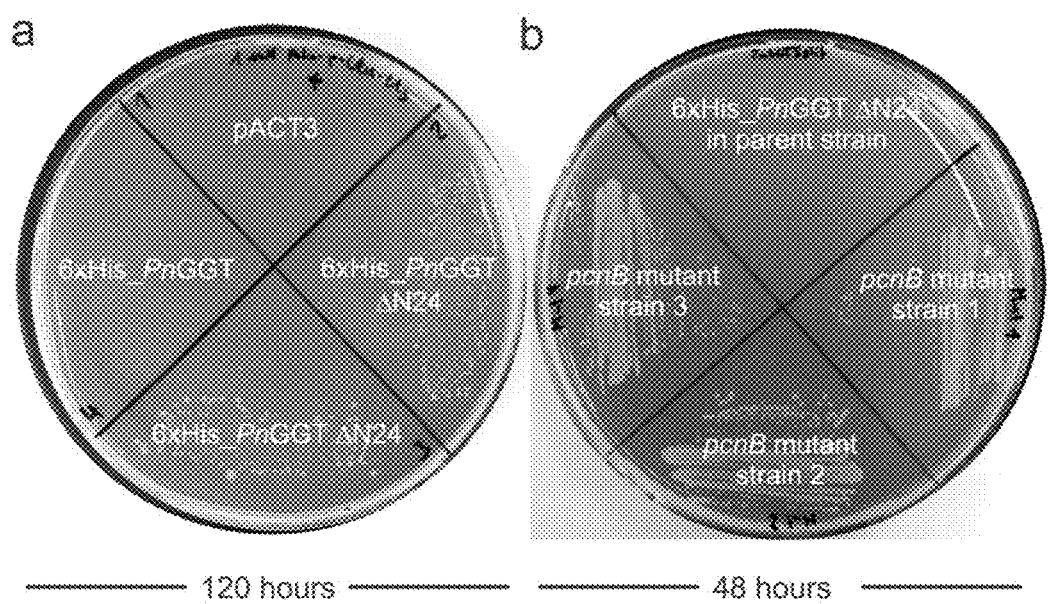

FIG. 11: Isolation of pcnB mutant strains. (a) Re-isolation of strain TK054 on M9 minimal medium supplemented with 0.5% glucose, 1 mM Ala-γ-Glu-Leu and 0.5 mM IPTG leads to poor growth after 4-5 days of incubation if 6×His_PnGGT ΔN24 is expressed. No growth was observed for an empty vector control (pACT3) or if 6×His_PnGGT was expressed. (b) Three colonies isolated from the initial experiment grew rapidly after re-isolation on the same medium. The parent strain is equivalent to the strain used in (a) and does not show colony formation after 48 hours of incubation at 37° C. Sequencing of all three strains revealed mutations in the gene pcnB.

Figure 12:
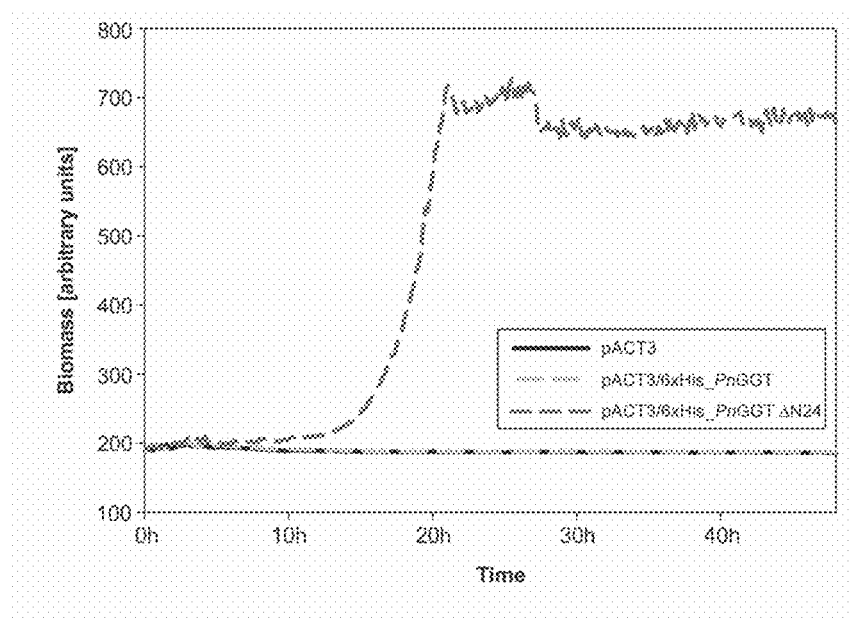

FIG. 12: Demonstration of the synthetic transport system in the pcnB knockout strain TK054 ΔpcnB in liquid medium. Growth of TK054 carrying different plasmids in liquid minimal medium supplemented with 0.5% glucose, 1 mM Ala-γ-Glu-Leu and 0.5 mM IPTG. Only if the cytoplasmic GGT variant was expressed from plasmid pACT3/ 6×His_PnGGT ΔN24, growth could be observed.

Figure 13:
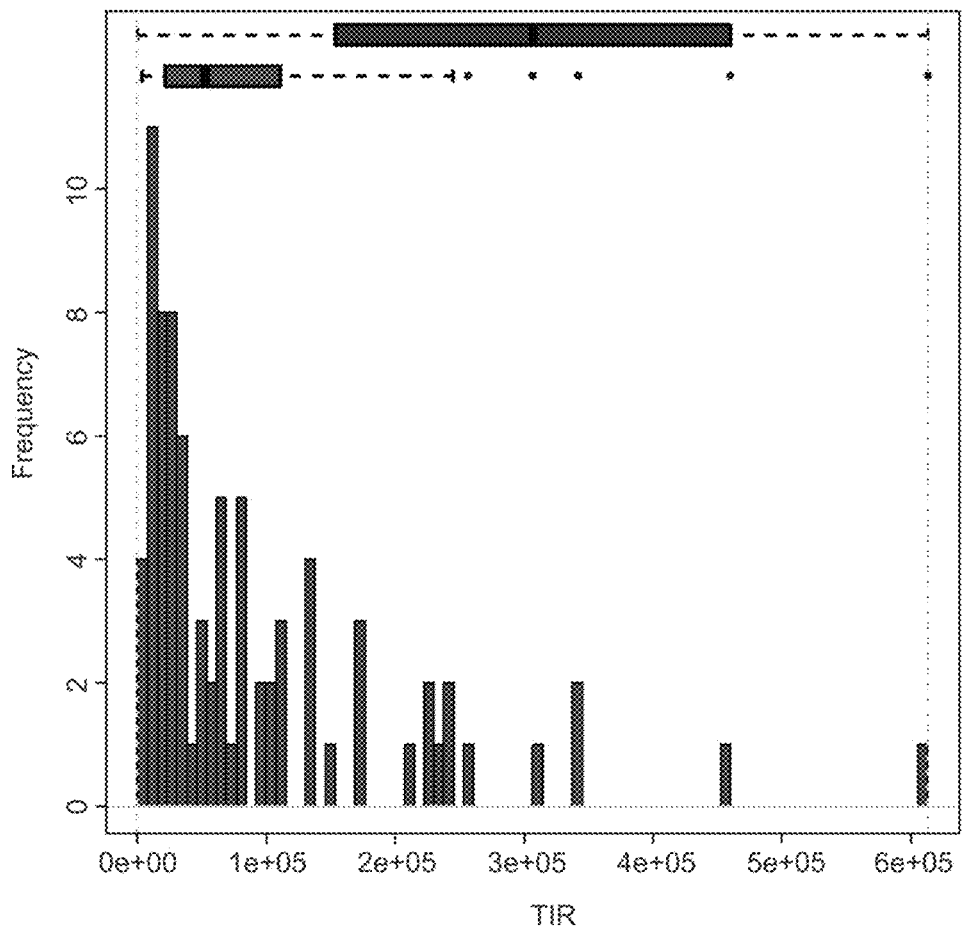

FIG. 13: Distribution of translation initiation ratios (TIRs) of the randomized HVVGGVGG RBS library. The library contains 81 different RBS sequences spanning a 166-fold range of TIRs. The frequency of RBS sequences within a specific TIR bin is represented on the y-axis. The blue box plot on top represents the ideal distribution of TIRs. The red box plot represents the actual distribution of TIRs, which is the distribution closest to the ideal distribution that can be reached with a library size of 81.

FIG. 14: Growth curves of JM101 with different 6×His_ PnGGT ΔN24 expression constructs in M9 medium supplemented with 0.5% glucose and 0.5 mM IPTG. Expression from the plasmid with the 6×His_PnGGT ΔN24 parent construct causes a long initial lag phase. If 6×His_PnGGT ΔN24 is expressed from plasmids with one of the five RBS variants under the same conditions, no extended lag phase can be observed.

FIG. 15: Scheme of a sulfonate based synthetic transport system. (a) Chemical structure of a γ-glutamyl amide (1), a glutaryl amide (2) and a sulfobutanoyl amide (3). (b) Scheme of the proposed transport system. A sulfobutanoyl amide is taken up by the cell via the sulfonate transporter SsuABC and intracellularly hydrolyzed by the enzyme GGT* to release the amine cargo molecule (R—NH$_2$).

Figure 16:
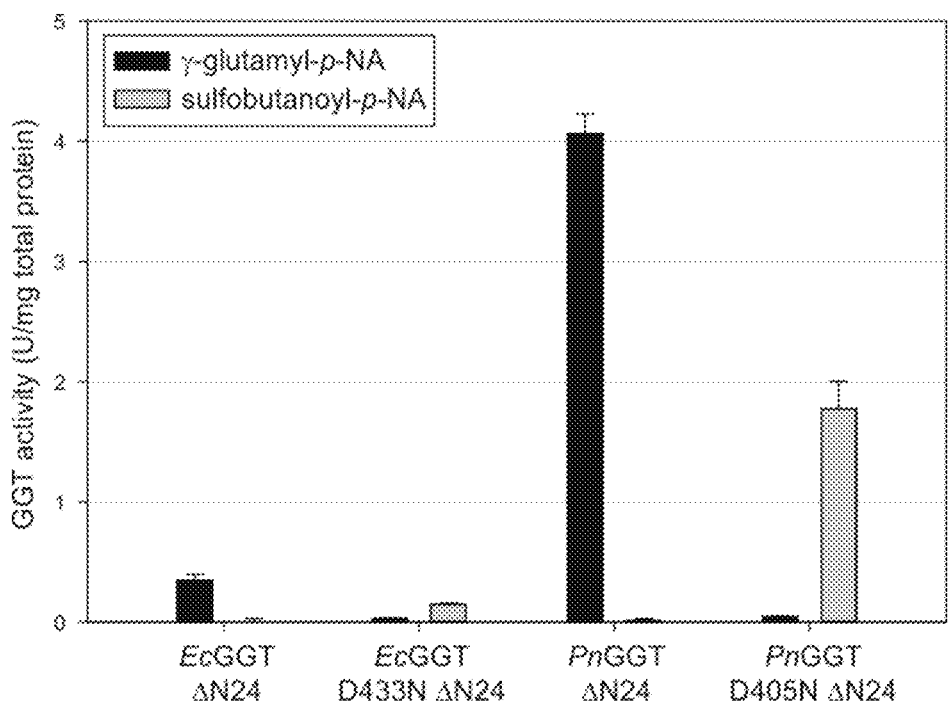

FIG. 16: Hydrolysis of γ-glutamyl-p-nitroanilide and sulfobutanoyl-p-nitroanilide by GGT variants. Cell free extracts containing different GGT variants were incubated with 4 mM of the substrate γ-glutamyl-p-nitroanilide or sulfobutanoyl-p-nitroanilide and the release of (3-carboxy-) 4-nitroanilide was quantified.

Figure 17:
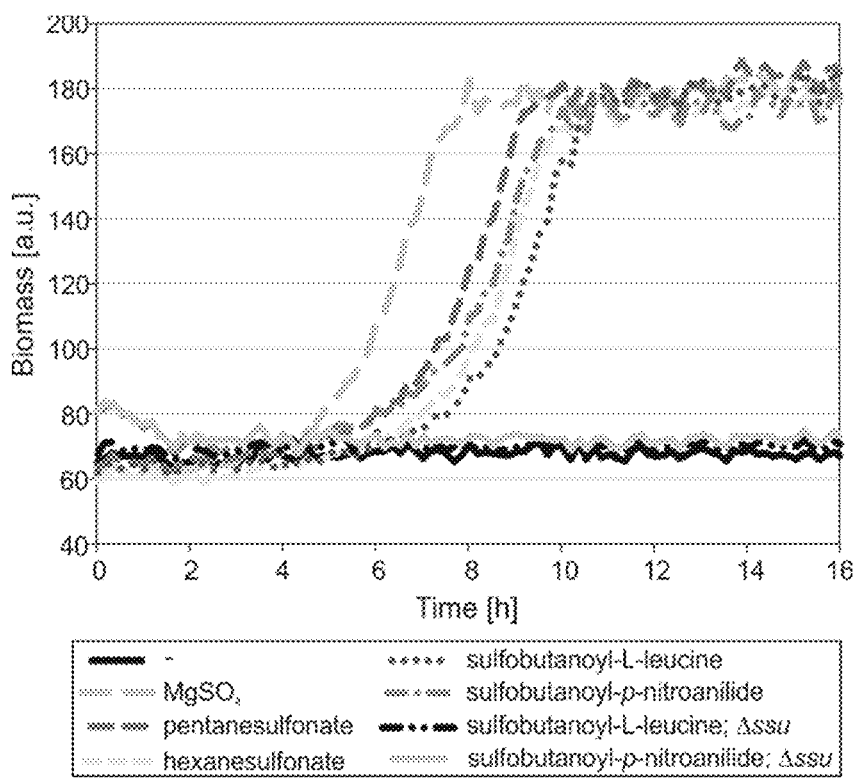

FIG. 17: Growth of E. coli deletion strains on different sulfur sources. Growth of strain BW25113 ΔleuB or BW25113 ΔleuB ΔssuEADCB (indicated in legend as Δssu) was compared in MS medium supplemented with 0.5% glucose, 0.4 mM leucine, 0.4 mM isoleucine and 1 mM of a sulfur source.

Figure 18:
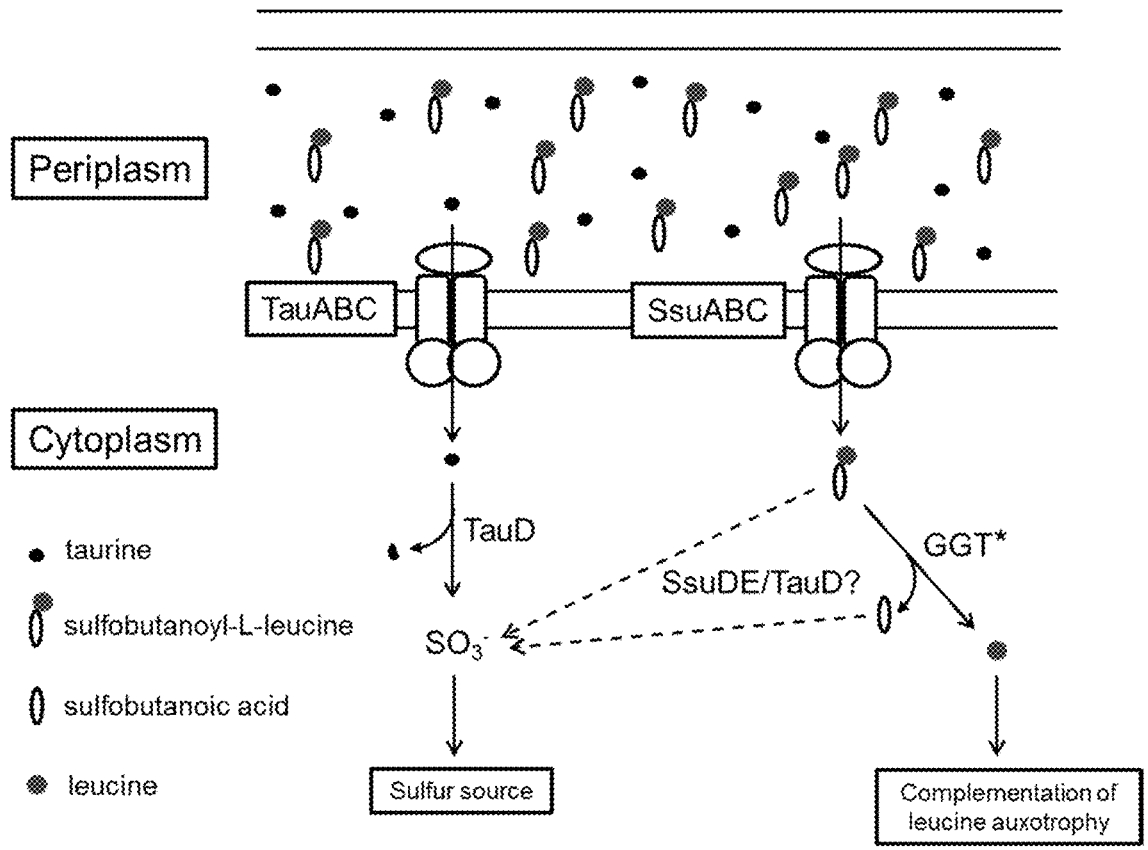

FIG. 18: Scheme of the proposed synthetic transport system exemplified for sulfobutanoyl-L-leucine. Taurine is taken up via the transporter TauABC and desulfonated by TauD to provide sulfite ions as sulfur source. Sulfobutanoyl-L-leucine is presumably taken up via SsuABC and can then be hydrolyzed by GGT* to provide leucine for complementation of the leucine auxotrophy. An alternative route for sulfobutanoyl-L-leucine would be the desulfonation by SsuDE and potentially TauD, which would make the substrate unavailable for further hydrolysis by GGT*.

Figure 19:
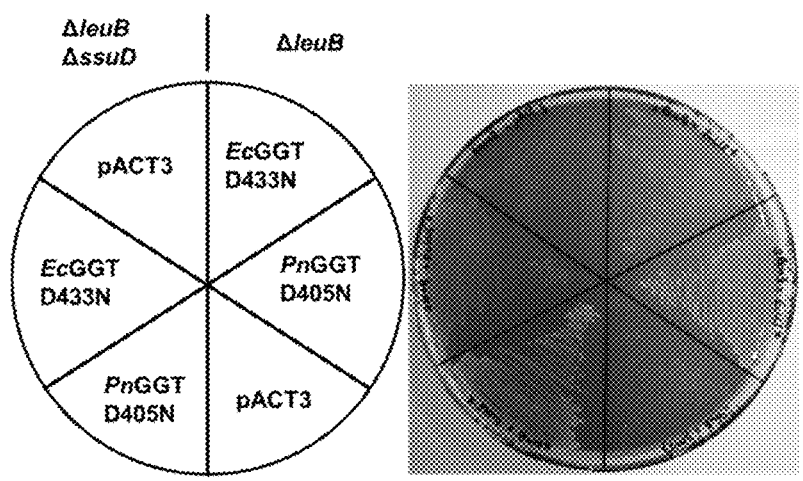

FIG. 19: Intracellular release of leucine from sulfobutanoyl-L-leucine by GGT*. The strains BW25113 ΔleuB and BW25113 ΔleuB ΔssuD were transformed with the expression plasmids pACT3/PnGGT_ΔN24_D405N, pACT3/EcGGT_ΔN24_D433N or the empty vector pACT3 and grown on MS medium supplemented with 0.5% glucose, 0.4 mM isoleucine, 0.5 mM taurine, 0.5 mM IPTG and 2 mM sulfobutanoyl-L-leucine.

Figure 20:
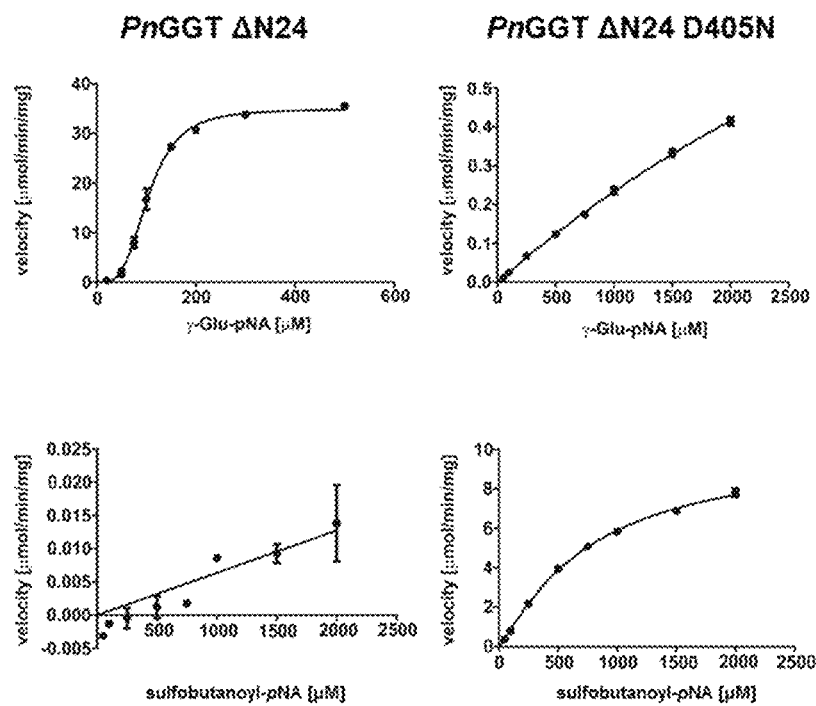

FIG. 20: Kinetic measurements with PnGGT ΔN24 and PnGGT ΔN24 D405N. PnGGT ΔN24 and PnGGT ΔN24 D405N were purified and kinetic measurements were performed with the substrates γ-Glu-p-nitroanilide and sulfobutanoyl-p-nitroanilide. Fitting of the kinetic data was performed with GraphPad Prism.

Figure 21:
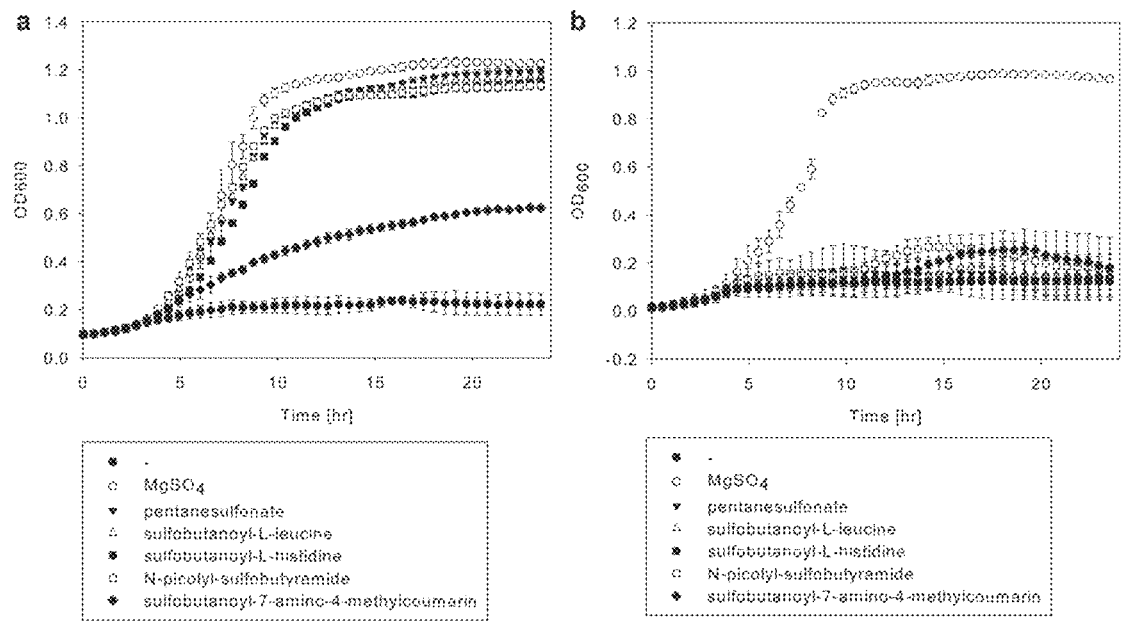

FIG. 21: Growth of E. coli on sulfonates. Strains TK080 (a; BW25113 ΔleuB) and TK082 (b; BW25113 ΔleuB ΔssuEADCB ΔtauD) were grown in MS minimal medium supplemented with 0.5% glucose, 0.4 mM L-leucine, 1 mM $MgCl_2$ and 1 mM of a sulfur source. TK080 was able to use the majority of the tested sulfur sources with a similar efficiency as sulfate. Only the substrate sulfobutanoyl-7-amino-4-methylcoumarin was utilized with a lower efficiency. Additional deletion of the operon ssuEADCB (TK082) prevented growth on all tested sulfonates, indicating that these compounds are mainly taken up via the transporter SsuABC. Dots represent the average of three independent measurements with standard deviations shown as error bars.

Figure 22:
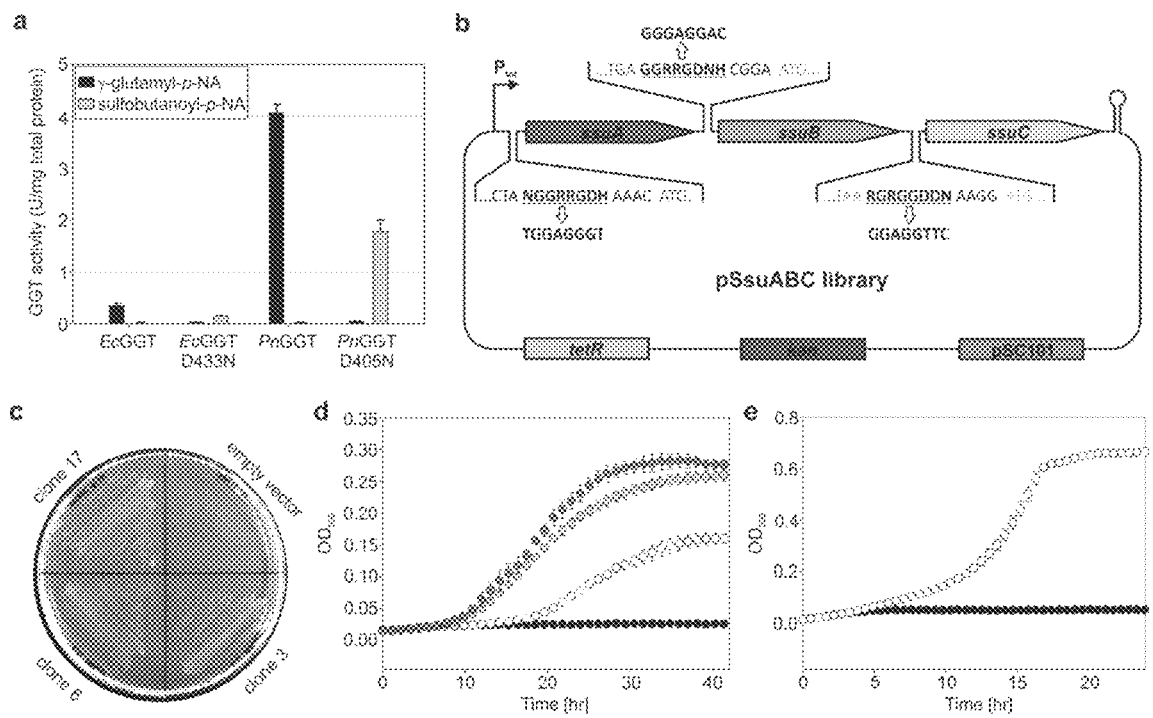

FIG. 22: Identification of GGT* activity and refactoring of the ssuABC operon. (a) Cell free extracts of strain TK018 synthesizing either EcGGT, EcGGT D433N, PnGGT or PnGGT D405N were incubated with 2 mM of the substrates γ-glutamyl-p-nitroanilide or sulfobutanoyl-p-nitroanilide (5), respectively. The release of 4-nitroaniline was quantified by measuring the absorption at 410 nm. (b) Plasmid map of the three-dimensional RBS-library for refactoring the ssuABC operon using 144 RBS variants per gene. RBS library sequences are underlined. Arrows point towards the final RBS sequences observed in plasmid pSsuABC. (c) Growth of strain TK082[pPnGGT*], transformed with either the empty vector pSEVA271 or the vector carrying different variants of the ssuABC libraries, on MS minimal medium supplemented with 0.5% glucose, 1 mM $MgSO_4$, 0.5 mM IPTG, 100 ng $ml^{-1}$ aTc and 0.5 mM sulfobutanoyl-L-leucine. (d) Growth of strain TK082[pSsuABC] transformed with the empty vector pACT3 (black circles), plasmid pPnGGT* (white circles), plasmid pPnGGT*_RBS3 (light grey circles) or pPnGGT*_RBS4 (dark grey circles) in liquid MS minimal medium supplemented with 0.5% glucose, 1 mM MgSO4, 0.5 mM IPTG, 100 ng $ml^{-1}$ aTc and 0.25 mM sulfobutanoyl-L-leucine. (e) Growth of strain TK088[pSsuABC]transformed with the empty vector pACT3 (black circles) or plasmid pPnGGT* (white circles) in liquid MS minimal medium supplemented with 0.5% glucose, 1 mM $MgSO_4$, 0.4 mM L-leucine, 0.5 mM IPTG, 100 ng $ml^{-1}$ aTc and 0.5 mM sulfobutanoyl-L-histidine. Bars and dots from panels (a), (d) and (e) represent the average of three independent measurements with standard deviations shown as error bars.

Figure 23:
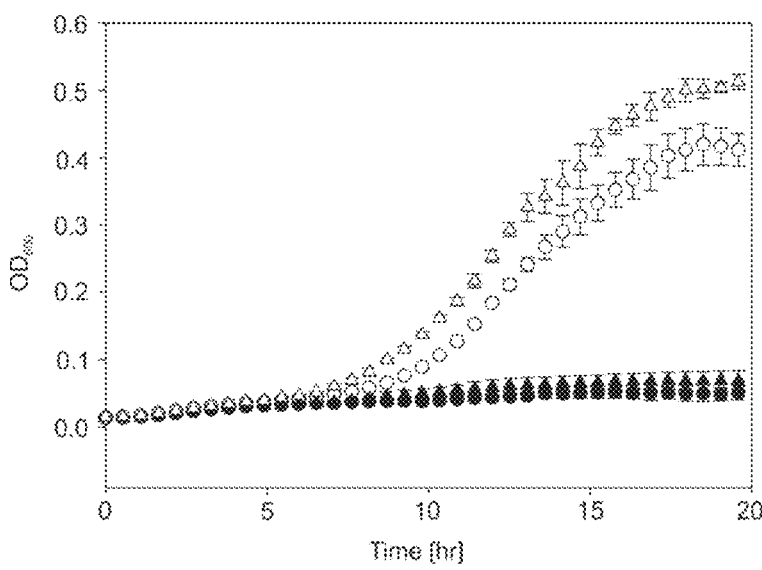

FIG. 23: Testing the transport system in different strain backgrounds. Strains TK080 (BW25113 ΔleuB; circles) and TK082 (BW25113 ΔleuB ΔssuEADCB ΔtauD; triangles) were transformed with plasmid pSsuABC and either the empty plasmid pACT3 (black symbols) or plasmid pPnGGT* (white symbols). Growth experiments in MS minimal medium supplemented with 0.5% glucose, 1 mM $MgSO_4$, 0.5 mM IPTG, 100 ng $ml^{-1}$ aTc and 1 mM sulfobutanoyl-L-leucine revealed a slight growth advantage of strain TK082. Dots represent the average of three independent measurements with standard deviations shown as error bars.

Figure 24:
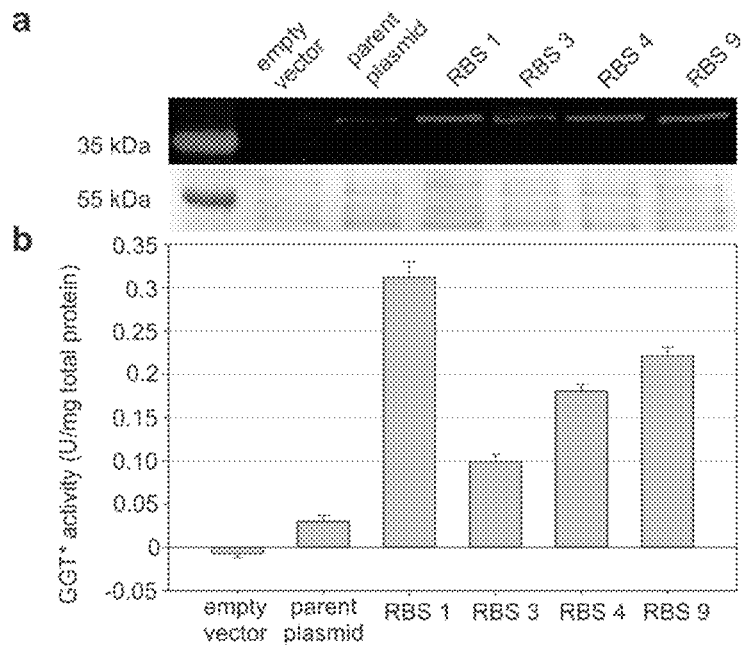

FIG. 24. Expression analysis of pPnGGT* RBS variants. (a) Western Blot with an antibody directed against the 6×His-tag at the N-terminus of the large subunit of PnGGT*. A fraction of an SDS gel loaded with the same samples is shown below to demonstrate loading of comparable protein amounts. (b) Quantification of PnGGT* levels in whole cell lysates with an enzyme assay using 2 mM of the substrate sulfobutanoyl-p-nitroanilide in 50 mM Tris/HCl (pH 7.0). Bars represent the average of three independent measurements with standard deviations shown as error bars.

Figure 25:
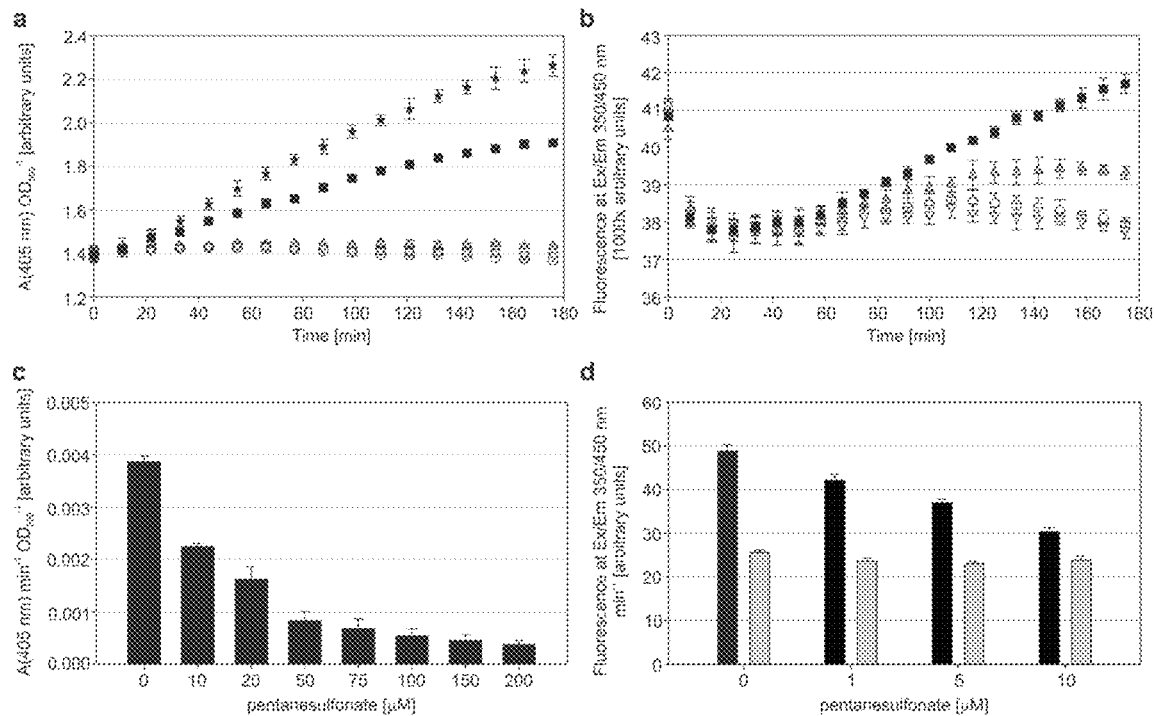

FIG. 25. Import of non-natural cargo molecules. Strain TK082 transformed with different plasmids was induced with 0.5 mM IPTG and 100 ng $ml^{-1}$ aTc for 2 hours before the addition of 0.5 mM sulfobutanoyl-p-nitroanilide (a) or 0.5 mM sulfobutanoyl-AMC (b). The release of 4-nitroaniline was monitored at 405 nm and normalized by $OD_{600}$. The release of AMC was monitored at λex=350 nm and λem=450 nm. White circles: pSEVA271 (empty parent plasmid of pSsuABC)+pACT3 (empty parent plasmid of pPnGGT*). Light grey inverted triangles: pSsuABC+pACT3. Dark grey triangles: pSEVA271+pPnGGT*. Black squares: pSsuABC+pPnGGT*. Black stars: pSsuABC+pPnGGT*_RBS4. (c) Release of 4-nitroaniline from 0.5 mM sulfobutanoyl-p-nitroanilide in the presence of different concentrations of pentanesulfonate in strain TK082[pSsuABC, pPnGGT*]. (d) Release of AMC from 0.5 mM sulfobutanoyl-AMC in the presence of different concentrations of pentanesulfonate in strain TK082[pSsuABC, pPnGGT*] (black bars) or TK082 [pSEVA271, pPnGGT*] (grey bars). Bars and curves represent the average of three independent measurements with standard deviations shown as error bars. Bars and dots from all panels represent the average of three independent measurements with standard deviations shown as error bars.

Figure 26:
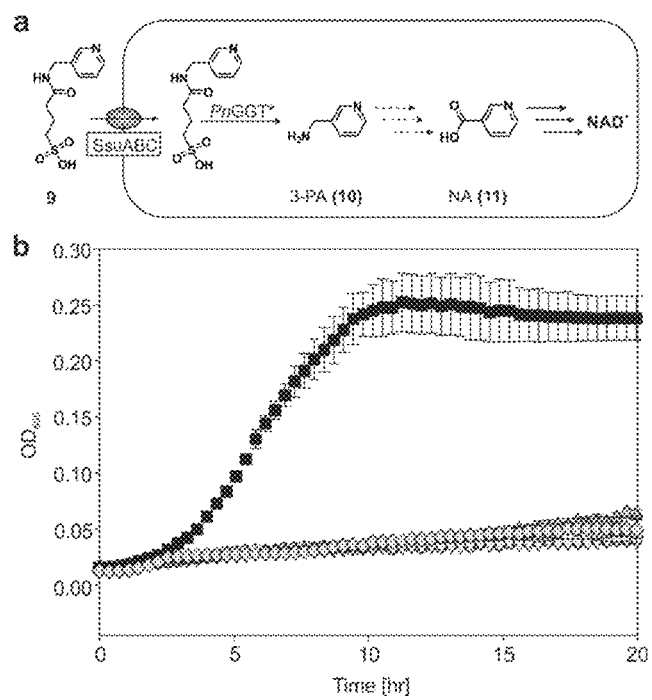

FIG. 26. Identification of a novel synthesis route towards nicotinic acid. (a) N-picolyl-sulfobutyramide (9) is taken up by the cell through the sulfonate transporter SsuABC and its cargo 3-picolylamine (10) is released inside the cell by PnGGT*. Via a so far unidentified pathway, 3-picolylamine is converted to nicotinic acid (11), which is then further converted to $NAD^+$ via the $NAD^+$ salvage pathway. (b) Growth of strain TK090 transformed with different plasmid combinations in spent MS minimal medium supplemented with 0.5% glucose, 1 mM $MgSO_4$, 0.4 mM L-leucine, 0.5 mM IPTG, 100 ng $ml^{-1}$ aTc and 25 µM N-picolyl-sulfobutyramide. White circles: pSEVA271+pACT3. Light grey inverted triangles: pSsuABC+pACT3. Dark grey triangles: pSEVA271+pPnGGT*. Black squares: pSsuABC+pPnGGT*. As a control, strain TK090[pSsuABC, pPnGGT*] was grown in MS minimal medium supplemented with 0.5% glucose, 1 mM $MgSO_4$, 0.4 mM L-leucine, 0.5 mM IPTG, 100 ng $ml^{-1}$ aTc and 50 µM 3-picolylamine (light blue diamonds). Dots represent the average of three independent measurements with standard deviations shown as error bars.

Figure 27:
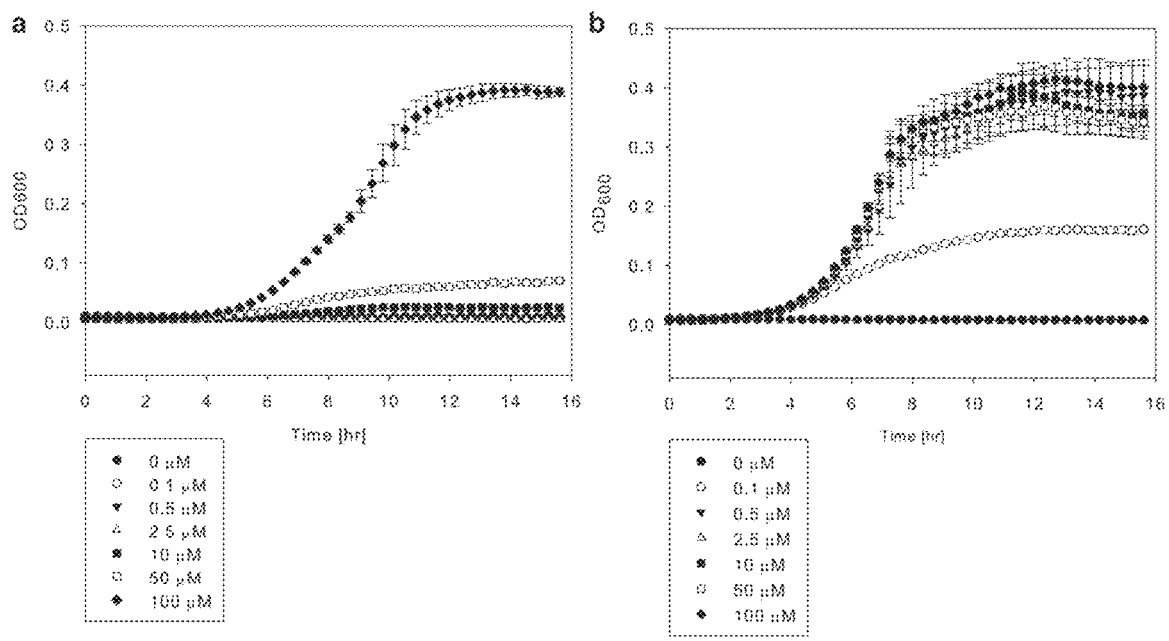

FIG. 27. Utilization of $NAD^+$ precursors. $NAD^+$ auxotrophic strain TK090 [pSsuABC; pPnGGT*] was grown in MS minimal medium containing 0.5% glucose, 1 mM $MgSO_4$, 0.4 mM leucine, 0.5 mM IPTG, 100 ng $ml^{-1}$ aTc and varying concentrations of either 3-picolylamine (a) or nicotinic acid (b). 3-picolylamine can only be efficiently used as NAD+ source by this strain if concentrations above 50 µM are added to the medium. On the other hand, sub-micromolar concentrations of nicotinic acid were sufficient to support growth of this strain. Dots represent the average of three independent measurements with standard deviations shown as error bars.

Figure 28:
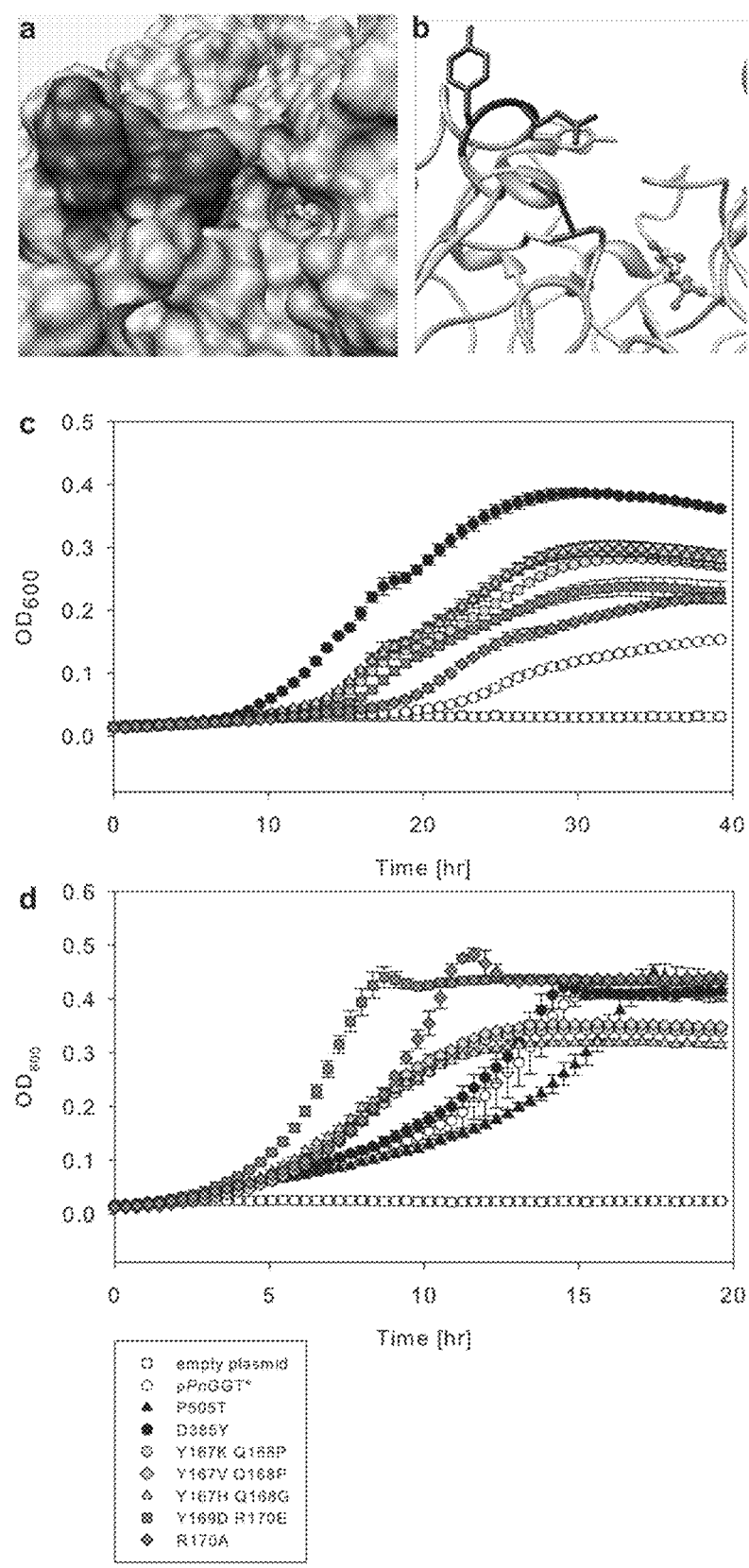

FIG. 28. Engineering of PnGGT*. (a) Surface of the substrate entry site of the PnGGT* homology model bound to SBA. The sulfobutanoyl-moiety is tightly bound in the substrate binding pocket of PnGGT*. Potential cargo molecules would be attached to the carboxyl group located at the exit site of the substrate binding pocket and be accommodated in a wider pocket. The surfaces of residues D385, Y167, Q168, Y169 and R170 are highlighted in dark grey. (b) The side chains of residues D385 (black), Y167 Q168 (light grey) and Y169 R170 (dark grey) lie in close spatial proximity to each other. (c) Growth assay with the leucine auxotrophic strain TK082[pSsuABC] transformed with the empty plasmid pACT3 (empty squares), the parent plasmid pPnGGT* (empty circles) or plasmids encoding the PnGGT*mutant variants P505T (black triangles), D385Y (black circles), Y167K Q168P (light grey circles), Y167V Q168P (light grey diamonds), Y167H Q168G (light grey triangles), Y169D R170E (dark grey squares) and R170A (dark grey diamonds) in MS minimal medium supplemented with 0.5% glucose, 1 mM MgSO$_4$, 0.5 mM IPTG, 100 ng ml$^{-1}$ aTc and 0.25 mM sulfobutanoyl-L-leucine as sole leucine source. (d) Similar growth assay with the histidine auxotrophic strain TK088[pSsuABC] in MS minimal medium supplemented with 0.5% glucose, 1 mM MgSO$_4$, 0.4 mM L-leucine, 0.5 mM IPTG, 100 ng ml$^{-1}$ aTc and 0.1 mM sulfobutanoyl-L-histidine as sole histidine source. Symbols from panels (c) and (d) represent the average of three independent measurements with standard deviations shown as error bars.

FIG. 29. Expression analysis of selected PnGGT* mutant variants. Strain TK018 was transformed with the empty vector pACT3, the parent plasmid pPnGGT* or selected mutant variants thereof and grown in LB medium to early exponential phase. Synthesis of the PnGGT* variants was induced for 4 hours by adding 0.5 mM IPTG to the culture. (a) GGT* activity assays with cell free extracts and 2 mM of the substrate sulfobutanoyl-p-nitroanilide. Of the selected mutants, only the P505T variant showed elevated activity towards sulfobutanoyl-p-nitroanilide. All other mutants had significantly reduced activity towards the substrate. Bars represent the average of three independent measurements with standard deviations shown as error bars. (b) SDS-PAGE of cell free extracts to confirm loading of similar protein amounts. (c) Western Blot of cell free extracts with an antibody directed against the large subunit of PnGGT* (38.5 kDa). Mutant variants Y167V Q168P and Y167H Q168G were synthesized slightly less efficiently than PnGGT*. All other mutant variants were synthesized with similar efficiency as PnGGT*.

FIG. 30. Multiple protein sequence alignment of Pseudomonas GGTs. Multiple protein sequence alignment of Pseudomonas nitroreducens GGT (position 480-539; accession number: BAJ16340.1) with GGT variants from Pseudomonas denitrificans (WP_015475590.1), Pseudomonas aeruginosa (WP_033895654.1), Pseudomonas putida (KTK91918.1), Pseudomonas syringae (WP_065832597.1) and Pseudomonas fluorescens (AGE09376.1). The sequences were downloaded on 4 Apr. 2017 and the alignment was created with Clustal Omega (Sievers et al., 2011).

FIG. 31. Sulfobutanoyl-p-nitroanilide hydrolysis kinetics of PnGGT* P505T. The kinetic parameters of PnGGT* P505T were determined in 50 mM Tris/HCl (pH 7.0) with the substrate sulfobutanoyl-p-nitroanilide added to the following concentrations: 50, 100, 250, 500, 750, 1000, 1500 and 2000 µM. The determined kinetic parameters of PnGGT* revealed a 27% lower K, an 8% improvement of $k_{cat}$ and a 39% improvement of catalytic efficiency ($k_{cat}/K_M$) over PnGGT*. Fitting of the kinetic data was performed with SigmaPlot v.12.2. Dots represent the average of three independent measurements with standard deviations shown as error bars.

Figure 32:
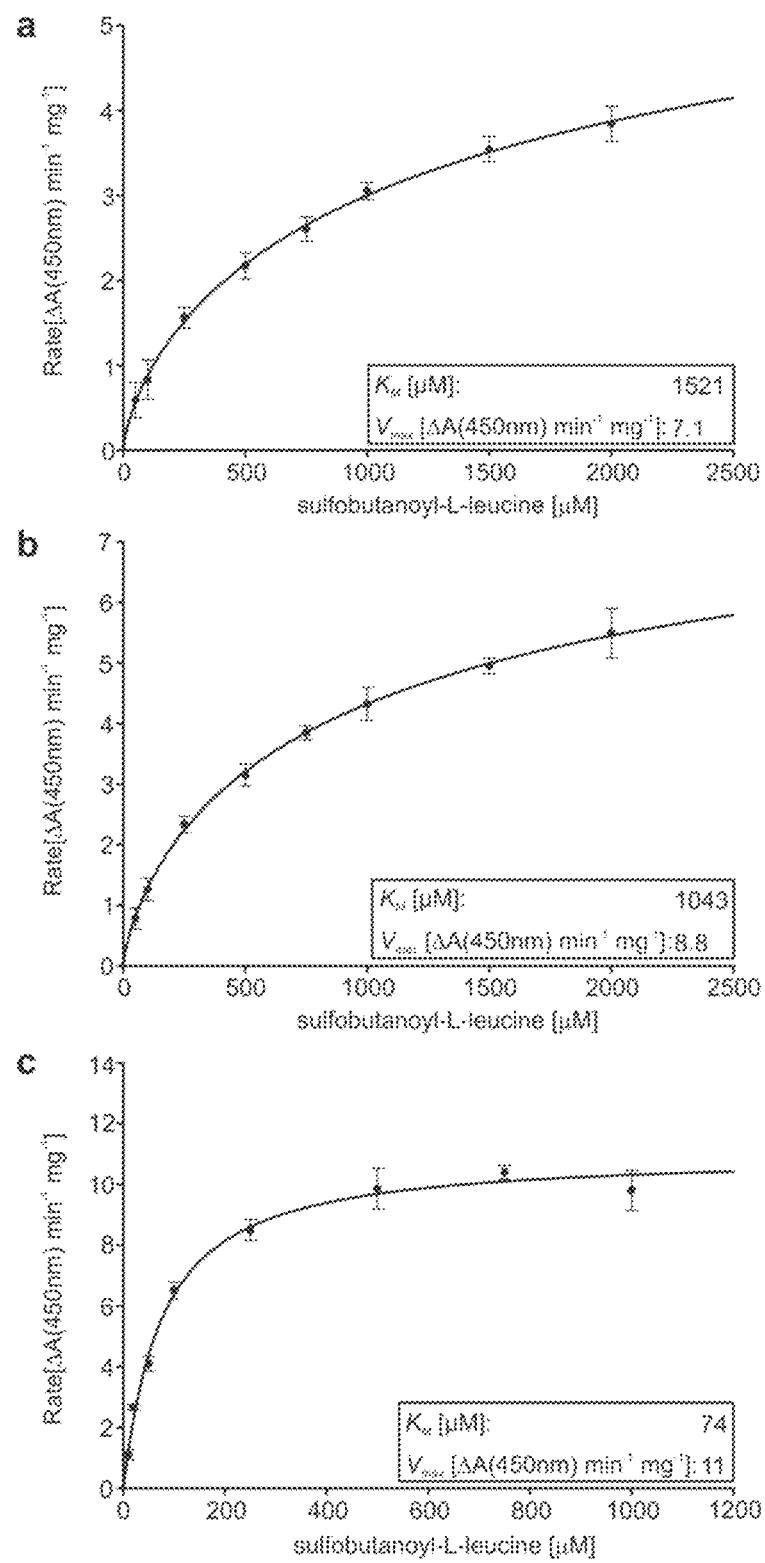

FIG. 32. Sulfobutanoyl-L-leucine hydrolysis kinetics of PnGGT* variants. To determine the kinetic parameters of PnGGT* with sulfobutanoyl-L-leucine, the reaction was coupled directly to a branched-chain amino acid kit to measure the release of leucine. Due to the unknown composition of the kit, absolute quantification of leucine was not possible and the results relating to reaction rates are plotted as changes in absorbance over time. (a) Kinetics of PnGGT* were determined in 50 mM Tris/HCl (pH 7.0) with 50, 100, 250, 500, 750, 1000, 1500 and 2000 µM sulfobutanoyl-L-leucine. The determined K value of 1521 µM was approximately three times higher than the K value determined with the substrate sulfobutanoyl-p-nitroanilide. While we cannot fully exclude that this is a consequence of the different assay conditions, we consider this unlikely due to the known insensitivity of the $K_M$ value to a broad range of experimental conditions. Therefore, we attribute this increase to a generally lower affinity of PnGGT* for the substrate sulfobutanoyl-L-leucine. (b) Kinetics of PnGGT* P505T were determined with the same substrate concentrations and buffer as for PnGGT*. For this variant a 46% reduction in $K_M$ and a 27% increase in $V_{max}$ in comparison to PnGGT* were measured, which corresponds well with the kinetic measurements of PnGGT* and PnGGT* P505T with the substrate sulfobutanoyl-p-nitroanilide (see Supplementary FIG. 9) and indicates the validity of the coupled enzyme assay. (c) Kinetics of PnGGT D385Y were determined in 50 mM Tris/HCl (pH 7.0) with 10, 20, 50, 100, 250, 500, 750 and 1000 µM sulfobutanoyl-L-leucine. For this variant a more than 20-fold reduced $K_M$ value was measured compared to PnGGT* which explains the extraordinary growth properties of strains expressing this variant at low sulfobutanoyl-L-leucine concentrations. At the same time, this variant had a 1.55-fold improved $V_{max}$ over PnGGT*. Fitting of the kinetic data was performed with SigmaPlot v.12.2. Dots represent the average of three independent measurements with standard deviations shown as error bars.

Figure 33:
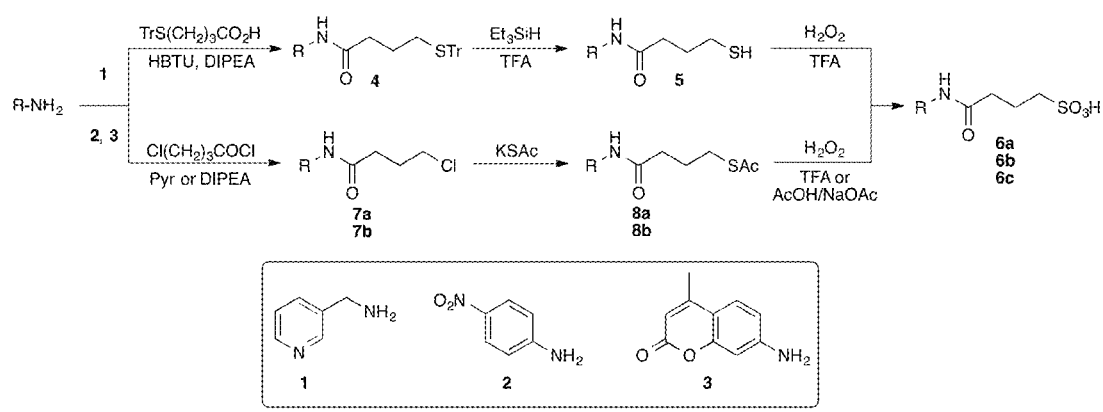

FIG. 33. Schematic illustration of the synthesis of sulfobutyramide analogues.

The invention will now be described by reference to the following examples which are merely illustrative and are not to be construed as a limitation of the scope of the present invention.

EXAMPLES

1. Materials and Methods 1.1 Strains and Media

A list of all bacterial strains used in this study is provided in Table 1. For cloning purposes E. coli strains Top10 or DH5a λpir were used. Growth experiments in selective medium were carried out in the leucine auxotrophic strains TK054 or TK054 ΔpcnB. For the construction of TK054, the genes ggt, leuB and brnQ were replaced with disrupted versions by P1 phage transduction using respective donor strains from the KEIO collection (Baba et al., 2006; Thomason et al., 2007). The livFGHMK operon was inactivated by λred recombination with a PCR fragment containing a kanamycin resistance gene amplified from pKD13 with the primers TK140 and TK141 (Datsenko and Wanner, 2000). To subsequently remove the kanamycin resistance gene, plasmid pCP20 was used (Cherepanov and Wackernagel, 1995). The gene pcnB was deleted by plasmid-based gene replacement (Martinez-Garcia and de Lorenzo, 2011; Martinez-Garcia and de Lorenzo, 2012). For this, 500 bp fragments upstream and downstream of pcnB (TS1 and TS2) were amplified, combined by PCR and cloned into plasmid pEMG via EcoRI and BamHI restriction sites. To integrate 6×His_PnGGT ΔN24 into the chromosome, the N-terminally tagged 6×His_PnGGT ΔN24 gene together with its promoter and the chloramphenicol resistance gene was amplified with the primers TK417 and TK418 using the plasmid as template. The PCR product was recombined with the E. coli chromosome in the intergenic region between yrhB and yhhA assisted by the λred genes expressed from pKD46 (Datsenko and Wanner, 2000).

For the experiments relating to the sulfonate based synthetic transport system, growth experiments in selective medium were carried out in the leucine auxotrophic strains BW25113 ΔleuB, BW25113 ΔleuB ΔssuEADCB or BS25113 ΔleuB ΔssuD. For the deletion of leuB and ssuD, the genes were replaced with disrupted versions by P1 phage transduction using respective donor strains from the KEIO collection (Baba et al., 2006; Thomason et al., 2007). The ssuEADCB operon was deleted by plasmid-based gene replacement (Martinez-Garcia and de Lorenzo, 2011; Martinez-Garcia and de Lorenzo, 2012). For this, 500 bp fragments upstream and downstream of the operon (TS1 and TS2) were amplified, combined by PCR and cloned into plasmid pEMG via EcoRI and BamHI restriction sites.

Additional growth experiments were carried out in the strains BW25113 ΔleuB ΔssuEADCB ΔtauD, BW25113 ΔleuB ΔssuEADCB ΔtauD ΔhisB and BW25113 ΔleuB ΔssuEADCB ΔtauD ΔnadAB. The genes hisB, nadA and tauD were replaced with disrupted versions by P1 phage transduction using respective donor strains from the KEIO collection (Baba et al., 2006; Thomason et al., 2007). The gene nadB was deleted by plasmid-based gene replacement (Martinez-Garcia and de Lorenzo, 2011; Martinez-Garcia and de Lorenzo, 2012). Flanking fragments were amplified with the primer pairs TK656/TK657 and TK658/TK659, combined via PCR using primers TK656/TK659 and cloned into pEMG via EcoRI and BamHI, yielding plasmid pEMG_nadB.

TABLE 1

Strains used in this study

| E. coli strain | Description | Reference |
|---|---|---|
| Top10 | F⁻ mcrA Δ(mrr hsdRMS⁻mcrBC) φ80lacZΔM15 ΔlacX74 nupG recA1 araD139 Δ(ara-leu)7697 galE15 galK16 rpsL(Str$^R$) endA1 λ⁻ | Life Technologies, Carlsbad, CA, USA |
| DH5α λpir | supE44, ΔacU169, (φ80 lacZDM15), hsdR17, (rk⁻ mk⁺), recA1, endA1, thi1, gyrA, relA, lysogenic λpir | (Platt et al., 2000) |
| JM101 | glnV44 thi- 1 Δ(lac-proAB) F'[lacI$^q$ZΔM15 traD36 proAB⁺] | (Messing et al., 1981; Yanisch-Perron et al., 1985) |
| BW25113 | F-, Δ(araD-araB)567, ΔlacZ4787(::rrnB-3), λ⁻, rph-1, Δ(rhaD-rhaB)568, hsdR514 | Yale, CGSG (Datsenko and Wanner, 2000) |
| JW3412 | BW25113 ggt::kan | Yale, CGSC (Baba et al., 2006) |
| JW5807 | BW25113 leuB::kan | Yale, CGSC (Baba et al., 2006) |
| JW0391 | BW25113 brnQ::kan | Yale, CGSC (Baba et al., 2006) |
| TK054 | JM101 ΔleuB Δggt Δliv ΔbrnQ | This study |
| TK054 ggt int | TK054 with 6xHis_PnGGT ΔN24 plasmid integrated in yrhB-yhhA intergenic region | This study |
| TK054 ΔpcnB | JM101 ΔleuB Δggt Δliv ΔbrnQ ΔpcnB | This study |
| TK054 ΔpcnB ggt int | TK054 ΔpcnB with 6xHis_PnGGT ΔN24 plasmid integrated in yrhB-yhhA intergenic region | This study |
| BW25113 ΔleuB | BW25113 ΔleuB | This study |
| BW25113 ΔleuB ΔssuEADCB | BW25113 ΔleuB ΔssuEADCB | This study |
| BW25113 ΔleuB ΔssuD | BW25113 ΔleuB ΔssuD | This study |
| JW0360 | BW25113 tauD::kan | Yale, CGSC (Baba et al., 2006) |
| JW0733 | BW25113 nadA::kan | Yale, CGSC (Baba et al., 2006) |
| JW2004 | BW25113 hisB::kan | Yale, CGSC (Baba et al., 2006) |
| TK018 | JM101 Δggt | This study |
| TK082 | BW25113 ΔleuB ΔssuEADBC ΔtauD | This study |
| TK088 | BW25113 ΔleuB ΔssuEADBC ΔtauD ΔhisB | This study |
| TK090 | BW25113 ΔleuB ΔssuEADBC ΔtauD ΔnadA ΔnadB | This study |

LB Miller broth (Becton Dickinson, Sparks, Md., USA) was used as standard growth medium for bacterial cultures (Sambrook, 2001). For the preparation of competent cells, SOB medium was used (Hanahan, 1983). Unless stated otherwise, growth experiments in selective medium were carried out in M9 minimal medium (Sambrook, 2001) supplemented with 0.5% glucose, 1 μg mL$^{-1}$ thiamine, 0.5 mM IPTG and 1 mM alanyl-γ-glutamyl-leucine (>95% purity, custom synthesized by Pepscan, Lelystad, Netherlands). For growth experiments on solid medium Bacto Agar (Becton Dickinson) was added to a final concentration of 1.5%. Growth experiments in liquid medium were performed either in a Tecan Infinite 200 Pro plate reader (Tecan, Mannedorf, Switzerland) or in a Biolector Basic Microbiorector System (m2p-labs, Baesweiler, Germany). All growth experiments were performed at 37° C. For selection purposes, antibiotics were added to the following concentrations: kanamycin (50 µg mL$^{-1}$); chloramphenicol (34 µg mL$^{-1}$); carbenicillin (100 µg mL$^{-1}$); gentamycin (10 µg mL$^{-1}$).

For the experiments relating to the sulfonate based synthetic transport system, unless stated otherwise, growth experiments in selective medium were carried out in sulfur free MS minimal medium (4 mM citric acid, 1 mM MgCl$_2$, 20 mM NH$_4$Cl, 50 mM KH$_2$PO$_4$ and 1×NTA mix (10 µM nitrilotriacetic acid, 3 µM CaCl$_2$, 3 µM FeCl$_3$, 1 µM MnCl$_2$, 0.3 µM ZnCl$_2$, 0.3 µM H$_3$B$_3$, 0.3 µM CrC$_3$, 0.3 µM COCl$_2$, 0.3 µM CuCl$_2$, 0.3 µM Ni$_2$C, 0.3 µM Na$_2$MoO$_4$, 0.3 µM Na$_2$SeO$_3$)) supplemented with 0.5% glucose. MgSO$_4$ (1 mM), MgCl$_2$ (1 mM), L-leucine (0.4 mM), IPTG (0.5 mM), aTc (100 ng mL-1), nicotinic acid (various concentrations), 3-picolylamine (various concentrations) and sulfonates (various concentrations) as indicated in the text. Sulfobutanoyl-L-leucine (>98% purity) and sulfobutanoyl-L-histidine (>90% purity) were custom synthesized by Pepscan, (Lelystad, Netherlands). Synthesis schemes for sulfobutanoyl-p-nitroanilide and other sulfonates are given below.

1.2 DNA Constructs

The *Pseudomonas nitroreducens* PnGGT coding sequence (GenBank entry AB548627.1) was chemically synthesized (Thermo Fisher Scientific, Regensburg, Germany). The *E. coli* EcGGT gene was amplified from genomic DNA of strain JM101. For PCR amplification of DNA Phusion High Fidelity DNA Polymerase (New England BioLabs, Ipswich, Mass., USA) was used. To construct truncated variants of EcGGT and PnGGT, the length of the signal peptide was first predicted using the SignalP 4.0 algorithm (Petersen et al., 2011). Then, alternative forward primers were used to remove the first 16 or 24 amino acids. All plasmids were constructed by conventional cloning using restriction enzymes and Quick Ligation Kit (both New England BioLabs). All DNA constructs were verified by Sanger sequencing (Microsynth, Balgach, Switzerland) and are summarized in Table 2.

For the experiments relating to the sulfonate based synthetic transport system, D to N mutations in EcGGT and PnGGT were introduced by PCR using primer pairs TK269/TK270 and TK275/TK276, respectively (Wang and Malcolm, 1999). Mutations in PnGGT* were introduced using the same method, but with template pPnGGT* and primer pairs TK595/TK596 (R94X), TK603/TK604 (T381X N383X), TK599/TK600 (E402X D405X), TK593/TK594 (F416X), TK601/TK602 (S434X S435), TK605/TK606 (G455X G456X), TK640/TK641 (D385X), TK642/TK643 (R170X) and TK644/TK645 (Y167X Q168X). Ribosome binding site libraries of pPnGGT* were prepared as described previously using primer pair TK534/TK535 (Kuenzl et al., 2017). All constructs used in this study are listed in Table 2. Oligonucleotides are listed in Table 3.

TABLE 2

Plasmids used in this study

| Plasmid | Description | Reference |
|---|---|---|
| pACT3 | Expression vector; pLlacO1; p15A ori; Cm$^R$, lacI$^q$ | (Dykxhoorn et al., 1996) |
| pSEVA271 | MCS; pSC101 ori, Kan$^R$ | (Martinez-Garcia et al., 2015) |
| pKD46 | λ Red recombination genes; araBp-gam-bet-exo; repA101 (ts); oriR101; Ap$^R$ | (Datsenko and Wanner, 2000) |
| pKD13 | FRT-Kan$^R$-FRT; oriR6K; Ap$^R$ | (Datsenko and Wanner, 2000) |
| pCP20 | yeast Flp recombinase gene; λ p$_R$ Rep$^{ts}$, Ap$^R$, Cm$^R$ | (Cherepanov and Wackernagel, 1995) |
| pEMG | Delivery vector for scarless deletion; oriR6K; lacZα with two flanking I-SceI sites; Kan$^R$ | (Martinez-Garcia and de Lorenzo, 2011) |
| pParaI-SceI | I-SceI gene under control of L-arabinose inducible promoter; p15A ori, Gm$^R$ | (Billerbeck and Panke, 2012) |
| pACT3/6xHis_EcGGT | EcGGT gene with N-terminal MRGSHHHHHHGSAC (SEQ ID NO: 32) sequence cloned in pACT3 | This study |
| pACT3/EcGGT_6xHis | EcGGT gene with C-terminal LEHHHHHH (SEQ ID NO: 33) sequence cloned in pACT3 | This study |
| pACT3/6xHis_EcGGT ΔN16 | EcGGT ΔN16 gene with N-terminal MRGSHHHHHHGSACEL (SEQ ID NO: 34) sequence cloned in pACT3 | This study |
| pACT3/6xHis_EcGGT ΔN24 (pEcGGT) | EcGGT ΔN24 gene with N-terminal MRGSHHHHHHGSACEL (SEQ ID NO: 35) sequence cloned in pACT3 | This study |
| pACT3/6xHis_PnGGT | PnGGT gene with N-terminal MRGSHHHHHHGSAC (SEQ ID NO: 36) sequence cloned in pACT3 | This study |
| pACT3/6xHis_PnGGT ΔN16 | PnGGT ΔN16 gene with N-terminal MRGSHHHHHHGSACEL (SEQ ID NO: 37) sequence cloned in pACT3 | This study |
| pACT3/6xHis_PnGGT ΔN24 (pPnGGT) | PnGGT ΔN24 gene with N-terminal MRGSHHHHHHGSACEL (SEQ ID NO: 38) sequence cloned in pACT3 | This study |
| pACT3/6xHis_PnGGT ΔN24 RBS 1 | 6xHis_PnGGT ΔN24 with standard RBS replaced by RBS mutant 1 | This study |
| pACT3/6xHis_PnGGT ΔN24 RBS 3 | 6xHis_PnGGT ΔN24 with standard RBS replaced by RBS mutant 3 | This study |
| pACT3/6xHis_PnGGT ΔN24 RBS 4 | 6xHis_PnGGT ΔN24 with standard RBS replaced by RBS mutant 4 | This study |
| pACT3/6xHis_PnGGT ΔN24 RBS 12 | 6xHis_PnGGT ΔN24 with standard RBS replaced by RBS mutant 12 | This study |
| pACT3/6xHis_PnGGT ΔN24 RBS 23 | 6xHis_PnGGT ΔN24 with standard RBS replaced by RBS mutant 23 | This study |
| pEMG-pcnB | pEMG bearing a 1.0 kb TS1-TS2 EcoRI-BamHI insert for deleting pcnB | This study |
| pACT3/EcGGT_ΔN24_D433N | EcGGT ΔN24 D433N gene with N-terminal MRGSHHHHHHGSACEL sequence cloned in pACT3 | This study |

TABLE 2-continued

Plasmids used in this study

| Plasmid | Description | Reference |
|---|---|---|
| pACT3/PnGGT_ΔN24_D405N | PnGGT ΔN24 D405N gene with N-terminal MRGSHHHHHHGSACEL sequence cloned in pACT3 | This study |
| pEMG-ssu | pEMG bearing a 1.0 kb TS1-TS2 EcoRI-BamHI insert for deleting ssu | This study |
| pAB92 | pSEVA vector backbone; MCS; pBR322 ori, Amp$^R$; $P_{tet}$-$P_{T7}$ fusion promoter | Bosshart et al., 2015) |
| pSEVA271_$P_{tet}$ | $P_{tet}$-$P_{T7}$; MCS; pSC101 ori, Kan$^R$ | This study |
| pEMG_ssuEADCB | pEMG bearing a 1.0 kb TS1-TS2 EcoRI-BamHI insert for deleting ssuEADCB | This study |
| pEMG_nadB | pEMG bearing a 1.0 kb TS1-TS2 EcoRI-BamHI insert for deleting nadB | This study |
| pEcGGT_D433N | pEcGGT with D433N mutation in ggt gene | This study |
| pPnGGT* (pPnGGT_D405N) | pPnGGT with D405N mutation in ggt gene | This study |
| pSsuABC | pSEVA271 backbone with $P_{tet}$-$P_{T7}$ fusion promoter from pAB92 and refactored ssuABC operon | This study |
| pPnGGT*_RBS1 | pPnGGT* with RBS sequence replaced by CCAGGGGG | This study |
| pPnGGT*_RBS3 | pPnGGT* with RBS sequence replaced by CGCGGGGG | This study |
| pPnGGT*_RBS4 | pPnGGT* with RBS sequence replaced by AGGGGGGG | This study |
| pPnGGT*_RBS9 | pPnGGT* with RBS sequence replaced by TACGGGGG | This study |
| pPnGGT*_D385Y | pPnGGT* with D385Y mutation in ggt gene | This study |
| pPnGGT*_P505T | pPnGGT* with P505T mutation in ggt gene | This study |
| pPnGGT*_Y167V_Q168P | pPnGGT* with Y167V and Q168P mutation in ggt gene | This study |
| pPnGGT*_Y167H_Q168G | pPnGGT* with Y167H and Q168G mutation in ggt gene | This study |
| pPnGGT*_Y169D_R170E | pPnGGT* with Y169D and R170E mutation in ggt gene | This study |
| pPnGGT*_R170A | pPnGGT* with R170A mutation in ggt gene | This study |

1.3 Protein Expression and Purification

For the expression of GGT variants, cells were grown to an approximate OD$_{600}$ of 0.5 and induced with 0.5 mM IPTG. After 20 hours expression at 20° C., cells were harvested and lysed in lysis buffer (50 mM NaH$_2$PO$_4$, 300 mM NaCl, 10 mM imidazole, 1 mg mL$^{-1}$ lysozyme, pH 8.0) for 30 minutes on ice. After a freeze/thaw cycle, samples were centrifuged and the supernatant containing the soluble protein fraction was collected. Purification of 6×His_EcGGT ΔN24 and 6×His_PnGGT ΔN24 was performed according to previous reports (Van Dyke et al., 1992) using Ni-NTA Superflow (Qiagen, Hilden, Germany). For fractionation of E. coli cells into periplasmic and cytoplasmic fraction PeriPreps Periplasting Kit (Epicentre, Madison, Wis., USA) was used according to the instructions of the manufacturers. Purity of the fractions was analyzed by measuring the activities of the enzymes alkaline phosphatase (providing 5 mM 4-methylumbelliferyl-phosphate as the substrate, 50 mM Tris/HCl pH 10.0 as the buffer for the reaction, 5 μL sample in 250 μL of total volume) and β-glucoronidase (5 mM 4-methylumbelliferyl-β-D-glucuronide, 50 mM Tris/HCl pH 7.5, 5 μL sample in 250 μL of total volume). In both cases, release of the fluorescent product 4-methylumbelliferone was measured using an excitation wavelength of 360 nm and emission wavelength of 449 nm.

Cell extracts and purified GGT variants were analyzed by SDS-PAGE as previously reported (Laemmli, 1970). For cell extracts, 10-20 μg of protein was loaded per well. For western blots, proteins were transferred to an Amersham Protran 0.45 nitrocellulose membrane (GE Healthcare, Little Chalfont, UK) using a Mini Trans-Blot Electrophoretic Transfer Cell (Bio-Rad, Hercules, Calif., USA) (Towbin et al., 1979). GGT variants fused to a 6×His-tag were detected using a primary mouse anti-His Tag antibody (GenScript, Piscataway, N.J., USA) and fluorescence labeled secondary IRDye 800CW Goat anti-Mouse IgG or IRDye 680RD Goat anti-Mouse IgG antibodies (LI-COR, Lincoln, Nebr., USA).

For the experiments relating to the sulfonate based synthetic transport system, purification of PnGGT ΔN24 and PnGGT ΔN24 D405N containing an N-terminal 6×His-tag was performed according to previous reports (Van Dyke et al., 1992) using Ni-NTA Superflow (Qiagen, Hilden, Germany). For kinetic studies, PnGGT variants were purified with the aid of the 6×His-tag located at the N-terminal end of the large subunit following the same procedure. To exchange the buffer, purified proteins were dialyzed against 50 mM Tris/HCl (pH 7.0).

1.4 Enzymatic GGT Assay

Determination of GGT activity was performed as described previously with slight modifications (Orlowski and Meister, 1970; Suzuki et al., 1986). For better solubility, the substrate L-glutamic acid γ-(3-carboxy-4-nitroanilide) (Sigma-Aldrich, St. Louis, Mo., USA) was used and added to a final concentration of 4 mM to start the reaction. To determine transpeptidase activity, 20 mM glycyl-glycine (Sigma-Aldrich) was added to the reaction. For determination of hydrolase activity, glycyl-glycine was omitted. As reaction buffer 50 mM Tris-HCl (pH 9.0) was used. To determine enzyme kinetics, absorption at 410 nm was constantly measured at 37° C. in a Tecan Infinite 200 Pro plate reader (Tecan). One unit is defined as the amount of enzyme required to catalyze the formation of 1 μmol of 3-carboxy-4-nitroaniline per minute.

For the experiments relating to the sulfonate based synthetic transport system, to determine the activity in whole cell lysates in 50 mM Tris-HCl (pH 9.0) the substrates L-glutamic acid γ-(3-carboxy-4-nitroanilide) (Sigma-Aldrich, St. Louis, Mo., USA) or sulfobutanoyl-p-nitroanilide were added to a final concentration of 4 mM to start the reaction. To determine enzyme activity, absorption at 410 nm was constantly measured at 37° C. in a Tecan Infinite 200 Pro plate reader (Tecan, Mannedorf, Switzerland). One unit is defined as the amount of enzyme required to catalyze the formation of 1 μmol of 3-carboxy-4-nitroaniline or 4-nitroaniline per minute.

To determine the kinetic parameters of PnGGT ΔN24 and PnGGT ΔN24 D405N the purified enzymes were preincubated in 50 mM Tris-HCl (pH 9.0). To start the reaction, varying concentrations of the substrates L-glutamic acid γ-(3-carboxy-4-nitroanilide) or sulfobutanoyl-p-nitroanilide were added to the mixtures. The results were evaluated using GraphPad Prism (GraphPad Software, La Jolla, Calif., USA).

1.5 Generation of RedLibs RBS Library

To generate the reduced ribosome binding site (RBS) library, first an initial RBS library using RBS calculator version 1.1 was generated (Espah Borujeni et al., 2014; Salis et al., 2009). For this, the RBS sequence of pACT3/6× His_PnGGT ΔN24 was randomized from position −8 to −15 (relative to the ATG start codon) with the degenerated base N, resulting in a library containing a total number of 65,536 sequences. To remove a large fraction of very weak or non-functional RBS sequences, we ran the RedLibs algorithm to reduce the library size to 81 variants (Jeschek et al., 2016). To introduce this library, the parent plasmid pACT3/6×His_PnGGT ΔN24 was amplified with primers TK534 and TK535, introducing the randomized RBS sequence (IUPAC nomenclature) HVVGGVGG (20 cycles, 61° C. (−0.2° C./cycle) annealing temperature, 8 minutes elongation time/cycle) (Wang and Malcolm, 1999). Subsequently, this PCR library was used to transform strain TK054 and plated on selective medium.

1.6 Genome Sequencing of Mutant Strains

Genomic DNA was isolated from the respective strains using High Pure PCR Template Preparation Kit (Roche Diagnostics, Basel, Switzerland). Libraries for sequencing were prepared using TruSeq DNA Sample Preparation Kit v2 (Illumina, San Diego, Calif., USA). The libraries were then purified using 0.7× Vol Agencourt AMPure XP beads (Beckman Coulter, Pasadena, Calif., USA) to exclude very short library fragments. Purified libraries were sequenced on the MiSeq (Illumina) PE 2×301 cycles using the 600-cycle v3 kit and converted to fastq files. For the alignment of reads the Bowtie 2 package was used (Langmead and Salzberg, 2012; Langmead et al., 2009). For analysis of sequences the deepSNV package (Gerstung et al., 2012; Gerstung et al., 2014) and Integrated Genome Viewer (Robinson et al., 2011; Thorvaldsdóttir et al., 2013) were used.

1.7 Oligonucleotides Used

Table 3 shows the oligonucleotides used. The restriction sites are underlined.

TABLE 3

| Primer | Sequence | Description |
|---|---|---|
| TK037 | ATAT<u>GAGCTC</u>AGGAGGATATACATATGAGAGGATCGCATCAC CATCACCATCACGGATCCGCATGCATAAAACCGACGTTTTTA CGCCGGG (SEQ ID NO: 12) | Forward primer for cloning of 6xHis_EcGGT (SacI) |
| TK040 | ATAT<u>GAGCTC</u>AGGAGGATATACATATGAGAGGATCGCATCAC CATCACCATCACGGATCCGCATGCGAACTCTCAGGAAGTTGT TTTAGCGCCGC (SEQ ID NO: 13) | Forward primer for cloning of 6xHis_EcGGT ΔN16 (SacI) |
| TK326 | ATAT<u>GAGCTC</u>AGGAGGATATACATATGAGAGGATCGCATCAC CATCACCATCACGGATCCGCATGCGAACTC GCCGCGCCTCCTG (SEQ ID NO: 14) | Forward primer for cloning of 6xHis_EcGGT ΔN24 (SacI) |
| TK038 | ATAT<u>CTGCAG</u>TCATCAGTACCCCGCCGTTAAATCATCCAC (SEQ ID NO: 15) | Reverse primer for cloning of 6xHis_EcGGT, 6xHis_EcGGT ΔN1S and 6xHis_EcGGT ΔN24 (PstI) |
| TK021 | ATAT<u>GAGCTC</u>AGGAGGATATACATATGATAAAACCGACGTTTT TACGCCGGG (SEQ ID NO: 16) | Forward primer for cloning of EcGGT_6xHis (SacI) |
| TK022 | ATAT<u>CTGCAG</u>TCATCAGTGGTGGTGGTGGTGCTCGAGGT ACCCCGCCGTTAAATCATCCACCG (SEQ ID NO: 17) | Reverse primer for cloning of EcGGT_6xHis (PstI) |
| TK053 | ATAT<u>GAGCTC</u>AGGAGGATATACATATGAGAGGATCGCATCAC CATCACCATCACGGATCCGCATGCATGCGCGTGTTCCACTTC AG (SEQ ID NO: 18) | Forward primer for cloning of 6xHis_PnGGT (SacI) |
| TK324 | ATAT<u>GAGCTC</u>AGGAGGATATACATATGAGAGGATCGCATCAC CATCACCATCACGGATCCGCATGCGAACTCGCGGCGAGTTC GTC (SEQ ID NO: 19) | Forward primer for cloning of 6xHis_PnGGT ΔN16 (SacI) |
| TK325 | ATAT<u>GAGCTC</u>AGGAGGATATACATATGAGAGGATCGCATCAC CATCACCATCACGGATCCGCATGCGAACTCACCCTCGACGG CG (SEQ ID NO: 20) | Forward primer for cloning of 6xHis_PnGGT ΔN24 (SacI) |
| TK054 | ATAT<u>CTGCAG</u>TCATCA GGGTTTGACCACCATCCCG (SEQ ID NO: 21) | Reverse primer for cloning of 6xHis_PnGGT, 6xHis_PnGGT ΔN1S and 6xHis_PnGGT ΔN24 |
| TK140 | AAAACAACATCACAACACACGTAATAACCAGAAGAATGGGGA TTCTCAGGGTGTAGGCTGGAGCTGCTTC (SEQ ID NO: 22) | Forward primer for amplification of liv operon knockout fragment from pKD13 |
| TK141 | TGTCACCTGTCTCAAAGGAGTCTTTTGACTCCCTATCAATCAA CGTGTTAATTCCGGGGATCCGTCGACC (SEQ ID NO: 23) | Reverse primer for amplification of liv operon knockout fragment from pKD13 |

TABLE 3-continued

| Primer | Sequence | Description |
|---|---|---|
| TK389 | ATATGAATTCGGTCACGCAATTTACTGACCAGC (SEQ ID NO: 24) | TS1F primer for scarless deletion of pcnB (EcoRI) |
| TK390 | GGACGACGAGTACGACGACGAGCGGCTAATCATAGCTCAGC (SEQ ID NO: 25) | TS1R primer for scarless deletion of pcnB |
| TK391 | GCTGAGCTATGATTAGCCGCTCGTCGTCGTACTCGTCGTCC (SEQ ID NO: 26) | TS2R primer for scarless deletion of pcnB |
| TK392 | TATAGGATCCGACGCAACATCTCCCCATCAGG (SEQ ID NO: 27) | TS2R primer for scarless deletion of pcnB (BamHI) |
| TK534 | CACACAGGAAACAGAATTCGAGCTHVVGGVGGTATACATATGAGAGGATCGCATCACC (SEQ ID NO: 28) | Forward primer for generation of pACT3/6xHis_PnGGT ΔN24 RBS library |
| TK535 | GGTGATGCGATCCTCTCATATGTATACCBCCBBDAGCTCGAATTCTGTTTCCTGTGTG (SEQ ID NO: 29) | Reverse primer for generation of pACT3/6xHis_PnGGT ΔN24 RBS library |
| TK417 | CGCGTATCCTCCTCTGAAGATATCCTTTAAGTTTACTCGCTTCCCGACAAAACGATGATTAATTCAGAGTTGTTGATACCGGGAAGCCCTG (SEQ ID NO: 30) | Forward primer for amplification of pACT3/6xHis_PnGGT ΔN24 for genome integration |
| TK418 | GAAATAAAAAAGGCTACCTTCGGCTTGCCCTGACAAAATAGCCCTCTTCCCACGAAGAGGGCCGCTAACCCAGAGCAAGAGATTACGCGCAG (SEQ ID NO: 31) | Reverse primer for amplification of pACT3/6xHis_PnGGT ΔN24 for genome integration |
| TK269 | AATAACCAGATGGATAATTTCTCCGCCAAACCGG (SEQ ID NO: 54) | Forward primer for introducing D433N mutation in EcGGT |
| TK270 | CCGGTTTGGCGGAGAAATTATCCATCTGGTTATT (SEQ ID NO: 55) | Reverse primer for introducing D433N mutation in EcGGT |
| TK275 | CGACGAGATGGATAACTTCAGCTCCAAGC (SEQ ID NO: 56) | Forward primer for introducing D405N mutation in PnGGT |
| TK276 | GCTTGGAGCTGAAGTTATCCATCTCGTCG (SEQ ID NO: 57) | Reverse primer for introducing D405N mutation in PnGGT |
| TK485 | ATATGAATTCTGGCACATCAATTTGCACGCC (SEQ ID NO: 58) | TS1F primer for scarless deletion of ssu (EcoRI) |
| TK486 | CCGAATGGCGGCAATAGCGCGGTCAGTCTGTCGGAGAGAC (SEQ ID NO: 59) | TS1R primer for scarless deletion of ssu |
| TK487 | GTCTCTCCGACAGACTGACCGCGCTATTGCCGCCATTCGG (SEQ ID NO: 60) | TS2R primer for scarless deletion of ssu |
| TK488 | TATAGGATCCGCTGGTGAGCAAGCAGTTCC (SEQ ID NO: 61) | TS2R primer for scarless deletion of ssu (BamHI) |
| TK593 | CGTGGCCAACGCCNNKGGCGTGGTGGGCAG (SEQ ID NO: 62) | Forward primer for randomization of residue F416 in PnGGT* |
| TK594 | CTGCCCACCACGCCMNNGGCGTTGGCCACG (SEQ ID NO: 63) | Reverse primer for randomization of residue F416 in PnGGT* |
| TK595 | GTACTTCCTCGACTACNNKGAGATCGCGCCGAAGG (SEQ ID NO: 64) | Forward primer for randomization of residue R94 in PnGGT* |
| TK596 | CCTTCGGCGCGATCTCMNNGTAGTCGAGGAAGTAC (SEQ ID NO: 65) | Reverse primer for randomization of residue R94 in PnGGT* |
| TK599 | GGCTTCCTGCTCAACGACNNKATGGATNNKTTCAGCTCCAAGCCGGGC (SEQ ID NO: 66) | Forward primer for randomization of residue E402 and D405 in PnGGT* |
| TK600 | GCCCGGCTTGGAGCTGAAMNNATCCATMNNGTCGTTGAGCAGGAAGCC (SEQ ID NO: 67) | Reverse primer for randomization of residue E402 and D405 in PnGGT* |

TABLE 3-continued

| Primer | Sequence | Description |
|---|---|---|
| TK601 | CGGGCAAGCGCATGCTCNNKNNKATGAGCCCGAGCATCGTC (SEQ ID NO: 68) | Forward primer for randomization of residue S434 and S435 in PnGGT* |
| TK602 | GACGATGCTCGGGCTCATMNNMNNGAGCATGCGCTTGCCCG (SEQ ID NO: 69) | Reverse primer for randomization of residue S434 and S435 in PnGGT* |
| TK603 | GCCGTCAGCAACACCTACNNKCTCNNKTGGGACTTCGGCAG CGGC (SEQ ID NO: 70) | Forward primer for randomization of residue T381 and N383 in PnGGT* |
| TK604 | GCCGCTGCCGAAGTCCCAMNNGAGMNNGTAGGTGTTGCTGA CGGC (SEQ ID NO: 71) | Reverse primer for randomization of residue T381 and N383 in PnGGT* |
| TK605 | GGTGCTGGGCACGCCCNNKNNKTCGCGGATCTTCACTTCG (SEQ ID NO: 72) | Forward primer for randomization of residue G455 and G456 in PnGGT* |
| TK606 | CGAAGTGAAGATCCGCGAMNNMNNGGGCGTGCCCAGCACC (SEQ ID NO: 73) | Reverse primer for randomization of residue G455 and G456 in PnGGT* |
| TK621 | CTATAGGGAGACCACAACGGTTTCCCTCTA AGGRGSHHAAAC ATGCGTAACATCATTAAACTGGCGC (SEQ ID NO: 74) | Forward primer for amplification of ssuA with an RBS library containing 32 variants and a 5' overhang for assembly with the pSEVA271_$P_{tet}$-$P_{T7}$ backbone |
| TK622 | TCATAATTGTTTTCCTTCCAGTTGAGTGG (SEQ ID NO: 75) | Reverse primer for amplification of ssuA |
| TK623 | CCCACTCAACTGGAAGGAAAACAATTATGA GGRGGWVBCGGA ATGAATACTGCTCGTCTGAACCAG (SEQ ID NO: 76) | Forward primer for amplification of ssuB with an RBS library containing 32 variants and a 5' overhang for assembly with ssuA |
| TK624 | TTACCCCTGTTTTCTCAGGCGAG (SEQ ID NO: 77) | Reverse primer for amplification of ssuB |
| TK625 | TCTGAAACTCGCCTGAGAAAACAGGGGTAA GGAGGDDNAAGG ATGGCAACGCCAGTGAAGAAG (SEQ ID NO: 78) | Forward primer for amplification of ssuC with an RBS library containing 32 variants and a 5' overhang for assembly with ssuB |
| TK626 | TCATACCGTGGCCTCCTTCAAATG (SEQ ID NO: 79) | Reverse primer for amplification of ssuC |
| TK627 | CGGCTTATCATTTGAAGGAGGCCACGGTATGACCTCCTGTGT GAAATTGTTATCCGC (SEQ ID NO: 80) | Forward primer for amplification of the pSEVA271_$P_{tet}$-$P_{T7}$ backbone with a 5' overhang for assembly with ssuC |
| TK628 | TAGAGGGAAACCGTTGTGGTC (SEQ ID NO: 81) | Reverse primer for amplification of the pSEVA271_$P_{tet}$-$P_{T7}$ backbone |
| TK635 | CTATAGGGAGACCACAACGGTTTCCCTCTA NGGRRGDHAAAC ATGCGTAACATCATTAAACTGGCGC (SEQ ID NO: 82) | Forward primer for amplification of ssuA with an RBS library containing 144 variants and a 5' overhang for assembly with the pSEVA271_$P_{tet}$-$P_{T7}$ backbone |
| TK636 | CCCACTCAACTGGAAGGAAAACAATTATGA GGRRGDNHCGGA ATGAATACTGCTCGTCTGAACCAG (SEQ ID NO: 83) | Forward primer for amplification of ssuB with an RBS library containing 144 variants and a 5' overhang for assembly with ssuA |
| TK637 | TCTGAAACTCGCCTGAGAAAACAGGGGTAA RGRGGDDNAAGG ATGGCAACGCCAGTGAAGAAG (SEQ ID NO:84) | Forward primer for amplification of ssuC with an RBS library containing 144 variants and a 5' overhang for assembly with ssuB |

TABLE 3-continued

| Primer | Sequence | Description |
|---|---|---|
| TK640 | CTACACCCTCAACTGGNNNTTCGGCAGCGGCGTGG (SEQ ID NO: 85) | Forward primer for randomization of residue D385 in PnGGT* |
| TK641 | CCACGCCGCTGCCGAANNNCCAGTTGAGGGTGTAG (SEQ ID NO 86) | Reverse primer for randomization of residue D385 in PnGGT* |
| TK642 | CAGCAGTACCAGTACNNNCAGGACGCCATCGCG (SEQ ID NO: 87) | Forward primer for randomization of residue R170 in PnGGT* |
| TK643 | CGCGATGGCGTCCTGNNNGTACTGGTACTGCTG (SEQ ID NO: 88) | Reverse primer for randomization of residue R170 in PnGGT* |
| TK644 | GGTCGCCGACCAGCAGNNKNNKTACCGCCAGGACGCC (SEQ ID NO: 89) | Forward primer for randomization of residues Y167 and Q168 in PnGGT* |
| TK645 | GGCGTCCTGGCGGTAMNNMNNCTGCTGGTCGGCGACC (SEQ ID NO: 90) | Reverse primer for randomization of residues Y167 and Q168 in PnGGT* |
| TK656 | ATAT<u>GAATTC</u>CGGGAAACCAGACTCGC (SEQ ID NO: 91) | TS1F primer for scarless deletion of nadB (EcoRI) |
| TK657 | CGCTGACCCAGGCTTTTTATCTG GTCACATGAATGTTCAGGGAGAG (SEQ ID NO: 92) | TS1R primer for scarless deletion of nadB |
| TK658 | CTCTCCCTGAACATTCATGTGAC CAGATAAAAAGCCTGGGTCAGCG (SEQ ID NO: 93) | TS2R primer for scarless deletion of nadB |
| TK659 | ATAT<u>GGATCC</u>GGAAAGTGAAGCTGCCGC (SEQ ID NO:94) | TS2R primer for scarless deletion of nadB (BamHI) |

1.8 Construction of pSsuABC

First, plasmid pSEVA271_P$_{tet}$ was constructed by cutting out the P$_{tet}$-P$_{T7}$ promoter together with the multiple cloning site (MCS) from pAB92 with the restriction enzymes PacI and SpeI (both New England Biolabs). The resulting fragment was ligated into the backbone of pSEVA271 that was digested with the same restriction enzymes. The reduced RBS libraries comprising either 36 or 144 variants were generated individually for each gene using the RedLibs algorithm (Jescheck et al., 2016). The single genes were amplified from the E. coli chromosome using forward primers encoding the respective RBS libraries and a 30 base pair sequence complementary to the upstream element in their 5'-overhangs. To construct the plasmid libraries, the respective ssuA, ssuB and ssuC fragments were assembled with the backbone of plasmid pSEVA271_P$_{tet}$ by Gibson assembly (New England Biolabs).

1.9 In Vivo Hydrolysis of Sulfobutanoyl-p-Nitroanilide and Sulfobutanoyl-AMC

Strain TK082 was transformed with plasmids as indicated in the text and grown at 37° C. in MS minimal medium supplemented with 0.5% glucose, 1 mM MgSO$_4$ and 0.4 mM L-leucine to an OD$_{600}$ of 0.5. At that stage, the synthesis of PnGGT* and/or SsuABC was induced for 2 hours by adding 0.5 mM IPTG and 100 ng mL$^{-1}$ aTc. Following this synthesis period, cells were washed in the same medium to remove proteins that had been released into the medium by cell lysis. After an additional centrifugation step, cells were resuspended in MS minimal medium supplemented with 0.5% glucose, 1 mM MgSO$_4$, 0.4 mM L-leucine, 0.5 mM IPTG, 100 ng mL$^{-1}$ aTc and 0.5 mM sulfobutanoyl-p-nitroanilide or sulfobutanoyl-AMC (see below for description of synthesis) and incubated in a Tecan Infinite 200 Pro plate reader at 37° C. To monitor cell density and the release of 4-nitroaniline, absorbance was constantly measured at 600 nm and 410 nm. The release of AMC was monitored by measuring the fluorescence at λex=350 nm and λem=450 nm. To determine the influence of competition for the sulfonate transporter SsuABC, different concentrations of pentanesulfonate (Sigma Aldrich) were added to the medium.

1.10 Complementation of an NAD$^+$ Auxotrophic Strain with N-Picolyl-Sulfobutyramide Selection experiments with NAD$^+$ auxotrophic strains are prone to contamination with unwanted NAD$^+$ sources and therefore demand special preparation of the precultures and medium. For the precultures, all tested strains were incubated overnight in MS minimal medium supplemented with 0.5% glucose, 1 mM MgSO$_4$, 0.4 mM L-leucine and 5 µM nicotinic acid. To guarantee complete consumption of nicotinic acid, precultures were then diluted 100-fold in MS minimal medium supplemented only with 0.5% glucose, 1 mM MgSO$_4$ and 0.4 mM L-leucine, but no additional NAD$^+$ source. Following an overnight incubation period, NAD$^+$-deprived cells were washed twice in the same medium and used for growth assays.

To prepare the medium for final growth assays, MS minimal medium was supplemented with 0.5% glucose, 1 mM MgSO$_4$, 0.4 mM L-leucine and 25 µM N-picolyl-sulfobutyramide (see below for description of synthesis). To remove all NAD$^+$ contaminants, the medium was inoculated overnight with strain TK090, which can utilize free NAD$^+$ precursors, but cannot take up or hydrolyze N-picolyl-sulfobutyramide due to the absence of SsuABC and PnGGT*. After an overnight incubation period, cells were separated from the medium by centrifugation and the supernatant was filtered using a Minisart 0.22 μm High Flow Syringe Filter (Sartorius, Goettingen, Germany). The filtered supernatant was then supplemented with the respective antibiotics and inducers and used for growth assays.

1.11 Kinetics with Sulfobutanoyl-L-Leucine

The hydrolysis of sulfobutanoyl-L-leucine by PnGGT* variants was measured by quantifying the release of leucine by PnGGT* using a branched-chain amino acid (BCAA) kit (Sigma-Aldrich). For that, 50 μL of the BCAA reaction mix containing 46 μL BCAA assay buffer, 2 μL BCAA enzyme mix and 2 μL WST substrate mix were pre-incubated with 35 μL BCAA assay buffer and 5 μL purified PnGGT* (final concentration approximately 0.05 mg mL-1) at 37° C. The reaction was started by adding 10 μL of sulfobutanoyl-L-leucine diluted in 50 mM Tris/HCl (pH 7.0) at different concentrations and absorbance at 450 nm was constantly measured at 37° C. in a Tecan Infinite 200 Pro plate reader. The reaction rate of PnGGT* variants was determined as the specific difference in absorption over time (ΔA (450 nm) per minute per mg of purified protein).

1.12 Protein Modeling

A homology model of PnGGT was created with the SWISS-MODEL workspace (Guex et al., 2009; Arnold et al. 2006; Kiefer et al., 2009; Biasini et al., 2014) using the crystal structure of *E. coli* GGT bound to glutamate (PDB accession number: 2DBX) as template (Okada et al., 2006). YASARA Structure (YASARA Biosciences GmBH, Vienna, Austria) was used to introduce mutation D405N into the homology model and to change the glutamate ligand to sulfobutanoic acid. After all modifications, energy minimization was performed using the YASARA force field with default settings. To visualize the protein structures, YASARA and Chimera (Pettersen et al., 2004) were used.

1.13 Synthesis of Sulfobutyramide Analogues

The synthesis of sulfobutyramide analogues is schematically illustrated in FIG. 33.

N-(3-Pyridinylmethyl)-4-[(triphenylmethyl)thio]-butyramide (4)

4-[(Triphenylmethyl)thio]butanoic acid (2.00 g, 5.51 mmol), which was prepared from 4-bromobutyric acid according to a literature procedure (Qvit et al., 2008), and O-(benzotriazol-1-yl)-N,N,N',N'-tetramethyluronium hexafluorophosphate (HBTU, 2.51 g, 6.62 mmol) were dissolved in dry DMF (25 mL) under a nitrogen atmosphere. This solution was cooled to 0° C. and 3-(aminomethyl)pyridine 1 (0.66 g, 0.62 mL, 6.10 mmol) was then added, followed by N,N-diisopropylethylamine (DIPEA, 2.85 g, 3.84 mL, 22.0 mmol). The reaction mixture was stirred overnight at room temperature. It was then diluted with ethyl acetate and washed with saturated aq. NaHCO$_3$, water, and a 1M solution of KHSO$_4$. The organic layer was dried over MgSO$_4$, filtered, and evaporated in vacuo to leave a crude residue that was purified by column chromatography (CH$_2$Cl$_2$:MeOH 95:5) to afford the title compound as a white solid (2.45 g, 98% yield). $^1$H NMR (300 MHz, CDCl$_3$): δ 8.49 (d, J=3.8 Hz, 1H, ArH), 8.45 (d, 1H, J=1.5 Hz, ArH), 7.57 (d, J=7.8 Hz, 1H, ArH), 7.43 (m, 6H, ArH), 7.30-7.19 (m, 10H, ArH, 6.25 (t, J=5.7 Hz, 1H, NH), 4.36 (d, J=5.9 Hz, 2H, NH—CH$_2$), 2.23 (t, J=7.0 Hz, 2H, CH$_2$), 2.17 (t, J=7.3 Hz, 2H, CH$_2$), 1.72 (quint, J=7.2 Hz, 2H, β-CH$_2$); $^{13}$C NMR (75 MHz, CDCl$_3$): δ 172.5, 149.4, 149.1, 145.1, 135.9, 134.4, 129.8, 128.2, 126.9, 123.9, 66.9, 41.2, 35.6, 31.7, 24.9; HRMS for C$_{29}$H$_{28}$N$_2$O$_1$S$_1$ [M+H]$^+$ calcd.: 453.1994, found: 453.1996.

N-(3-Pyridinylmethyl)sulfobutyramide sodium salt (N-picolyl-sulfobutyramide; 6a)

Compound 4 (0.551 g, 1.22 mmol) was dissolved in CH$_2$Cl$_2$ (5 mL) and the resulting solution was cooled to 0° C. Trifluoroacetic acid (5 mL) was then added followed by triethylsilane (0.71 g, 0.98 mL, 6.09 mmol) and the mixture was stirred at room temperature for 1.5 h. After removal of all the volatiles in vacuo, the crude residue was quickly purified by column chromatography (CH$_2$Cl$_2$:MeOH 9:1) to give N-(3-pyridinylmethyl)-4-mercapto-butyramide 5 as a colourless oil (0.26 g; HRMS for C$_{10}$H$_{14}$N$_2$O$_1$S$_1$ [M+H]$^+$ calcd.: 211.0899, found: 211.0898). To a stirred solution of 5 (0.357 g, 1.70 mmol) in THF (2 mL) cooled at 0° C. was added trifluoroacetic acid (1.66 mL) followed by the dropwise addition of a 35% aq. solution of hydrogen peroxide (0.98 mL). The ice-bath was removed and the reaction mixture was stirred at room temperature for 40 min. After removal of all the volatiles in vacuo, the crude residue was purified by reverse phase (C18) HPLC (H$_2$O:CH$_3$CN), the collected eluate was subsequently passed through a column containing the ion-exchanger Amberlite® IR 120 Na$^+$ form, and purified once more by reverse phase HPLC to afford the sodium salt of 6a as a white solid (34%). $^1$H NMR (500 MHz, D$_2$O): δ 8.62 (br s, 2H, ArH), 8.27 (d, J=8.1 Hz, 1H, ArH, 7.85-7.83 (m, 1H, ArH), 4.53 (s, 2H, NH—CH$_2$), 2.89 (t, J=7.6 Hz, 2H, CH$_2$), 2.48 (t, J=7.5 Hz, 2H, CH$_2$), 2.03 (quint, J=7.5 Hz, 2H, β-CH$_2$); $^{13}$C NMR (125 MHz, D$_2$O): δ 176.0, 142.6, 142.5, 142.4, 137.5, 126.3, 50.0, 40.2, 34.0, 20.6; HRMS for C$_{10}$H$_{14}$N$_2$O$_4$S$_1$ [M−H]$^-$ calcd.: 257.0601, found: 257.0602.

N-(4-Nitrophenyl)sulfobutyramide sodium salt (sulfobutanoyl-p-nitroanilide; 6b)

4-Nitroaniline 2 (5.0 g, 36 mmol) was dissolved in dry CH$_2$Cl$_2$ (100 mL) and cooled to 0° C. DIPEA (13 mL, 72 mmol) was then added, followed by the dropwise addition of 4-chlorobutyryl chloride (4.8 mL, 43 mmol), and the reaction mixture was stirred at room temperature overnight. After completion, a saturated aq. NaHCO$_3$ solution was added and the solution was extracted with CH$_2$Cl$_2$. The organic layers were combined, dried over MgSO$_4$, and evaporated in vacuo to give crude product 7a. Compound 7a was then dissolved in dry DMF (25 mL) and potassium thioacetate (12.3 g, 108 mmol) was added, and the reaction mixture was stirred at 40° C. overnight. After completion, the solvent was removed in vacuo, water was added and extracted with CH$_2$C$_2$. The organic layers were combined, dried over MgSO$_4$, and evaporated in vacuo to afford compound 8a as a brown oil, which was used in the next step without further purification. Compound 8a was suspended in acetic acid and CH$_3$COONa (11 g, 144 mmol) was then added. The reaction mixture was warmed to 40° C., 35% aq. H$_2$O$_2$ was then added dropwise, and the mixture was stirred overnight at 40° C. After disappearance of the starting material (TLC), the solvent was evaporated in vacuo and the resulting residue was treated with saturated aq. NaHCO$_3$ and stirred for 2 h until the effervescence stopped. This aqueous solution was washed with diethyl ether and CH$_2$Cl$_2$, and the water layer was lyophilized to afford a yellow powder. The residue was purified by silica gel column chromatography using isopropanol and water as elution system to remove the excess of salts. The yellow solid thus obtained was redissolved in a minimum amount of water, purified by reverse phase (C-18) HPLC (H$_2$O:CH$_3$CN), and lyophilized to afford pure 6b as yellowish solid in 20% overall yield. $^1$H NMR (300 MHz, D$_2$O): δ 8.27 (2H, d, J=9.0 Hz, ArH), 7.81 (2H, d, J=9.0 Hz, ArH), 2.90 (2H, m, CH$_2$), 2.56 (2H, m, CH$_2$), 2.04 (2H, m, CH$_2$), $^{13}$C NMR (75 MHz, D$_2$O): δ 175.8, 143.6, 142.7, 124.7, 119.6, 49.6, 33.4, 20.2: HRMS (ESI) for C$_{10}$H$_{11}$N$_2$O$_6$S [M−H]$^−$ calcd.: 287.0343; found 287.0336.

N-(4-Methyl-2-oxo-2H-1-benzopyran-7-yl)chlorobutyramide (7b)

7-Amino-4-methylcoumarin 3 (0.100 g, 0.57 mmol) was dissolved in a mixture of dry CH$_2$Cl$_2$ (10 mL) and DMF (2 mL) under an argon atmosphere, and then cooled to 0° C. in an ice-bath. Subsequently, dry pyridine (0.09 mL, 1.14 mmol) was added, followed by the dropwise addition of 4-chlorobutyryl chloride (0.08 mL, 0.86 mmol). The reaction mixture was then stirred overnight at 35° C. After partial removal of all the volatiles in vacuo, water was then added. The solid precipitate was washed repeatedly with water, collected by filtration through a Buchner funnel, and dried in vacuo to afford the title compound in the form of a white solid (0.135 g, 84% yield). $^1$H NMR (300 MHz, DMSO): δ 10.4 (s, 1H, NH), 7.74 (s, 1H, H-8), 7.69 (d, J=8.7 Hz, 1H, H-5), 7.46 (d, J=8.5 Hz, 1H, H-6), 6.23 (s, 1H, H-3), 3.70 (t, J=6.4 Hz, 2H, γ-CH$_2$), 3.32 (s, 3H, CH$_3$), 2.53 (t, J=7.3 Hz, 2H, α-CH$_2$), 2.04 (t, J=6.93 Hz, 2H, 3-CH$_2$); $^{13}$C NMR (75 MHz, DMSO): δ 171.1, 160.2, 153.8, 153.2, 142.6, 126.0, 115.2, 115.0, 112.3, 105.7, 45.1, 33.7, 27.8, 18.1; HRMS for C$_{14}$H$_{14}$Cl$_1$N$_1$O$_3$ [M+H]$^+$ calcd.: 280.0735, found: 280.0732.

N-(4-Methyl-2-oxo-2H-1-benzopyran-7-yl)sulfobutyramide (sulfobutanoyl-AMC; 6c)

Compound 7b (0.135 g, 0.48 mmol) was dissolved in dry DMF (5 mL) under an argon atmosphere, and then potassium thioacetate (0.066 g, 0.58 mmol) was added. The mixture was stirred at room temperature overnight. The solvent was then removed in vacuo to leave a crude residue, which was washed repeatedly with water. After filtration through a Buchner funnel, thioester 8b was isolated as a tanned solid (0.110 g; HRMS for C$_{16}$H$_{17}$N$_1$O$_4$S$_1$ [M−H]$^−$ calcd.: 318.0805, found: 318.0805), dried in vacuo, and used as such in the following step. To a stirred solution of thioester 8b (0.092 g, 0.29 mmol) in trifluoroacetic acid (0.28 mL) cooled at 0° C. was added dropwise a 35% aq. solution of hydrogen peroxide (0.16 mL). The ice-bath was removed and the reaction mixture was stirred at room temperature for 30 min. After removal of all the volatiles in vacuo, the crude residue was purified by reverse phase (C$_{18}$) HPLC (H$_2$O:CH$_3$CN) to afford pure 3 as a white fluffy solid (0.048 g) in 38% yield over two steps. $^1$H NMR (300 MHz, D$_2$O): δ 7.31 (d, J=8.6 Hz, 1H, H-5), 7.17 (d, J=1.7 Hz, 1H, H-8), 7.01 (dd, J=8.4, 1.8 Hz, 1H, H-6), 5.97 (s, 1H, H-3), 2.91 (t, J=7.2 Hz, 2H, CH$_2$), 2.48 (t, J=7.5 Hz, 2H, CH$_2$), 2.12 (s, 3H, CH$_3$), 1.98 (t, J=7.5 Hz, 2H, β-CH$_2$); $^{13}$C NMR (75 MHz, D$_2$O): δ 173.6, 163.7. 155.4, 152.5, 140.6, 125.3, 116.0, 115.6, 111.4, 106.4, 49.8, 34.8, 20.0, 17.4; HRMS for C$_{14}$H$_{15}$N$_1$O$_6$S$_1$ [M−H]$^−$ calcd.: 324.047, found: 324.0558.

2. Example 1: Comparison of E. coli and Pseudomonas nitroreducens GGT

In order to ensure efficient cargo release in the cytoplasm of E. coli, it was important to ensure (I) efficient expression in the cytoplasm of E. coli, (II) high hydrolytic and low transpeptidase activity even in the presence of a suitable peptide or amino acid acceptor, and (III) a high promiscuity regarding the γ-glutamyl substrate. As promising candidates the EcGGT from E. coli has been identified which is well-characterized (Suzuki and Kumagai, 2002; Suzuki et al., 1986) and for which a protein structure is available (Okada et al., 2006), and the PnGGT from P. nitroreducens, which was reported with a higher hydrolytic than transpeptidase activity and a broad substrate range (Imaoka et al., 2010).

First, the influence of the location of a hexahistidine tag (6×His-tag) on expression and activity of both variants was investigated. To determine expression levels, western blot analysis with an antibody against the 6×His-tag was performed. Activity was determined using the substrate L-glutamic acid γ-(3-carboxy-4-nitroanilide) under two conditions, either in the presence or absence of glycyl-glycine as a second substrate, allowing either hydrolytic and transpeptidase or only hydrolytic activity, respectively. Both activities lead to the formation of the yellow dye 3-carboxy-4-nitroaniline, but previous experiments (Suzuki et al., 1986) and own observations (data not shown) suggest that transpeptidase activity is revealed in this assay by an increase in product formation on top of the product release due to hydrolysis. In other words, identical product release rates in the presence and absence of glycyl-glycine indicate absence of transpeptidase activity.

Fusion of the 6×His-tag to the C-terminus of EcGGT led to partial accumulation of the presumably inactive precursor polypeptide and reduced GGT activity in cell lysates compared to a variant with N-terminal 6×His-tag (FIG. 9 and FIG. 10). Based on this observation, N-terminal 6×His-tag fusions were used for further experiments.

To directly compare the activities of EcGGT and PnGGT, N-terminal 6×His-tag fusion variants 6×His_EcGGT ΔN24 and 6×His_PnGGT ΔN24 (for description see below) were purified and specific activities were determined. For EcGGT, the product release rate was 3-fold higher in the presence of glycyl-glycine, suggesting a considerable transpeptidase activity. In contrast, similar activities were measured for PnGGT in the absence and presence of glycyl-glycine (FIG. 4b), confirming the enzyme's preference for transferring the γ-glutamyl moiety to a water molecule (Imaoka et al., 2010). Due to its significantly higher activity in the absence of an amino acid or peptide acceptor molecule and its demonstrated broad substrate range (Imaoka et al., 2010), PnGGT was selected as the preferred GGT candidate for further experiments.

3. Example 2: Cytoplasmic Expression of PnGGT

For efficient intracellular cargo release, GGT has to operate in the cytoplasm instead of its natural reaction space, the periplasm. As suggested by a bioinformatics analysis (Petersen et al., 2011), the wild type gene encodes a 25 amino acid residues signal peptide at the 5' end of the gene, and previous work with EcGGT suggested interference of the His-tag with the secretion of GGT to the periplasmic space (Lo et al., 2008). The expression of PnGGT was tested with an N-terminal 6×His-tag added in front of the signal peptide of the precursor. A high GGT activity was determined in cell lysates, but the large subunit, which in the case of retention in the cytoplasm could have been expected to remain attached to the His-tag via the signal peptide, was hardly detectable in western blot analysis (FIG. 4c and FIG. 9). This suggested that the 6×His-tag was cleaved off from the large subunit, possibly together with the signal peptide during secretion to the periplasmic space. Therefore, to retain PnGGT in the cytoplasmic space, variants of PnGGT with a partially (6×His_PnGGT ΔN16) and an almost entirely deleted signal peptide (6×His_PnGGT ΔN24) were generated. After expression of both variants, broad bands around 40 kDa were detected after western blotting, corresponding well to the size of the large subunit of PnGGT (FIG. 4c and FIG. 9). The truncated PnGGT variants showed higher GGT activities in whole cell lysates compared to the PnGGT variant with full signal peptide, indicating more efficient expression and/or maturation of 6×His_PnGGT ΔN16 and 6×His_PnGGT ΔN24 (FIG. 4c).

To determine the cellular localization of PnGGT, the variants with and without signal peptide (6×His_PnGGT and 6×His_PnGGT ΔN24, respectively) were expressed again in *E. coli* and the periplasmic protein fraction was separated from the cytoplasmic fraction by osmotic shock. To analyze the purity of the periplasmic and cytoplasmic fraction, activities of the periplasmic enzyme alkaline phosphatase and the cytoplasmic enzyme β-glucoronidase were determined in both fractions, and the fractions were found to be around 80% (periplasmic) and 90% (cytoplasmic) pure. In a strain expressing 6×His_PnGGT 78% of GGT activity was detected in the periplasmic fraction, consistent with the notion that an N-terminally 6×His-tagged protein variant with the full signal peptide is indeed efficiently exported into the periplasmic space. However, in cells expressing 6×His__PnGGT ΔN24, 80% of the GGT activity was found in the cytoplasm, consistent with the notion that deletion of the signal peptide effectively prevents secretion to the periplasmic space (FIG. 5).

4. Example 3: Applying 6×His_PnGGT ΔN24 in a Synthetic Transport System

The possibility to express 6×His_PnGGT ΔN24 in the cytoplasm of *E. coli* and the enzyme's relaxed substrate specificity (Imaoka et al., 2010) opened up the possibility to selectively hydrolyze γ-glutamyl compounds within the cytoplasm. To demonstrate the activity of 6×His_PnGGT ΔN24 in an in vivo situation, it was aimed at unloading of a cargo molecule from a γ-glutamyl peptide after uptake through a peptide transporter. As a cargo, leucine was chosen, whose successful release could be easily detected by restoring growth to a leucine auxotrophic strain. For this, *E. coli* strain JM101 was made leucine auxotrophic (ΔleuB). Additional deletions were made in the chromosome of this strain, specifically in the ggt gene, to exclude effects caused by endogenous EcGGT, and in the leucine transporter genes brnQ and livFGHMK (Adams et al., 1990; Ohnishi et al., 1988). While deletion of these transporters reduces the uptake of free leucine from the medium, it is of note that it does not completely abolish it (FIG. 6c). The resulting strain was called TK054. Next, TK054 cells were plated with the plasmid pACT3/6×His_PnGGT ΔN24 on minimal medium supplemented with 0.5% glucose, 1 mM of the peptide alanyl-γ-glutamyl-leucine (Ala-γ-Glu-Leu) as sole source of leucine (FIG. 3) and 0.5 mM IPTG to induce protein expression. In general, poor growth of the leucine auxotrophic strain was observed, even if plates were incubated at 37° C. for 5 days or more. At the same time, there was no growth of the same strain expressing the periplasmic variant 6×His_PnGGT or carrying an empty vector control (FIG. 11a). These results were at least partially consistent with the notion that cytoplasmic expression of 6×His_PnGGT ΔN24 is essential for unloading of the leucine cargo, but pointed towards the requirement of further refinement of the system.

Interestingly, this initial growth experiment had produced a few colonies at the end of an extended incubation period of 5 days, raising the possibility that these cells had acquired a mutation that led to the improved growth phenotype. These colonies were re-isolated on the same medium and three isolates showed improved growth on selective medium with notable growth already after 2 days (FIG. 11b). Genomic DNA from each of the isolated strains was isolated for next generation sequencing and the genome sequences of the isolated were compared with that of the parental strain. All three isolates revealed mutations in the gene pcnB, encoding the enzyme poly(A) polymerase I (PAP I), that is responsible for the polyadenylation of most RNAs in *E. coli* and plays an important role in initiation of RNA decay (Mohanty and Kushner, 1999; Mohanty and Kushner, 2006). One of the strains harbored a point mutation leading to an amino acid exchange from glycine (GGC) to aspartic acid (GAC) at position 152 of the predicted PcnB protein sequence, which lies in close proximity to the active site of the protein at position D162 (Raynal and Carpousis, 1999). The second mutant strain had a deletion of a guanine nucleotide in pcnB at the codon R54 leading to a frame shift and causing premature termination of translation, and the third strain had a 339 base pair deletion in pcnB between position G67 and V181. These results suggested that a partial or even complete inactivation of the PcnB activity was in some way beneficial for the functionality of the synthetic transport system. Besides the mutations in pcnB, no other mutations were detected.

To verify that the beneficial effects to growth with Ala-γ-Glu-Leu were caused by activity reducing mutations in pcnB, the entire gene was removed from the unmutated leucine auxotrophic selection strain, resulting in strain TK054 ΔpcnB. On M9 minimal medium containing 0.5% glucose and 1 mM Ala-γ-Glu-Leu as the only source of leucine, no growth of this strain was detected if the inducer IPTG was omitted (FIG. 6a). In the presence of IPTG, the strain expressing the gene for 6×His_PnGGT ΔN24 grew rapidly, confirming the beneficial effect of the pcnB deletion. In contrast, if the strain was transformed with the empty vector or an expression vector for the periplasmic variant 6×His_PnGGT, no growth was detected after two days (FIG. 6b), confirming that growth depended on the cytoplasmic expression of the GGT. All transformed strains were also re-isolated on a minimal medium on which cells were not expected to require functional GGT, i.e. containing 0.5% glucose, 1 mM leucine and 0.5 mM IPTG. All variants showed similar but slower growth rates compared to medium supplemented with the Ala-γ-Glu-Leu peptide, confirming that the pcnB deletion does not impair growth on mineral medium as such and that free leucine is only slowly taken up by this strain (FIG. 6c).

Comparable results were obtained for growth in liquid medium (FIG. 12).

5. Example 4: Investigation of the Effects of pcnB on the Synthetic Transport System In *E. coli*, the pcnB-encoded enzyme PAP I is responsible for the polyadenylation of RNAs and was shown to contribute to the destabilization of mRNAs (Blum et al., 1999; Yehudai-Resheff and Schuster, 2000). A deletion of pcnB can therefore delay the onset of RNA degradation and thus result in increased mRNA half-life. The amino acid sequence of the *E. coli* pcnB-encoded enzyme PAP I is shown in SEQ ID NO:11. On the other hand, pcnB is also involved in copy number maintenance of ColE1 and p15A plasmids: As the replication of these plasmids is initiated by the small RNAII, a deletion of pcnB leads to an extended functional half-life of the antagonistic RNAI, resulting in decreased copy numbers of plasmids that replicate by this mechanism (Hershfield et al., 1974; Xu et al., 1993). Therefore, deletion of pcnB most likely results in upregulation of crucial players of the synthetic transport system like peptide transporters, peptidases or 6×His_PnGGT ΔN24 due to prolonged mRNA half-life, and/or in lower expression of 6×His_PnGGT ΔN24 due to reduced copy number due to the location of the gene on a p15A-type replicon. To differentiate between these two groups of influences, the effect of expressing GGT at reduced level was investigated in a pcnB+ background. The pertinent parts of the 6×His_PnGGT ΔN24 expression plasmid were integrated into the chromosome of strains TK054 and TK054 ΔpcnB, resulting in strains TK054 ggt int and TK054 ΔpcnB ggt int, respectively. Chromosomal integration of the GGT gene results in a single gene copy per genome in contrast to plasmids where it was expected to have between 16 and 22 copies per genome in a wild-type strain (Chang and Cohen, 1978). Indeed, reduced expression of 6×His_PnGGT ΔN24 showed beneficial effects on mineral medium supplemented with glucose and Ala-γ-Glu-Leu as the sole source of leucine: As expected, neither TK054 nor TK054 ΔpcnB grew if they were transformed with the empty plasmid pACT3. When the two strains were transformed with the plasmid pACT3/6×His_PnGGT ΔN24, only TK054 ΔpcnB was able to grow, as observed in previous experiments. If, however, 6×His_PnGGT ΔN24 was expressed from the chromosome (FIG. 7a, 6×His_PnGGT ΔN24 int A & B), regular growth was observed after two days of incubation at 37° C. both for the strain with and without a functional pcnB copy, suggesting that the pcnB deletion has no longer a beneficial effect if the gene for GGT is present in only a single copy per genome and thus its activity reduced.

This interpretation was also supported by total activity data for the different strains. Cells were lysed after overnight expression in rich medium and GGT activity of whole cell lysates was measured. The highest GGT activity was detected when 6×His_PnGGT ΔN24 was expressed from a plasmid in a strain with a functional pcnB gene, a combination for which no growth was detected on selective medium. In the pcnB deletion strain transformed with the same plasmid, GGT activity dropped more than ten-fold, correlating with the reduction in plasmid copy number of the p15A-type expression plasmid (data not shown). If the gene for 6×His_PnGGT ΔN24 was integrated into the chromosome, equally low GGT activities were detected for strains with and without a functional pcnB copy, consistent with the notion that the gene copy number no longer depended on PcnB (FIG. 7b). In conclusion, all variants with improved growth on selective medium had low GGT activities in a comparable range. Finally, these observations were further confirmed by western blot analysis with an anti-hexahistidine antibody to detect the large subunit of 6×His_PnGGT ΔN24 (FIG. 7c). These results consistently indicate that the beneficial effect of the pcnB deletion on the performance of the synthetic transport system when the GGT gene is plasmid borne is most likely caused by a reduction of cytoplasmic GGT activity, achieved by a reduction in plasmid copy number leading to lower 6×His_PnGGT ΔN24 levels in the cell.

6. Example 5: Optimization of 6×His_PnGGT ΔN24 Expression from Plasmids

To construct an optimized strain for the synthetic transport system it was then aimed at identifying the optimal expression level of 6×His_PnGGT ΔN24. To maintain flexibility, the ggt gene was retained on a plasmid, the plasmid pACT3/6×His_PnGGT ΔN24 was used as starting point, and its ribosome binding site (RBS) was engineered to obtain a wide distribution of translation initiation rates (TIRs) (Espah Borujeni et al., 2014; Salis et al., 2009). By using the RedLibs algorithm (Jeschek et al., 2016), a reduced RBS library was generated of 81 variants (sequence HVVGGVGG, original sequence CAGGAGGA) covering a predicted translation range from 0.1 fold to 14 fold relative to the RBS of the parent construct (translation initiation ratios (TIRs) ranging from 3'693 to 613'384 arbitrary units, with the TIR of the wild type RBS predicted at 42'646 (Espah Borujeni et al., 2014; Salis et al., 2009)) (FIG. 13). The library was used to transform the leucine auxotrophic and pcnB+ strain TK054. Transformants were plated out on selective minimal medium and after three days of incubation the 24 largest colonies were re-isolated. The plasmids of all 24 candidates were isolated and their RBS sequences were analyzed by Sanger sequencing. Among these 24, one sequence was found five times and four sequences were found twice. Ten sequences were found only once and one sequence gave unclear sequencing results. The majority of these RBS sequences have predicted TIRs ranging from 4'422 to 31'744, while only one of the RBS sequences found during selection has a predicted TIR stronger than the RBS of the parent plasmid (Table 4).

TABLE 4

RBS sequence and translation initiation rates of the 24 fastest growing variants

| Clone # | Sequence | TIR |
|---|---|---|
| 17 | ACAGGCGG (SEQ ID NO: 39) | 21171.47 |
| 18 | ACAGGCGG (SEQ ID NO: 39) | 21171.47 |
| 20 | ACAGGCGG (SEQ ID NO: 39) | 21171.47 |
| 21 | ACAGGCGG (SEQ ID NO: 39) | 21171.47 |
| 23 | ACAGGCGG (SEQ ID NO: 39) | 21171.47 |
| 1 | CGGGGCGG (SEQ ID NO: 40) | 10974.66 |
| 7 | CGGGGCGG (SEQ ID NO: 40) | 10974.66 |
| 3 | ACGGGCGG (SEQ ID NO: 41) | 21171.47 |
| 16 | ACGGGCGG (SEQ ID NO: 41) | 21171.47 |
| 4 | CGCGGGGG (SEQ ID NO: 42) | 27985.38 |
| 8 | CGCGGGGG (SEQ ID NO: 42) | 27985.38 |

TABLE 4-continued

RBS sequence and translation initiation rates of the 24 fastest growing variants

| Clone # | Sequence | TIR |
|---|---|---|
| 12 | TCGGGCGG (SEQ ID NO: 43) | 13620.97 |
| 15 | TCGGGCGG (SEQ ID NO: 43) | 13620.97 |
| 2 | TCCGGCGG (SEQ ID NO: 44) | 4421.58 |
| 5 | TACGGCGG (SEQ ID NO: 45) | 10304.52 |
| 6 | CCAGGCGG (SEQ ID NO: 46) | 20607.43 |
| 9 | CAGGGAGG (SEQ ID NO: 47) | 130429.9 |
| 11 | CAAGGCGG (SEQ ID NO: 48) | 31743.72 |
| 13 | ACCGGCGG (SEQ ID NO: 49) | 10304.52 |
| 14 | CAGGGCGG (SEQ ID NO: 50) | 17212.46 |
| 19 | CGAGGCGG (SEQ ID NO: 51) | 26995.73 |
| 22 | TGGGGCGG (SEQ ID NO: 52) | 6113.69 |
| 24 | TGAGGCGG (SEQ ID NO: 53) | 19700.56 |
| 10 | — | — |

However, it should be noted that these predictions, while a useful tool to qualitatively estimate the strength of a TIR, are not a reliable predictor of the absolute TIR of any given RBS (Salis et al., 2009). Therefore, the fact that RBS's with a TIR prediction lower than wild type were strongly enriched among fast growing strains is another clear indication that a reduction of total cytoplasmic activity of GGT is beneficial. To corroborate the estimates with activity and protein level data, western blot and colorimetric activity analysis data after growth on rich medium were used again. The highest GGT levels were detected in the strain harboring the pACT3/6×His_PnGGT ΔN24 parent plasmid, while strains carrying a plasmid with one of the five most frequently isolated RBS variants led to significantly lower levels of the large subunit (FIG. 8c). Furthermore, highest enzyme activity was measured again when 6×His_PnGGT ΔN24 was expressed from the parent plasmid and the cell-specific activity for strains carrying variant versions of the RBS showed a 9 to 24-fold lower activity (FIG. 8b). Thus, both assays consistently showed that expression from all five RBS mutant plasmids was weaker compared to expression from the parent plasmid and these results are in good agreement with the predicted TIR values.

To conclude this section, the original proof-of-concept experiment for leucine portage that had only delivered poor growth when using the original pACT3/6×His_PnGGT ΔN24 parent plasmid was repeated. For this, strain TK054 was transformed with the parent plasmids and the five RBS variants and the resulting strains were grown again on solid selective medium containing 0.5% glucose, 1 mM Ala-γ-Glu-Leu and 0.5 mM IPTG at 37° C. After two days, no growth was detectable where the strain had been transformed with the pACT3/6×His_PnGGT ΔN24 parent plasmid. In contrast, transformation of the same strain with plasmids containing the mutant RBS sequences led to dense and rapid growth over the same period (FIG. 8a).

7. Example 6: Toxicity of High Levels of Cytoplasmic GGT

From the results presented above, it becomes clear that high intracellular levels of GGT are not tolerated by E. coli on selective medium. This could be due to a variety of reasons. For example, GGT is known to hydrolyze glutamine to glutamate (Imaoka et al., 2010) and could thus establish a futile cycle of glutamine synthesis when expressed in the cytoplasm or simply a reduction of glutamine levels. It was also shown previously that supplementation of a medium with certain leucine containing peptides can be toxic for E. coli, because essential enzymes can be inhibited by too high concentrations of leucine (Gollop et al., 1982; Tavori et al., 1981). In order to investigate whether the beneficial effect of lower 6×His_PnGGT ΔN24 expression on viability is independent from the fact that we used leucine for auxotrophy complementation in this study, the leucine prototrophic strain JM101 was transformed with the pACT3/6×His_PnGGT ΔN24 parent plasmid and the five RBS mutant variants. These transformants were grown in minimal medium supplemented with 0.5% glucose and 0.5 mM IPTG (i.e. without the leucine-containing peptide as substrate) and compared the growth behavior of the different transformants. The strain harboring the pACT3/6×His_PnGGT ΔN24 parent plasmid exhibited a significantly increased lag phase of approximately 30 hours. All strains harboring a pACT3/6×His_PnGGT ΔN24 plasmid with mutated RBS sequence showed rapid growth after a significantly shorter lag phase (FIG. 14). These results clearly show that higher levels of GGT alone are already sufficient to cause the toxic effect for the cell. Interestingly, the addition of external glutamine did not alleviate the growth problems (data not shown), indicating that either glutamine hydrolysis is much faster than import and/or that additional or altogether different side reactions are responsible.

8. Example 7: Exploring the Potential of GGT to Hydrolyze 4-Sulfobutanoyl Amides To ensure efficient release of cargo molecules from a sulfobutanoyl transport vector in the cytoplasm of E. coli, it is essential to confirm enzymatic activity for the hydrolysis of sulfobutanoyl amides. As outlined above, a synthetic transport system was set up by recruiting the promiscuous enzyme GGT for the release of different cargo molecules from γ-glutamyl backbones. Interestingly, it was previously demonstrated that introducing an aspartate to asparagine mutation in a variant of the E. coli GGT (EcGGT D433N) endows the enzyme with glutaryl-7-aminocephalosporanic acid (GL-7-ACA) acylase activity (Suzuki et al., 2004; Yamada et al., 2008). Given the structural similarity between the glutaryl moiety of GL-7-ACA and the sulfobutanoyl moiety, EcGGT D433N was investigated as a starting point for generating an enzyme that is capable of hydrolyzing sulfobutanoyl amides.

To test for the desired activity a colorimetric enzyme assay was chosen and the substrate sulfobutanoyl-p-nitroanilide was synthesized for this purpose. Hydrolysis of this colorless substrate by a GGT variant into sulfobutanoic acid and the yellow dye 4-nitroaniline can be quantified photometrically at 410 nm. For that, cytoplasmic GGT variants containing an N-terminal 6×His-tag were first expressed from E. coli (EcGGT ΔN24) and Pseudomonas nitroreducens (PnGGT ΔN24), as well as EcGGT ΔN24 D433N and the corresponding mutant variant PnGGT ΔN24 D405N. Position D405 of PnGGT was identified to fulfill the same function as position D433 of EcGGT by sequence alignment and homology modeling between EcGGT and PnGGT. Then the ability of whole cell lysates containing the respective enzymes was tested to hydrolyze L-glutamic acid γ-(3-carboxy-4-nitroanilide) or sulfobutanoyl-p-nitroanilide. As expected, EcGGT ΔN24 and PnGGT ΔN24 were both able to hydrolyze L-glutamic acid γ-(3-carboxy-4-nitroanilide), but showed no activity towards sulfobutanoyl-p-nitroanilide (FIG. 16). Interestingly, while EcGGT ΔN24 D433N still had detectable activity towards L-glutamic acid γ-(3-carboxy-4-nitroanilide), both mutant variants had acquired the ability to hydrolyze 4-sulfobutanoyl-p-nitroanilide, with PnGGT ΔN24 D405N having significantly higher activity than EcGGT ΔN24 D433N.

To further characterize the hydrolysis of γ-glutamyl-p-nitroanilide and sulfobutanoyl-p-nitroanilide by PnGGT ΔN24 and PnGGT ΔN24 D405N, the kinetic parameters of the two enzymes with both substrates was determined (Table 5, FIG. 20). PnGGT ΔN24 was able to hydrolyze γ-glutamyl-p-nitroanilide ($K_M$: 105 µM; $k_{cat}$: 34.5 s$^{-1}$) but showed no detectable activity towards sulfobutanoyl-p-nitroanilide. In contrast, PnGGT ΔN24 D405N exhibited reduced activity towards γ-glutamyl-p-nitroanilide ($K_M$: 6498 µM; $k_{cat}$: 1.8 s$^{-1}$), but was able to hydrolyze sulfobutanoyl-p-nitroanilide ($K_M$: 767 µM; $k_{cat}$: 10.2$^{-1}$).

growth experiments were carried out with a strain lacking the more promiscuous sulfonate transporter SsuABC and the alkanesulfonate monooxygenase SsuDE (BW25113 ΔleuB ΔssuEADCB). Deletion of this broad specificity sulfonate transporter prevented growth on both sulfobutanoyl amides suggesting that uptake and desulfonation of the sulfobutanoyl amides is facilitated by these proteins.

10. Example 9: Intracellular Release of Leucine from Sulfobutanoyl-L-Leucine

It was then tested if sulfobutanoyl-L-leucine can also be hydrolyzed intracellularly by GGT*. Strains BW25113 ΔleuB or BW25113 ΔleuB ΔssuD were transformed either with the empty vector pACT3 or the expression plasmids pACT3/EcGGT_ΔN24_D433N and pACT3/PnGGT_ΔN24_D405N. All transformed strains were grown on plates containing minimal medium supplemented with 0.5% glucose, 0.4 mM isoleucine, 0.5 mM taurine, 0.5 mM IPTG and 2 mM sulfobutanoyl-L-leucine. Strain BW25113 ΔleuB ΔssuD was tested in parallel to prevent desulfonation of sulfobutanoyl-L-leucine by SsuDE, which would render the substrate unavailable for hydrolysis by GGT*. In principle, sulfobutanoyl-L-leucine can be used by E. coli as leucine source through hydrolysis by GGT* and also as sulfur source through desulfonation of either sulfobutanoyl-L-leucine itself or the GGT* hydrolysis product sulfobutanoic acid by the enzymes SsuDE and/or TauD (FIG. 18). Taurine is taken up exclusively via TauABC and solely desulfonated by TauD. Addition of an excess of taurine should therefore not lead to competition with sulfobutanoyl-L-leucine for the SsuABC transporter and prevent TauD from using sulfobutanoyl-L-leucine as substrate, ensuring

TABLE 5

Kinetic parameters of PnGGT ΔN24 and PnGGT ΔN24 D405N

| | PnGGT ΔN24 | | PnGGT ΔN24 D405N | |
|---|---|---|---|---|
| | γ-Glu-p-nitroanilide | sulfobutanoyl-p-nitroanilide | γ-Glu-p-nitroanilide | sulfobutanoyl-p-nitroanilide |
| $K_M$ [µM] | 105 +/− 2 | ND | 6498 +/− 3212 | 767 +/− 40 |
| $V_{max}$ [µmol/min/mg] | 34.94 +/− 0.47 | ND | 1.79 +/− 0.61 | 10.35 +/−0.28 |
| $k_{cat}$ [s$^{-1}$] | 34.5 | ND | 1.8 | 10.2 |
| $k_{cat}/K_M$ [1/mM s$^{-1}$] | 328.57 | ND | 0.28 | 13.30 |

ND = not determined

9. Example 8: Uptake of Sulfobutanoyl Amides by E. coli

The sulfonate transporters SsuABC and TauABC transport a wide variety of sulfonate compounds (Eichhorn et al., 2000) and can thus be exploited for the present synthetic transport system. As such, the uptake and utilization of sulfobutanoyl-L-leucine was assessed. The leucine auxotrophic strain BW25113 ΔleuB was tested for growth in minimal medium supplemented with 0.5% glucose, 0.4 mM leucine, 0.4 mM isoleucine and 1 mM of a sulfur-containing compound as the sole sulfur source. It was observed that growth on sulfobutanoyl-L-leucine and sulfobutanoyl-p-nitroanilide was comparable to growth on other sulfonates like pentanesulfonate or hexanesulfonate and only slightly less efficient compared to growth on magnesium sulfate (FIG. 17) indicating that sulfobutanoyl-L-leucine could be efficiently taken up and utilized.

Next, it was identified which transport system is responsible for uptake of the sulfobutanoyl amides, and so similar that the majority of sulfobutanoyl-L-leucine is hydroluzed by GGT*. At the same time taurine does not lead to repression of the ssu operon and allows efficient expression of these genes which is essential for functionality of the transport system.

BW25113 ΔleuB grows best on this medium when expressing PnGGT ΔN24 D405N while expression of EcGGT ΔN24 D433N leads to slower growth, which is in good agreement with the activity measurements of the two GGT* variants (FIG. 19, FIG. 16). Additional inactivation of the desulfonating enzyme SsuD (BW25113 ΔleuB ΔssuD) did not significantly improve growth on sulfobutanoyl-L-leucine, suggesting that even in the presence of SsuD enough sulfobutanoyl-L-leucine is being metabolized by GGT to support growth of a leucine auxotrophic strain. Interestingly, weak growth was also observed with the pACT3 empty vector control. One possibility is that the relatively high concentration of sulfobutanoyl-L-leucine in the medium increases the risk that free leucine from chemical decomposition of sulfobutanoyl-L-leucine is taken up.

11. Example 10: Testing Other Sulfur Sources than Taurine

To further improve the system TauD is deleted in order to eliminate a potential sink for sulfobutanoyl-L-leucine.

Deletion TauD prevents the use of taurine as a sulfur source and as such another source will have to be identified. Unfortunately, most commonly used sulfur sources like sulfate, sulfite or cysteine cannot be used in this setting because they lead to a repression of the ssu operon, which would prevent the uptake of sulfobutanoyl-L-leucine into the cell. Therefore, a sulfur source is identified that can be rapidly utilized by E. coli, does not cause repression of the ssu operon and does not compete with sulfobutanoyl-L-leucine for the transporter SsuABC. Thiosulfate is expected to fulfill all the mentioned criteria which is further investigated.

12. Example 11: Increasing the Affinity of GGT* for Sulfobutanoyl-L-Leucine

Kinetic studies with PnGGT ΔN24 D405N and sulfobutanoyl-L-leucine revealed that the affinity of the enzyme for the substrate is relatively low ($K_M$ of 734 µM), which might be a limiting factor for the efficiency of the transport system. Therefore, the functionality of the transport system is improved by engineering GGT* with the goal to increase the affinity towards sulfobutanoyl amides. In a previous publication it was shown for EcGGT that mutations in several residues of the substrate binding pocket can lead to improved binding of glutaryl substrates (Yamada et al., 2008), opening up the possibility that mutations in these residues can also lead to improved binding of sulfobutanoyl substrates. To test this, saturation mutagenesis of 10 residues in the substrate binding pockets of EcGGT and PnGGT, respectively, is performed with the goal to identify a variant that allows faster growth on sulfobutanoyl-L-leucine (Table 6).

TABLE 6

Sites in EcGGT and PnGGT targeted for saturation mutagenesis

| EcGGT | PnGGT |
| --- | --- |
| R114 | R94 |
| T409 & N411 | T381 & N383 |
| Q430 & D433 | E402 & D405 |
| Y444 | F416 |
| S462 & S463 | S434 & S435 |
| G483 & G484 | G455 & G456 |

13. Example 12: Improving the Affinity of the Synthetic Transport System by Whole Strain Mutagenesis In order to further improve the functionality of the synthetic transport system a whole strain mutagenesis is performed. There is a possibility that the efficiency of the transport system suffers from toxic side products of sulfobutanoyl-L-leucine hydrolysis, like for example sulfobutanoic acid or 4-oxobutanoic acid. Another possibility is that the efficiency of the transport system is negatively influenced by regulatory processes, leading to reduced uptake or hydrolysis of sulfobutanoyl-L-leucine. To address these issues, the selection strain BW25113 ΔleuB is converted into a temporary mutator strain by overexpressing an inactive variant of the DNA polymerase subunit DnaQ which is responsible for proofreading activity. The strain is then plated on medium with gradually decreasing concentrations of sulfobutanoyl-L-leucine and colonies that grow faster or at lower substrate concentration are then selected. Through genome sequencing mutations can be identified that improve the functionality of the synthetic transport system.

14. Example 13: Further Applications of the Synthetic Transport System

Complementation of a histidine auxotrophic strain is demonstrated by feeding sulfobutanoyl-L-histidine to the cells. Sulfobutanoyl amides containing the dyes 4-nitroaniline, 3-carboxy-4-nitronaniline, 7-amino-4-methyl-coumarin and 7-amino-4-acetyl-coumarin are further synthesized. These substrates allow to easily visualize the functionality of the transport system. Sulfobutanoyl-picolylamide (also termed herein N-picolyl-sulfobutyramide) is tested which results in the release of picolylamine, a precursor of nicotinamide. The successful release of this compound can be easily assayed by complementation of a suitable nictotinamide auxotrophy.

15. Example 14: Import: Refactoring the Ssu Operon

After ensuring efficient cargo release from sulfobutanoyl amides, the efficient import into E. coli cells was addressed. Growth assays in minimal medium showed that sulfobutanoyl amides were taken up with a similar efficiency as other sulfonates, presumably via the transporter SsuABC (FIG. 21). However, expression of the ssuEADCB operon from the E. coli chromosome was shown previously to be tightly regulated by the availability of sulfur sources in the medium, with, for example, sulfate leading to strong repression of these genes already at minute levels (van Der Ploeg et al., 1999). To entirely disconnect the ssu system from standard sulfur regulons and thus make it impervious to trivial yet fatal obstacles such as frequently encountered sulfur impurities in the medium, the operon was refactored and thereby deregulated the expression of the transporter genes. To this end, first the leucine auxotrophic strain TK082 (BW25113 ΔleuB ΔssuEADCB ΔtauD) was constructed which lacks the genes encoding the sulfonate transporter SsuABC as well as the enzymes SsuDE and TauD, which might otherwise desulfonate sulfobutanoyl amides intracellularly and thus render them unavailable for PnGGT* (Eichhorn et al., 1997 and Eichhorn et al., 1999). To re-enable uptake of sulfobutanoyl amides, a plasmid containing the synthetic operon ssuABC under control of a tetracycline-inducible promoter was constructed (FIG. 22b). As recombinant expression of membrane or exported proteins often leads to growth impairments (Freigasser et al., 2009), yet substrate import rate is expected to be a crucial parameter for the use of the synthetic import system, we optimized the expression levels of the ssuABC operon. Each gene was amplified with a 5' overhang encoding a reduced ribosome binding site (RBS) library covering a broad range of translation initiation rates (TIRs). The libraries were specifically designed for each gene using the RedLibs algorithm (Espah Borujeni et al., 2014, Salis et al., 2009 and Jeschek et al., 2016). In total, two plasmid-based multidimensional libraries containing either 36 or 144 RBS variants per gene of the synthetic ssuABC operon were generated, one with in principle 46'656 variants, and the other with in principle 2'985'984 different operon variants.

To identify variants with well-balanced transporter protein levels based on optimal leucine import, both plasmid libraries were used to transform strain TK082[pPnGGT*]. For selection purposes, approximately 100'000 variants from each library were plated on MS minimal medium supplemented with glucose, $MgSO_4$ (as sulfur source), IPTG (for synthesis of PnGGT*), anhydrotetracycline (aTc, for expression of ssuABC) and 0.5 mM sulfobutanoyl-L-leucine as the sole source of leucine. Growth on this medium is only possible if sulfobutanoyl-L-leucine is taken up via the transiently expressed SsuABC transporter and hydrolyzed intracellularly by PnGGT* to complement the leucine auxotrophy of strain TK082. After 2 days of incubation at 37° C., colonies of different sizes were obtained. Re-isolation of cells from the largest colonies resulted in strains that showed rapid growth, while a control strain carrying the empty plasmid pSEVA271 without ssuABC did not grow at all (FIG. 22c). Clones originating from both libraries were among the fastest growing variants, but we could not draw solid conclusions from TIRs predicted after sequencing the operons recovered from fast growing strains as can be derived from Table 7.

TABLE 7

Summary of pSsuABC variants.

| | ssuA RBS sequence | TIR [ssuA] | ssuB RBS sequence | TIR [ssuB] | ssuC RBS sequence | TIR [ssuC] |
|---|---|---|---|---|---|---|
| cl.3 | AGGGGCTT | 2'491 | GGAGGTCT | 83'162 | GGAGGTTT | 547 |
| cl.6 | AGGGGCTT | 2'491 | GGAGGTCT | 83'162 | GGAGGTTT | 547 |
| cl.17 | TGGAGGGT | 4'274 | GGGAGGAC | 11'944 | GGAGGTTC | 5'481 |

The fastest growing clone 17, carrying a plasmid from here on called pSsuABC, originated from the larger library, indicating that this library might allow more accurate fine-tuning of the system, even though it has to be noted that the library was not exhaustively tested. The identical clones 3 and 6 were selected from the smaller library.

Experiments in liquid medium supplemented with sulfobutanoyl-L-leucine confirmed that the leucine auxotrophic strain TK082[pSsuABC] only grew when cells were synthesizing PnGGT* (FIG. 22d). When the experiment was repeated in the parent strain of TK082 that still contained the ssu and tau genes, it was verified that the deletion of ssuEADCB and tauD led to slightly improved growth, but was not critical for the function of the synthetic transport system. This suggests that the system can be easily transferred into other strain backgrounds (FIG. 23). Entirely equivalent results were obtained when these experiments were repeated using sulfobutanoyl-L-histidine instead of sulfobutanoyl-L-leucine and the histidine auxotrophic strain TK088 (FIG. 22e), confirming already at least a minimum of flexibility of the synthetic transport system.

16. Example 15: Cargo Release: Optimizing the Expression of PnGGT*

As flux control can be distributed over multiple steps (Kacser & Burns, 1995), the next experiments focused on the PnGGT* expression for flux optimization.

In earlier experiments, low intracellular levels of the parent enzyme PnGGT had to be maintained when unloading cargo from γ-glutamyl amides, presumably to prevent the futile hydrolysis of glutamine to glutamate (Kuenzl, et al., 2017). As the variant enzyme PnGGT* no longer possesses significant reactivity to γ-glutamyl-p-nitroanilide (FIG. 22a), it was reasoned that with PnGGT* and the sulfonate-based synthetic transport system such toxicity concerns should no longer apply and increasing the levels of PnGGT* in the cell might improve the performance of the synthetic transport system.

To identify the optimal intracellular level of PnGGT*, another round of RBS engineering was performed, this time on the basis of plasmid pPnGGT*. An RBS library with 81 members was used to transform strain TK082[pSsuABC] and the fastest growing colonies were re-isolated on MS minimal medium containing 0.25 mM sulfobutanoyl-L-leucine as the sole leucine source. It is of note that the reduced concentration of the leucine source compared to the previous selections. Two of the isolated clones were confirmed to reliably grow faster in liquid medium than a strain carrying the parent plasmid pPnGGT* (FIG. 22d). Two further variants were identified to lead to higher cell densities than the parent strain, but resulted in a multiphasic growth behavior in liquid medium (data not shown). Sequencing of plasmids from these strains showed that the predicted TIRs of all four RBS variants were up to tenfold higher than the parent plasmid's TIR as can be derived from Table 8.

TABLE 8

Summary of PnGGT* RBS variants.

| | RBS sequence | TIR |
|---|---|---|
| pPnGGT* | TTAGCAGG | 8'009 |
| RBS 1 | CCAGGGGG | 63'482 |
| RBS 3 | CGCGGGGG | 27'985 |
| RBS 4 | AGGGGGGG | 66'405 |
| RBS 9 | TACGGGGG | 83'162 |

These data suggested an increased protein level which was confirmed by Western blotting and enzyme activity assays in cell free extracts using the substrate sulfobutanoyl-p-nitroanilide (FIG. 24). Testing the same RBS variants in the histidine auxotrophic strain TK088[pSsuABC] for growth in minimal medium supplemented with sulfobutanoyl-L-histidine did not result in improved growth (data not shown), presumably because the metabolic burden of elevated PnGGT* synthesis overweighs the faster release of histidine.

17. Example 16: Uptake of Non-Natural Cargo Molecules

To further illustrate the versatility of the synthetic transport system, it was tested for in vivo release of the colorimetric dye 4-nitroaniline and the fluorescent dye 7-amino-4-methyl coumarin (AMC) in the cytoplasm of E. coli. Therefore, the substrates sulfobutanoyl-p-nitroanilide and sulfobutanoyl-AMC were prepared, which only turn colorimetric or fluorescent once the cargo is released from the SBA moiety. In a growing E. coli culture containing strain TK082 with different plasmid combinations, 4-nitroaniline was only released from the SBA moiety when SsuABC and PnGGT* were simultaneously synthesized by the cells, while no release took place if one or both components were missing (FIG. 25a). Consistent with in vitro data, faster release of 4-nitroaniline was detected if PnGGT* was synthesized from a plasmid containing a stronger RBS sequence. Similar results were obtained with sulfobutanoyl-AMC, however, some release of the dye was detected in a strain expressing only PnGGT*, but no SsuABC (FIG. 25b). Release of AMC in the absence of SsuABC most likely results from hydrolysis of the sulfonate by PnGGT* that leaked into the medium from lysed cells. This assumption can presumably be explained by the slow uptake of sulfobutanoyl-AMC through SsuABC (FIG. 21), which caused a low signal-to-noise ratio with this substrate during the in vivo studies. Furthermore, addition of low concentrations of pentanesulfate, a good substrate for transport by SsuABC (FIG. 21), were sufficient to slow down the release of 4-nitroaniline, consistent with the competition between pentanesulfate and sulfobutanoyl-p-nitroanilide for the SsuABC transporter and the resulting reduction in intracellular hydrolysis rate of sulfobutanoyl-p-nitroanilide (FIG. 25c). Similar results were obtained with the substrate sulfobutanoyl-AMC. While the presumably extracellular release of AMC in a strain lacking SsuABC was not affected by pentanesulfonate, already minute concentrations of pentanesulfonate were sufficient to slow down the release of AMC in the presence of SsuABC, indicating that at least a fraction of AMC was released inside the cell, after the sulfonate was taken up by SsuABC (FIG. 25d). The observation that such low concentrations of pentanesulfonate inhibit the intracellular release of AMC further supports the assumption that SsuABC has a low affinity for sulfobutanoyl-AMC.

18. Example 17: Identification of Novel Metabolic Routes

To demonstrate the potential of the synthetic transport system for biotechnological applications, this Example aimed to implement an alternative route for the in vivo biosynthesis of the commercially interesting product nicotinic acid (11; vitamin B3). Synthesis of nicotinic acid in *E. coli* involves a 5 step reaction from aspartate to $NAD^+$, and an additional 3 step reaction from the NAD salvage pathway to obtain nicotinic acid (Begley et al., 2001). To shortcut this reaction, we reasoned that the substrate 3-picolylamine (10) can potentially be converted to nicotinic acid in a two-step reaction involving a transamination and an oxidation step (FIG. 26a). However, due to the positive charge of its amine group and its absence from *E. coli*'s metabolism, uptake of 3-picolylamine is expected to be a limiting factor when implementing a novel pathway.

Initial growth experiments with the $NAD^+$ auxotrophic strain TK090 revealed that *E. coli* indeed possesses the enzymatic machinery to convert 3-picolylamine into $NAD^+$, but approximately 500 to 1000-fold higher concentrations of 3-picolylamine were necessary to complement the $NAD^+$ auxotrophy when compared to growth with nicotinic acid (FIG. 27). This discrepancy can either be explained by insufficient uptake of 3-picolylamine into the cell or inefficient conversion of 3-picolylamine to $NAD^+$. To address potential transport problems, 3-picolylamine was attached to SBA to yield N-picolyl-sulfobutyramide and added to the growth medium as the sole source of $NAD^+$. Consistent with previous results, growth of the $NAD^+$ auxotrophic strain was only observed when both the sulfonate transporter SsuABC and PnGGT* were synthesized simultaneously, while no growth was observed when one of the components was missing or in the presence of equimolar concentrations of free 3-picolylamine (FIG. 26b). These results indicate that insufficient uptake of 3-picolylamine is at least partly responsible for its inefficient utilization by *E. coli*.

19. Example 18: Engineering of PnGGT*

Initial growth experiments revealed that sulfobutanoyl-L-leucine and sulfobutanoyl-L-histidine were used as sulfur sources by *E. coli* with comparable efficiencies (FIG. 21).

Further growth experiments with auxotrophic strains harboring the synthetic transport system, however, revealed that cells grown in the presence of sulfubutanoyl-L-histidine grew significantly faster and to higher cell densities compared to cells grown with the same concentration of sulfobutanoyl-L-leucine (FIG. 22d and FIG. 22e). This discrepancy can most likely be explained either by a higher leucine demand of *E. coli* compared to histidine or by slower intracellular release of leucine from sulfobutanoyl-L-leucine by PnGGT*. Even though the demand of *E. coli* for leucine is indeed approximately 4-fold higher (Bennett, et al., 2009; Kaleta et al., 2013 and Spahr, 1962), we reason that sulfobutanoyl-L-leucine is a promising substrate for engineering the activity PnGGT*.

In a first round of engineering, several residues that lie in close proximity to the sulfobutanoyl moiety of sulfobutanoyl-L-leucine were randomized by site-directed mutagenesis, either individually (R94, F416) or in pairs of two (T381 N383, E402 D405, S434 S435, G455 G456). The libraries obtained with the template pPnGGT* were used to transform strain TK082[pSsuABC] and approximately 10'000 to 100'000 variants from each library were isolated on selective medium containing only 0.1 mM sulfobutanoyl-L-leucine as the only source of leucine. However, sequence analysis of isolated plasmids from the fastest growing variants revealed that none of them carried a mutation in a residue targeted by site-directed mutagenesis. Instead, several variants with either a random mutation from aspartate to tyrosine at position 385 or a proline to threonine mutation at position 505 were detected. In addition, various mutations in a loop formed by residue 167-170 were detected in the isolated variants.

Interestingly, the homology model of PnGGT* suggests that residue D385 and the loop formed by residue 167-170 are in spatial proximity and delineate a pocket where the cargo molecule is accommodated (FIG. 28a and FIG. 28b). Site-directed mutagenesis of residue D385 with a degenerated oligonucleotide showed that tyrosine is strongly favored at this position when selected on sulfobutanoyl-L-leucine, with all of the six fastest growing variants isolated from the corresponding library carrying the D385Y mutation. Randomization of residues Y167 and Q168 or alternatively residue R170 resulted in several variants with improved growth on sulfobutanoyl-L-leucine when compared to the same strain carrying the parent plasmid pPnGGT* (FIG. 28c). The localization of these mutations in the cargo pocket suggests that these mutations might specifically facilitate binding and hydrolysis of the substrate sulfobutanoyl-L-leucine, but not necessarily of other sulfobutanoyl amides. Indeed, additional growth assays with the substrate sulfobutanoyl-L-histidine in strain TK088[pSsuABC] revealed that only the mutations in the loop formed by residues 167-170 still had a positive effect on growth (FIG. 28d). To further investigate this issue, cell free extracts containing the different PnGGT* mutant variants were tested in vitro for activity against sulfobutanoyl-p-nitroanilide. In this case, all variants with mutations in the cargo pocket were significantly less active towards sulfobutanoyl-p-nitroanilide when compared to PnGGT*, while the expression of these variants was only partly affected (FIG. 29). These results indicate that mutations in these sites do not seem to have an overall positive effect on the performance of the synthetic transport system, but, as their position in the cargo pocket suggests, rather allow to fine tune the performance of the system for certain cargo molecules.

The homology model places residue P505 at quite a distance from the substrate binding site of PnGGT*. A mutation from proline to threonine led to improved utilization of sulfobutanoyl-L-leucine, while having a slightly negative effect on the utilization of sulfobutanoyl-L-histidine (FIGS. 28c and d). Interestingly, this mutant also had slightly elevated in vitro activity towards sulfobutanoyl-p-nitroanilide, indicating that this mutation has a more subtle effect on substrate specificity of the enzyme (FIG. 29). A sequence alignment of GGT variants from different Pseudomonas species revealed that threonine and alanine residues seem to be evolutionary favored in this position, which is consistent with the notion that the introduction of a threonine residue at this position can have beneficial effects (FIG. 30).

To further confirm that the faster growth of strains synthesizing mutated PnGGT* variants on sulfobutanoyl-L-leucine was indeed mediated by mutations in PnGGT*, the kinetic parameters of mutants P505T and D385Y were determined. For PnGGT* P505T, a lower $K_M$ and a slightly higher $V_{max}$ were measured with sulfobutanoyl-p-nitroanilide and sulfobutanoyl-L-leucine when compared to PnGGT* (FIG. 31 and FIG. 32). This improvement in catalytic efficiency is consistent with the faster growth on sulfobutanoyl-L-leucine observed with strains synthesizing this enzyme variant. Due to the low activity of PnGGT* D385Y towards sulfobutanoyl-p-nitroanilide, the kinetic parameters of this variant were determined only with the substrate sulfobutanoyl-L-leucine and resulted in a 21-fold reduction of $K_M$ and a 1.55-fold improvement of $V_{max}$ over PnGGT* (FIG. 32). This drastic improvement in affinity for sulfobutanoyl-L-leucine corresponds well with the significantly improved growth behavior on this substrate.

REFERENCES

Adams, M. D., Wagner, L. M., Graddis, T. J., Landick, R., Antonucci, T. K., Gibson, A. L., Oxender, D. L., 1990. Nucleotide sequence and genetic characterization reveal six essential genes for the LIV-1 and LS transport systems of Escherichia coli. J Biol Chem. 265, 11436-11443.

Ames, B. N., Ames, G. F., Young, J. D., Tsuchiya, D., Lecocq, J., 1973. Illicit transport: the oligopeptide permease. Proc Natl Acad Sci USA. 70, 456-458.

Arnold, K., Bordoli, L., Kopp, J., Schwede, T., 2006. The SWISS-MODEL workspace: a web-based environment for protein structure homology modelling. Bioinformatics. 22, 195-201.

Baba, T., Ara, T., Hasegawa, M., Takai, Y., Okumura, Y., Baba, M., Datsenko, K. A., Tomita, M., Wanner, B. L., Mori, H., 2006. Construction of Escherichia coli K-12 in-frame, single-gene knockout mutants: the Keio collection. Mol Syst Biol. 2, 2006.0008.

Begley, T. P., Kinsland, C., Mehl, R. A., Osterman, A. & Dorrestein, P. The biosynthesis of nicotinamide adenine dinucleotides in bacteria. Vitamins and hormones 61, 103-119 (2001).

Bennett, B. D. et al. Absolute metabolite concentrations and implied enzyme active site occupancy in Escherichia coli. Nature chemical biology 5, 593-599 (2009).

Biasini, M., Bienert, S., Waterhouse, A., Arnold, K., Studer, G., Schmidt, T., Kiefer, F., Gallo Cassarino, T., Bertoni, M., Bordoli, L., Schwede, T., 2004. SWISS-MODEL: modelling protein tertiary and quaternary structure using evolutionary information. Nucleic Acids Res. 42, W252-258.

Billerbeck, S., Panke, S., 2012. A genetic replacement system for selection-based engineering of essential proteins. Microb Cell Fact. 11, 110.

Birmingham, W. R., Starbird, C. A., Panosian, T. D., Nannemann, D. P., Iverson, T. M., Bachmann, B. O., 2014. Bioretrosynthetic construction of a didanosine biosynthetic pathway. Nat Chem Biol. 10, 392-399.

Blum, E., Carpousis, A. J., Higgins, C. F., 1999. Polyadenylation promotes degradation of 3'-structured RNA by the Escherichia coli mRNA degradosome in vitro. J Biol Chem. 274, 4009-4016.

Boehm, J. C., Kingsbury, W. D., Perry, D., Gilvarg, C., 1983. The use of cysteinyl peptides to effect portage transport of sulfhydryl-containing compounds in Escherichia coli. J Biol Chem. 258, 14850-14855.

Bosshart, A., Hee, C. S., Bechtold, M., Schirmer, T., Panke, S. 2015. Directed divergent evolution of a thermostable D-tagatose epimerase towards improved activity for two hexose substrates. Chembiochem. 16, 592-601.

Chang, A. C., Cohen, S. N., 1978. Construction and characterization of amplifiable multicopy DNA cloning vehicles derived from the P15A cryptic miniplasmid. J Bacteriol. 134, 1141-1156.

Cherepanov, P. P., Wackernagel, W., 1995. Gene disruption in Escherichia coli: TcR and KmR cassettes with the option of Flp-catalyzed excision of the antibiotic-resistance determinant. Gene. 158, 9-14.

Cowan, S. W., Schirmer, T., Rummel, G., Steiert, M., Ghosh, R., Pauptit, R. A., Jansonius, J. N., Rosenbusch, J. P., 1992. Crystal structures explain functional properties of two E. coli porins. Nature. 358, 727-733.

Datsenko, K. A., Wanner, B. L., 2000. One-step inactivation of chromosomal genes in Escherichia coli K-12 using PCR products. Proc Natl Acad Sci USA. 97, 6640-6645.

Dunten, P., Mowbray, S. L., 1995. Crystal structure of the dipeptide binding protein from Escherichia coli involved in active transport and chemotaxis. Protein Sci. 4, 2327-2334.

Dykxhoorn, D. M., St Pierre, R., Linn, T., 1996. A set of compatible tac promoter expression vectors. Gene. 177, 133-136.

Eichhorn, E., van der Ploeg, J. R., Kertesz, M. A., Leisinger, T., 1997. Characterization of alpha-ketoglutarate-dependent taurine dioxygenase from Escherichia coli. The Journal of biological chemistry. 272, 23031-6.

Eichhorn, E., van der Ploeg, J. R., Leisinger, T., 1999. Characterization of a two-component alkanesulfonate monooxygenase from Escherichia coli. The Journal of biological chemistry. 274, 26639-46.

Eichhorn, E., van der Ploeg, J. R., Leisinger, T., 2000. Deletion analysis of the Escherichia coli taurine and alkanesulfonate transport systems. J Bacteriol. 182, 2687-95.

Espah Borujeni, A., Channarasappa, A. S., Salis, H. M., 2014. Translation rate is controlled by coupled trade-offs between site accessibility, selective RNA unfolding and sliding at upstream standby sites. Nucleic Acids Res. 42, 2646-2659.

Fickel, T. E., Gilvarg, C., 1973. Transport of impermeant substances in *E. coli* by way of oligopeptide permease. Nat New Biol. 241, 161-163.

Finidori, J., Laperche, Y., Haguenauertsapis, R., Barouki, R., Guellaen, G., Hanoune, J., 1984. In vitro biosynthesis and membrane insertion of gamma-glutamyl transpeptidase. J Biol Chem. 259, 4687-4690.

Freigassner, M., Pichler, H. & Glieder, A. Tuning microbial hosts for membrane protein production. *Microbial cell factories* 8, 69 (2009).

Gerstung, M., Beisel, C., Rechsteiner, M., Wild, P., Schraml, P., Moch, H., Beerenwinkel, N., 2012. Reliable detection of subclonal single-nucleotide variants in tumour cell populations. Nat Commun. 3, 811.

Gerstung, M., Papaemmanuil, E., Campbell, P. J., 2014. Subclonal variant calling with multiple samples and prior knowledge. Bioinformatics. 30, 1198-1204.

Gollop, N., Tavori, H., Barak, Z., 1982. Acetohydroxy acid synthase is a target for leucine containing peptide toxicity in *Escherichia coli*. J Bacteriol. 149, 387-390.

Guex, N., Peitsch, M. C., Schwede, T., 2009. Automated comparative protein structure modeling with SWISS-MODEL and Swiss-PdbViewer: a historical perspective. Electrophoresis. 30, S162-173.

Guyer, C. A., Morgan, D. G., Staros, J. V., 1986. Binding specificity of the periplasmic oligopeptide-binding protein from *Escherichia coli*. J Bacteriol. 168, 775-779.

Hanahan, D., 1983. Studies on transformation of *Escherichia coli* with plasmids. J Mol Biol. 166, 557-580.

Hanigan, M. H., 2014. Gamma-glutamyl transpeptidase: redox regulation and drug resistance. Adv Cancer Res. 122, 103-141.

Hershfield, V., Boyer, H. W., Yanofsky, C., Lovett, M. A., Helinski, D. R., 1974. Plasmid ColE1 as a molecular vehicle for cloning and amplification of DNA. Proc Natl Acad Sci USA. 71, 3455-3459.

Hong, N. J., Park, Y. T., 1993. Portage transport of toxophoric agent, N-hydroxyalanine, through oligopeptide permease in *Escherichia coli*. Bull Korean Chem Soc. 14, 674-678.

Hwang, S. Y., Berges, D. A., Taggart, J. J., Gilvarg, C., 1989. Portage transport of sulfanilamide and sulfanilic acid. J Med Chem. 32, 694-698.

Imaoka, M., Yano, S., Okumura, M., Hibi, T., Wakayama, M., 2010. Molecular cloning and characterization of gamma-glutamyltranspeptidase from *Pseudomonas nitroreducens* IFO12694. Biosci Biotechnol Biochem. 74, 1936-1939.

Jeschek, M., Gerngross, D., Panke, S., 2016. Rationally reduced libraries for combinatorial pathway optimization minimizing experimental effort. Nat Commun. 7, 11163.

Kacser, H. & Burns, J. A. The control of flux. *Biochemical Society transactions* 23, 341-366 (1995).

Kaleta, C., Schauble, S., Rinas, U. & Schuster, S. Metabolic costs of amino acid and protein production in *Escherichia coli*. Biotechnology journal 8, 1105-1114 (2013).

Kiefer, F., Arnold, K., Kunzli, M., Bordoli, L., Schwede, T., 2009. The SWISS-MODEL Repository and associated resources. Nucleic Acids Res. 37, D387-392.

Kingsbury, W. D., Boehm, J. C., Perry, D., Gilvarg, C., 1984. Portage of various compounds into bacteria by attachment to glycine residues in peptides. Proc Natl Acad Sci USA. 81, 4573-4576.

Klepsch, M. M., Kovermann, M., Low, C., Balbach, J., Permentier, H. P., Fusetti, F., de Gier, J. W., Slotboom, D. J., Berntsson, R. P., 2011. *Escherichia coli* peptide binding protein OppA has a preference for positively charged peptides. *J Mol Biol*. 414, 75-85.

Krewinkel M, Dworeck T, Fioroni M. 2011. Engineering of an *E. coli* outer membrane protein FhuA with increased channel diameter. J Nanobiotechnology 9:33.

Kuenzl T, Sroka M, Srivastava P, Herdewijn P, Marlière P, Panke S. Overcoming the membrane barrier: Recruitment of γ-glutamyl transferase for intracellular release of metabolic cargo from peptide vectors. Metabolic Engineering doi:http://dx.doi.org/10.1016/j.ymben.2016.10.016.

Kuenzl T, Panke S. 2016. Potential applications of γ-glutamyl transferases in synthetic biology. New Biotechnology 33, Supplement:S186.

Laemmli, U. K., 1970. Cleavage of structural proteins during the assembly of the head of bacteriophage T4. Nature. 227, 680-685.

Langmead, B., Salzberg, S. L., 2012. Fast gapped-read alignment with Bowtie 2. Nat Methods. 9, 357-359.

Langmead, B., Trapnell, C., Pop, M., Salzberg, S. L., 2009. Ultrafast and memory-efficient alignment of short DNA sequences to the human genome. Genome Biol. 10, R25.

Lo, H. F., Chou, W. M., Chen, P. J., Lin, L. L., 2008. Influence of signal-peptide truncations on the functional expression of *Escherichia coli* gamma-glutamyltranspeptidase. J Basic Microbiol. 48, 260-268.

Lou K L, Saint N, Prilipov A, Rummel G, Benson S A, Rosenbusch J P, Schirmer T. 1996. Structural and functional characterization of OmpF porin mutants selected for larger pore size. I. Crystallographic analysis. J Biol Chem 271:20669-20675.

Malyshev, D. A., Dhami, K., Lavergne, T., Chen, T., Dai, N., Foster, J. M., Correa, I. R., Jr., Romesberg, F. E., 2014. A semi-synthetic organism with an expanded genetic alphabet. Nature. 509, 385-388.

Martinez-Garcia, E., Aparicio, T., Goni-Moreno, A., Fraile, S., de Lorenzo, V., 2015. SEVA 2.0: an update of the Standard European Vector Architecture for de-/reconstruction of bacterial functionalities. Nucleic Acids Res. 43, 1183-1189.

Martinez-Garcia, E., de Lorenzo, V., 2011. Engineering multiple genomic deletions in Gram-negative bacteria: analysis of the multi-resistant antibiotic profile of *Pseudomonas putida* KT2440. Environ Microbiol. 13, 2702-2716.

Martinez-Garcia, E., de Lorenzo, V., 2012. Transposon-based and plasmid-based genetic tools for editing genomes of gram-negative bacteria. Methods Mol Biol. 813, 267-283.

Messing, J., Crea, R., Seeburg, P. H., 1981. A system for shotgun DNA sequencing. Nucleic Acids Res. 9, 309-321.

Minami, H., Suzuki, H., Kumagai, H., 2003. Salt-tolerant gamma-glutamyltranspeptidase from *Bacillus subtilis* 168 with glutaminase activity. Enzyme Microb. Technol. 32, 431-438.

Mohanty, B. K., Kushner, S. R., 1999. Analysis of the function of *Escherichia coli* poly(A) polymerase I in RNA metabolism. Mol Microbiol. 34, 1094-1108.

Mohanty, B. K., Kushner, S. R., 2006. The majority of *Escherichia coli* mRNAs undergo post-transcriptional modification in exponentially growing cells. Nucleic Acids Res. 34, 5695-5704.

Muhammad N, Dworeck T, Fioroni M, Schwaneberg U. 2011. Engineering of the *E. coli* outer membrane protein FhuA to overcome the hydrophobic mismatch in thick polymeric membranes. J Nanobiotechnology 9:8.

Nickitenko, A. V., Trakhanov, S., Quiocho, F. A., 1995. 2 A resolution structure of DppA, a periplasmic dipeptide transport/chemosensory receptor. Biochemistry. 34, 16585-16595.

Ohnishi, K., Hasegawa, A., Matsubara, K., Date, T., Okada, T., Kiritani, K., 1988. Cloning and nucleotide sequence of the brnQ gene, the structural gene for a membrane-associated component of the LIV-II transport system for branched-chain amino acids in *Salmonella typhimurium*. Jpn J Genet. 63, 343-357.

Okada, T., Suzuki, H., Wada, K., Kumagai, H., Fukuyama, K., 2006. Crystal structures of gamma-glutamyltranspeptidase from *Escherichia coli*, a key enzyme in glutathione metabolism, and its reaction intermediate. Proc Natl Acad Sci USA. 103, 6471-6476.

Orlowski, M., Meister, A., 1970. The gamma-glutamyl cycle: a possible transport system for amino acids. Proc Natl Acad Sci USA. 67, 1248-1255.

Payne, J. W., Morley, J. S., Armitage, P., Payne, G. M., 1984. Transport and hydrolysis of antibacterial peptide analogues in *Escherichia coli*: backbone-modified aminoxy peptides. J Gen Microbiol. 130, 2253-2265.

Perry, D., Gilvarg, C., 1984. Spectrophotometric determination of affinities of peptides for their transport systems in *Escherichia coli*. J Bacteriol. 160, 943-948.

Petersen, T. N., Brunak, S., von Heijne, G., Nielsen, H., 2011. SignalP 4.0: discriminating signal peptides from transmembrane regions. Nat Methods. 8, 785-786.

Pettersen, E. F., Goddard, T. D., Huang, C. C., Couch, G. S., Greenblatt, D. M., Meng, E. C., Ferrin, T. E., 2004. UCSF Chimera—a visualization system for exploratory research and analysis. J. Comput. Chem. 25, 1605-1612.

Platt, R., Drescher, C., Park, S. K., Phillips, G. J., 2000. Genetic system for reversible integration of DNA constructs and lacZ gene fusions into the *Escherichia coli* chromosome. Plasmid. 43, 12-23.

Qvit, N., Reuveni, H., Gazal, S., Zundelevich, A., Blum, G., Niv, M Y., Feldstein, A., Meushar, S., Shalev, D. E., Friedler, A., Gilon, C., 2008. Synthesis of a novel macrocyclic library: discovery of an IGF-1R inhibitor. J. Comb. Chem. 10, 256-266.

Raynal, L. C., Carpousis, A. J., 1999. Poly(A) polymerase I of *Escherichia coli*: characterization of the catalytic domain, an RNA binding site and regions for the interaction with proteins involved in mRNA degradation. Mol Microbiol. 32, 765-775.

Robinson, J. T., Thorvaldsdóttir, H., Winckler, W., Guttman, M., Lander, E. S., Getz, G., Mesirov, J. P., 2011. Integrative Genomics Viewer. Nat Biotechnol. 29, 24-26.

Saint N, Lou K L, Widmer C, Luckey M, Schirmer T, Rosenbusch J P. 1996. Structural and functional characterization of OmpF porin mutants selected for larger pore size. II. Functional characterization. J Biol Chem 271: 20676-20680.

Salis, H. M., Mirsky, E. A., Voigt, C. A., 2009. Automated Design of Synthetic Ribosome Binding Sites to Precisely Control Protein Expression. Nat Biotechnol. 27, 946-950.

Sambrook, J., Russell, D. W., 2001. Molecular cloning: a laboratory manual. Cold Spring Harbor Laboratory Press, Cold Spring Harbor, N.Y.

Sievers, F. et al. Fast, scalable generation of high-quality protein multiple sequence alignments using Clustal Omega. *Mol Syst Biol* 7, 539 (2011).

Sleigh, S. H., Seavers, P. R., Wilkinson, A. J., Ladbury, J. E., Tame, J. R., 1999. Crystallographic and calorimetric analysis of peptide binding to OppA protein. J Mol Biol. 291, 393-415.

Smith, M. W., Tyreman, D. R., Payne, G. M., Marshall, N. J., Payne, J. W., 1999. Substrate specificity of the periplasmic dipeptide-binding protein from *Escherichia coli*: experimental basis for the design of peptide prodrugs. Microbiology. 145, 2891-2901.

Spahr, P. F. Amino acid composition of ribosomes from *Escherichia coli*. *Journal of molecular biology* 4, 395-406 (1962).

Suzuki, H., Kumagai, H., 2002. Autocatalytic processing of gamma-glutamyltranspeptidase. J Biol Chem. 277, 43536-43543.

Suzuki, H., Kumagai, H., Tochikura, T., 1986. Gamma-glutamyltranspeptidase from *Escherichia coli* K-12: purification and properties. J Bacteriol. 168, 1325-1331.

Suzuki, H., Miwa, C., Ishihara, S., Kumagai, H., 2004. A single amino acid substitution converts gamma-glutamyltranspeptidase to a class IV cephalosporin acylase (glutaryl-7-aminocephalosporanic acid acylase). Applied and environmental microbiology. 70, 6324-8.

Tame, J. R., Dodson, E. J., Murshudov, G., Higgins, C. F., Wilkinson, A. J., 1995. The crystal structures of the oligopeptide-binding protein OppA complexed with tripeptide and tetrapeptide ligands. Structure. 3, 1395-1406.

Tavori, H., Kimmel, Y., Barak, Z., 1981. Toxicity of leucine-containing peptides in *Escherichia coli* caused by circumvention of leucine transport regulation. J Bacteriol. 146, 676-683.

Thomason, L. C., Costantino, N., Court, D. L., 2007. *E. coli* genome manipulation by P1 transduction. Current protocols in molecular biology. Chapter 1, Unit 1.17.

Thorvaldsdóttir, H., Robinson, J. T., Mesirov, J. P., 2013. Integrative Genomics Viewer (IGV): high-performance genomics data visualization and exploration. Brief Bioinform. 14, 178-192.

Towbin, H., Staehelin, T., Gordon, J., 1979. Electrophoretic transfer of proteins from polyacrylamide gels to nitrocellulose sheets: procedure and some applications. Proc Natl Acad Sci USA. 76, 4350-4354.

van Der Ploeg, J. R., Iwanicka-Nowicka, R., Bykowski, T., Hryniewicz, M. M. & Leisinger, T. The *Escherichia coli* ssuEADCB gene cluster is required for the utilization of sulfur from aliphatic sulfonates and is regulated by the transcriptional activator Cbl. *The Journal of biological chemistry* 274, 29358-29365 (1999).

Van Dyke, M. W., Sirito, M., Sawadogo, M., 1992. Single-step purification of bacterially expressed polypeptides containing an oligo-histidine domain. Gene. 111, 99-104.

Van Gelder P, Dumas F, Bartoldus I, Saint N, Prilipov A, Winterhalter M, Wang Y, Philippsen A, Rosenbusch J P, 2002. Sugar Transport through Maltoporin of *Escherichia coli*: Role of the Greasy Slide. J Bacteriol 184:2994-2999.

Van Gelder P, Dutzler R, Dumas F, Koebnik R, Schirmer T. 2001. Sucrose transport through maltoporin mutants of *Escherichia coli*. Protein Eng Des Sel 14:943-948.

Wang, W., Malcolm, B. A., 1999. Two-stage PCR protocol allowing introduction of multiple mutations, deletions and insertions using QuikChange Site-Directed Mutagenesis. Biotechniques. 26, 680-682.

Xu, F., Lin-Chao, S., Cohen, S. N., 1993. The *Escherichia coli* pcnB gene promotes adenylylation of antisense RNAI of ColE1-type plasmids in vivo and degradation of RNAI decay intermediates. Proc Natl Acad Sci USA. 90, 6756-6760.

Yanisch-Perron, C., Vieira, J., Messing, J., 1985. Improved M13 phage cloning vectors and host strains: nucleotide sequences of the M13mp18 and pUC19 vectors. Gene. 33, 103-119.

Yamada, C., Kijima, K., Ishihara, S., Miwa, C., Wada, K., Okada, T., Fukuyama, K., Kumagai, H., Suzuki, H., 2008. Improvement of the glutaryl-7-aminocephalosporanic acid acylase activity of a bacterial gamma-glutamyltranspeptidase. Applied and environmental microbiology. 74, 3400-9.

Yehudai-Resheff, S., Schuster, G., 2000. Characterization of the *E. coli* poly(A) polymerase: nucleotide specificity, RNA-binding affinities and RNA structure dependence. Nucleic Acids Res. 28, 1139-1144.

The invention claimed is:

1. A cellular transport system for bringing a sulfonic acid construct of the following formula (I) or a physiologically acceptable salt thereof

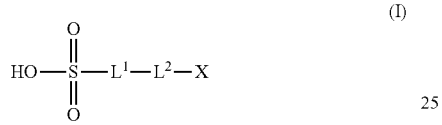

(I)

wherein:
- $L^1$ is a group —$(CH_2)_{1-6}$—, wherein said group —$(CH_2)_{1-6}$— is optionally substituted with one or more groups $R^{L11}$, and further wherein one or more —$CH_2$— units comprised in said group —$(CH_2)_{1-6}$— are each optionally replaced by a group $R^{L12}$;
- $L^2$ is —C(=O)— or —C(=S)—;
- X is a chemical moiety which is attached to $L^2$ via a heteroatom comprised in said chemical moiety, wherein said heteroatom is selected from oxygen, sulfur, nitrogen and selenium;
- each $R^{L11}$ is independently selected from $C_{1-5}$ alkyl, $C_{2-5}$ alkenyl, $C_{2-5}$ alkynyl, —$(C_{0-3}$ alkylene)-OH, —$(C_{0-3}$ alkylene)-O$(C_{1-5}$ alkyl), —$(C_{0-3}$ alkylene)-O$(C_{1-5}$ alkylene)-OH, —$(C_{0-3}$ alkylene)-O$(C_{1-5}$ alkylene)-O$(C_{1-5}$ alkyl), —$(C_{0-3}$ alkylene)-SH, —$(C_{0-3}$ alkylene)-S$(C_{1-5}$ alkyl), —$(C_{0-3}$ alkylene)-S$(C_{1-5}$ alkylene)-SH, —$(C_{0-3}$ alkylene)-S$(C_{1-5}$ alkylene)-S$(C_{1-5}$ alkyl), —$(C_{0-3}$ alkylene)-NH$_2$, —$(C_{0-3}$ alkylene)-NH$(C_{1-5}$ alkyl), —$(C_{0-3}$ alkylene)-N$(C_{1-5}$ alkyl)$(C_{1-5}$ alkyl), —$(C_{0-3}$ alkylene)-halogen, —$(C_{0-3}$ alkylene)-$(C_{1-5}$ haloalkyl), —$(C_{0-3}$ alkylene)-O—$(C_{1-5}$ haloalkyl), —$(C_{0-3}$ alkylene)-CF$_3$, —$(C_{0-3}$ alkylene)-CN, —$(C_{0-3}$ alkylene)-NO$_2$, —$(C_{0-3}$ alkylene)-CHO, —$(C_{0-3}$ alkylene)-CO—$(C_{1-5}$ alkyl), —$(C_{0-3}$ alkylene)-COOH, —$(C_{0-3}$ alkylene)-CO—O—$(C_{1-5}$ alkyl), —$(C_{0-3}$ alkylene)-O—CO—$(C_{1-5}$ alkyl), —$(C_{0-3}$ alkylene)-CO—NH$_2$, —$(C_{0-3}$ alkylene)-CO—NH$(C_{1-5}$ alkyl), —$(C_{0-3}$ alkylene)-CO—N$(C_{1-5}$ alkyl)$(C_{1-5}$ alkyl), —$(C_{0-3}$ alkylene)-NH—CO—$(C_{1-5}$ alkyl), —$(C_{0-3}$ alkylene)-N$(C_{1-5}$ alkyl)-CO—$(C_{1-5}$ alkyl), —$(C_{0-3}$ alkylene)-SO$_2$—NH$_2$, —$(C_{0-3}$ alkylene)-SO$_2$—NH$(C_{1-5}$ alkyl), —$(C_{0-3}$ alkylene)-SO$_2$—N$(C_{1-5}$ alkyl)$(C_{1-5}$ alkyl), —$(C_{0-3}$ alkylene)-NH—SO$_2$—$(C_{1-5}$ alkyl), —$(C_{0-3}$ alkylene)-N$(C_{1-5}$ alkyl)-SO$_2$—$(C_{1-5}$ alkyl), —$(C_{0-3}$ alkylene)-carbocyclyl, and —$(C_{0-3}$ alkylene)-heterocyclyl, wherein the carbocyclyl moiety comprised in said —$(C_{0-3}$ alkylene)-carbocyclyl and the heterocyclyl moiety comprised in said —$(C_{0-3}$ alkylene)-heterocyclyl are each optionally substituted with one or more groups $R^{L15}$, and further wherein any two groups $R^{L11}$ that are attached to different carbon atoms comprised in $L^1$ may also be mutually linked to form together a group —$R^{L13}$—, and wherein any two groups $R^{L11}$ that are attached to the same carbon atom comprised in $L^1$ may also be mutually linked to form, together with the carbon atom that they are attached to, a cycloalkyl or a heterocycloalkyl, wherein said cycloalkyl or said heterocycloalkyl is optionally substituted with one or more groups $R^{L15}$;
- each $R^{L12}$ is independently selected from —O—, —CO—, —C(=O)O—, —O—C(=O)—, —N($R^{L14}$)—, —N($R^{L14}$)—CO—, —CO—N($R^{L14}$)—, —S—, —SO—, —SO$_2$—, —SO$_2$—N($R^{L14}$)— and —N($R^{L14}$)—SO$_2$—;
- each $R^{L13}$ is independently selected from $C_{1-6}$ alkylene and $C_{2-6}$ alkenylene, wherein said alkylene or said alkenylene is optionally substituted with one or more groups independently selected from $C_{1-4}$ alkyl, —OH, —O$(C_{1-4}$ alkyl), —NH$_2$, —NH$(C_{1-4}$ alkyl), —N$(C_{1-4}$ alkyl)$(C_{1-4}$ alkyl), halogen, —CF$_3$, and —CN, and further wherein one or more —CH$_2$— units comprised in said alkylene or in said alkenylene are each optionally replaced by a group independently selected from —O—, —CO—, —NH—, —N$(C_{1-5}$ alkyl)- and —S—;
- each $R^{L14}$ is independently selected from hydrogen and $C_{1-5}$ alkyl; and
- each $R^{L15}$ is independently selected from $C_{1-5}$ alkyl, $C_{2-5}$ alkenyl, $C_{2-5}$ alkynyl, —$(C_{0-3}$ alkylene)-OH, —$(C_{0-3}$ alkylene)-O$(C_{1-5}$ alkyl), —$(C_{0-3}$ alkylene)-O$(C_{1-5}$ alkylene)-OH, —$(C_{0-3}$ alkylene)-O$(C_{1-5}$ alkylene)-O$(C_{1-5}$ alkyl), —$(C_{0-3}$ alkylene)-SH, —$(C_{0-3}$ alkylene)-S$(C_{1-5}$ alkyl), —$(C_{0-3}$ alkylene)-S$(C_{1-5}$ alkylene)-SH, —$(C_{0-3}$ alkylene)-S$(C_{1-5}$ alkylene)-S$(C_{1-5}$ alkyl), —$(C_{0-3}$ alkylene)-NH$_2$, —$(C_{0-3}$ alkylene)-NH$(C_{1-5}$ alkyl), —$(C_{0-3}$ alkylene)-N$(C_{1-5}$ alkyl)$(C_{1-5}$ alkyl), —$(C_{0-3}$ alkylene)-halogen, —$(C_{0-3}$ alkylene)-$(C_{1-5}$ haloalkyl), —$(C_{0-3}$ alkylene)-O—$(C_{1-5}$ haloalkyl), —$(C_{0-3}$ alkylene)-CF$_3$, —$(C_{0-3}$ alkylene)-CN, —$(C_{0-3}$ alkylene)-NO$_2$, —$(C_{0-3}$ alkylene)-CHO, —$(C_{0-3}$ alkylene)-CO—$(C_{1-5}$ alkyl), —$(C_{0-3}$ alkylene)-COOH, —$(C_{0-3}$ alkylene)-CO—O—$(C_{1-5}$ alkyl), —$(C_{0-3}$ alkylene)-O—CO—$(C_{1-5}$ alkyl), —$(C_{0-3}$ alkylene)-CO—NH$_2$, —$(C_{0-3}$ alkylene)-CO—NH$(C_{1-5}$ alkyl), —$(C_{0-3}$ alkylene)-CO—N$(C_{1-5}$ alkyl)$(C_{1-5}$ alkyl), —$(C_{0-3}$ alkylene)-NH—CO—$(C_{1-5}$ alkyl), —$(C_{0-3}$ alkylene)-N$(C_{1-5}$ alkyl)-CO—$(C_{1-5}$ alkyl), —$(C_{0-3}$ alkylene)-SO$_2$—NH$_2$, —$(C_{0-3}$ alkylene)-SO$_2$—NH ($C_{1-5}$ alkyl), —($C_{0-3}$ alkylene)-$SO_2$—N($C_{1-5}$ alkyl)($C_{1-5}$ alkyl), —($C_{0-3}$ alkylene)-NH—$SO_2$—($C_{1-5}$ alkyl), and —($C_{0-3}$ alkylene)-N($C_{1-5}$ alkyl)-$SO_2$—($C_{1-5}$ alkyl);

- into a cell and releasing a cargo from the sulfonic acid construct of formula (I) in the cell's cytoplasm, wherein said cargo is a compound H—X wherein X is as defined in formula (I), and wherein the cellular transport system comprises:
- (i) a sulfonate transporter located in the membrane of the cell wherein said sulfonate transporter is capable of transporting the sulfonic acid construct of formula (I) across the cytoplasm membrane into the cytoplasm; and
- (ii) a γ-glutamyl transferase (GGT; EC 2.3.2.2) which is modified to be located in the cytoplasm of the cell, wherein said γ-glutamyl transferase is capable of hydrolyzing the sulfonic acid construct of formula (I) to release the compound H—X.

2. The cellular transport system according to claim 1, wherein $L^1$ is —$(CH_2)_3$— and wherein $L^2$ is —C(=O)—.

3. The cellular transport system according to claim 1, wherein the γ-glutamyl transferase (GGT) is modified to be located in the cytoplasm of the cell by a signal-peptide truncation.

4. The cellular transport system according to claim 1, wherein the γ-glutamyl transferase (GGT) has an amino acid sequence as shown in SEQ ID NO:1 or an amino acid sequence having at least 30% sequence identity to SEQ ID NO:1 and lacking at least 16 N-terminal amino acids, wherein the enzymatically active form of said γ-glutamyl transferase is capable of hydrolyzing said sulfonic acid construct of formula (I) to release the compound H—X.

5. The cellular transport system according to claim 1, wherein the sulfonate transporter located in the cytoplasm membrane of the cell is a TauABC transporter or an SsuABC transporter derived from *E. coli*.

6. The cellular transport system according to claim 1, wherein the cell is a eukaryotic cell or a prokaryotic cell.

7. The cellular transport system according to claim 6, wherein the eukaryotic cell is a yeast cell.

8. The cellular transport system according to claim 6, wherein the prokaryotic cell is a gram negative bacterial cell.

9. The cellular transport system according to claim 8, wherein the gram negative bacterial cell a *E. coli* cell.

10. The cellular transport system according to claim 1, wherein X is selected from the group consisting of an amino acid, a sugar, a nucleobase, a nucleoside, a nucleotide, a phosphate containing organic group or a lipid.

11. The cellular transport system according to claim 1, wherein the γ-glutamyl transferase has an amino acid sequence as shown in SEQ ID NO:1 or an amino acid sequence having at least 30% sequence identity to SEQ ID NO:1 in which the amino acid residue at position 433 in the amino acid sequence shown in SEQ ID NO:1 or at a position corresponding to this position is substituted with another amino acid residue.

12. The cellular transport system according to claim 1, wherein the γ-glutamyl transferase has an amino acid sequence as shown in SEQ ID NO:2 or an amino acid sequence having at least 30% sequence identity to SEQ ID NO:2 in which the amino acid residue at position 405 in the amino acid sequence shown in SEQ ID NO:2 or at a position corresponding to this position is substituted with another amino acid residue.

13. A method for transporting a cargo molecule into a cell comprising incubating a cell comprising the transport system of claim 1 in a medium containing a sulfonic acid construct of formula (I) whereby said sulfonic acid construct is transported into the cell and is hydrolyzed within the cell by said GGT releasing in the cell from said sulfonic acid construct the cargo as H—X, wherein X is as defined in formula (I).

14. A composition comprising:
- (a) the sulfonic acid construct of formula (1); and
- (b) a cell comprising the cellular transport system of claim 1.

* * * * *

SEQUENCE LISTING

```
<160> NUMBER OF SEQ ID NOS: 94

<210> SEQ ID NO 1
<211> LENGTH: 580
<212> TYPE: PRT
<213> ORGANISM: Escherichia coli

<400> SEQUENCE: 1

Met Ile Lys Pro Thr Phe Leu Arg Arg Val Ala Ile Ala Ala Leu Leu
1               5                   10                  15

Ser Gly Ser Cys Phe Ser Ala Ala Ala Pro Pro Ala Pro Pro Val
            20                  25                  30

Ser Tyr Gly Val Glu Glu Asp Val Phe His Pro Val Arg Ala Lys Gln
        35                  40                  45

Gly Met Val Ala Ser Val Asp Ala Thr Ala Thr Gln Val Gly Val Asp
    50                  55                  60

Ile Leu Lys Glu Gly Gly Asn Ala Val Asp Ala Ala Val Ala Val Gly
65                  70                  75                  80

Tyr Ala Leu Ala Val Thr His Pro Gln Ala Gly Asn Leu Gly Gly Gly
                85                  90                  95

Gly Phe Met Leu Ile Arg Ser Lys Asn Gly Asn Thr Thr Ala Ile Asp
            100                 105                 110

Phe Arg Glu Met Ala Pro Ala Lys Ala Thr Arg Asp Met Phe Leu Asp
        115                 120                 125

Asp Gln Gly Asn Pro Asp Ser Lys Lys Ser Leu Thr Ser His Leu Ala
    130                 135                 140

Ser Gly Thr Pro Gly Thr Val Ala Gly Phe Ser Leu Ala Leu Asp Lys
145                 150                 155                 160

Tyr Gly Thr Met Pro Leu Asn Lys Val Val Gln Pro Ala Phe Lys Leu
                165                 170                 175

Ala Arg Asp Gly Phe Ile Val Asn Asp Ala Leu Ala Asp Asp Leu Lys
            180                 185                 190

Thr Tyr Gly Ser Glu Val Leu Pro Asn His Glu Asn Ser Lys Ala Ile
        195                 200                 205

Phe Trp Lys Glu Gly Glu Pro Leu Lys Lys Gly Asp Thr Leu Val Gln
    210                 215                 220

Ala Asn Leu Ala Lys Ser Leu Glu Met Ile Ala Glu Asn Gly Pro Asp
225                 230                 235                 240

Glu Phe Tyr Lys Gly Thr Ile Ala Glu Gln Ile Ala Gln Glu Met Gln
                245                 250                 255

Lys Asn Gly Gly Leu Ile Thr Lys Glu Asp Leu Ala Ala Tyr Lys Ala
            260                 265                 270

Val Glu Arg Thr Pro Ile Ser Gly Asp Tyr Arg Gly Tyr Gln Val Tyr
```

```
            275                 280                 285
Ser Met Pro Pro Ser Ser Gly Gly Ile His Ile Val Gln Ile Leu
    290                 295                 300

Asn Ile Leu Glu Asn Phe Asp Met Lys Lys Tyr Gly Phe Gly Ser Ala
305                 310                 315                 320

Asp Ala Met Gln Ile Met Ala Glu Ala Lys Tyr Ala Tyr Ala Asp
                325                 330                 335

Arg Ser Glu Tyr Leu Gly Asp Pro Asp Phe Val Lys Val Pro Trp Gln
            340                 345                 350

Ala Leu Thr Asn Lys Ala Tyr Ala Lys Ser Ile Ala Asp Gln Ile Asp
                355                 360                 365

Ile Asn Lys Ala Lys Pro Ser Ser Glu Ile Arg Pro Gly Lys Leu Ala
370                 375                 380

Pro Tyr Glu Ser Asn Gln Thr Thr His Tyr Ser Val Val Asp Lys Asp
385                 390                 395                 400

Gly Asn Ala Val Ala Val Thr Tyr Thr Leu Asn Thr Thr Phe Gly Thr
                405                 410                 415

Gly Ile Val Ala Gly Glu Ser Gly Ile Leu Leu Asn Asn Gln Met Asp
            420                 425                 430

Asp Phe Ser Ala Lys Pro Gly Val Pro Asn Val Tyr Gly Leu Val Gly
                435                 440                 445

Gly Asp Ala Asn Ala Val Gly Pro Asn Lys Arg Pro Leu Ser Ser Met
450                 455                 460

Ser Pro Thr Ile Val Val Lys Asp Gly Lys Thr Trp Leu Val Thr Gly
465                 470                 475                 480

Ser Pro Gly Gly Ser Arg Ile Ile Thr Thr Val Leu Gln Met Val Val
                485                 490                 495

Asn Ser Ile Asp Tyr Gly Leu Asn Val Ala Glu Ala Thr Asn Ala Pro
            500                 505                 510

Arg Phe His His Gln Trp Leu Pro Asp Glu Leu Arg Val Glu Lys Gly
                515                 520                 525

Phe Ser Pro Asp Thr Leu Lys Leu Leu Glu Ala Lys Gly Gln Lys Val
530                 535                 540

Ala Leu Lys Glu Ala Met Gly Ser Thr Gln Ser Ile Met Val Gly Pro
545                 550                 555                 560

Asp Gly Glu Leu Tyr Gly Ala Ser Asp Pro Arg Ser Val Asp Asp Leu
                565                 570                 575

Thr Ala Gly Tyr
                580

<210> SEQ ID NO 2
<211> LENGTH: 556
<212> TYPE: PRT
<213> ORGANISM: Pseudomonas nitroreducens

<400> SEQUENCE: 2

Met Arg Val Phe His Phe Ser Lys Leu Pro Leu Gly Val Ala Ile Leu
1               5                   10                  15

Ala Ala Ser Ser Ser Val Phe Ala Thr Leu Asp Gly Gly Ala Val Ala
                20                  25                  30

Ala Pro Asp Gln Tyr Gly Ala Lys Val Ala Ala Glu Ile Leu Lys Lys
            35                  40                  45

Gly Gly Asn Ala Val Asp Ala Val Ala Thr Ala Phe Thr Leu Ala
            50                  55                  60
```

```
Val Thr Tyr Pro Glu Ala Gly Asn Ile Gly Gly Gly Phe Met Thr
 65                  70                  75                  80

Leu Tyr Val Asp Gly Lys Pro Tyr Phe Leu Asp Tyr Arg Glu Ile Ala
                 85                  90                  95

Pro Lys Ala Ala Thr Lys Thr Met Tyr Leu Asn Glu Lys Gly Glu Val
                100                 105                 110

Ile Glu Asn Leu Ser Leu Val Gly Ala Lys Ala Gly Val Pro Gly
            115                 120                 125

Thr Val Met Gly Leu Trp Glu Ala His Gln Arg Phe Gly Lys Leu Lys
            130                 135                 140

Trp Ser Glu Leu Leu Thr Pro Ala Ile Gly Tyr Ala Gln Thr Gly Phe
145                 150                 155                 160

Lys Val Ala Asp Gln Gln Tyr Gln Tyr Arg Gln Asp Ala Ile Ala Leu
                165                 170                 175

Phe Asn Gly Lys Thr Asn Phe Gly Asp Tyr Phe Gly Thr Met Lys Pro
            180                 185                 190

Gly Glu Val Phe Lys Gln Pro Glu Leu Ala Lys Thr Leu Glu Arg Ile
            195                 200                 205

Ala Asp Lys Gly Pro Asp Asp Phe Tyr Lys Gly Glu Thr Ala Lys Leu
            210                 215                 220

Leu Ile Ala Gln Met Lys Gln Asp Gly Gly Leu Ile Thr Ser Asp Asp
225                 230                 235                 240

Leu Val Asp Tyr Gln Ala Lys Trp Arg Glu Pro Met Arg Ile Asp Trp
                245                 250                 255

Gln Gly Asn Thr Leu Tyr Thr Ala Pro Leu Pro Ser Ser Gly Gly Ile
            260                 265                 270

Ala Leu Ala Gln Leu Ile Gly Ile Lys Glu Gln Arg Ala Ala Asp Phe
            275                 280                 285

Lys Gly Val Glu Leu Asn Ser Ala Lys Tyr Ile His Leu Leu Ser Glu
            290                 295                 300

Ile Glu Lys Arg Val Phe Ala Asp Arg Ala Asp Tyr Leu Gly Asp Pro
305                 310                 315                 320

Gln Phe Ser Lys Val Pro Val Ala Gln Leu Thr Asp Pro Lys Tyr Ile
                325                 330                 335

Ala Lys Arg Ala Gly Glu Val Asn Pro Asp Ala Ile Ser Ala Thr Glu
            340                 345                 350

Lys Val Arg Pro Gly Leu Glu Pro His Gln Thr Thr His Phe Ser Ile
            355                 360                 365

Val Asp Lys Asp Gly Asn Ala Val Ser Asn Thr Tyr Thr Leu Asn Trp
            370                 375                 380

Asp Phe Gly Ser Gly Val Val Lys Gly Ala Gly Phe Leu Leu Asn
385                 390                 395                 400

Asp Glu Met Asp Asp Phe Ser Ser Lys Pro Gly Val Ala Asn Ala Phe
                405                 410                 415

Gly Val Val Gly Ser Asp Ala Asn Ala Ile Glu Pro Gly Lys Arg Met
            420                 425                 430

Leu Ser Ser Met Ser Pro Ser Ile Val Thr Arg Asp Gly His Val Ser
            435                 440                 445

Leu Val Leu Gly Thr Pro Gly Gly Ser Arg Ile Phe Thr Ser Ile Phe
            450                 455                 460

Gln Val Leu Asn Asn Val Tyr Asp Phe His Leu Pro Leu Glu Lys Ala
465                 470                 475                 480

Val Ala Ala Gln Arg Val His His Gln Leu Leu Pro Lys Asp Thr Ile
```

```
                        485                 490                 495
Tyr Tyr Asp Ala Tyr Ala Pro Leu Pro Gly Lys Val Ala Asp Glu Leu
                500                 505                 510

Lys Ala Met Gly Tyr Thr Leu Glu Asp Gln Gly Trp Asn Met Gly Asp
            515                 520                 525

Ile Gln Ala Ile Arg Val Asn Gly Lys Ala Leu Glu Thr Ala Ser Asp
        530                 535                 540

Pro Arg Gly Arg Gly Val Gly Met Val Val Lys Pro
545                 550                 555

<210> SEQ ID NO 3
<211> LENGTH: 572
<212> TYPE: PRT
<213> ORGANISM: Artificial Sequence
<220> FEATURE:
<223> OTHER INFORMATION: EcGGT ΔN24

<400> SEQUENCE: 3

Met Arg Gly Ser His His His His His His Gly Ser Ala Cys Glu Leu
1               5                   10                  15

Ala Ala Pro Pro Ala Pro Pro Val Ser Tyr Gly Val Glu Glu Asp Val
            20                  25                  30

Phe His Pro Val Arg Ala Lys Gln Gly Met Val Ala Ser Val Asp Ala
        35                  40                  45

Thr Ala Thr Gln Val Gly Val Asp Ile Leu Lys Glu Gly Gly Asn Ala
    50                  55                  60

Val Asp Ala Ala Val Ala Val Gly Tyr Ala Leu Ala Val Thr His Pro
65                  70                  75                  80

Gln Ala Gly Asn Leu Gly Gly Gly Phe Met Leu Ile Arg Ser Lys
                85                  90                  95

Asn Gly Asn Thr Thr Ala Ile Asp Phe Arg Glu Met Ala Pro Ala Lys
            100                 105                 110

Ala Thr Arg Asp Met Phe Leu Asp Asp Gln Gly Asn Pro Asp Ser Lys
        115                 120                 125

Lys Ser Leu Thr Ser His Leu Ala Ser Gly Thr Pro Gly Thr Val Ala
    130                 135                 140

Gly Phe Ser Leu Ala Leu Asp Lys Tyr Gly Thr Met Pro Leu Asn Lys
145                 150                 155                 160

Val Val Gln Pro Ala Phe Lys Leu Ala Arg Asp Gly Phe Ile Val Asn
                165                 170                 175

Asp Ala Leu Ala Asp Leu Lys Thr Tyr Gly Ser Glu Val Leu Pro
            180                 185                 190

Asn His Glu Asn Ser Lys Ala Ile Phe Trp Lys Glu Gly Glu Pro Leu
        195                 200                 205

Lys Lys Gly Asp Thr Leu Val Gln Ala Asn Leu Ala Lys Ser Leu Glu
    210                 215                 220

Met Ile Ala Glu Asn Gly Pro Asp Glu Phe Tyr Lys Gly Thr Ile Ala
225                 230                 235                 240

Glu Gln Ile Ala Gln Glu Met Gln Lys Asn Gly Gly Leu Ile Thr Lys
                245                 250                 255

Glu Asp Leu Ala Ala Tyr Lys Ala Val Glu Arg Thr Pro Ile Ser Gly
            260                 265                 270

Asp Tyr Arg Gly Tyr Gln Val Tyr Ser Met Pro Pro Pro Ser Ser Gly
        275                 280                 285

Gly Ile His Ile Val Gln Ile Leu Asn Ile Leu Glu Asn Phe Asp Met
```

```
                290                 295                 300
Lys Lys Tyr Gly Phe Gly Ser Ala Asp Ala Met Gln Ile Met Ala Glu
305                 310                 315                 320

Ala Glu Lys Tyr Ala Tyr Ala Asp Arg Ser Glu Tyr Leu Gly Asp Pro
                325                 330                 335

Asp Phe Val Lys Val Pro Trp Gln Ala Leu Thr Asn Lys Ala Tyr Ala
                340                 345                 350

Lys Ser Ile Ala Asp Gln Ile Asp Ile Asn Lys Ala Lys Pro Ser Ser
                355                 360                 365

Glu Ile Arg Pro Gly Lys Leu Ala Pro Tyr Glu Ser Asn Gln Thr Thr
370                 375                 380

His Tyr Ser Val Val Asp Lys Asp Gly Asn Ala Val Ala Val Thr Tyr
385                 390                 395                 400

Thr Leu Asn Thr Thr Phe Gly Thr Gly Ile Val Ala Gly Glu Ser Gly
                405                 410                 415

Ile Leu Leu Asn Asn Gln Met Asp Asp Phe Ser Ala Lys Pro Gly Val
                420                 425                 430

Pro Asn Val Tyr Gly Leu Val Gly Gly Asp Ala Asn Ala Val Gly Pro
                435                 440                 445

Asn Lys Arg Pro Leu Ser Ser Met Ser Pro Thr Ile Val Val Lys Asp
                450                 455                 460

Gly Lys Thr Trp Leu Val Thr Gly Ser Pro Gly Gly Ser Arg Ile Ile
465                 470                 475                 480

Thr Thr Val Leu Gln Met Val Val Asn Ser Ile Asp Tyr Gly Leu Asn
                485                 490                 495

Val Ala Glu Ala Thr Asn Ala Pro Arg Phe His His Gln Trp Leu Pro
                500                 505                 510

Asp Glu Leu Arg Val Glu Lys Gly Phe Ser Pro Asp Thr Leu Lys Leu
                515                 520                 525

Leu Glu Ala Lys Gly Gln Lys Val Ala Leu Lys Glu Ala Met Gly Ser
                530                 535                 540

Thr Gln Ser Ile Met Val Gly Pro Asp Gly Glu Leu Tyr Gly Ala Ser
545                 550                 555                 560

Asp Pro Arg Ser Val Asp Asp Leu Thr Ala Gly Tyr
                565                 570

<210> SEQ ID NO 4
<211> LENGTH: 548
<212> TYPE: PRT
<213> ORGANISM: Artificial Sequence
<220> FEATURE:
<223> OTHER INFORMATION: PnGGT ΔN24

<400> SEQUENCE: 4

Met Arg Gly Ser His His His His His His Gly Ser Ala Cys Glu Leu
1               5                   10                  15

Thr Leu Asp Gly Gly Ala Val Ala Ala Pro Asp Gln Tyr Gly Ala Lys
                20                  25                  30

Val Ala Ala Glu Ile Leu Lys Lys Gly Gly Asn Ala Val Asp Ala Ala
                35                  40                  45

Val Ala Thr Ala Phe Thr Leu Ala Val Thr Tyr Pro Glu Ala Gly Asn
                50                  55                  60

Ile Gly Gly Gly Gly Phe Met Thr Leu Tyr Val Asp Gly Lys Pro Tyr
65                  70                  75                  80

Phe Leu Asp Tyr Arg Glu Ile Ala Pro Lys Ala Ala Thr Lys Thr Met
```

```
                       85                  90                  95
Tyr Leu Asn Glu Lys Gly Glu Val Ile Glu Asn Leu Ser Leu Val Gly
                100                 105                 110

Ala Lys Ala Ala Gly Val Pro Gly Thr Val Met Gly Leu Trp Glu Ala
            115                 120                 125

His Gln Arg Phe Gly Lys Leu Lys Trp Ser Glu Leu Leu Thr Pro Ala
        130                 135                 140

Ile Gly Tyr Ala Gln Thr Gly Phe Lys Val Ala Asp Gln Gln Tyr Gln
145                 150                 155                 160

Tyr Arg Gln Asp Ala Ile Ala Leu Phe Asn Gly Lys Thr Asn Phe Gly
                165                 170                 175

Asp Tyr Phe Gly Thr Met Lys Pro Gly Glu Val Phe Lys Gln Pro Glu
            180                 185                 190

Leu Ala Lys Thr Leu Glu Arg Ile Ala Asp Lys Gly Pro Asp Asp Phe
        195                 200                 205

Tyr Lys Gly Glu Thr Ala Lys Leu Leu Ile Ala Gln Met Lys Gln Asp
    210                 215                 220

Gly Gly Leu Ile Thr Ser Asp Asp Leu Val Asp Tyr Gln Ala Lys Trp
225                 230                 235                 240

Arg Glu Pro Met Arg Ile Asp Trp Gln Gly Asn Thr Leu Tyr Thr Ala
                245                 250                 255

Pro Leu Pro Ser Ser Gly Gly Ile Ala Leu Ala Gln Leu Ile Gly Ile
            260                 265                 270

Lys Glu Gln Arg Ala Ala Asp Phe Lys Gly Val Glu Leu Asn Ser Ala
        275                 280                 285

Lys Tyr Ile His Leu Leu Ser Glu Ile Glu Lys Arg Val Phe Ala Asp
    290                 295                 300

Arg Ala Asp Tyr Leu Gly Asp Pro Gln Phe Ser Lys Val Pro Val Ala
305                 310                 315                 320

Gln Leu Thr Asp Pro Lys Tyr Ile Ala Lys Arg Ala Gly Glu Val Asn
                325                 330                 335

Pro Asp Ala Ile Ser Ala Thr Glu Lys Val Arg Pro Gly Leu Glu Pro
            340                 345                 350

His Gln Thr Thr His Phe Ser Ile Val Asp Lys Asp Gly Asn Ala Val
        355                 360                 365

Ser Asn Thr Tyr Thr Leu Asn Trp Asp Phe Gly Ser Gly Val Val
    370                 375                 380

Lys Gly Ala Gly Phe Leu Leu Asn Asp Glu Met Asp Asp Phe Ser Ser
385                 390                 395                 400

Lys Pro Gly Val Ala Asn Ala Phe Gly Val Val Gly Ser Asp Ala Asn
                405                 410                 415

Ala Ile Glu Pro Gly Lys Arg Met Leu Ser Ser Met Ser Pro Ser Ile
            420                 425                 430

Val Thr Arg Asp Gly His Val Ser Leu Val Leu Gly Thr Pro Gly Gly
        435                 440                 445

Ser Arg Ile Phe Thr Ser Ile Phe Gln Val Leu Asn Asn Val Tyr Asp
    450                 455                 460

Phe His Leu Pro Leu Glu Lys Ala Val Ala Gln Arg Val His His
465                 470                 475                 480

Gln Leu Leu Pro Lys Asp Thr Ile Tyr Tyr Asp Ala Tyr Ala Pro Leu
                485                 490                 495

Pro Gly Lys Val Ala Asp Glu Leu Lys Ala Met Gly Tyr Thr Leu Glu
            500                 505                 510
```

```
Asp Gln Gly Trp Asn Met Gly Asp Ile Gln Ala Ile Arg Val Asn Gly
            515                 520                 525

Lys Ala Leu Glu Thr Ala Ser Asp Pro Arg Gly Arg Gly Val Gly Met
        530                 535                 540

Val Val Lys Pro
545

<210> SEQ ID NO 5
<211> LENGTH: 320
<212> TYPE: PRT
<213> ORGANISM: Escherichia coli

<400> SEQUENCE: 5

Met Ala Ile Ser Ser Arg Asn Thr Leu Leu Ala Ala Leu Ala Phe Ile
1               5                   10                  15

Ala Phe Gln Ala Gln Ala Val Asn Val Thr Val Ala Tyr Gln Thr Ser
            20                  25                  30

Ala Glu Pro Ala Lys Val Ala Gln Ala Asp Asn Thr Phe Ala Lys Glu
        35                  40                  45

Ser Gly Ala Thr Val Asp Trp Arg Lys Phe Asp Ser Gly Ala Ser Ile
    50                  55                  60

Val Arg Ala Leu Ala Ser Gly Asp Val Gln Ile Gly Asn Leu Gly Ser
65                  70                  75                  80

Ser Pro Leu Ala Val Ala Ala Ser Gln Gln Val Pro Ile Glu Val Phe
                85                  90                  95

Leu Leu Ala Ser Lys Leu Gly Asn Ser Glu Ala Leu Val Val Lys Lys
            100                 105                 110

Thr Ile Ser Lys Pro Glu Asp Leu Ile Gly Lys Arg Ile Ala Val Pro
        115                 120                 125

Phe Ile Ser Thr Thr His Tyr Ser Leu Leu Ala Ala Leu Lys His Trp
    130                 135                 140

Gly Ile Lys Pro Gly Gln Val Glu Ile Val Asn Leu Gln Pro Pro Ala
145                 150                 155                 160

Ile Ile Ala Ala Trp Gln Arg Gly Asp Ile Asp Gly Ala Tyr Val Trp
                165                 170                 175

Ala Pro Ala Val Asn Ala Leu Glu Lys Asp Gly Lys Val Leu Thr Asp
            180                 185                 190

Ser Glu Gln Val Gly Gln Trp Gly Ala Pro Thr Leu Asp Val Trp Val
        195                 200                 205

Val Arg Lys Asp Phe Ala Glu Lys His Pro Glu Val Val Lys Ala Phe
    210                 215                 220

Ala Lys Ser Ala Ile Asp Ala Gln Gln Pro Tyr Ile Ala Asn Pro Asp
225                 230                 235                 240

Val Trp Leu Lys Gln Pro Glu Asn Ile Ser Lys Leu Ala Arg Leu Ser
                245                 250                 255

Gly Val Pro Glu Gly Asp Val Pro Gly Leu Val Lys Gly Asn Thr Tyr
            260                 265                 270

Leu Thr Pro Gln Gln Thr Ala Glu Leu Thr Gly Pro Val Asn Lys
        275                 280                 285

Ala Ile Ile Asp Thr Ala Gln Phe Leu Lys Glu Gln Gly Lys Val Pro
    290                 295                 300

Ala Val Ala Asn Asp Tyr Ser Gln Tyr Val Thr Ser Arg Phe Val Gln
305                 310                 315                 320
```

```
<210> SEQ ID NO 6
<211> LENGTH: 255
<212> TYPE: PRT
<213> ORGANISM: Escherichia coli

<400> SEQUENCE: 6

Met Leu Gln Ile Ser His Leu Tyr Ala Asp Tyr Gly Gly Lys Pro Ala
1               5                   10                  15

Leu Glu Asp Ile Asn Leu Thr Leu Glu Ser Gly Glu Leu Leu Val Val
            20                  25                  30

Leu Gly Pro Ser Gly Cys Gly Lys Thr Thr Leu Leu Asn Leu Ile Ala
        35                  40                  45

Gly Phe Val Pro Tyr Gln His Gly Ser Ile Gln Leu Ala Gly Lys Arg
    50                  55                  60

Ile Glu Gly Pro Gly Ala Glu Arg Gly Val Val Phe Gln Asn Glu Gly
65                  70                  75                  80

Leu Leu Pro Trp Arg Asn Val Gln Asp Asn Val Ala Phe Gly Leu Gln
                85                  90                  95

Leu Ala Gly Ile Glu Lys Met Gln Arg Leu Glu Ile Ala His Gln Met
            100                 105                 110

Leu Lys Lys Val Gly Leu Glu Gly Ala Glu Lys Arg Tyr Ile Trp Gln
        115                 120                 125

Leu Ser Gly Gly Gln Arg Gln Arg Val Gly Ile Ala Arg Ala Leu Ala
    130                 135                 140

Ala Asn Pro Gln Leu Leu Leu Asp Glu Pro Phe Gly Ala Leu Asp Ala
145                 150                 155                 160

Phe Thr Arg Asp Gln Met Gln Thr Leu Leu Lys Leu Trp Gln
                165                 170                 175

Glu Thr Gly Lys Gln Val Leu Leu Ile Thr His Asp Ile Glu Glu Ala
            180                 185                 190

Val Phe Met Ala Thr Glu Leu Val Leu Ser Ser Gly Pro Gly Arg
        195                 200                 205

Val Leu Glu Arg Leu Pro Leu Asn Phe Ala Arg Arg Phe Val Ala Gly
    210                 215                 220

Glu Ser Ser Arg Ser Ile Lys Ser Asp Pro Gln Phe Ile Ala Met Arg
225                 230                 235                 240

Glu Tyr Val Leu Ser Arg Val Phe Glu Gln Arg Glu Ala Phe Ser
                245                 250                 255

<210> SEQ ID NO 7
<211> LENGTH: 275
<212> TYPE: PRT
<213> ORGANISM: Escherichia coli

<400> SEQUENCE: 7

Met Ser Val Leu Ile Asn Glu Lys Leu His Ser Arg Arg Leu Lys Trp
1               5                   10                  15

Arg Trp Pro Leu Ser Arg Gln Val Thr Leu Ser Ile Gly Thr Leu Ala
            20                  25                  30

Val Leu Leu Thr Val Trp Trp Thr Val Ala Thr Leu Gln Leu Ile Ser
        35                  40                  45

Pro Leu Phe Leu Pro Pro Gln Gln Val Leu Glu Lys Leu Leu Thr
    50                  55                  60

Ile Ala Gly Pro Gln Gly Phe Met Asp Ala Thr Leu Trp Gln His Leu
65                  70                  75                  80

Ala Ala Ser Leu Thr Arg Ile Met Leu Ala Leu Phe Ala Ala Val Leu
```

```
                        85                  90                  95
Phe Gly Ile Pro Val Gly Ile Ala Met Gly Leu Ser Pro Thr Val Arg
            100                 105                 110
Gly Ile Leu Asp Pro Ile Ile Glu Leu Tyr Arg Pro Val Pro Pro Leu
            115                 120                 125
Ala Tyr Leu Pro Leu Met Val Ile Trp Phe Gly Ile Gly Glu Thr Ser
            130                 135                 140
Lys Ile Leu Leu Ile Tyr Leu Ala Ile Phe Ala Pro Val Ala Met Ser
145                 150                 155                 160
Ala Leu Ala Gly Val Lys Ser Val Gln Gln Val Arg Ile Arg Ala Ala
            165                 170                 175
Gln Ser Leu Gly Ala Ser Arg Ala Gln Val Leu Trp Phe Val Ile Leu
            180                 185                 190
Pro Gly Ala Leu Pro Glu Ile Leu Thr Gly Leu Arg Ile Gly Leu Gly
            195                 200                 205
Val Gly Trp Ser Thr Leu Val Ala Ala Glu Leu Ile Ala Ala Thr Arg
            210                 215                 220
Gly Leu Gly Phe Met Val Gln Ser Ala Gly Glu Phe Leu Ala Thr Asp
225                 230                 235                 240
Val Val Leu Ala Gly Ile Ala Val Ile Ala Ile Ala Phe Leu Leu
            245                 250                 255
Glu Leu Gly Leu Arg Ala Leu Gln Arg Arg Leu Thr Pro Trp His Gly
            260                 265                 270
Glu Val Gln
        275

<210> SEQ ID NO 8
<211> LENGTH: 319
<212> TYPE: PRT
<213> ORGANISM: Escherichia coli

<400> SEQUENCE: 8

Met Arg Asn Ile Ile Lys Leu Ala Leu Ala Gly Leu Leu Ser Val Ser
1               5                   10                  15
Thr Phe Ala Val Ala Ala Glu Ser Ser Pro Glu Ala Leu Arg Ile Gly
            20                  25                  30
Tyr Gln Lys Gly Ser Ile Gly Met Val Leu Ala Lys Ser His Gln Leu
            35                  40                  45
Leu Glu Lys Arg Tyr Pro Glu Ser Lys Ile Ser Trp Val Glu Phe Pro
    50                  55                  60
Ala Gly Pro Gln Met Leu Glu Ala Leu Asn Val Gly Ser Ile Asp Leu
65                  70                  75                  80
Gly Ser Thr Gly Asp Ile Pro Pro Ile Phe Ala Gln Ala Ala Gly Ala
            85                  90                  95
Asp Leu Val Tyr Val Gly Val Glu Pro Pro Lys Pro Lys Ala Glu Val
            100                 105                 110
Ile Leu Val Ala Glu Asn Ser Pro Ile Lys Thr Val Ala Asp Leu Lys
            115                 120                 125
Gly His Lys Val Ala Phe Gln Lys Gly Ser Ser His Asn Leu Leu
            130                 135                 140
Leu Arg Ala Leu Arg Gln Ala Gly Leu Lys Phe Thr Asp Ile Gln Pro
145                 150                 155                 160
Thr Tyr Leu Thr Pro Ala Asp Ala Arg Ala Ala Phe Gln Gln Gly Asn
            165                 170                 175
```

```
Val Asp Ala Trp Ala Ile Trp Asp Pro Tyr Tyr Ser Ala Ala Leu Leu
            180                 185                 190

Gln Gly Gly Val Arg Val Leu Lys Asp Gly Thr Asp Leu Asn Gln Thr
        195                 200                 205

Gly Ser Phe Tyr Leu Ala Ala Arg Pro Tyr Ala Glu Lys Asn Gly Ala
    210                 215                 220

Phe Ile Gln Gly Val Leu Ala Thr Phe Ser Glu Ala Asp Ala Leu Thr
225                 230                 235                 240

Arg Ser Gln Arg Glu Gln Ser Ile Ala Leu Ala Lys Thr Met Gly
                245                 250                 255

Leu Pro Ala Pro Val Ile Ala Ser Tyr Leu Asp His Arg Pro Pro Thr
                260                 265                 270

Thr Ile Lys Pro Val Asn Ala Glu Val Ala Ala Leu Gln Gln Gln Thr
                275                 280                 285

Ala Asp Leu Phe Tyr Glu Asn Arg Leu Val Pro Lys Lys Val Asp Ile
            290                 295                 300

Arg Gln Arg Ile Trp Gln Pro Thr Gln Leu Glu Gly Lys Gln Leu
305                 310                 315

<210> SEQ ID NO 9
<211> LENGTH: 255
<212> TYPE: PRT
<213> ORGANISM: Escherichia coli

<400> SEQUENCE: 9

Met Asn Thr Ala Arg Leu Asn Gln Gly Thr Pro Leu Leu Leu Asn Ala
1               5                   10                  15

Val Ser Lys His Tyr Ala Glu Asn Ile Val Leu Asn Gln Leu Asp Leu
            20                  25                  30

His Ile Pro Ala Gly Gln Phe Val Ala Val Gly Arg Ser Gly Gly
        35                  40                  45

Gly Lys Ser Thr Leu Leu Arg Leu Leu Ala Gly Leu Glu Thr Pro Thr
    50                  55                  60

Ala Gly Asp Val Leu Ala Gly Thr Thr Pro Leu Ala Glu Ile Gln Glu
65                  70                  75                  80

Asp Thr Arg Met Met Phe Gln Asp Ala Arg Leu Leu Pro Trp Lys Ser
                85                  90                  95

Val Ile Asp Asn Val Gly Leu Gly Leu Lys Gly Gln Trp Arg Asp Ala
            100                 105                 110

Ala Arg Arg Ala Leu Ala Ala Val Gly Leu Glu Asn Arg Ala Gly Glu
        115                 120                 125

Trp Pro Ala Ala Leu Ser Gly Gly Gln Lys Gln Arg Val Ala Leu Ala
    130                 135                 140

Arg Ala Leu Ile His Arg Pro Gly Leu Leu Leu Leu Asp Glu Pro Leu
145                 150                 155                 160

Gly Ala Leu Asp Ala Leu Thr Arg Leu Glu Met Gln Asp Leu Ile Val
                165                 170                 175

Ser Leu Trp Gln Glu His Gly Phe Thr Val Leu Leu Val Thr His Asp
            180                 185                 190

Val Ser Glu Ala Val Ala Met Ala Asp Arg Val Leu Leu Ile Glu Glu
        195                 200                 205

Gly Lys Ile Gly Leu Asp Leu Thr Val Asp Ile Pro Arg Pro Arg Arg
    210                 215                 220

Leu Gly Ser Val Arg Leu Ala Glu Leu Glu Ala Glu Val Leu Gln Arg
225                 230                 235                 240
```

-continued

```
Val Met Gln Arg Gly Glu Ser Glu Thr Arg Leu Arg Lys Gln Gly
            245                 250                 255

<210> SEQ ID NO 10
<211> LENGTH: 263
<212> TYPE: PRT
<213> ORGANISM: Escherichia coli

<400> SEQUENCE: 10

Met Ala Thr Pro Val Lys Lys Trp Leu Leu Arg Val Ala Pro Trp Phe
1               5                   10                  15

Leu Pro Val Gly Ile Val Ala Val Trp Gln Leu Ala Ser Ser Val Gly
            20                  25                  30

Trp Leu Ser Thr Arg Ile Leu Pro Ser Pro Glu Gly Val Val Thr Ala
        35                  40                  45

Phe Trp Thr Leu Ser Ala Ser Gly Glu Leu Trp Gln His Leu Ala Ile
    50                  55                  60

Ser Ser Trp Arg Ala Leu Ile Gly Phe Ser Ile Gly Gly Ser Leu Gly
65                  70                  75                  80

Leu Ile Leu Gly Leu Ile Ser Gly Leu Ser Arg Trp Gly Glu Arg Leu
                85                  90                  95

Leu Asp Thr Ser Ile Gln Met Leu Arg Asn Val Pro His Leu Ala Leu
            100                 105                 110

Ile Pro Leu Val Ile Leu Trp Phe Gly Ile Asp Glu Ser Ala Lys Ile
        115                 120                 125

Phe Leu Val Ala Leu Gly Thr Leu Phe Pro Ile Tyr Ile Asn Thr Trp
    130                 135                 140

His Gly Ile Arg Asn Ile Asp Arg Gly Leu Val Glu Met Ala Arg Ser
145                 150                 155                 160

Tyr Gly Leu Ser Gly Ile Pro Leu Phe Ile His Val Ile Leu Pro Gly
                165                 170                 175

Ala Leu Pro Ser Ile Met Val Gly Val Arg Phe Ala Leu Gly Leu Met
            180                 185                 190

Trp Leu Thr Leu Ile Val Ala Glu Thr Ile Ser Ala Asn Ser Gly Ile
        195                 200                 205

Gly Tyr Leu Ala Met Asn Ala Arg Glu Phe Leu Gln Thr Asp Val Val
    210                 215                 220

Val Val Ala Ile Ile Leu Tyr Ala Leu Leu Gly Lys Leu Ala Asp Val
225                 230                 235                 240

Ser Ala Gln Leu Leu Glu Arg Leu Trp Leu Arg Trp Asn Pro Ala Tyr
                245                 250                 255

His Leu Lys Glu Ala Thr Val
            260

<210> SEQ ID NO 11
<211> LENGTH: 465
<212> TYPE: PRT
<213> ORGANISM: Escherichia coli

<400> SEQUENCE: 11

Met Phe Thr Arg Val Ala Asn Phe Cys Arg Lys Val Leu Ser Arg Glu
1               5                   10                  15

Glu Ser Glu Ala Glu Gln Ala Val Ala Arg Pro Gln Val Thr Val Ile
            20                  25                  30

Pro Arg Glu Gln His Ala Ile Ser Arg Lys Asp Ile Ser Glu Asn Ala
        35                  40                  45
```

```
Leu Lys Val Met Tyr Arg Leu Asn Lys Ala Gly Tyr Glu Ala Trp Leu
    50                  55                  60

Val Gly Gly Val Arg Asp Leu Leu Leu Gly Lys Lys Pro Lys Asp
65                  70                  75                  80

Phe Asp Val Thr Thr Asn Ala Thr Pro Glu Gln Val Arg Lys Leu Phe
                85                  90                  95

Arg Asn Cys Arg Leu Val Gly Arg Phe Arg Leu Ala His Val Met
            100                 105                 110

Phe Gly Pro Glu Ile Ile Glu Val Ala Thr Phe Arg Gly His His Glu
            115                 120                 125

Gly Asn Val Ser Asp Arg Thr Thr Ser Gln Arg Gly Gln Asn Gly Met
    130                 135                 140

Leu Leu Arg Asp Asn Ile Phe Gly Ser Ile Glu Glu Asp Ala Gln Arg
145                 150                 155                 160

Arg Asp Phe Thr Ile Asn Ser Leu Tyr Tyr Ser Val Ala Asp Phe Thr
                165                 170                 175

Val Arg Asp Tyr Val Gly Gly Met Lys Asp Leu Lys Asp Gly Val Ile
            180                 185                 190

Arg Leu Ile Gly Asn Pro Glu Thr Arg Tyr Arg Glu Asp Pro Val Arg
            195                 200                 205

Met Leu Arg Ala Val Arg Phe Ala Ala Lys Leu Gly Met Arg Ile Ser
    210                 215                 220

Pro Glu Thr Ala Glu Pro Ile Pro Arg Leu Ala Thr Leu Leu Asn Asp
225                 230                 235                 240

Ile Pro Pro Ala Arg Leu Phe Glu Glu Ser Leu Lys Leu Leu Gln Ala
                245                 250                 255

Gly Tyr Gly Tyr Glu Thr Tyr Lys Leu Leu Cys Glu Tyr His Leu Phe
            260                 265                 270

Gln Pro Leu Phe Pro Thr Ile Thr Arg Tyr Phe Thr Glu Asn Gly Asp
            275                 280                 285

Ser Pro Met Glu Arg Ile Ile Glu Gln Val Leu Lys Asn Thr Asp Thr
    290                 295                 300

Arg Ile His Asn Asp Met Arg Val Asn Pro Ala Phe Leu Phe Ala Ala
305                 310                 315                 320

Met Phe Trp Tyr Pro Leu Leu Glu Thr Ala Gln Lys Ile Ala Gln Glu
                325                 330                 335

Ser Gly Leu Thr Tyr His Asp Ala Phe Ala Leu Ala Met Asn Asp Val
            340                 345                 350

Leu Asp Glu Ala Cys Arg Ser Leu Ala Ile Pro Lys Arg Leu Thr Thr
            355                 360                 365

Leu Thr Arg Asp Ile Trp Gln Leu Gln Leu Arg Met Ser Arg Arg Gln
    370                 375                 380

Gly Lys Arg Ala Trp Lys Leu Leu Glu His Pro Lys Phe Arg Ala Ala
385                 390                 395                 400

Tyr Asp Leu Leu Ala Leu Arg Ala Glu Val Glu Arg Asn Ala Glu Leu
                405                 410                 415

Gln Arg Leu Val Lys Trp Trp Gly Glu Phe Gln Val Ser Ala Pro Pro
            420                 425                 430

Asp Gln Lys Gly Met Leu Asn Glu Leu Asp Glu Pro Ser Pro Arg
            435                 440                 445

Arg Arg Thr Arg Arg Pro Arg Lys Arg Ala Pro Arg Arg Glu Gly Thr
    450                 455                 460
```

Ala
465

<210> SEQ ID NO 12
<211> LENGTH: 91
<212> TYPE: DNA
<213> ORGANISM: Artificial Sequence
<220> FEATURE:
<223> OTHER INFORMATION: TK037: Forward primer for cloning of
      6xHis_EcGGT (SacI)

<400> SEQUENCE: 12
atatgagctc aggaggatat acatatgaga ggatcgcatc accatcacca tcacggatcc    60
gcatgcataa aaccgacgtt tttacgccgg g                                   91

<210> SEQ ID NO 13
<211> LENGTH: 95
<212> TYPE: DNA
<213> ORGANISM: Artificial Sequence
<220> FEATURE:
<223> OTHER INFORMATION: TK040: Forward primer for cloning of
      6xHis_EcGGT ΔN16 (SacI)

<400> SEQUENCE: 13
atatgagctc aggaggatat acatatgaga ggatcgcatc accatcacca tcacggatcc    60
gcatgcgaac tctcaggaag ttgttttagc gccgc                               95

<210> SEQ ID NO 14
<211> LENGTH: 85
<212> TYPE: DNA
<213> ORGANISM: Artificial Sequence
<220> FEATURE:
<223> OTHER INFORMATION: TK326: Forward primer for cloning of
      6xHis_EcGGT ΔN24 (SacI)

<400> SEQUENCE: 14
atatgagctc aggaggatat acatatgaga ggatcgcatc accatcacca tcacggatcc    60
gcatgcgaac tcgccgcgcc tcctg                                          85

<210> SEQ ID NO 15
<211> LENGTH: 40
<212> TYPE: DNA
<213> ORGANISM: Artificial Sequence
<220> FEATURE:
<223> OTHER INFORMATION: TK038: Reverse primer for cloning of
      6xHis_EcGGT, 6xHis_EcGGT ΔN16 and 6xHis_EcGGT ΔN24 (PstI)

<400> SEQUENCE: 15
atatctgcag tcatcagtac cccgccgtta aatcatccac                          40

<210> SEQ ID NO 16
<211> LENGTH: 52
<212> TYPE: DNA
<213> ORGANISM: Artificial Sequence
<220> FEATURE:
<223> OTHER INFORMATION: TK021: Forward primer for cloning of
      EcGGT_6xHis (SacI)

<400> SEQUENCE: 16
atatgagctc aggaggatat acatatgata aaaccgacgt ttttacgccg gg            52

<210> SEQ ID NO 17
<211> LENGTH: 66
<212> TYPE: DNA
<213> ORGANISM: Artificial Sequence

```
<220> FEATURE:
<223> OTHER INFORMATION: TK022: Reverse primer for cloning of
      EcGGT_6xHis (PstI)

<400> SEQUENCE: 17
atatctgcag tcatcagtgg tggtggtggt ggtgctcgag gtaccccgcc gttaaatcat      60
ccaccg                                                                 66

<210> SEQ ID NO 18
<211> LENGTH: 86
<212> TYPE: DNA
<213> ORGANISM: Artificial Sequence
<220> FEATURE:
<223> OTHER INFORMATION: TK053: Forward primer for cloning of
      6xHis_PnGGT (SacI)

<400> SEQUENCE: 18
atatgagctc aggaggatat acatatgaga ggatcgcatc accatcacca tcacggatcc      60
gcatgcatgc gcgtgttcca cttcag                                           86

<210> SEQ ID NO 19
<211> LENGTH: 86
<212> TYPE: DNA
<213> ORGANISM: Artificial Sequence
<220> FEATURE:
<223> OTHER INFORMATION: TK324: Forward primer for cloning of
      6xHis_PnGGT ΔN16 (SacI)

<400> SEQUENCE: 19
atatgagctc aggaggatat acatatgaga ggatcgcatc accatcacca tcacggatcc      60
gcatgcgaac tcgcggcgag ttcgtc                                           86

<210> SEQ ID NO 20
<211> LENGTH: 85
<212> TYPE: DNA
<213> ORGANISM: Artificial Sequence
<220> FEATURE:
<223> OTHER INFORMATION: TK325: Forward primer for cloning of
      6xHis_PnGGT ΔN24 (SacI)

<400> SEQUENCE: 20
atatgagctc aggaggatat acatatgaga ggatcgcatc accatcacca tcacggatcc      60
gcatgcgaac tcaccctcga cggcg                                            85

<210> SEQ ID NO 21
<211> LENGTH: 35
<212> TYPE: DNA
<213> ORGANISM: Artificial Sequence
<220> FEATURE:
<223> OTHER INFORMATION: TK054: Reverse primer for cloning of
      6xHis_PnGGT, 6xHis_PnGGT ΔN16 and 6xHis_PnGGT ΔN24

<400> SEQUENCE: 21
atatctgcag tcatcagggt ttgaccacca tcccg                                 35

<210> SEQ ID NO 22
<211> LENGTH: 70
<212> TYPE: DNA
<213> ORGANISM: Artificial Sequence
<220> FEATURE:
<223> OTHER INFORMATION: TK140: Forward primer for amplification of liv
      operon knockout fragment from pKD13

<400> SEQUENCE: 22
```
aaaacaacat cacaacacac gtaataacca gaagaatggg gattctcagg gtgtaggctg    60
gagctgcttc                                                            70

<210> SEQ ID NO 23
<211> LENGTH: 70
<212> TYPE: DNA
<213> ORGANISM: Artificial Sequence
<220> FEATURE:
<223> OTHER INFORMATION: TK141: Reverse primer for amplification of liv
      operon knockout fragment from pKD13

<400> SEQUENCE: 23
tgtcacctgt ctcaaaggag tcttttgact ccctatcaat caacgtgtta attccgggga    60
tccgtcgacc                                                            70

<210> SEQ ID NO 24
<211> LENGTH: 33
<212> TYPE: DNA
<213> ORGANISM: Artificial Sequence
<220> FEATURE:
<223> OTHER INFORMATION: TK389: TS1F primer for scarless deletion of
      pcnB (EcoRI)

<400> SEQUENCE: 24
atatgaattc ggtcacgcaa tttactgacc agc                                  33

<210> SEQ ID NO 25
<211> LENGTH: 41
<212> TYPE: DNA
<213> ORGANISM: Artificial Sequence
<220> FEATURE:
<223> OTHER INFORMATION: TK390: TS1R primer for scarless deletion of
      pcnB

<400> SEQUENCE: 25
ggacgacgag tacgacgacg agcggctaat catagctcag c                         41

<210> SEQ ID NO 26
<211> LENGTH: 41
<212> TYPE: DNA
<213> ORGANISM: Artificial Sequence
<220> FEATURE:
<223> OTHER INFORMATION: TK391: TS2R primer for scarless deletion of
      pcnB

<400> SEQUENCE: 26
gctgagctat gattagccgc tcgtcgtcgt actcgtcgtc c                         41

<210> SEQ ID NO 27
<211> LENGTH: 32
<212> TYPE: DNA
<213> ORGANISM: Artificial Sequence
<220> FEATURE:
<223> OTHER INFORMATION: TK392: TS2R primer for scarless deletion of
      pcnB (BamHI)

<400> SEQUENCE: 27
tataggatcc gacgcaacat ctccccatca gg                                   32

<210> SEQ ID NO 28
<211> LENGTH: 58
<212> TYPE: DNA
<213> ORGANISM: Artificial Sequence
<220> FEATURE:
<223> OTHER INFORMATION: TK534: Forward primer for generation of
      pACT3/6xHis_PnGGT ΔN24 RBS library -continued

<400> SEQUENCE: 28
cacacaggaa acagaattcg agcthvvggv ggtatacata tgagaggatc gcatcacc    58

<210> SEQ ID NO 29
<211> LENGTH: 58
<212> TYPE: DNA
<213> ORGANISM: Artificial Sequence
<220> FEATURE:
<223> OTHER INFORMATION: TK535: Reverse primer for generation of
     pACT3/6xHis_PnGGT ΔN24 RBS library

<400> SEQUENCE: 29
ggtgatgcga tcctctcata tgtataccbc cbbdagctcg aattctgttt cctgtgtg    58

<210> SEQ ID NO 30
<211> LENGTH: 91
<212> TYPE: DNA
<213> ORGANISM: Artificial Sequence
<220> FEATURE:
<223> OTHER INFORMATION: TK417: Forward primer for amplification of
     pACT3/6xHis_PnGGT ΔN24 for genome integration

<400> SEQUENCE: 30
cgcgtatcct cctctgaaga tatcctttaa gtttactcgc ttcccgacaa aacgatgatt    60
aattcagagt tgttgatacc gggaagccct g                                   91

<210> SEQ ID NO 31
<211> LENGTH: 92
<212> TYPE: DNA
<213> ORGANISM: Artificial Sequence
<220> FEATURE:
<223> OTHER INFORMATION: TK418: Reverse primer for amplification of
     pACT3/6xHis_PnGGT ΔN24 for genome integration

<400> SEQUENCE: 31
gaaataaaaa aggctaccttt cggcttgccc tgacaaaata gccctcttcc cacgaagagg    60
gccgctaacc cagagcaaga gattacgcgc ag                                  92

<210> SEQ ID NO 32
<211> LENGTH: 14
<212> TYPE: PRT
<213> ORGANISM: Artificial Sequence
<220> FEATURE:
<223> OTHER INFORMATION: N-terminal sequence cloned to the EcGGT gene in
     pACT3

<400> SEQUENCE: 32

Met Arg Gly Ser His His His His His His Gly Ser Ala Cys
1               5                   10

<210> SEQ ID NO 33
<211> LENGTH: 8
<212> TYPE: PRT
<213> ORGANISM: Artificial Sequence
<220> FEATURE:
<223> OTHER INFORMATION: C-terminal sequence cloned to the EcGGT gene in
     pACT3

<400> SEQUENCE: 33

Leu Glu His His His His His His
1               5

<210> SEQ ID NO 34
<211> LENGTH: 16

```
<212> TYPE: PRT
<213> ORGANISM: Artificial Sequence
<220> FEATURE:
<223> OTHER INFORMATION: N-terminal sequence cloned to the EcGGT ΔN16
      gene to the in pACT3

<400> SEQUENCE: 34

Met Arg Gly Ser His His His His His His Gly Ser Ala Cys Glu Leu
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: N-terminal sequence cloned to the EcGGT ΔN24
      gene in pACT3

<400> SEQUENCE: 35

Met Arg Gly Ser His His His His His His Gly Ser Ala Cys Glu Leu
1               5                   10                  15

<210> SEQ ID NO 36
<211> LENGTH: 14
<212> TYPE: PRT
<213> ORGANISM: Artificial Sequence
<220> FEATURE:
<223> OTHER INFORMATION: N-terminal sequence cloned to the EcGGT gene in
      pACT3

<400> SEQUENCE: 36

Met Arg Gly Ser His His His His His His Gly Ser Ala Cys
1               5                   10

<210> SEQ ID NO 37
<211> LENGTH: 16
<212> TYPE: PRT
<213> ORGANISM: Artificial Sequence
<220> FEATURE:
<223> OTHER INFORMATION: N-terminal sequence cloned PnGGT ΔN16 gene in
      pACT3

<400> SEQUENCE: 37

Met Arg Gly Ser His His His His His His Gly Ser Ala Cys Glu Leu
1               5                   10                  15

<210> SEQ ID NO 38
<211> LENGTH: 16
<212> TYPE: PRT
<213> ORGANISM: Artificial Sequence
<220> FEATURE:
<223> OTHER INFORMATION: N-terminal sequence cloned to the PnGGT ΔN24
      gene in pACT3

<400> SEQUENCE: 38

Met Arg Gly Ser His His His His His His Gly Ser Ala Cys Glu Leu
1               5                   10                  15

<210> SEQ ID NO 39
<211> LENGTH: 8
<212> TYPE: DNA
<213> ORGANISM: Artificial Sequence
<220> FEATURE:
<223> OTHER INFORMATION: RBS sequence

<400> SEQUENCE: 39 acaggcgg                                                         8
```

```
<210> SEQ ID NO 40
<211> LENGTH: 8
<212> TYPE: DNA
<213> ORGANISM: Artificial Sequence
<220> FEATURE:
<223> OTHER INFORMATION: RBS sequence

<400> SEQUENCE: 40 cggggcgg                                                                8

<210> SEQ ID NO 41
<211> LENGTH: 8
<212> TYPE: DNA
<213> ORGANISM: Artificial Sequence
<220> FEATURE:
<223> OTHER INFORMATION: RBS sequence

<400> SEQUENCE: 41 acgggcgg                                                                8

<210> SEQ ID NO 42
<211> LENGTH: 8
<212> TYPE: DNA
<213> ORGANISM: Artificial Sequence
<220> FEATURE:
<223> OTHER INFORMATION: RBS sequence

<400> SEQUENCE: 42 cgcggggg                                                                8

<210> SEQ ID NO 43
<211> LENGTH: 8
<212> TYPE: DNA
<213> ORGANISM: Artificial Sequence
<220> FEATURE:
<223> OTHER INFORMATION: RBS sequence

<400> SEQUENCE: 43 tcgggcgg                                                                8

<210> SEQ ID NO 44
<211> LENGTH: 8
<212> TYPE: DNA
<213> ORGANISM: Artificial Sequence
<220> FEATURE:
<223> OTHER INFORMATION: RBS sequence

<400> SEQUENCE: 44 tccggcgg                                                                8

<210> SEQ ID NO 45
<211> LENGTH: 8
<212> TYPE: DNA
<213> ORGANISM: Artificial Sequence
<220> FEATURE:
<223> OTHER INFORMATION: RBS sequence

<400> SEQUENCE: 45 tacggcgg                                                                8

<210> SEQ ID NO 46
<211> LENGTH: 8
<212> TYPE: DNA
<213> ORGANISM: Artificial Sequence
<220> FEATURE:
<223> OTHER INFORMATION: RBS sequence
```

<400> SEQUENCE: 46 ccaggcgg                                                                 8

<210> SEQ ID NO 47
<211> LENGTH: 8
<212> TYPE: DNA
<213> ORGANISM: Artificial Sequence
<220> FEATURE:
<223> OTHER INFORMATION: RBS sequence

<400> SEQUENCE: 47 cagggagg                                                                 8

<210> SEQ ID NO 48
<211> LENGTH: 8
<212> TYPE: DNA
<213> ORGANISM: Artificial Sequence
<220> FEATURE:
<223> OTHER INFORMATION: RBS sequence

<400> SEQUENCE: 48 caaggcgg                                                                 8

<210> SEQ ID NO 49
<211> LENGTH: 8
<212> TYPE: DNA
<213> ORGANISM: Artificial Sequence
<220> FEATURE:
<223> OTHER INFORMATION: RBS sequence

<400> SEQUENCE: 49 accggcgg                                                                 8

<210> SEQ ID NO 50
<211> LENGTH: 8
<212> TYPE: DNA
<213> ORGANISM: Artificial Sequence
<220> FEATURE:
<223> OTHER INFORMATION: RBS sequence

<400> SEQUENCE: 50 cagggcgg                                                                 8

<210> SEQ ID NO 51
<211> LENGTH: 8
<212> TYPE: DNA
<213> ORGANISM: Artificial Sequence
<220> FEATURE:
<223> OTHER INFORMATION: RBS sequence

<400> SEQUENCE: 51 cgaggcgg                                                                 8

<210> SEQ ID NO 52
<211> LENGTH: 8
<212> TYPE: DNA
<213> ORGANISM: Artificial Sequence
<220> FEATURE:
<223> OTHER INFORMATION: RBS sequence

<400> SEQUENCE: 52 tggggcgg                                                                 8

<210> SEQ ID NO 53

```
<211> LENGTH: 10
<212> TYPE: DNA
<213> ORGANISM: Artificial Sequence
<220> FEATURE:
<223> OTHER INFORMATION: RBS sequence

<400> SEQUENCE: 53
tgaggcggaa                                                          10

<210> SEQ ID NO 54
<211> LENGTH: 34
<212> TYPE: DNA
<213> ORGANISM: Artificial Sequence
<220> FEATURE:
<223> OTHER INFORMATION: TK269: Forward primer for introducing D433N
      mutation in EcGGT

<400> SEQUENCE: 54
aataaccaga tggataattt ctccgccaaa ccgg                               34

<210> SEQ ID NO 55
<211> LENGTH: 34
<212> TYPE: DNA
<213> ORGANISM: Artificial Sequence
<220> FEATURE:
<223> OTHER INFORMATION: TK270: Reverse primer for introducing D433N
      mutation in EcGGT

<400> SEQUENCE: 55
ccggtttggc ggagaaatta tccatctggt tatt                               34

<210> SEQ ID NO 56
<211> LENGTH: 29
<212> TYPE: DNA
<213> ORGANISM: Artificial Sequence
<220> FEATURE:
<223> OTHER INFORMATION: TK275: Forward primer for introducing D405N
      mutation in PnGGT

<400> SEQUENCE: 56
cgacgagatg gataacttca gctccaagc                                     29

<210> SEQ ID NO 57
<211> LENGTH: 29
<212> TYPE: DNA
<213> ORGANISM: Artificial Sequence
<220> FEATURE:
<223> OTHER INFORMATION: TK276: Reverse primer for introducing D405N
      mutation in PnGGT

<400> SEQUENCE: 57
gcttggagct gaagttatcc atctcgtcg                                     29

<210> SEQ ID NO 58
<211> LENGTH: 31
<212> TYPE: DNA
<213> ORGANISM: Artificial Sequence
<220> FEATURE:
<223> OTHER INFORMATION: TK485: TS1F primer for scarless deletion of ssu
      (EcoRI)

<400> SEQUENCE: 58
atatgaattc tggcacatca atttgcacgc c                                  31

<210> SEQ ID NO 59
<211> LENGTH: 40
<212> TYPE: DNA
```

<213> ORGANISM: Artificial Sequence
<220> FEATURE:
<223> OTHER INFORMATION: TK486: TS1R primer for scarless deletion of ssu

<400> SEQUENCE: 59
ccgaatggcg gcaatagcgc ggtcagtctg tcggagagac          40

<210> SEQ ID NO 60
<211> LENGTH: 40
<212> TYPE: DNA
<213> ORGANISM: Artificial Sequence
<220> FEATURE:
<223> OTHER INFORMATION: TK487: TS2R primer for scarless deletion of ssu

<400> SEQUENCE: 60
gtctctccga cagactgacc gcgctattgc cgccattcgg          40

<210> SEQ ID NO 61
<211> LENGTH: 30
<212> TYPE: DNA
<213> ORGANISM: Artificial Sequence
<220> FEATURE:
<223> OTHER INFORMATION: TK488: TS2R primer for scarless deletion of ssu
      (BamHI)

<400> SEQUENCE: 61
tataggatcc gctggtgagc aagcagttcc          30

<210> SEQ ID NO 62
<211> LENGTH: 30
<212> TYPE: DNA
<213> ORGANISM: Artificial Sequence
<220> FEATURE:
<223> OTHER INFORMATION: TK293:Forward primer for randomization of
      residue F416 in PnGGT*
<220> FEATURE:
<221> NAME/KEY: variation
<222> LOCATION: 14,15
<223> OTHER INFORMATION: /replace="a,t,c,g"

<400> SEQUENCE: 62
cgtggccaac gccnnkggcg tggtgggcag          30

<210> SEQ ID NO 63
<211> LENGTH: 30
<212> TYPE: DNA
<213> ORGANISM: Artificial Sequence
<220> FEATURE:
<223> OTHER INFORMATION: TK594: Reverse primer for randomization of
      residue F416 in PnGGT*
<220> FEATURE:
<221> NAME/KEY: variation
<222> LOCATION: 16,17
<223> OTHER INFORMATION: /replace="a,t,c,g"

<400> SEQUENCE: 63
ctgcccacca cgccmnnggc gttggccacg          30

<210> SEQ ID NO 64
<211> LENGTH: 35
<212> TYPE: DNA
<213> ORGANISM: Artificial Sequence
<220> FEATURE:
<223> OTHER INFORMATION: TK595: Forward primer for randomization of
      residue R94 in PnGGT*
<220> FEATURE:
<221> NAME/KEY: variation
<222> LOCATION: 17,18
<223> OTHER INFORMATION: /replace="a,t,c,g"

```
<400> SEQUENCE: 64
gtacttcctc gactacnnkg agatcgcgcc gaagg                               35

<210> SEQ ID NO 65
<211> LENGTH: 35
<212> TYPE: DNA
<213> ORGANISM: Artificial Sequence
<220> FEATURE:
<223> OTHER INFORMATION: TK596: Reverse primer for randomization of
      residue R94 in PnGGT*
<220> FEATURE:
<221> NAME/KEY: variation
<222> LOCATION: 18,19
<223> OTHER INFORMATION: /replace="a,t,c,g"

<400> SEQUENCE: 65
ccttcggcgc gatctcmnng tagtcgagga agtac                               35

<210> SEQ ID NO 66
<211> LENGTH: 48
<212> TYPE: DNA
<213> ORGANISM: Artificial Sequence
<220> FEATURE:
<223> OTHER INFORMATION: TK599: Forward primer for randomization of
      residue E402 and D405 in PnGGT*
<220> FEATURE:
<221> NAME/KEY: variation
<222> LOCATION: 19,20,28,29
<223> OTHER INFORMATION: /replace="a,t,c,g"

<400> SEQUENCE: 66
ggcttcctgc tcaacgacnn katggatnnk ttcagctcca agccgggc                 48

<210> SEQ ID NO 67
<211> LENGTH: 48
<212> TYPE: DNA
<213> ORGANISM: Artificial Sequence
<220> FEATURE:
<223> OTHER INFORMATION: TK600: Reverse primer for randomization of
      residue E402 and D405 in PnGGT*
<220> FEATURE:
<221> NAME/KEY: variation
<222> LOCATION: 20,21,29,30
<223> OTHER INFORMATION: /replace="a,t,c,g"

<400> SEQUENCE: 67
gcccggcttg gagctgaamn natccatmnn gtcgttgagc aggaagcc                 48

<210> SEQ ID NO 68
<211> LENGTH: 41
<212> TYPE: DNA
<213> ORGANISM: Artificial Sequence
<220> FEATURE:
<223> OTHER INFORMATION: TK601: Forward primer for randomization of
      residue S434 and S435 in PnGGT*
<220> FEATURE:
<221> NAME/KEY: variation
<222> LOCATION: 18,19,21,22
<223> OTHER INFORMATION: /replace="a,t,c,g"

<400> SEQUENCE: 68
cgggcaagcg catgctcnnk nnkatgagcc cgagcatcgt c                        41

<210> SEQ ID NO 69
<211> LENGTH: 41
<212> TYPE: DNA
<213> ORGANISM: Artificial Sequence
<220> FEATURE:
```

```
<223> OTHER INFORMATION: TK602: Reverse primer for randomization of
      residue S434 and S435 in PnGGT*
<220> FEATURE:
<221> NAME/KEY: variation
<222> LOCATION: 20,21,23,24
<223> OTHER INFORMATION: /replace="a,t,c,g"

<400> SEQUENCE: 69
gacgatgctc gggctcatmn nmnngagcat gcgcttgccc g                    41

<210> SEQ ID NO 70
<211> LENGTH: 45
<212> TYPE: DNA
<213> ORGANISM: Artificial Sequence
<220> FEATURE:
<223> OTHER INFORMATION: TK603: Forward primer for randomization of
      residue T381 and N383 in PnGGT*
<220> FEATURE:
<221> NAME/KEY: variation
<222> LOCATION: 19,20,25,26
<223> OTHER INFORMATION: /replace="a,t,c,g"

<400> SEQUENCE: 70
gccgtcagca acacctacnn kctcnnktgg gacttcggca gcggc                45

<210> SEQ ID NO 71
<211> LENGTH: 45
<212> TYPE: DNA
<213> ORGANISM: Artificial Sequence
<220> FEATURE:
<223> OTHER INFORMATION: TK604: Reverse primer for randomization of
      residue T381 and N383 in PnGGT*
<220> FEATURE:
<221> NAME/KEY: variation
<222> LOCATION: 20,21,26,27
<223> OTHER INFORMATION: /replace="a,t,c,g"

<400> SEQUENCE: 71
gccgctgccg aagtcccamn ngagmnngta ggtgttgctg acggc                45

<210> SEQ ID NO 72
<211> LENGTH: 40
<212> TYPE: DNA
<213> ORGANISM: Artificial Sequence
<220> FEATURE:
<223> OTHER INFORMATION: TK605: Forward primer for randomization of
      residue G455 and G456 in PnGGT*
<220> FEATURE:
<221> NAME/KEY: variation
<222> LOCATION: 17,18,20,21
<223> OTHER INFORMATION: /replace="a,t,c,g"

<400> SEQUENCE: 72
ggtgctgggc acgcccnnkn nktcgcggat cttcacttcg                      40

<210> SEQ ID NO 73
<211> LENGTH: 40
<212> TYPE: DNA
<213> ORGANISM: Artificial Sequence
<220> FEATURE:
<223> OTHER INFORMATION: TK606: Reverse primer for randomization of
      residue G455 and G456 in PnGGT*
<220> FEATURE:
<221> NAME/KEY: variation
<222> LOCATION: 20,21,23,24
<223> OTHER INFORMATION: /replace="a,t,c,g"

<400> SEQUENCE: 73
cgaagtgaag atccgcgamn nmnngggcgt gcccagcacc                      40
```

<210> SEQ ID NO 74
<211> LENGTH: 67
<212> TYPE: DNA
<213> ORGANISM: Artificial Sequence
<220> FEATURE:
<223> OTHER INFORMATION: TK621: Forward primer for amplification of ssuA
      with an RBS library containing 32 variants and a 5' overhang for
      assembly with the pSEVA271_Ptet-PT7 backbone

<400> SEQUENCE: 74
ctatagggag accacaacgg tttccctcta aggrgshhaa acatgcgtaa catcattaaa      60
ctggcgc      67

<210> SEQ ID NO 75
<211> LENGTH: 29
<212> TYPE: DNA
<213> ORGANISM: Artificial Sequence
<220> FEATURE:
<223> OTHER INFORMATION: TK622: Reverse primer for amplification of ssuA

<400> SEQUENCE: 75
tcataattgt tttccttcca gttgagtgg      29

<210> SEQ ID NO 76
<211> LENGTH: 66
<212> TYPE: DNA
<213> ORGANISM: Artificial Sequence
<220> FEATURE:
<223> OTHER INFORMATION: TK623: Forward primer for amplification of ssuB
      with an RBS library containing 32 variants and a 5' overhang for
      assembly with ssuA

<400> SEQUENCE: 76
cccactcaac tggaaggaaa acaattatga ggrggwvbcg gaatgaatac tgctcgtctg      60
aaccag      66

<210> SEQ ID NO 77
<211> LENGTH: 23
<212> TYPE: DNA
<213> ORGANISM: Artificial Sequence
<220> FEATURE:
<223> OTHER INFORMATION: TK624: Reverse primer for amplification of ssuB

<400> SEQUENCE: 77
ttacccctgt tttctcaggc gag      23

<210> SEQ ID NO 78
<211> LENGTH: 63
<212> TYPE: DNA
<213> ORGANISM: Artificial Sequence
<220> FEATURE:
<223> OTHER INFORMATION: TK625: Forward primer for amplification of ssuC
      with an RBS library containing 32 variants and a 5' overhang for
      assembly with ssuB
<220> FEATURE:
<221> NAME/KEY: variation
<222> LOCATION: 38
<223> OTHER INFORMATION: /replace="a,t,c,g"

<400> SEQUENCE: 78
tctgaaactc gcctgagaaa acaggggtaa ggaggddnaa ggatggcaac gccagtgaag      60
aag      63

<210> SEQ ID NO 79
<211> LENGTH: 24

<212> TYPE: DNA
<213> ORGANISM: Artificial Sequence
<220> FEATURE:
<223> OTHER INFORMATION: TK626: Reverse primer for amplification of ssuC

<400> SEQUENCE: 79
tcataccgtg gcctccttca aatg                                            24

<210> SEQ ID NO 80
<211> LENGTH: 57
<212> TYPE: DNA
<213> ORGANISM: Artificial Sequence
<220> FEATURE:
<223> OTHER INFORMATION: TK627: Forward primer for amplification of the
      pSEVA271_Ptet-PT7 backbone with a 5' overhang for assembly with
      ssuC

<400> SEQUENCE: 80
cggcttatca tttgaaggag gccacggtat gacctcctgt gtgaaattgt tatccgc        57

<210> SEQ ID NO 81
<211> LENGTH: 21
<212> TYPE: DNA
<213> ORGANISM: Artificial Sequence
<220> FEATURE:
<223> OTHER INFORMATION: TK628: Reverse primer for amplification of the
      pSEVA271_Ptet-PT7 backbone

<400> SEQUENCE: 81
tagagggaaa ccgttgtggt c                                               21

<210> SEQ ID NO 82
<211> LENGTH: 67
<212> TYPE: DNA
<213> ORGANISM: Artificial Sequence
<220> FEATURE:
<223> OTHER INFORMATION: TK635: Forward primer for amplification of ssuA
      with an RBS library containing 144 variants and a 5' overhang for
      assembly with the pSEVA271_Ptet-PT7 backbone
<220> FEATURE:
<221> NAME/KEY: variation
<222> LOCATION: 31
<223> OTHER INFORMATION: /replace="a,t,c,g"

<400> SEQUENCE: 82
ctatagggag accacaacgg tttccctcta nggrrgdhaa acatgcgtaa catcattaaa     60
ctggcgc                                                               67

<210> SEQ ID NO 83
<211> LENGTH: 66
<212> TYPE: DNA
<213> ORGANISM: Artificial Sequence
<220> FEATURE:
<223> OTHER INFORMATION: TK636: Forward primer for amplification of ssuB
      with an RBS library containing 144 variants and a 5' overhang for
      assembly with ssuA
<220> FEATURE:
<221> NAME/KEY: variation
<222> LOCATION: 37
<223> OTHER INFORMATION: /replace="a,t,c,g"

<400> SEQUENCE: 83
cccactcaac tggaaggaaa acaattatga ggrrgdnhcg aatgaatac tgctcgtctg      60 aaccag                                                                66

<210> SEQ ID NO 84
<211> LENGTH: 63

```
<212> TYPE: DNA
<213> ORGANISM: Artificial Sequence
<220> FEATURE:
<223> OTHER INFORMATION: TK637: Forward primer for amplification of ssuC
      with an RBS library containing 144 variants and a 5' overhang for
      assembly with ssuB
<220> FEATURE:
<221> NAME/KEY: variation
<222> LOCATION: 38
<223> OTHER INFORMATION: /replace="a,t,c,g"

<400> SEQUENCE: 84
tctgaaactc gcctgagaaa acaggggtaa rgrggddnaa ggatggcaac gccagtgaag      60
aag                                                                   63

<210> SEQ ID NO 85
<211> LENGTH: 35
<212> TYPE: DNA
<213> ORGANISM: Artificial Sequence
<220> FEATURE:
<223> OTHER INFORMATION: TK640: Forward primer for randomization of
      residue D385 in PnGGT*
<220> FEATURE:
<221> NAME/KEY: variation
<222> LOCATION: 17,18,19
<223> OTHER INFORMATION: /replace="a,t,c,g"

<400> SEQUENCE: 85
ctacaccctc aactggnnnt tcggcagcgg cgtgg                                 35

<210> SEQ ID NO 86
<211> LENGTH: 34
<212> TYPE: DNA
<213> ORGANISM: Artificial Sequence
<220> FEATURE:
<223> OTHER INFORMATION: TK641: Reverse primer for randomization of
      residue D385 in PnGGT*
<220> FEATURE:
<221> NAME/KEY: variation
<222> LOCATION: 16,17,18
<223> OTHER INFORMATION: /replace="a,t,c,g"

<400> SEQUENCE: 86
cacgccgctg ccgaannncc agttgagggt gtag                                 34

<210> SEQ ID NO 87
<211> LENGTH: 33
<212> TYPE: DNA
<213> ORGANISM: Artificial Sequence
<220> FEATURE:
<223> OTHER INFORMATION: TK642: Forward primer for randomization of
      residue R170 in PnGGT*
<220> FEATURE:
<221> NAME/KEY: variation
<222> LOCATION: 16,17,18
<223> OTHER INFORMATION: /replace="a,t,c,g"

<400> SEQUENCE: 87
cagcagtacc agtacnnnca ggacgccatc gcg                                  33

<210> SEQ ID NO 88
<211> LENGTH: 33
<212> TYPE: DNA
<213> ORGANISM: Artificial Sequence
<220> FEATURE:
<223> OTHER INFORMATION: TK643: Reverse primer for randomization of
      residue R170 in PnGGT*
<220> FEATURE:
<221> NAME/KEY: variation
<222> LOCATION: 16,17,18
```

<223> OTHER INFORMATION: /replace="a,t,c,g"

<400> SEQUENCE: 88
cgcgatggcg tcctgnnngt actggtactg ctg                          33

<210> SEQ ID NO 89
<211> LENGTH: 37
<212> TYPE: DNA
<213> ORGANISM: Artificial Sequence
<220> FEATURE:
<223> OTHER INFORMATION: TK644: Forward primer for randomization of
      residues Y167 and Q168 in PnGGT*
<220> FEATURE:
<221> NAME/KEY: variation
<222> LOCATION: 17,18,20,21
<223> OTHER INFORMATION: /replace="a,t,c,g"

<400> SEQUENCE: 89
ggtcgccgac cagcagnnkn nktaccgcca ggacgcc                      37

<210> SEQ ID NO 90
<211> LENGTH: 37
<212> TYPE: DNA
<213> ORGANISM: Artificial Sequence
<220> FEATURE:
<223> OTHER INFORMATION: TK645: Reverse primer for randomization of
      residues Y167 and Q168
      in PnGGT*
<220> FEATURE:
<221> NAME/KEY: variation
<222> LOCATION: 17,18,20,21
<223> OTHER INFORMATION: /replace="a,t,c,g"

<400> SEQUENCE: 90
ggcgtcctgg cggtamnnmn nctgctggtc ggcgacc                      37

<210> SEQ ID NO 91
<211> LENGTH: 27
<212> TYPE: DNA
<213> ORGANISM: Artificial Sequence
<220> FEATURE:
<223> OTHER INFORMATION: TK656: TS1F primer for scarless deletion of
      nadB (EcoRI)

<400> SEQUENCE: 91
atatgaattc cgggaaacca gactcgc                                 27

<210> SEQ ID NO 92
<211> LENGTH: 46
<212> TYPE: DNA
<213> ORGANISM: Artificial Sequence
<220> FEATURE:
<223> OTHER INFORMATION: TK657: TS1R primer for scarless deletion of
      nadB

<400> SEQUENCE: 92
cgctgaccca ggctttttat ctggtcacat gaatgttcag ggagag            46

<210> SEQ ID NO 93
<211> LENGTH: 46
<212> TYPE: DNA
<213> ORGANISM: Artificial Sequence
<220> FEATURE:
<223> OTHER INFORMATION: TK658: TS2R primer for scarless deletion of
      nadB

<400> SEQUENCE: 93
ctctccctga acattcatgt gaccagataa aaagcctggg tcagcg            46

```
<210> SEQ ID NO 94
<211> LENGTH: 28
<212> TYPE: DNA
<213> ORGANISM: Artificial Sequence
<220> FEATURE:
<223> OTHER INFORMATION: TK659: TS2R primer for scarless deletion of
      nadB (BamHI)

<400> SEQUENCE: 94
atatggatcc ggaaagtgaa gctgccgc                                          28
```